(12) United States Patent
Liu et al.

(10) Patent No.: US 8,158,634 B2
(45) Date of Patent: Apr. 17, 2012

(54) COMPOUNDS AND COMPOSITIONS AS INHIBITORS OF CANNABINOID RECEPTOR 1 ACTIVITY

(75) Inventors: Hong Liu, San Diego, CA (US);
Xiaohui He, San Diego, CA (US);
Ha-Soon Choi, San Diego, CA (US);
Kunyong Yang, San Diego, CA (US);
David Woodmansee, San Diego, CA (US); Zhicheng Wang, San Diego, CA (US); David Archer Ellis, San Diego, CA (US); Baogen Wu, San Diego, CA (US); Yun He, San Diego, CA (US);
Truc Ngoc Nguyen, Vista, CA (US)

(73) Assignee: IRM LLC, Hamilton (BM)

( * ) Notice: Subject to any disclaimer, the term of this patent is extended or adjusted under 35 U.S.C. 154(b) by 1134 days.

(21) Appl. No.: 11/718,016

(22) PCT Filed: Oct. 26, 2005

(86) PCT No.: PCT/US2005/038361
§ 371 (c)(1),
(2), (4) Date: Apr. 26, 2007

(87) PCT Pub. No.: WO2006/047516
PCT Pub. Date: May 4, 2006

(65) Prior Publication Data
US 2009/0247517 A1    Oct. 1, 2009

Related U.S. Application Data

(60) Provisional application No. 60/622,508, filed on Oct. 26, 2004, provisional application No. 60/672,670, filed on Apr. 18, 2005.

(51) Int. Cl.
C07D 487/04 (2006.01)
A61K 31/519 (2006.01)
A61P 3/04 (2006.01)
C07D 471/04 (2006.01)
C07D 473/30 (2006.01)
A61K 31/5025 (2006.01)
A61K 31/5365 (2006.01)

(52) U.S. Cl. ............ 514/262.1; 544/262; 544/254; 544/264; 544/255; 544/350; 546/118; 514/249; 514/260.1; 514/261.1; 514/263.1; 514/303

(58) Field of Classification Search ............ 544/265; 514/265.1
See application file for complete search history.

(56) References Cited

U.S. PATENT DOCUMENTS

| | | | |
|---|---|---|---|
| 6,956,033 B2 | 10/2005 | Ogawa et al. | |
| 2004/0214838 A1 | 10/2004 | Carpino et al. | |
| 2004/0259870 A1 * | 12/2004 | Feng et al. | 514/229.2 |

FOREIGN PATENT DOCUMENTS

| | | |
|---|---|---|
| EP | 1514552 | 3/2005 |
| JP | 2-101078 | 4/1990 |
| WO | WO 95/21838 | 8/1995 |
| WO | WO 02/26718 | 4/2002 |
| WO | WO 0226718 * | 4/2002 |
| WO | WO 2004/012671 | 2/2004 |
| WO | WO 2004/037176 | 5/2004 |
| WO | WO 2004/037823 | 5/2004 |
| WO | WO 2004/087053 | 10/2004 |
| WO | WO 2004/094417 | 11/2004 |
| WO | WO 2004/096130 | 11/2004 |
| WO | WO 2005/049613 | 6/2005 |

OTHER PUBLICATIONS

Nielsen, et al., "Phosphorus Pentoxide in Organic Synthesis-I", Tetrahedron, 1982, pp. 1435-1441, vol. 38, No. 10, Pergason Press Ltd., Great Britain.
Oertel, et al., "Synthese and Reaktionen substituierter Pyrazolo [3,4-d] pyrimidine" Pharmazie, 1992, pp. 251-254, vol. 47, No. 4, Germany.
Nielsen, et al., Phosphorus Pentoxide in Organic Synthesis, Chemica Scripta, 1984, pp. 208-223, vol. 24.
El-Emary, et al., "Facile synthesis of some new pyrazolo{3,4-b] pyrazines and their antifungal activity", II Farmaco, 1998, pp. 383-388, vol. 53, Elsevier Science S.A.
Sicker, et al., "Eine vereinfachte Synthese fur Pyrazolo[3,4-b] pyrazine", Journal f. prakt. Chemie, 1990, pp. 584-586, vol. 332, No. 4, Germany. Wang, et al., "A Facile Synthesis of 6-Alkoxyl (Aroxyl)-1,5-Dihydropyrazolo-[3,4-d]Pyrimidin-4-One Derivatives", Heterocyclic Communications, 2004, vol. 10, Nos. 2-3.
He, et al., "Synthesis and characterization of a novel heterocycle: 1-substituted-4-arylazamethylene-6-arylpyrazolo[5,4-d]-1,3-oxazine", Journal of Heterocyclic Chemistry, 2008, pp. 365-369, vol. 45, No. 2, American Chemical Socirty, US.
Rangneckar et al., "Synthesis of 5-hetarylpyrazolo[3,4-b]pyrazines and their use as disperse dyes for polyester fibres", Dyes and Pigments, 1990, pp. 241-250, vol. 13, No. 4, Elsevier Science Ltd.
Colombo, et al., "Synthesis of Pyrazolo [3,4-b]diazepines and Pyrazolo[3,4-b] pyrazines", Journal of Heterocyclic Chemistry, 1989, pp. 949-955, Vol. 26.
Muccioli, "Blocking the Cannbinoid Receptors: Drug Candidates and Therpeutic Promises", Chemistry and Biodiversity, 2007, pp. 1805-1827, vol. 4, Verlag Helvetica Chimica Actua AG, Zurich, Switzerland.
Muccioli, et al., "Current Knowledge on the Antagonists and Inverse Agonists of Cannabinoid Receptors", Current Medicinal Chemistry, 2005, pp. 1361-2394, vol. 12, Bentham Science Publishers, Ltd.

* cited by examiner

*Primary Examiner* — Susanna Moore
(74) *Attorney, Agent, or Firm* — Chihang Amy Smith; Genomics Institute of the Novartis Research Foundation

(57) ABSTRACT

The invention provides compounds having Formula Ia,

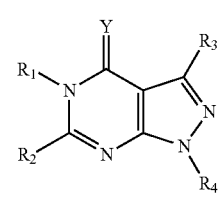

Ia or a pharmaceutically acceptable salt thereof, wherein $R_1$, $R_2$, $R_3$, $R_4$ and Y are as defined in the specification; as well as pharmaceutical compositions comprising such compounds and methods of using such compounds to treat or prevent diseases or disorders associated with the activity of Cannabinoid Receptor 1 (CB1).

11 Claims, No Drawings

COMPOUNDS AND COMPOSITIONS AS INHIBITORS OF CANNABINOID RECEPTOR 1 ACTIVITY

CROSS-REFERENCE TO RELATED APPLICATIONS

This application is the National Stage of Application No. PCT/US2005/038361, filed on Oct. 26, 2005 which claims benefit under 35 U.S.C. §119(e) of U.S. Provisional Application Nos. 60/622,508, filed Oct. 26, 2004, and 60/672,670, filed Apr. 18, 2005, the contents of which are incorporated herein by reference in their entirety.

BACKGROUND OF THE INVENTION

1. Field of the Invention

The invention provides compounds, pharmaceutical compositions comprising such compounds and methods of using such compounds to treat or prevent diseases or disorders associated with the activity of Cannabinoid Receptor 1 (CB1).

2. Background

The cannabinoids are psychoactive ingredients of marijuana, principally delta-9-tetrahydrocannabinol. Two cannabinoid receptors have been cloned, CB1 and CB2. CB1 is predominantly expressed in the central nervous system whereas CB2 is expressed in peripheral tissues, principally in the immune system. Both receptors are members of the G-protein coupled class and their inhibition is linked to adenylate cyclase activity.

The novel compounds of this invention inhibit the activity of CB1 and are, therefore, expected to be useful in the treatment of CB1-associated diseases or disorders such as, but not limited to, psychosis, memory deficit, cognitive disorders, migraine, neuropathy, neuroinflammatory disorders, cerebral vascular accidents, head trauma, anxiety disorders, substance abuse (such as smoking cessation), stress, epilepsy, Parkinson's disease, schizophrenia, osteoporosis, constipation, chronic intestinal pseudo-obstruction, cirrhosis of the liver, asthma, obesity, and other eating disorders associated with excessive food intake.

SUMMARY OF THE INVENTION

In one aspect, the present invention provides compound selected from Formula Ia, Ib, Ic, Id, Ie, If, Ig, Ih, Ii, Ij and Ik:

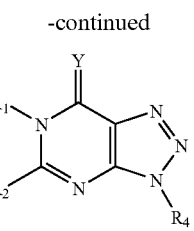

in which:

Y is selected from O, NR$_7$ and S; wherein R$_7$ is selected from hydrogen, hydroxy and C$_{1-6}$alkyl;

R$_1$ is selected from C$_{5-10}$heteroaryl, C$_{3-12}$cycloalkyl, phenyl and benzyl; wherein said heteroaryl, cycloalkyl, phenyl and benzyl of R$_1$ is optionally substituted with 1 to 3 radicals independently selected from halo, hydroxy, cyano, nitro, C$_{1-6}$alkyl, C$_{1-6}$alkoxy, halo-substituted C$_{1-6}$alkyl, halo-substituted C$_{1-6}$alkoxy, —NR$_8$R$_9$, —S(O)$_{0-2}$R$_8$, —C(O)OR$_8$ and R$_{10}$;

R$_2$ is selected from C$_{3-8}$heterocycloalkyl, C$_{5-10}$heteroaryl, phenyl and phenoxy; wherein said heterocycloalkyl, heteroaryl, phenyl or phenoxy of R$_2$ is optionally substituted with 1 to 3 radicals independently selected from halo, hydroxy, cyano, nitro, C$_{1-6}$alkyl, C$_{1-6}$alkoxy, halo-substituted C$_{1-6}$alkyl, C$_{1-6}$alkenyl, halo-substituted C$_{1-6}$alkoxy, —XNR$_8$R$_9$, —XOR$_8$, —XC(O)R$_8$, —XS(O)$_{0-2}$R$_8$, —XC(O)NR$_8$R$_9$, —XC(O)OR$_8$, —XOR$_{10}$, —XNR$_8$XR$_{10}$ and —XR$_{10}$; wherein each X is independently selected from a bond, C$_{1-4}$alkylene and C$_{2-4}$alkenylene;

R$_3$ is selected from hydrogen, halo, hydroxy, cyano, cyano-C$_{1-6}$alkyl, nitro, C$_{1-6}$alkyl, C$_{1-6}$alkoxy, halo-substituted-C$_{1-6}$alkyl, halo-substituted C$_{1-6}$alkoxy, —XNR$_8$R$_9$, —XR$_{10}$, —XS(O)$_{0-2}$R$_9$, —XC(O)R$_{10}$, —XC(O)NR$_8$R$_9$, —XC(O)NR$_8$R$_{10}$ and —XC(O)OR$_8$;

R$_4$ is selected from C$_{1-6}$alkyl, halo-substituted C$_{1-6}$alkyl, C$_{6-10}$aryl-C$_{0-4}$alkyl, C$_{5-10}$heteroaryl, C$_{3-12}$cycloalkyl, C$_{3-8}$heterocycloalkyl and C(O)R$_{11}$; wherein R$_{11}$ is selected from C$_{3-8}$heterocycloalkyl and C$_{3-8}$heteroaryl; wherein any alkyl of R$_4$ can optionally have a methylene replaced with O, S(O)$_{0-2}$ and NR$_8$; wherein any cycloalkyl, heterocycloalkyl, aryl or heteroaryl of R$_4$ can optionally be substituted with 1 to 3 radicals independently selected from halo, hydroxy, cyano, nitro, C$_{1-6}$alkyl, C$_{1-6}$alkoxy, halo-substituted-C$_{1-6}$alkyl, halo-substituted-C$_{1-6}$alkoxy, —XOR$_8$, —XR$_{10}$, —XC(O)R$_{10}$, —XS(O)$_{0-2}$R$_8$, —XNR$_8$R$_9$, —XC(O)NR$_8$R$_9$, —XC(O)NR$_8$R$_{10}$, —XC(O)NR$_8$XNR$_8$R$_9$, —XC(O)NR$_8$XOR$_9$ and —XC(O)OR$_8$;

R$_5$ is selected from hydrogen, halo, hydroxy, C$_{1-6}$alkyl, C$_{1-6}$alkoxy, halo-substituted-C$_{1-6}$alkyl, halo-substituted-C$_{1-6}$alkoxy, hydroxy-substituted-C$_{1-6}$alkyl, hydroxy-substituted-C$_{1-6}$alkoxy, —NR$_8$R$_9$, —OXOR$_8$, —OXR$_{10}$, —NR$_8$XOR$_9$, —OXNR$_8$R$_9$ and —C(O)OR$_8$; wherein X is independently selected from a bond, C$_{1-4}$alkylene and C$_{2-4}$alkenylene;

R$_6$ is selected from hydrogen, halo, hydroxy, cyano, nitro, C$_{1-6}$alkyl, C$_{1-6}$alkoxy, halo-substituted C$_{1-6}$alkyl, halo-substituted C$_{1-6}$alkoxy, —XNR$_8$R$_9$, —XNR$_8$XOR$_9$, —XNR$_8$NR$_8$R$_9$, —XOXNR$_8$R$_9$, —XNR$_8$S(O)$_2$R$_9$, —XS(O)$_2$R$_9$, and —XC(O)OR$_8$;

R$_8$ and R$_9$ are independently selected from hydrogen, C$_{1-6}$alkyl and C$_{2-6}$alkenyl; or R$_8$ and R$_9$ together with the nitrogen atom to which both are attached form C$_{3-8}$heterocycloalkyl or C$_{5-10}$heteroaryl; and R$_{10}$ is selected from C$_{5-10}$heteroatyl, C$_{3-8}$heterocycloalkyl, C$_{3-12}$cycloalkyl and phenyl; wherein said heteroaryl or heterocycloalkyl of R$_{10}$ or the combination of R$_8$ and R$_9$ and additionally the cycloalkyl or phenyl of R$_{10}$ is optionally substituted with 1 to 3 radicals independently selected from halo, hydroxy, cyano, cyano-C$_{1-6}$ alkyl, nitro, C$_{1-6}$alkyl, C$_{1-6}$alkoxy, halo-substituted-C$_{1-6}$ alkyl, halo-substituted-C$_{1-6}$alkoxy, hydroxy-substituted-C$_{1-6}$ alkyl, hydroxy-substituted-C$_{1-6}$alkoxy, phenyl, —NR$_8$R$_8$, —S(O)$_{0-2}$R$_8$ and —C(O)OR$_8$; wherein each R$_8$ is independently selected from hydrogen, C$_{1-6}$alkyl and C$_{2-6}$alkenyl; and the pharmaceutically acceptable salts, hydrates, solvates and isomers thereof; with the proviso that compounds of Formula Ia do not include compounds of Formula II (as detailed infra).

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of CB1 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which CB1 activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. C$_{1-6}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3] dioxole, imidazolyl, benzo-imidazolyl, pyrsmidinyl, furanyl, oxazolyl, isoxazolyl, triazolyl, tetrazolyl, pyrazolyl, thienyl, 1H-pyridin-2-onyl, 6-oxo-1,6-dihydro-pyridin-3-yl, etc. "C$_{6-10}$ arylC$_{0-4}$alkyl" means an aryl as described above connected via a alkylene grouping. For example, C$_{6-10}$arylC$_{0-4}$ alkyl includes phenethyl, benzyl, etc. Heteroaryl also includes the N-oxide derivatives, for example, pyridine N-oxide derivatives with the following structure:

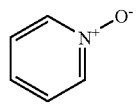

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, 2-oxo-pyrrolidin-1-yl, 2-oxo-piperidin-1-yl, etc.

"Compounds of Formula II" are defined as: 5-(4-Isopropyl-phenyl)-1-phenyl-6-p-tolyl-1,5-dihydro-pyrazolo[3,4-d]pyrimidin-4-one; 6-(4-Bromo-phenyl)-1-phenyl-5-p-tolyl-1,5-dihydro-pyrazolo[3,4-d]pyrimidin-4-one; 1-Phenyl-5,6-di-m-tolyl-1,5-dihydro-pyrazolo[3,4-d]pyrimidin-4-one; 1-Phenyl-5,6-di-m-tolyl-1,5-dihydro-pyrazolo[3,4-d]pyrimidin-4-one; 1,5-Diphenyl-6-m-tolyl-1,5-dihydro-pyrazolo[3,4-d]pyrimidin-4-one; 1-Phenyl-5-o-tolyl-6-p-tolyl-1,5-dihydro-pyrazolo[3,4-d]pyrimidin-4-one; 5-(4-Ethoxy-phenyl)-1-phenyl-6-p-tolyl-1,5-dihydro-pyrazolo[3,4-d]pyrimidin-4-one; 5-(4-Chloro-phenyl)-1-phenyl-6-p-tolyl-1,5-dihydro-pyrazolo[3,4-d]pyrimidin-4-one; 5-(4-Isopropyl-phenyl)-1,6-diphenyl-1,5-dihydro-pyrazolo[3,4-d]pyrimidin-4-one; 5-(4-Bromo-phenyl)-6-(2-fluoro-phenyl)-1-phenyl-1,5-dihydro-pyrazolo[3,4-d]pyrimidin-4-one; 5-(4-Methoxy-phenyl)-1-phenyl-6-p-tolyl-1,5-dihydro-pyrazolo[3,4-d]pyrimidin-4-one; 6-(2-Fluoro-phenyl)-1-phenyl-5-m-tolyl-1,5-dihydro-pyrazolo[3,4-d]pyrimidin-4-one; 5-(4-Fluoro-phenyl)-6-(2-fluoro-phenyl)-1-phenyl-1,5-dihydro-pyrazolo[3,4-d]pyrimidin-4-one; 5-(4-Bromo-phenyl)-1-phenyl-6-m-tolyl-1,5-dihydro-pyrazolo[3,4-d]pyrimidin-4-one; 5-(4-Chloro-phenyl)-1-phenyl-6-m-tolyl-1,5-dihydro-pyrazolo[3,4-d]pyrimidin-4-one; 6-(2-Fluoro-phenyl)-5-(4-methoxy-phenyl)-1-phenyl-1,5-dihydro-pyrazolo[3,4-d]pyrimidin-4-one; 1-Phenyl-6-mtolyl-5-p-tolyl-1,5-dihydro-pyrazolo[3,4-d]pyrimidin-4-one; 6-(4-Chloro-phenyl)-5-(4-fluoro-phenyl)-1-phenyl-1,5-dihydro-pyrazolo[3,4-d]pyrimidin-4-one; 5-(3-Chloro-phenyl)-1-phenyl-6-m-tolyl-1,5-dihydro-pyrazolo[3,4-d]pyrimidin-4-one; 1-Phenyl-5,6-di-p-tolyl-1,5-dihydro-pyrazolo[3,4-d]pyrimidin-4-one; 6-(4-Chloro-phenyl)-5-(4-ethoxy-phenyl)-1-phenyl-1,5-dihydro-pyrazolo[3,4-d]pyrimidin-4-one; 5-(4-Chloro-phenyl)-1-phenyl-6-p-tolyl-1,5-dihydro-pyrazolo[3,4-d]pyrimidin-4-one; 5,6-Bis-(4-bromo-phenyl)-1-phenyl-1,5-dihydro-pyrazolo[3,4-d]pyrimidin-4-one; 5,6-Bis-(4-chloro-phenyl)-1-phenyl-1,5-dihydro-pyrazolo[3,4-d]pyrimidin-4-one; 5-(3-Chloro-phenyl)-6-(2-fluoro-phenyl)-1-phenyl-1,5-dihydro-pyrazolo[3,4-d]pyrimidin-4-one; 6-(2-Fluoro-phenyl)-1,5-diphenyl-1,5-dihydro-pyrazolo[3,4-d]pyrimidin-4-one; 1,5-Phenyl-6-p-tolyl-1,5-dihydro-pyrazolo[3,4-d]pyrimidin-4-one; 5-(3-Chloro-phenyl)-6-(4-chloro-phenyl)-1-phenyl-1,5-dihydro-pyrazolo[3,4-d]pyrimidin-4-one; 5-(4-Methoxy-phenyl)-1,6-diphenyl-1,5-dihydro-pyrazolo[3,4-d]pyrimidin-4-one; 5-(3-Chloro-phenyl)-1-phenyl-6-p-tolyl-1,5-dihydro-pyrazolo[3,4-d]pyrimidin-4-one; 1-Phenyl-5,6-di-p-tolyl-1,5-dihydro-pyrazolo[3,4-d]pyrimidin-4-one; 6-(4-Chloro-phenyl)-1-phenyl-5-p-tolyl-1,5-dihydro pyrazolo[3,4-d]pyrimidin-4-one; 6-(4-Bromo-phenyl)-5-(2,4-dimethyl-phenyl)-1-phenyl-1,5-dihydro-pyrazolo[3,4-d]pyrimidin-4-one; 6-(4-Chloro-phenyl)-1-phenyl-5-m-tolyl-1,5-dihydro-pyrazolo[3,4-d]pyrimidin-4-one; 6-(4-Bromo-phenyl)-1-phenyl-5-o-tolyl-1,5-dihydro-pyrazolo[3,4-d]pyrimidin-4-one; 6-(2-Fluoro-phenyl)-1-phenyl-5-o-tolyl-1,5-dihydro-pyrazolo[3,4-d]pyrimidin-4-one; 5-(4-Isopropyl-phenyl)-1-phenyl-6-m-tolyl-1,5-dihydro-pyrazolo[3,4-d]pyrimidin-4-one; 6-(4-Bromo-phenyl)-1-phenyl-5-m-tolyl-1,5-dihydro-pyrazolo[3,4-d]pyrimidin-4-one; 6-(4-Bromo-phenyl)-5-(4-ethoxy-phenyl)-1-phenyl-1,5-dihydro-pyrazolo[3,4-d]pyrimidii>4-one; 5-(4-Chloro-phenyl)-6-(2-fluoro-phenyl)-1-phenyl-1,5-dihydro-pyrazolo[3,4-d]pyrimidin-4-one; 5-(3-Chloro-phenyl)-1-phenyl-6-o-tolyl-1,5-dihydro-pyrazolo[3,4-d]pyrimidin-4-one; 5-(3,5-Dimethyl-phenyl)-1-phenyl-6-m-tolyl-1,5-dihydro-pyrazolo[3,4-d]pyrimidin-4-one; 6-(4-Bromo-phenyl)-5-(4-fluoro-phenyl)-1-phenyl-1,5-dihydro-pyrazolo[3,4-d]pyrimidin-4-one; 5-(4-Fluoro-phenyl)-1-phenyl-6-o-tolyl-1,5-dihydro-pyrazolo[3,4-d]pyrimidin-4-one; 1-Phenyl-5-m-tolyl-6-p-tolyl-1,5-dihydro-pyrazolo[3,4-d]pyrimidin-4-one; 5-(4-Bromo-phenyl)-1,6-diphenyl-1,5-dihydro-pyrazolo[3,4-d]pyrimidin-4-one; 5-(3-Chloro-phenyl)-1,6-diphenyl-1,5-dihydro-pyrazolo[3,4-d]pyrimidin-4-one; 1,6-Diphenyl-5-m-tolyl-1,5-dihydro-pyrazolo[3,4-d]pyrimidin-4-one; 5-(4-Ethoxy-phenyl)-1,6-diphenyl-1,5-dihydro-pyrazolo[3,4-d]pyrimidin-4-one; 6-(4-Bromo-phenyl)-5-(3-chloro-phenyl)-1-phenyl-1,5-dihydro-pyrazolo[3,4-d]pyrimidin-4-one; 6-(4-Chloro-phenyl)-1-phenyl-5-o-tolyl-1,5-dihydro-pyrazolo[3,4-d]pyrimidin-4-one; 6-(4-Chloro-phenyl)-5-(3,5-dimethyl-phenyl)-1-phenyl-1,5-dihydro-pyrazolo[3,4-d]pyrimidin-4-one; 1-Phenyl-6-o-tolyl-5-p-tolyl-1,5-dihydro-pyrazolo[3,4-d]pyrimidin-4-one; 1,5,6-Triphenyl-1,5-dihydro-pyrazolo[3,4-d]pyrimidin-4-one; 5-(4-Bromo-phenyl)-6-(4-chloro-phenyl)-1-phenyl)-5-dihydro-pyrazolo[3,4-d]pyrimidin-4-one; 6-(2-Fluoro-phenyl)-5-(4-isopropyl-phenyl)-1-phenyl-1,5-dihydro-pyrazolo[3,4-d]pyrimidin-4-one; 6-(2-Fluoro-phenyl)-1-phenyl-5-p-tolyl-1,5-dihydro-pyrazolo[3,4-d]pyrimidin-4-one; 6-(4-Bromo-phenyl)-5-(4-isopropyl-phenyl)-1-phenyl-1,5-dihydro-pyrazolo[3,4-d]pyrimidin-4-one; 6-(4-Bromo-phenyl)-5-(4-chloro-phenyl)-1-phenyl-1,5-dihydro-pyrazolo[3,4-d]pyrimidin-4-one; 5-(4-Fluoro-phenyl)-1-phenyl-6-m-tolyl-1,5-dihydro-pyrazolo[3,4-d]pyrimidin-4-one; 1,6-Diphenyl-5-o-tolyl 1,5-dihydro-pyrazolo[3,4-d]pyrimidin-4-one; 5-(4-Ethoxy-phenyl)-6-(2-fluorophenyl)-1-phenyl-1,5-dihydro-pyrazolo[3,4-d]pyrimidin-4-one; and 1,6-Diphenyl-5-p-tolyl-1,5-dihydro-pyrazolo[3,4-d]pyrimidin-4-one.

"Halogen" (or halo) preferably represents chloro or fluoro, but can also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which inhibition of CB1 activity can prevent, inhibit or ameliorate the pathology and/or symptomology of the diseases, which method comprises administering to the animal a therapeutically effective amount of a compound of Formula I.

In one embodiment, with reference to compounds of the invention, $R_1$ is selected from phenyl and cyclohexyl; wherein said phenyl and cyclohexyl are optionally substituted with 1 to 3 radicals independently selected from halo, hydroxy, cyano, nitro, $C_{1-6}$alkyl, $C_{1-6}$alkoxy, halo-substituted-$C_{1-6}$alkyl, halo-substituted-$C_{1-6}$alkoxy, —$NR_8R_9$, —$S(O)_2R_8$, —$C(O)OR_8$ and $R_{10}$; wherein $R_8$ and $R_9$ are independently selected from hydrogen, $C_{1-6}$alkyl and $C_{2-6}$alkenyl; or $R_8$ and $R_9$ together with the nitrogen atom to which both are attached form $C_{3-8}$heterocycloalkyl or $C_{5-10}$heteroaryl; and $R_{10}$ is selected from $C_{5-10}$heteroaryl, $C_{3-8}$heterocycloalkyl, $C_{3-12}$cycloalkyl and phenyl; wherein said phenyl of $R_1$ and heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, nitro, $C_{1-6}$alkyl, $C_{1-6}$alkoxy, halo-substituted-$C_{1-6}$alkyl, halo-substituted-$C_{1-6}$alkoxy, phenyl, —$NR_8R_8$ and —$C(O)OR_8$; wherein each $R_8$ is independently selected from hydrogen, $C_{1-6}$alkyl and $C_{2-6}$alkenyl.

In another embodiment, $R_2$ is selected from piperazinyl, morpholino, benzthiazolyl, pyridinyl, pyrazolyl, phenyl and phenoxy; wherein said piperazinyl, morpholino, benzthiazolyl, pyridinyl, pyrazolyl, phenyl or phenoxy is optionally substituted with 1 to 3 radicals independently selected from halo, hydroxy, cyano, nitro, $C_{1-6}$alkyl, $C_{1-6}$alkoxy, halo-substituted $C_{1-6}$alkyl, halo-substituted $C_{1-6}$alkoxy, —$XNR_8R_9$, —$XOR_8$, —$XC(O)R_8$, $XS(O)_{0-2}R_8$, —$XC(O)NR_8R_9$, —$XC(O)OR_8$, —$XOR_{10}$, —$XNR_8R_{10}$ and $XR_{10}$; wherein each X is independently selected from a bond, $C_{1-4}$alkylene and $C_{2-4}$alkenylene; and $R_8$ and $R_9$ are independently selected from hydrogen, $C_{1-6}$alkyl and $C_{2-6}$alkenyl; or $R_8$ and $R_9$ together with the nitrogen atom to which both are attached form $C_{3-8}$heterocycloalkyl or $C_{5-10}$heteroaryl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, cyano-$C_{1-6}$alkyl, nitro, $C_{1-6}$alkyl, $C_{1-6}$alkoxy, halo-substituted-$C_{1-6}$alkyl, halo-substituted-$C_{1-6}$alkoxy, phenyl, —$NR_8R_8$ and —$C(O)OR_8$; wherein each $R_8$ is independently selected from hydrogen, $C_{1-6}$alkyl and $C_{2-6}$alkenyl.

In another embodiment, $R_4$ is selected from $C_{1-6}$alkyl, phenyl, $C_{5-10}$heteroaryl, $C_{3-8}$heterocycloalkyl, $C_{3-8}$heterocycloalkyl-carbonyl and $C_{3-12}$cycloalkyl; wherein any phenyl, cycloalkyl, heteroaryl or heterocycloalkyl of $R_4$ can optionally be substituted with 1 to 3 radicals independently selected from halo, hydroxy, cyano, nitro, $C_{1-6}$alkyl, $C_{1-6}$alkoxy, halo-substituted $C_{1-6}$alkyl, halo-substituted $C_{1-6}$alkoxy, —$XS(O)_{0-2}R_8$, —$XNR_8R_9$, —$XC(O)NR_8R_9$, —$XC(O)NR_8R_{10}$, —$XC(O)NR_8XNR_8R_9$, $XC(O)NR_8XOR_9$, —$XOR_8$, —$XC(O)R_{10}$ and —$XC(O)OR_9$; wherein each X is independently selected from a bond, $C_{1-4}$alkylene and $C_{2-4}$alkenylene; each $R_8$ is independently selected from hydrogen, $C_{1-6}$alkyl and $C_{2-6}$alkenyl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, cyano-$C_{1-6}$alkyl, nitro, $C_{1-6}$alkyl, $C_{1-6}$alkoxy, halo-substituted-$C_{1-6}$alkyl, halo-substituted-$C_{1-6}$alkoxy, phenyl, —$NR_8R_8$ and —$C(O)OR_8$; wherein each $R_8$ is independently selected from hydrogen, $C_{1-6}$alkyl and $C_{2-6}$alkenyl.

In another embodiment, $R_5$ is selected from ethoxy, chloro, hydroxy, dimethyl-amino, morpholino-ethoxy, methoxy, amino, hydroxy-ethoxy, dimethyl-amino-ethoxy, hydroxy-ethyl-amino, morpholino-propoxy and methyl-piperazinyl-ethoxy.

In another embodiment are compounds Formula Ia:

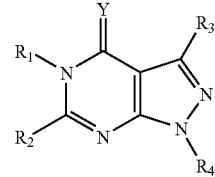

in which: Y is O; and $R_3$ is selected from hydrogen, cyano, halo, halo-substituted-$C_{1-6}$alkyl, cyano-$C_{1-6}$alkyl, $C_{1-6}$alkyl, —$XS(O)_{0-2}R_{9a}$, —$XC(O)NR_{8a}R_{9a}$, —$XC(O)OR_{8n}$, —$XR_{10}$ and —$XC(O)R_{10}$; wherein each $R_{8a}$ and $R_{9a}$ are independently selected from hydrogen and $C_{1-6}$alkyl; or $R_{8a}$ and $R_{9a}$ together with the nitrogen atom to which both are attached form $C_{3-8}$heterocycloalkyl or $C_{5-10}$heteroaryl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_{8a}$ and $R_{9a}$ and additionally the cycloalkyl or phenyl of $R_{10}$ is optionally substituted with 1 to 3 radicals independently selected from halo, hydroxy, cyano, cyano-$C_{1-6}$alkyl, nitro, $C_{1-6}$alkyl, $C_{1-6}$alkoxy, halo-substituted-$C_{1-6}$alkyl, halo-substituted $C_{1-6}$alkoxy, phenyl, —$NR_{8a}R_{8a}$ and —$C(O)OR_{8a}$; wherein each $R_{8a}$ is independently selected from hydrogen and $C_{1-6}$alkyl.

In a further embodiment, with respect to compounds of Formula Ia, $R_1$ is selected from phenyl and cyclohexyl; wherein said phenyl and cyclohexyl is optionally substituted with 1 to 2 radicals independently selected from chloro, bromo, fluoro, methyl, cyano, methyl-sulfanyl, t-butyl, methoxy-carbonyl, butoxy, trifluoromethoxy, trifluoromethyl, methoxy, isopropyl, piperidinyl and phenyl optionally substituted with halo.

In a further embodiment, $R_2$ is selected from piperazinyl, morpholino, pyridinyl, pyrazolyl, benzthiazolyl, phenyl and phenoxy; wherein said piperazinyl, morpholino, pyridinyl, pyrazolyl, benzthiazolyl, phenyl or phenoxy is optionally substituted with 1 to 2 radicals independently selected from: bromo; chloro; fluoro; iodo; hydroxy; isopropyl; methyl; cyclohexyl; oxazolyl; isoxazolyl optionally substituted with 1 to 2 methyl radicals; pyrazolidinyl; methyl-carbonyl; amino-carbonyl; morpholino; thienyl; furanyl; cyclohexyl-amino optionally substituted with an amino radical; methyl-sulfonyl; trichloromethyl; methoxy-carbonyl; chloro-methyl; butoxy-ethenyl; butoxy-ethyl; trifluoromethyl; trifluoromethoxy; ethoxy-carbonyl; t-butyl; amino-carbonyl; ethyl; propyl; methoxy; methoxy-methyl; carboxy; piperidinyl; piperidinyl-methyl; morpholino-methyl; diethyl-amino-methyl; isobutyl-amino-methyl; cyclopropyl-methyl-amino-methyl; isopropoxy-methyl; ethenyl; cyclopropyl; butoxy; [1,2,4]oxadiazol-5-yl optionally substituted with methyl; piperazinyl optionally substituted with 1 to 2 radicals independently selected from methyl, isopropyl and methyl-sulfonyl; 2-oxo-piperidin-1-yl; 2-oxo-pyrrolidin-1-yl; 2H-[1,2,4]triazol-3-yl; 1-methyl-1H-[1,2,4]triazol-3-yl; pyrazolyl optionally substituted with methyl; pyridazinyl; pyrazinyl optionally substituted with 1 to 2 radicals independently selected from cyano and methyl; pyridinyl optionally substituted with 1 to 2 radicals independently selected from halo, methyl and amino; pyridinyl-N-oxide optionally substituted with methyl; pyrimidinyl optionally substituted with 1 to 2 radicals independently selected from halo, methyl and amino; phenyl optionally substituted with 1 to 2 radicals independently selected from halo, methyl and trifluoromethyl; imidazolyl optionally substituted with 1 to 2 radicals independently selected from methyl, ethyl and cyano-methyl; and 6-oxo-1,6-dihydro-pyridin-3-yl.

In a further embodiment, $R_3$ is selected from hydrogen, methyl, methyl-sulfonyl, t-butoxy-carbonyl-methyl, amino-carbonyl-methyl, methyl-[1,2,4]oxadiazolyl, cyano-methyl, carboxy, ethoxy-carbonyl, methyl-amino-carbonyl, dimethyl-amino-carbonyl, benzyl, furanyl, pyridinyl, indolyl, morpholino-carbonyl, piperidinyl-amino-carbonyl, piperidinyl-carbonyl, isopropoxy-carbonyl, amino-carbonyl, methyl-sulfanyl, methyl-amino-carbonyl, cyano, methyl-sulfonyl, methyl-piperazinyl, benzyl and phenyl optionally substituted with 1 to 2 radicals independently selected from methyl, methoxy, fluoro, chloro, bromo, iodo, cyano, nitro, hydroxy-methyl, ethoxy-carbonyl, methyl-sulfonyl, dimethyl-ammo, methyl-amino, cyclopropyl-aminocarbonyl, isopropoxy, trifluoromethyl and trifluoromethoxy.

In a further embodiment, $R_4$ is methyl, hydroxy-ethyl, t-butyl, phenyl, benzyl, cyclohexyl, cyclopropyl, pyridinyl, furanyl, morpholino-carbonyl, tetrahydro-thiopyranyl, tetrahydro-thiopyranyl 1,1-dioxide and quinolinyl; wherein said phenyl, benzyl, cyclohexyl, cyclopropyl, pyridinyl, furanyl, morpholino-carbonyl, tetrahydro-thiopyranyl, tetrahydro-thiopyranyl 1,1-dioxide and quinolinyl of $R_4$ is optionally substituted with 1 to 2 radicals independently selected from methyl, cyano, carboxy, aminocarbonyl, methoxy, trifluoromethyl, isopropoxy, methyl-sulfanyl, dimethyl-amino, ethoxy-carbonyl, trifluoromethoxy, cyclopropyl-aminocarbonyl, pyridinyl-aminocarbonyl, cyclohexyl-aminocarbonyl, isoxazolyl-aminocarbonyl, dimethylamino-ethyl-aminocarbonyl, methoxy-ethyl-aminocarbonyl, nitro, amino, fluoro, chloro, bromo, hydroxymethyl, methyl-piperazinyl-carbonyl, morpholino-carbonyl and piperidinyl-carbonyl.

In another embodiment are compounds of Formula Ic:

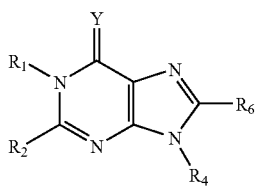

Ic in which: Y is O; and $R_6$ is selected from hydrogen, halo, cyano, $C_{1-6}$alkyl, $C_{1-6}$alkoxy, halo-substituted $C_{1-6}$alkyl, —$XNR_8R_9$, —$XNR_8S(O)_2R_9$, —$XR_{10}$, —$XOXNR_8R_9$ and —$XNR_8NR_8R_9$; wherein each X is independently selected from a bond, $C_{1-4}$alkylene and $C_{2-4}$alkenylene; each $R_8$ is independently selected from hydrogen, $C_{1-6}$alkyl and $C_{2-6}$alkenyl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, cyano-$C_{1-6}$alkyl, nitro, $C_{1-6}$alkyl, $C_{1-6}$alkoxy, halo-substituted-$C_{1-6}$alkyl, halo-substituted-$C_{1-6}$alkoxy, phenyl, —$NR_8R_8$ and —$C(O)OR_8$; wherein each $R_8$ is independently selected from hydrogen, $C_{1-6}$alkyl and $C_{2-6}$alkenyl.

In a further embodiment, with respect to compounds of Formula Ic, $R_1$ is selected from phenyl and cyclohexyl; wherein said phenyl and cyclohexyl is optionally substituted with 1 to 2 radicals independently selected from chloro, bromo, fluoro, methyl, cyano, methyl-sulfanyl, t-butyl, methoxy-carbonyl, butoxy, trifluoromethoxy, trifluoromethyl, methoxy, isopropyl, piperidinyl and phenyl optionally substituted with halo.

In a further embodiment, $R_2$ is selected from piperazinyl, morpholino, pyridinyl, pyrazolyl, benzthiazolyl, phenyl and phenoxy; wherein said piperazinyl, morpholino, pyridinyl, pyrazolyl, benzthiazolyl, phenyl or phenoxy is optionally substituted with 1 to 2 radicals independently selected from: bromo; chloro; fluoro; iodo; hydroxy; isopropyl; methyl; cyclohexyl; oxazolyl; isoxazolyl optionally substituted with 1 to 2 methyl radicals; pyrazolidinyl; methyl-carbonyl; amino-carbonyl; morpholino; thienyl; furanyl; cyclohexyl-amino optionally substituted with an amino radical; methyl-sulfonyl; trichloromethyl; methoxy-carbonyl; chloro-methyl; butoxy-ethenyl; butoxy-ethyl; trifluoromethyl; trifluoromethoxy; ethoxy-carbonyl; t-butyl; amino-carbonyl; ethyl; propyl; methoxy; methoxy-methyl; carboxy; piperidinyl; piperidinyl-methyl; morpholino-methyl; diethyl-amino-methyl; isobutyl-amino-methyl; cyclopropyl-methyl-amino-methyl; isopropoxy-methyl; ethenyl; cyclopropyl; butoxy; [1,2,4]oxadiazol-5-yl optionally substituted with methyl; piperazinyl optionally substituted with 1 to 2 radicals independently selected from methyl, isopropyl and methyl-sulfonyl; 2-oxo-piperidin-1-yl; 2-oxo-pyrrolidin-1-yl; 2H-[1,2,4]triazol-3-yl; 1-methyl-1H-[1,2,4]triazol-3-yl; pyrazolyl optionally substituted with methyl; pyridazinyl; pyrazinyl optionally substituted with 1 to 2 radicals independently selected from cyano and methyl; pyridinyl optionally substituted with 1 to 2 radicals independently selected from halo, methyl and amino; pyridinyl-N-oxide optionally substituted with methyl; pyrimidinyl optionally substituted with 1 to 2 radicals independently selected from halo, methyl and amino; phenyl optionally substituted with 1 to 2 radicals independently selected from halo, methyl and trifluoromethyl; imidazolyl optionally substituted with 1 to 2 radicals independently selected from methyl, ethyl and cyano-methyl; and 6-oxo-1,6-dihydro-pyridin-3-yl.

In a further embodiment, $R_4$ is methyl, hydroxy-ethyl, t-butyl, phenyl, benzyl, cyclohexyl, cyclopropyl, pyridinyl, furanyl, morpholino-carbonyl, tetrahydro-thiopyranyl, tetrahydro-thiopyranyl 1,1-dioxide and quinolinyl; wherein said phenyl, benzyl, cyclohexyl, cyclopropyl, pyridinyl, furanyl, morpholino-carbonyl, tetrahydro-thiopyranyl, tetrahydro-thiopyranyl 1,1-dioxide and quinolinyl of $R_4$ is optionally substituted with 1 to 2 radicals independently selected from methyl, cyano, carboxy, aminocarbonyl, methoxy, trifluoromethyl, isopropoxy, methyl-sulfanyl, dimethyl-amino, ethoxy-carbonyl, trifluoromethoxy, cyclopropyl-aminocarbonyl, pyridinyl-aminocarbonyl, cyclohexyl-aminocarbonyl, isoxazolyl-aminocarbonyl, dimethylamino-ethyl-aminocarbonyl, methoxy-ethyl-aminocarbonyl, nitro, amino, fluoro, chloro, bromo, hydroxymethyl, methyl-piperazinyl-carbonyl, morpholino-carbonyl and piperidinyl-carbonyl.

In a further embodiment, $R_6$ is selected from methyl-sulfonyl-aminomethyl, bromomethyl, methyl-sulfonyl-methyl, ethyl(methyl)amino, dimethylamino, methyl, ethyl, cyano, bromo, chloro, fluoro, morpholino, methyl-piperazinyl, dimethyl-amino-ethoxy, methyl-amino-amino and hydroxyethyl (methyl)amino and methoxy.

In another embodiment, are compounds selected from Formula Ie, Ig and Ih:

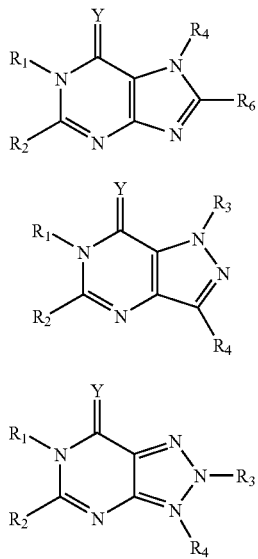

in which: Y is O; and is selected from hydrogen, halo, cyano, $C_{1-4}$alkyl, $C_{1-6}$alkoxy, halo-substituted $C_{1-6}$alkyl, —$XNR_8R_9$, —$XNR_8S(C-)_2R_9$, —$XR_{10}$, —$XOXNR_8R_9$ and —$XNR_8NR_8R_9$; wherein each X is independently selected from a bond, $C_{1-6}$alkylene and $C_{2-4}$alkenylene; each $R_9$ is independently selected from hydrogen, $C_{1-6}$alkyl and $C_{2-6}$alkenyl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, cyano-$C_{1-6}$alkyl, nitro, $C_{1-6}$alkyl, $C_{1-6}$alkoxy, halo-substituted-$C_{1-6}$alkyl, halo-substituted-$C_{1-6}$alkoxy, phenyl, —$NR_8R_8$ and —$C(O)OR_8$; wherein each $R_8$ is independently selected from hydrogen, $C_{1-6}$alkyl and $C_{2-6}$alkenyl.

In a further embodiment, with respect to compounds of Formula Ie, Ig and Ih, $R_1$ is selected from phenyl and cyclohexyl; wherein said phenyl and cyclohexyl is optionally substituted with 1 to 2 radicals independently selected from chloro, bromo, fluoro, methyl, cyano, methyl-sulfanyl, t-butyl, methoxy-carbonyl, butoxy, trifluoromethoxy, trifluoromethyl, methoxy, isopropyl, piperidinyl and phenyl optionally substituted with halo.

In a further embodiment, $R_2$ is selected from piperazinyl, morpholino, pyridinyl, pyrazolyl, benzthiazolyl, phenyl and phenoxy; wherein said piperazinyl, morpholino, pyridinyl, pyrazolyl, benzthiazolyl, phenyl or phenoxy is optionally substituted with 1 to 2 radicals independently selected from: bromo; chloro; fluoro; iodo; hydroxy; isopropyl; methyl; cyclohexyl; oxazolyl; isoxazolyl optionally substituted with 1 to 2 methyl radicals; pyrazolidinyl; methyl-carbonyl; amino-carbonyl; morpholino; thienyl; furanyl; cyclohexyl-amino optionally substituted with an amino radical; methyl-sulfonyl; trichloromethyl; methoxy-carbonyl; chloro-methyl; butoxy-ethenyl; butoxy-ethyl; trifluoromethyl; trifluoromethoxy; ethoxy-carbonyl; t-butyl; amino-carbonyl; ethyl; propyl; methoxy; methoxy-methyl; carboxy; piperidinyl; piperidinyl-methyl; morpholino-methyl; diethyl-amino-methyl; isobutyl-amino-methyl; cyclopropyl-methyl-amino-methyl; isopropoxy-methyl; ethenyl; cyclopropyl; butoxy; [1,2,4]oxadiazol-5-yl optionally substituted with methyl; piperazinyl optionally substituted with 1 to 2 radicals independently selected from methyl, isopropyl and methyl-sulfonyl; 2-oxo-piperidin-1-yl; 2-oxo-pyrrolidin-1-yl; 2H-[1,2,4]triazol-3-yl; 1-methyl-1H-[1,2,4]triazol-3-yl; pyrazolyl optionally substituted with methyl; pyridazinyl; pyrazinyl optionally substituted with 1 to 2 radicals independently selected from cyano and methyl; pyridinyl optionally substituted with 1 to 2 radicals independently selected from halo, methyl and amino; pyridinyl-N-oxide optionally substituted with methyl; pyrimidinyl optionally substituted with 1 to 2 radicals independently selected from halo, methyl and amino; phenyl optionally substituted with 1 to 2 radicals independently selected from halo, methyl and trifluoromethyl; imidazolyl optionally substituted with 1 to 2 radicals independently selected from methyl, ethyl and cyano-methyl; and 6-oxo-1,6-dihydro-pyridin-3-yl.

In a further embodiment, $R_3$ is selected from hydrogen, methyl, methyl-sulfonyl, t-butoxy-carbonyl-methyl, amino-carbonyl-methyl, methyl-[1,2,4]oxadiazolyl, cyano-methyl, carboxy, ethoxy-carbonyl, methyl-amino-carbonyl, dimethyl-amino-carbonyl, benzyl, furanyl, pyridinyl, indolyl, morpholino-carbonyl, piperidinyl-amino-carbonyl, piperidinyl-carbonyl, isopropoxy-carbonyl, amino-carbonyl, methyl-sulfanyl, methyl-amino-carbonyl, cyano, methyl-sulfonyl, methyl-piperazinyl, benzyl and phenyl optionally substituted with 1 to 2 radicals independently selected from methyl, methoxy, fluoro, chloro, bromo, iodo, cyano, nitro, hydroxy-methyl, ethoxy-carbonyl, methyl-sulfonyl, dimethyl-amino, methyl-amino, cyclopropyl-aminocarbonyl, isopropoxy, trifluoromethyl and trifluoromethoxy.

In a further embodiment, $R_4$ is methyl, hydroxy-ethyl, t-butyl, phenyl, benzyl, cyclohexyl, cyclopropyl, pyridinyl, furanyl, morpholino-carbonyl, tetrahydro-thiopyranyl, tetrahydro-thiopyranyl 1,1-dioxide and quinolinyl; wherein said phenyl, benzyl, cyclohexyl, cyclopropyl, pyridinyl, furanyl, morpholino-carbonyl, tetrahydro-thiopyranyl, tetrahydro-thiopyranyl 1,1-dioxide and quinolinyl of $R_4$ is optionally substituted with 1 to 2 radicals independently selected from methyl, cyano, carboxy, aminocarbonyl, methoxy, trifluoromethyl, isopropoxy, methyl-sulfanyl, dimethyl-amino, ethoxy-carbonyl, trifluoromethoxy, cyclopropyl-aminocarbonyl, pyridinyl-aminocarbonyl, cyclohexyl-aminocarbonyl, isoxazolyl-aminocarbonyl, dimethylamino-ethyl-aminocarbonyl, methoxy-ethyl-aminocarbonyl, nitro, amino, fluoro, chloro, bromo, hydroxymethyl, methyl-piperazinyl-carbonyl, morpholino-carbonyl and piperidinyl-carbonyl.

In a further embodiment, $R_6$ is selected from methyl-sulfonyl-aminomethyl, bromomethyl, methyl-sulfonyl-methyl, ethyl(methyl)amino, dimethylamino, methyl, ethyl, cyano, bromo, chloro, fluoro, morpholino, methyl-piperazinyl, dimethyl-amino-ethoxy, methyl-amino-amino and hydroxyethyl (methyl)amino and methoxy.

Preferred compounds of the invention are selected from 5-(4-Chloro-phenyl)-6-(2,4-dichloro-phenyl)-1-phenyl-1,5-dihydro-pyrazolo[3,4-d]pyrimidin-4-one; 5-(4-bromo-phenyl)-1-phenyl-6-p-tolyl-1,5-dihydro-pyrazolo[3,4-d]pyrimidin-4-one; 5-(4-chloro-phenyl)-6-(2,4-dichloro-phenyl)-1-phenyl-1H-pyrazolo[3,4-b]pyridin-4-ylamine; 5-(4-Chloro-phenyl)-6-(2,4-dichloro-phenyl)-1-phenyl-1H-pyrazolo[3,4-b]pyridine; 5-(4-chloro-phenyl)-6-(2,4-dichloro-phenyl)-4-ethoxy-1-phenyl-1H-pyrazolo[3,4-b]pyridine; 5-(4-Chloro-phenyl)-6-(2,4-dichloro-phenyl)-1-(4-nitro-phenyl)-1,5-dihydro-pyrazolo[3,4-d]pyrimidin-4-one; 5-(4-Chloro-phenyl)-6-(2,4-dichloro-phenyl)-1-(2-nitro-phenyl)-1,5- dihydro-pyrazolo[3,4-d]pyrimidin-4-one; 1-(4-Aminophenyl)-5-(4-chloro-phenyl)-6-(2,4-dichloro-phenyl)-1,5-dihydro-pyrazolo[3,4-d]pyrimidin-4-one; 5-(4-Bromo-phenyl)-6-(2-fluoro-phenyl)-1-quinolin-2-yl-1,5-dihydro-pyrazolo[3,4-d]pyrimidin-4-one; 5-(4-bromo-phenyl)-6-(4-fluoro-phenyl)-1-phenyl-1,5-dihydro-pyrazolo[3,4-d]pyrimidin-4-one; 5-(4-Bromo-phenyl)-1-pyridin-2-yl-6-o-tolyl-1,5-dihydro-pyrazolo[3,4-d]pyrimidin-4-one; 5-(4-Bromo-phenyl)-6-(2-fluoro-phenyl)-1-(2-hydroxy-ethyl)-1,5-dihydro-pyrazolo[3,4-d]pyrimidin-4-one; 5-(2,4-Dichloro-phenyl)-6-(2-fluoro-phenyl)-1-phenyl-1,5-dihydro-pyrazolo[3,4-d]pyrimidin-4-one; 5-(4-Bromo-phenyl)-6-(2,4-dichloro-phenyl)-1-phenyl-1,5-dihydro-pyrazolo[3,4-d]pyrimidin-4-one; 6-(2,4-Dichlorophenyl)-5-(4-fluoro-phenyl)-1-phenyl-1,5-dihydro-pyrazolo[3,4-d]pyrimidin-4-one; 6-(4-Chloro-phenyl)-5-(2,4-dichloro-phenyl)-1-phenyl-1,5-dihydro-pyrazolo[3,4-d]pyrimidin-4-one; 5-(4-Chloro-2-fluoro-phenyl)-6-(4-chloro-phenyl)-1-phenyl-1,5-dihydro-pyrazolo[3,4-d]pyrimidin-4-one; 6-(4-Chloro-phenyl)-5-(2,4-difluoro-phenyl)-1-phenyl-1,5-dihydro-pyrazolo[3,4-d]pyrimidin-4-one; 5-(4-bromo-phenyl)-6-(2-chloro-phenyl)-1-phenyl-1,5-dihydro-pyrazolo[3,4-d]pyrimidin-4-one; 5-(4-bromo-phenyl)-6-(3-chloro-phenyl)-1-phenyl-1,5-dihydro-pyrazolo[3,4-d]pyrimidin-4-one; 5-(4-bromo-phenyl)-6-(2-bromo-phenyl)-1-phenyl-1,5-dihydro-pyrazolo[3,4-d]pyrimidin-4-one; 5-(4-bromo-phenyl)-6-(2,4-difluoro-phenyl)-1-phenyl-1,5-dihydro-pyrazolo[3,4-d]pyrimidin-4-one; 6-biphenyl-4-yl-5-(4-bromo-phenyl)-1-phenyl-1,5-dihydro-pyrazolo[3,4-d]pyrimidin-4-one; 5-(4-bromo-phenyl)-6-(3,4-dichloro-phenyl)-1-phenyl-1,5-dihydro-pyrazolo[3,4-d]pyrimidin-4-one; 6-(4-Chloro-phenyl)-1,5-diphenyl-1,5-dihydro-pyrazolo[3,4-d]pyrimidin-4-one; 5-(4-bromo-phenyl)-6-(2-fluoro-phenyl)-1-pyridin-2-yl-1,5-dihydro-pyrazolo[3,4-d]pyrimidin-4-one; 5-(4-bromo-phenyl)-1-phenyl-6-o-tolyl-1,5-dihydro-pyrazolo[3,4-d]pyrimidin-4-one; 5-(4-bromo-phenyl)-6-(3-fluoro-phenyl)-1-phenyl-1,5-dihydro-pyrazolo[3,4-d]pyrimidin-4-one; 5-(4-bromo-phenyl)-1-cyclohexyl-6-(2-fluoro-phenyl)-1,5-dihydro-pyrazolo[3,4-d]pyrimidin-4-one; 5-(4-Bromo-phenyl)-1-tert-butyl-6-(2-fluoro-phenyl)-1,5-dihydro-pyrazolo[3,4-d]pyrimidin-4-one; 5-(4-Bromo-phenyl)-6-(2-fluoro-phenyl)-1-(4-methoxy-phenyl)-1,5-dihydro-pyrazolo[3,4-d]pyrimidin-4-one; 5-(4-Chloro-phenyl)-6-(2,4-dichloro-phenyl)-4-methoxy-1-phenyl-1H-pyrazolo[3,4-b]pyridine; 5-(4-Bromo-phenyl)-1-(3-fluoro-phenyl)-6-(2-fluoro-phenyl)-1,5-dihydro-pyrazolo[3,4-d]pyrimidin-4-one; 4-[5-(4-Bromo-phenyl)-6-(2-fluoro-phenyl)-4-oxo-4,5-dihydro-pyrazolo[3,4-d]pyrimidin-1-yl]-benzonitrile; 5-(4-Bromo-phenyl)-6-(2-fluoro-phenyl)-1-m-tolyl-1,5-dihydro-pyrazolo[3,4-d]pyrimidin-4-one; 5-(4-Bromo-phenyl)-6-(2-fluoro-phenyl)-1-(4-trifluoromethyl-phenyl)-1,5-dihydro-pyrazolo[3,4-d]pyrimidin-4-one; 5-(4-bromo-phenyl)-6-(4-methoxy-phenyl)-1-phenyl-1,5-dihydro-pyrazolo[3,4-d]pyrimidin-4-one; 5-(4-bromo-phenyl)-1-phenyl-6-(4-trifluoromethoxy-phenyl)-1,5-dihydro-pyrazolo[3,4-d]pyriraidin-4-one; 5-(4-bromo-phenyl)-6-(4-tert-butyl-phenyl)-1-phenyl-1,5-dihydro-pyrazolo[3,4-d]pyrimidin-4-one; 5-(4-bromo-phenyl)-1-phenyl-6-(2-trifluoromethyl-phenyl)-1,5-dihydro-pyrazolo[3,4-d]pyrimidin-4-one; 5-(4-bromo-phenyl)-6-(2,6-difluoro-phenyl)-1-phenyl-1,5-dihydro-pyrazolo[3,4-d]pyrimidin-4-one; 5-(4-bromo-phenyl)-6-(2,6-dichloro-phenyl)-1-phenyl-1,5-dihydro-pyrazolo[3,4-d]pyrimidin-4-one; 5-(4-bromo-phenyl)-1-phenyl-6-(2,4,6-trifluoro-phenyl)-1,5-dihydro-pyrazolo[3,4-d]pyrimidin-4-one; 5-(4-bromo-phenyl)-6-(2-methoxy-phenyl)-1-phenyl-1,5-dihydro-pyrazolo[3,4-d]pyrimidin-4-one; 5-(4-bromo-phenyl)-1-phenyl-6-(4-trifluoromethyl-phenyl)-1,5-dihydro-pyrazolo[3,4-d]pyrimidin-4-one; 6-biphenyl-4-yl-5-(4-chloro phenyl)-1-phenyl-1,5-dihydro-pyrazolo[3,4-d]pyrimidin-4-one; 1-(4-Bromo-phenyl)-2-(2-fluoro-phenyl)-9-phenyl-1,9-dihydro-purin-6-one; 4-[6-(2-Fluoro-phenyl)-4-oxo 1-phenyl-1,4-dihydro-pyrazolo[3,4-d]pyrimidin-5-yl]-benzonitrile; 6-(2-Fluoro-phenyl)-5-(4-methylsulfanyl-phenyl)-1-phenyl-1,5-dihydro-pyrazolo[3,4-d]pyrimidin-4-one; 5-(4-tert-Butyl-phenyl)-6-(2-fluoro-phenyl)-1-phenyl-1,5-dihydro-pyrazolo[3,4-d]pyrimidin-4-one; 4-[6-(2-Fluoro-phenyl)-4-oxo-1-phenyl-1,4-dihydro-pyrazolo[3,4-d]pyrimidin-5-yl]-benzoic acid methyl ester; 5-(4-Butoxy-phenyl)-6-(2-fluoro-phenyl)-1-phenyl-1,5-dihydro-pyrazolo[3,4-d]pyrimidin-4-one; 5-Biphenyl-4-yl-6-(2-fluoro-phenyl)-1-phenyl-1,5-dihydro-pyrazolo[3,4-d]pyrimidin-4-one; 6-(2-Fluoro-phenyl)-1-phenyl-5-(4-trifluoromethoxy-phenyl)-1,5-dihydro-pyrazolo[3,4-d]pyrimidin-4-one; 6-(2-Fluoro-phenyl)-1-phenyl-5-(4-trifluoromethyl-phenyl)-1,5-dihydro-pyrazolo[3,4-d]pyrimidin-4-one; 5-Benzyl-6-(2-fluoro-phenyl)-1-phenyl-1,5-dihydro-pyrazolo[354-d]pyrimidin-4-one; 5-Cyclohexyl-6-(2-fluoro-phenyl)-1-phenyl-1,5-dihydro-pyrazolo[3,4-d]pyrimidin-4-one; 5-(4-Bromo-phenyl)-6-(2-fluoro-phenyl)-1-methyl-1,5-dihydro-pyrazolo[3,4-d]pyrimidin-4-one; 4-Chloro-5-(4-chloro-phenyl)-6-(2,4-dichloro-phenyl)-1-phenyl-1H-pyrazolo[3,4-b]pyridine; 5,6-Bis-(4-chloro-phenyl)-1-phenyl-1H-pyrazolo[3,4-b]pyridin-4-ol; 5,6-Bis-(4-chloro-phenyl)-4-methoxy-1-phenyl-1H-pyrazolo[3,4-b]pyridine; 6-(4-Chloro-phenyl)-5-(2,4-dichloro-phenyl)-3-phenyl-3H-imidazo[4,5-b]pyridin-7-ylamine; 1-(4-Bromo-phenyl)-2-(2,4-dichloro-phenyl)-9-p-tolyl-1,9-dihydro-purin-6-one; 1-(4-Bromo-phenyl)-2-(2,4-dichloro-phenyl)-9-phenyl 1,9-dihydro-purin-6-one; 1-(4-Bromo-phenyl)-2-(4-chlorophenyl)-9-phenyl)-9-dihydro-purin-6-one; 1-(4-Bromo-phenyl)-2-(3,4-dichloro-phenyl)-9-phenyl-1,9-dihydro-purin-6-one; 1-(4-Bromo-phenyl)-9-phenyl-2-p-tolyl-1,9-dihydro-purin-6-one; 1-(4-Bromo-phenyl)-9-phenyl-2-(4-trifluoromethyl-phenyl)-1,9-dihydro-purin-6-one; 5-(4-bromo-phenyl)-6-(2-fluoro-phenyl)-1-(morpholine-4-carbonyl)-1,5-dihydro-pyrazolo[3,4-d]pyrimidin-4-one; 5,6-Bis-(4-chloro-phenyl)-1-phenyl-1H-pyrazolo[3,4-b]pyrazine; 2-[5-(4-Chloro-phenyl)-6-(2,4-dichloro-phenyl)-1-phenyl-1H-pyrazolo[3,4-b]pyridin-4-yloxy]-ethanol; 5-(4-Bromo-phenyl)-6-(2-fluoro-phenyl)-1-(tetrahydro-thiopyran-4-yl)-1,5-dihydro-pyrazolo[3,4-d]pyrimidin-4-one; [5,6-Bis-(4-chloro-phenyl)-1-phenyl-1H-pyrazolo[3,4-b]pyridin-4-yl]-dimethyl-amine; 5-(4-Bromo-phenyl)-1-(1,1-dioxo-hexahydro-1$\lambda^6$-thiopyran-4-yl)-6-(2-fluoro-phenyl)-1,5-dihydro-pyrazolo[3,4-d]pyrimidin-4-one; 5-(4-Chloro-phenyl)-6-[4-(3-methyl-[1,2,4]oxadiazol-5-yl)-phenyl]-1-phenyl-1,5-dihydro-pyrazolo[3,4-d]pyrimidin-4-one; 5-(4-Chloro-phenyl)-6-(4-isoxazol-5-yl-phenyl)-1-phenyl-1,5-dihydro-pyrazolo[3,4-d]pyrimidin-4-one; 5-(4-Chloro-phenyl)-1-phenyl-6-[4-(2H-pyrazol-3-yl)-phenyl]-1,5-dihydro-pyrazolo[3,4-d]pyrimidin-4-one; 6-(4-Acetyl-phenyl)-5-(4-chloro-phenyl)-1-phenyl-1,5-dihydro-pyrazolo[3,4-d]pyrimidin-4-one; 4-[5-(4-Chloro-phenyl)-4-oxo-1-phenyl-4,5-dihydro-1H-pyrazolo[3,4-d]pyrimidin-6-yl]-benzamide; 6-[4-(2-Amino-pyrimidin-4-yl)-phenyl]-5-(4-chloro-phenyl)-1-phenyl-1,5-dihydro-pyrazolo[3,4-d]pyrimidin-4-one; 5-(4-Chloro-phenyl)-1-phenyl-6-(4-pyrimidin-4-yl-phenyl)-1,5-dihydro-pyrazolo[3,4-d]pyrimidin-4-one; 5-(4-Chloro-phenyl)-6-[4-(2-methyl-pyrimidin-4-yl)-phenyl]-1-phenyl-1,5-dihydro-pyrazolo[3,4-d]pyrimidin-4-one; 5-(4-Chloro-phenyl)-1-phenyl-6-[4-(2H-[1,2,4]triazol-3-yl)-phenyl]-1,5-dihydro-pyrazolo[3,4-d]pyrimidin-4-one; 5-(4-Chloro-phenyl)-6-(4-[1,2,4]

oxadiazol-5-yl-phenyl)-1-phenyl-1,5-dihydro-pyrazolo[3,4-d]pyrimidin-4-one; 6-Biphenyl-4-yl-5-(4-chloro-phenyl)-4-oxo-1-phenyl-4,5-dihydro-1H-pyrazolo[3,4-d]pyrimidine-3-carboxylic acid amide; 6-Biphenyl-4-yl-5-(4-chloro-phenyl)-4-oxo-1-phenyl-4,5-dihydro-1H-pyrazolo[3,4-d]pyrimidine-3-carboxylic acid ethyl ester; 5-(4-chloro-phenyl)-6-(3'-fluoro-biphenyl-4-yl)-1-phenyl-1,5-dihydro-pyrazolo[3,4-d]pyrimidin-4-one; 5-(4-chloro-phenyl)-6-(4-morpholin-4-yl-phenyl)-1-phenyl-1,5-dihydro-pyrazolo[3,4-d]pyrimidin-4-one; 5-(4-chloro-phenyl)-6-(4-imidazol-1-yl-phenyl)-1-phenyl-1,5-dihydro-pyrazolo[3,4-d]pyrimidin-4-one; 5-(4-chloro-phenyl)-1-phenyl-6-(4-pyridin-2-yl-phenyl)-1,5-dihydro-pyrazolo[3,4-d]pyrimidin-4-one; 5-(4-chloro-phenyl)-1-phenyl-6-(4-phenyl-piperazin-1-yl)-1,5-dihydro-pyrazolo[3,4-d]pyrimidin-4-one; 6-benzothiazol 2-yl-5-(4-chloro-phenyl)-1-phenyl-1,5-dihydro-pyrazolo[3,4-d]pyrimidin-4-one; 5-(4-chloro-phenyl)-1-phenyl-6-p-tolyloxy-1,5-dihydro-pyrazolo[3,4-d]pyrimidln-4-one; 6-(4-bromo-phenyl)-3-phenyl-5-p-tolyl-1,6-dihydro-pyrazolo[4,3-d]pyrimidin-7-one; 1-(4-Chloro-phenyl)-2-(4-isopropyl-phenyl)-9-phenyl-1,9-dihydro-purin-6-one; 1-(4-Chloro-phenyl)-2-(4-methoxymethyl-phenyl)-9-phenyl-1,9-dihydro-purin-6-one; 5-(4-Bromo-phenyl)-1-phenyl-6-pyridin-3-yl-1,5-dihydro-pyrazolo[3,4-d]pyrimidin-4-one; 6-(2-Fluoro-phenyl)-1-phenyl-5-pyridin-3-yl-1,5-dihydro-pyrazolo[3,4-d]pyrimidin-4-one; 5-(4-Bromo-phenyl)-6-(2-fluoro-phenyl)-1-(tetrahydro-pyran-4-yl) 1,5-dihydro-pyrazolo[3,4-d]pyrimidin-4-one; 5-(4-Chloro-phenyl)-6-(4-iodo-phenyl)-1-phenyl-1,5-dihydro-pyrazolo[3,4-d]pyrimidin-4-one; 5-(4-Chloro-phenyl)-6-(4'-fluoro-biphenyl-4-yl)-1-phenyl-1,5-dihydro-pyrazolo[3,4-d]pyrimidin-4-one; 5-(4-Chloro-phenyl)-6-(2'-fluoro-biphenyl-4-yl)-1-phenyl-1,5-dihydro-pyrazolo[3,4-d]pyrimidin-4-one; 6-(2-Fluoro-phenyl)-1-phenyl-5-(4-piperidin-1-yl-phenyl)-1,5-dihydro-pyrazolo[3,4-d]pyrimidin-4-one; 5-C4-Chloro-phenyl)-1-phenyl-6-(4'-trifluoromethyl-biphenyl-4-yl)-1,5-dihydro-pyrazolo[3,4-d]pyrimidin-4-one; 5-(4-Chloro-phenyl)-1-phenyl-6-(4-thiophen-3-yl-phenyl)-1,5-dihydro-pyrazolo[3,4-d]pyrimidin-4-one; 5-(4-Chloro-phenyl)-6-[4-(4-methyl-piperazin-1-yl)-phenyl]-1-phenyl-1,5-dihydro-pyrazolo[3,4-d]pyrimidin-4-one; {2-[5-(4-Chloro-phenyl)-6-(2,4-dichloro-phenyl)-1-phenyl-1H-pyrazolo[3,4-b]pyridin-4-yloxy]-ethyl}-dimethyl-amine; 2-[5-(4-Chloro-phenyl)-6-(2,4-dichloro-phenyl)-1-phenyl-1H-pyrazolo[3,4-b]pyridin-4-ylamino]-ethanol; 5-(4-Chloro-phenyl)-6-(2,4-dichloro-phenyl)-4-(3-morpholin-4-yl-propoxy)-1-phenyl-1H-pyrazolo[3,4-b]pyridine; 5-(4-Chloro-phenyl)-6-(2,4-dichloro-phenyl)-4-[2-(4-methyl-piperazin-1-yl)-ethoxy]-1-phenyl-1H-pyrazolo[3,4-b]pyridine; 5-(4-Chloro-phenyl)-6-(2,4-dichloro-phenyl)-4-(2-morpholin-4-yl-ethoxy)-1-phenyl-1H-pyrazolo[3,4-b]pyridine; 1-(4-Chloro-phenyl)-9-phenyl-2-(4-pyridin-2-yl-phenyl)-1,9-dihydro-purin-6-one; 5-(4-Chloro-phenyl)-1-phenyl-6-(4-piperidin-1-yl-phenyl)-1,5-dihydro-pyrazolo[3,4-d]pyrimidin-4-one; 6-(4-Bromo-phenyl)-5-(4-chloro-phenyl)-1-phenyl-1,5-dihydro-pyrazolo[3,4-d]pyrimidin-4-one; 5-(4-Chloro-phenyl)-6-(4-phenoxy-phenyl)-1-phenyl-1,5-dihydro-pyrazolo[3,4-d]pyrimidin-4-one; 5-(4-Bromo-phenyl)-1-phenyl-6-(4-phenyl-piperazin-1-yl)-1,5-dihydro-pyrazolo[3,4-d]pyrimidin-4-one; 5-(4-Bromo-phenyl)-6-[4-(4-fluoro-phenyl)-piperazin-1-yl]-1-phenyl-1,5-dihydro-pyrazolo[3,4-d]pyrimidin-4-one; 6-(4-Bromo-2-fluoro-phenyl)-5-(4-chloro-phenyl)-1-phenyl-1,5-dihydro-pyrazolo[3,4-d]pyrimidin-4-one; 6-(4-Bromo-2-chloro-phenyl)-5-(4-chloro-phenyl)-1-phenyl-1,5-dihydro-pyrazolo[3,4-d]pyrimidin-4-one; 5-(4-Chloro-phenyl)-6-(2-fluoro-4-morpholin-4-yl-phenyl)-1-phenyl-1,5-dihydro-pyrazolo[3,4-d]pyrimidin-4-one; 6-(2-Chloro-4-morpholin-4-yl-phenyl)-5-(4-chloro-phenyl)-1-phenyl-1,5-dihydro-pyrazolo[3,4-d]pyrimidin-4-one; 5-(4-Chloro-phenyl)-6-(3-fluoro-biphenyl-4-yl)-1-phenyl-1,5-dihydro-pyrazoto[3,4-d]pyrimidin-4-one; 6-(3-Chloro-biphenyl-4-yl)-5-(4-chloro-phenyl)-1-phenyl-1,5-dihydro-pyrazolo[3,4-d]pyrimidin-4-one; 5-(4-Chloro-phenyl)-6-(4-furan-3-yl-phenyl)-1-phenyl-1,5-dihydro-pyrazolo[3,4-d]pyrimidin-4-one; 5-(4-Chloro-phenyl)-1-phenyl-6-(4-pyridin-3-yl-phenyl)-1,5-dihydro-pyrazolo[3,4-d]pyiimidin-4-one; 5-(4-Chloro-phenyl)-1-phenyl-6-(4-pyridin-4-yl-phenyl)-1,5-dihydro-pyrazolo[3,4-d]pyrimidin-4-one; 5-(4-Chloro-phenyl)-6-[4-(3,5-dimethyl-isoxazol-4-yl)-phenyl]-1-phenyl-1,5-dihydro-pyrazolo[3,4-d]pyrimidin-4-one; 6-Biphenyl-4-yl-5-(4-chloro-phenyl)-1-(tetrahydro-pyran-4-yl)-1,5-dihydro-pyrazolo[3,4-d]pyrimidin-4-one; 5-(4-Chloro-phenyl)-6-[1-(3-fluoro-phenyl)-1H-pyrazol-4-yl]-1-phenyl-1,5-dihydro-pyrazolo[3,4-d]pyrimidin-4-one; 4-[5-(4-Chloro-phenyl)-4-oxo-1-phenyl-4,5-dihydro-1H-pyrazolo[3,4-d]pyrimidin-6-yl]-benzoic acid methyl ester; 5-(4-Bromo-phenyl)-6-morpholin-4-yl-1-phenyl-1,5-dihydro-pyrazolo[3,4-d]pyrimidin-4-one; 5-(4-Bromo-phenyl)-6-(4-isopropyl-piperazin-1-yl)-1-phenyl-1,5-dihydro-pyrazolo[3,4-d]pyrimidin-4-one; 5-(4-Chloro-phenyl)-1-phenyl-6-(4-pyrazol-1-yl-phenyl)-1,5-dihydro-pyrazolo[3,4-d]pyrimidin-4-one; 6-[4-(2-amino-cyclohexylamino)-phenyl]-5-(4-chloro-phenyl)-1-phenyl-1,5-dihydro-pyrazolo[3,4-d]pyrimidin-4-one; 6-(4-Bromo-3-fluoro-phenyl)-5-(4-chloro-phenyl)-1-phenyl-1,5-dihydro-pyrazoto[3,4-d]pyrimidin-4-one; 4-[5-(4-Chloro-phenyl)-4-oxo-1-phenyl-4,5-dihydro-1H-pyrazolo[3,4-d]pyrimidin-6-yl]-benzoic acid ethyl ester; 5-(4-Chloro-phenyl)-6-(2-fluoro-biphenyl-4-yl)-1-phenyl-1,5-dihydro-pyrazolo[3,4-d]pyrimidin-4-one; 5-(4-Chbro-phenyl)-6-(3-fluoro-4-morpholin-4-yl-phenyl)-1-phenyl-1,5-dihydro-pyrazolo[3,4-d]pyrimidin-4-one; 5-(4-Chloro-phenyl)-6-[3-fluoro-4-(4-methyl-piperazin-1-yl)-phenyl]-1-phenyl-1,5-dihydro-pyrazolo[3,4-d]pyrimidin-4-one; 5-(4-Chloro-phenyl)-6-[3-fluoro-4-(4-isopropyl-piperazin-1-yl)-phenyl]-1-phenyl-1,5-dihydro-pyrazolo[3,4-d]pyrimidin-4-one; 5-(4-Chloro-phenyl)-6-(2'-methyl-biphenyl-4-yl)-1-phenyl-1,5-dihydro-pyrazolo[3,4-d]pyiimidin-4-one; 5-(4-Chloro-phenyl)-6-(3'-methyl-biphenyl-4-yl)-1-phenyl-1,5-dihydro-pyrazolo[3,4-d]pyrimidin-4-one; 5-(4-Chloro-phenyl)-6-(4'-methyl-biphenyl-4-yl)-lphenyl-1,5-dihydro-pyrazolo[3,4-d]pyrimidin-4-one; 5-(4-Chloro-phenyl)-6-[2-fluoro-4-(4-methyl-piperazin-1-yl)-phenyl]-1-phenyl-1,5-dihydro-pyrazolo[3,4-d]pyrimidin-4-one; 5-(4-Chloro-phenyl)-6-[2-fliioro-4-(4-isopropyl-piperazin-1-yl)-phenyl]-1-phenyl-1,5-dihydro-pyrazolo[3,4-d]pyrimidin-4-one; 6-[2-Chloro-4-(4-methyl-piperazin-1-yl)-phenyl]-5-(4-chloro-phenyl)-1-phenyl-1,5-dihydro-pyrazolo[3,4-d]pyrimidin-4-one; 6-[2-Chloro-4-(4-isopropyl-piperazin-1-yl)-phenyl]-5-(4-chloro-phenyl)-1-phenyl-1,5-dihydro-pyrazolo[3,4-d]pyrimidin-4-one; 5-(4-Chloro-phenyl)-1-phenyl-6-o-tolyloxy-1,5-dihydro-pyrazolo[3,4-d]pyrimidin-4-one; 5-(4-Chloro-phenyl)-1-phenyl-6-m-tolyloxy-1,5-dihydro-pyrazolo[3,4-d]pyrimidin-4-one; 5-(4-Chloro-phenyl)-1-phenyl-6-p-tolyl-1,5-dihydro-pyrazolo[3,4-d]pyrimidin-4-one; 5-(4-Chloro-phenyl)-1-phenyl-6-(4-trifluoromethyl-phenyl)-1,5-dihydro-pyrazolo[3,4-d]pyriinidin-4-one; 5-(4-Chloro-phenyl)-6-(4-methanesulfonyl-piperazin-1-yl)-1-phenyl-1,5-dihydro-pyrazolo[3,4-d]pyrimidin-4-one; 7-Benzyl-1-(4-chloro-phenyl)-2-(2,4-dichloro-phenyl)-1,7-dihydro-purin-6-one; 9-Benzyl-1-(4-chloro-phenyl)-2-(2,4-dichloro-phenyl)-1,9-dihydro-purin-6-one; 1-(4-Bromo-phenyl)-2-(2,4-dichlorophenyl)-7-phenyl-1,7-dihydro-purin-6-one; 1-(4-Bromo-phenyl)-9-cyclopropyl-2-(2,4-dichloro-phenyl)-1,9-dihydro-purin-6-one; 3-[1-(4-Chloro-phenyl)-2-(2,4-dichloro-phenyl)-6-oxo-1,6-dihydro-purin-7-yl]-benzonitrile; 1-(4-Chloro-phenyl)-9-phenyl-2-(4-thiophen-3-yl-phenyl)-1,9-dihydro-purin-6-one; 1-(4-Bromo-phenyl)-2-(2,4-dichloro-phenyl)-8-methyl-9-phenyl-1,9-dihydro-purin-6-one; 1-(4-Chloro-phenyl)-2-(2,4-dichloro-phenyl)-8-ethyl-9-phenyl-1,9-dihydro-purin-6-one; 1-(4-Chloro-phenyl)-9-phenyl-2-(4-pyridin-4-yl-phenyl)-1,9-dihydro-purin-6-one; 1-(4-Bromo-phenyl)-2-(2-fluoro-phenyl)-9-phenyl-1,9-dihydro-purin-6-one; 1-Biphenyl-4-yl-2-(4-chloro-phenyl)-7-phenyl-1,7-dihydro-purin-6-one; 1,2-Bis-(4-chloro-phenyl)-7-phenyl-1,7-dihydro-purin-6-one; 1-(4-Chloro-phenyl)-2-(2,4-dichloro-phenyl)-9-phenyl-1,9-dihydro-purin-6-one; 1-(4-Bromo-phenyl)-2-(2,4-dichloro-phenyl)-9-phenyl-1,9-dihydro-purin-6-one; 2-Biphenyl-4-yl-1-(4-chloro-phenyl)-9-phenyl-1,9-dihydro-purin-6-one; 4-[1-(4-Bromo-phenyl)-2-(2,4-dichloro-phenyl)-6-oxo-1,6-dihydro-purin-9-yl]-benzonitrile; 1-(4-Bromo-phenyl)-9-phenyl-2-(2-trifluoromethyl-phenyl)-1,9-dihydro-purin-6-one; 1-(4-Bromo-phenyl)-9-phenyl-2-m-tolyl-1,9-dihydro-purin-6-one; 1-(4-Bromo-phenyl)-9-phenyl-2-o-tolyl-1,9-dihydro-purin-6-one; 1-(4-Bromo-phenyl)-2-(4-methoxy-phenyl)-9-phenyl-1,9-dihydro-purin-6-one; 1-(4-Bromo-phenyl)-2-(2,3-difluoro-phenyl)-9-phenyl-1,9-dihydro-purin-6-one; 1-(4-Bromo-phenyl)-2-(4-fluoro-3-methyl-phenyl)-9-phenyl-1,9-dihydro-purin-6-one; 1-(4-Chloro-phenyl)-2-(2,4-dichloro-phenyl)-7-(3-nitro-phenyl)-1,7-dihydro-purin-6-one; 1-(4-Chloro-phenyl)-2-(2,4-dichloro-phenyl)-7-furan-3-yl-1,7-dihydro-purin-6-one; 1-(4-Chloro-phenyl)-2-(2,4-dichloro-phenyl)-9-(2-trifluoromethyl-phenyl)-1,9-dihydro-purin-6-one; 1-(4-Chloro-phenyl)-2-(2,4-dichloro-phenyl)-9-(3,5-difluoro-phenyl)-1,9-dihydro-purin-6-one; 1-(4-Chloro-phenyl)-2-(2,4-dichloro-phenyl)-9-(2-isopropoxy-phenyl)-1,9-dihydro-purin-6-one; 1-(4-Chloro-phenyl)-2-(2,4-dichloro-phenyl)-7-(3-trifluoromethoxy-phenyl)-1,7-dihydro-purin-6-one; 1-(4-Chloro-phenyl)-2-(2,4-dichloro-phenyl)-7-(3,5-dimethyl-phenyl)-1,7-dihydro-purin-6-one; 1-(4-Chloro-phenyl)-2-(2,4-dichloro-phenyl)-9-(3-trifluoromethoxy-phenyl)-1,9-dihydro-purin-6-one; 1-(4-Chloro-phenyl)-2-(2,4-dichloro-phenyl)-9-(3,5-dimethyl-phenyl)-1,9-dihydro-purin-6-one; 2-(4-Bromo-phenyl)-1-(2,4-dichlorophenyl)-7-phenyl-1,7-dihydro-purin-6-one; 1-(4-Chloro-phenyl)-2-(2,4-dichloro-phenyl)-9-(3-nitro-phenyl)-1,9-dihydro-purin-6-one; 3-[1-(4-Choro-phenyl)-2-(2,4-dichloro-phenyl)-6-oxo-1,6-dihydro-purin-9-yl]-benzonitrile; 1-(4-Chloro-phenyl)-2-(2,4-dichloro-phenyl)-9-furan-3-yl-1,9-dihydro-purin-6-one; 1-(4-Chloro-phenyl)-2-(2,4-dichloro-phenyl)-7-(3,5-dichloro-phenyl)-1,7-dihydro-purin-6-one; 1-(4-Chloro-phenyl)-2-(2,4-dichloro-phenyl)-9-(2-methoxy-5-methylphenyl)-1,9-dihydro-purin-6-one; 2-(4-Chloro-phenyl)-1-(2-fluoro-phenyl)-7-phenyl-1,7-dihydro-purin-6-one; 1-(4-Chloro-phenyl)-2-(2,4-dichloro-phenyl)-7-(5-fluoro-2-methoxy-phenyl)-1,7-dihydro-purin-6-one; 1-(4-Chloro-phenyl)-2-(2,4-dichloro-phenyl)-7-(2-trifluoromethyl-phenyl)-1,7-dihydro-purin-6-one; 1-(4-Bromo-phenyl)-2-(4-tert-butyl-phenyl)-9-phenyl-1,9-dihydro-purin-6-one; 1-(4-Bromo-phenyl)-2-(3-fluoro-phenyl)-9-phenyl-1,9-dihydro-purin-6-one; 1-(4-Chloro-phenyl)-2-(4-iodo-phenyl)-9-phenyl-1,9-dihydro-purin-6-one; 1-(4-Chloro-phenyl)-2-(3',5'-difluoro-biphenyl-4-yl)-9-phenyl-1,9-dihydro-purin-6-one; 1-(4-Chloro-phenyl)-2-(2'-fluoro-biphenyl-4-yl)-9-phenyl-1,9-dihydro-purin-6-one; 1-(4-Chloro-phenyl)-2-(3'-fluoro-biphenyl-4-yl)-9-phenyl-1,9-dihydro-purin-6-one; 1-(4-Chloro-phenyl)-2-(4'-fluoro-biphenyl-4-yl)-9-phenyl-1,9-dihydro-purin-6-one; 1-(4-Chloro-phenyl)-2-(2,4-dichloro-phenyl)-7-pyridin-3-yl-1,7-dihydro-purin-6-one; 1-(4-Chloro-phenyl)-2-(2,4-dichloro-phenyl)-9-pyridin-3-yl-1,9-dihydro-purin-6-one; 1-(4-Chloro-phenyl)-2-(2,4-dichloro-phenyl)-7-pyridin-4-yl-1,7-dihydro-purin-6-one; 1-(4-Chloro-phenyl)-2-(2,4-dichloro-phenyl)-7-(2-fluoro-phenyl)-3,7-dihydro-purin-6-one; 1-(4-Chloro-phenyl)-2-(2,4-dichloro-phenyl)-9-(2-fluoro-phenyl)-1,9-dihydropurin-6-one; 2-[1-(4-Chloro-phenyl)-2-(2,4-dichloro-phenyl)-6-oxo-1,6-dihydro-purin-7-yl]indole-1-carboxylic acid tert-butyl ester; 1-(4-Chloro-phenyl)-2-(2,4-dichloro-phenyl)-7-(4-hydroxymethyl-phenyl)-1,7-dihydro-purin-6-one; 1-(4-Chloro-phenyl)-2-(2,4-dichloro-phenyl)-9-(4-hydroxymethyl-phenyl)-1,9-dihydro-purin-6-one; 1-(4-Chloro-phenyl)-2-(2,4-dichlorophenyl)-7-(2,5-difluoro-phenyl)-1,7-dihydro-purin-6-one; 1-(4-Chloro-phenyl)-2-(2,4-dichloro-phenyl)-9-(2,5-difluoro-phenyl)-1,9-dihydro-purin-6-one; 7-(5-Chloro-2-methyl-phenyl)-1-(4-chloro-phenyl)-2-(2,4-dichloro-phenyl)-1,7-dihydropurin-6-one; 9-(5-Chloro-2-methyl-phenyl)-1-(4-chloro-phenyl)-2-(2,4-dichloro-phenyl) 1,9-dihydro-purin-6-one; 1-(4-Chloro-phenyl)-2-(2,4-dichloro-phenyl)-7-(2,5-dichloro-phenyl)-1,7-dihydro-purin-6-one; 1-(4-Chloro-phenyl)-2-(2,4-dichloro-phenyl)-9-(2,5-dichloro-phenyl)-1,9-dilrydro-purin-6-one; 1-(4-Chloro-phenyl)-2-(2,4-dichloro-phenyl)-7-(2-nitro-phenyl)-1,7-dihydro-purin-6-one; 1-(4-Chloro-phenyl)-2-(2,4-dichloro-phenyl)-9-(2-nitro-phenyl)-1,9-dihydro-purin-6-one; 3-[1-(4-Chloro-phenyl)-2-(2,4-dichloro-phenyl)-6-oxo-1,6-dihydro-purin-7-yl]-benzoic acid ethyl ester; 3-[1-(4-Chloro-phenyl)-2-(2,4-dichloro-phenyl)-6-oxo-1,6-dihydro-purin-9-yl]-benzoic acid ethyl ester; 4-[1-(4-Chloro-phenyl)-2-(2,4-dichloro-phenyl)-6-oxo-1,6-dihydro-purin-7-yl]-N-cyclopropyl-benzamide; 4-[1-(4-Chloro-phenyl)-2-(2,4-dichloro-phenyl)-6-oxo-1,6-dihydro-purin-9-yl]-N-cyclopropy 1-benzamide; 1-(4-Chloro-phenyl) 2-(2,4-dichloro-phenyl)-7-(4-fluoro-2-methyl-phenyl)-1,7-dihydro-purin-6-one; 1-(4-Chloro-phenyl)-2-(2,4-dichloro-phenyl)-9-(5-fluoro-2-methyl-phenyl)-1,9-dihydro-purin-6-one; 1-(4-Chloro-phenyl)-2-(2,4-dichloro-phenyl)-7-(3-methoxy-phenyl)-1,7-dihydro-purin-6-one; 1-(4-Chloro-phenyl)-2-(2,4-dichloro-phenyl)-9-(3-methoxy-phenyl)-1,9-dihydro-purin-6-one; 1-(4-Chloro-phenyl)-2-(2,4-dichloro-phenyl)-7-(4-methanesulfonyl-phenyl)-1,7-dihydro-purin-6-one; 1-(4-Chloro-phenyl)-2-(2,4-dichloro-phenyl)-9-(4-methanesulfonyl-phenyl)-1,9-dihydro-purin-6-one; 1-(4-Chloro-phenyl)-2-(2,4-dichloro-phenyl)-7-(4-dimethylamino-phenyl)-1,7-dihydro-purin-6-one; 1-(4-Chloro-phenyl)-2-(2,4-dichloro-phenyl)-9-(4-dimethylamino-phenyl)-1,9-dihydro-purin-6-one; 1-(4-Chloro-phenyl)-7-(2-chloro-phenyl)-2-(2,4-dichloro-phenyl)-1,7-dihydro-purin-6-one; 1-(4-Chloro-phenyl)-2-(2,4-dichloro-phenyl)-7-(2,5-dimethyl-phenyl)-1,7-dihydro-purin-6-one; 1-(4-Chloro-phenyl)-2-(2,4-dichloro-phenyl)-9-(2,5-dimethyl-phenyl)-1,9-dihydro-purin-6-one; 4-[1-(4-Chloro-phenyl)-2-(2,4-dichloro-phenyl)-6-oxo-1,6-dihydro-purin-7-yl]-benzoic acid ethyl ester; 4-[1-(4-Chloro-phenyl)-2-(2,4-dichloro-phenyl)-6-oxo-1,6-dihydro-purin-9-yl]-benzoic acid ethyl ester; 1-(4-Chloro-phenyl)-2-(2,4-dichloro-phenyl)-7-(4-methylamino-phenyl)-1,7-dihydro-purin-6-one; 1-(4-Chloro-phenyl)-2-(2,4-dichloro-phenyl)-8-methyl-9-phenyl-1,9-dihydro-purin-6-one; 1-(4-Bromo-phenyl)-2-(3-fluoro-4-trifluoromethyl-phenyl)-9-phenyl-1,9-dihydro-purin-6-one; 1-(4-Bromo-phenyl)-2-(4-ethyl-phenyl)-9-phenyl-1,9-dihydro-purin-6-one; 1-(4-Bromo-phenyl)-2-(2,4-dichloro-phenyl)-8-ethyl-9-phenyl-1,9-dihydro-purin-6-one; 1-(4-Bromo phenyl)-9-phenyl-2-(4-propyl-phenyl)-1,9-dihydro-purin-6-one; 1-(4-Bromophenyl)-2-(2,4-dichloro-phenyl)-9-(3-trifluoromethoxy-phenyl)-1,9-dihydro-purin-6-one; 1-(4-Bromo-phenyl)-9-(2-methoxy-5-methyl-phenyl)-2-p-tolyl-1,9-dihydro-purin-6-one; 3-[1-(4-Bromo-phenyl)-6-oxo-2-p-tolyl-1,6-dihydro-purin-9-yl]-benzonitrile; 3-[1-(4-Bromo-phenyl)-2-(2,4-dichloro-phenyl)-6-oxo-1,6-dihydro-purin-9-yl]-benzonitrile; 1-(4-Bromophenyl)-8-ethyl-9-phenyl-2-(4-propy 1-phenyl)-1,9-dihydro-purin-6-one; 1-(4-Bromo-phenyl)-8-ethyl-2-(4-ethyl-phenyl)-9-phenyl-1,9-dihydro-purin-6-one; 1-(4-Bromo-phenyl)-8-ethyl-9-phenyl-2-(4-trifluoromethyl-phenyl)-1,9-dihydro-purin-6-one; 1-(4-Bromo-phenyl)-2-(2,4-dichloro-phenyl)-9-(2-methoxy-5-methyl-phenyl)-1,9-dihydro-purin-6-one; 1-(4-Bromo-phenyl)-8-ethy)-9-phenyl-2-p-tolyl-1,9-dihydro-purin-6-one; 1-(4-Chloro-phenyl)-2-(2-fluoro-4-methyl-phenyl)-9-phenyl-1,9-dihydro-purin-6-one; 1-(4-Chloro-phenyl)-2-(2-fluoro-4-trifluoromethyl-phenyl)-9-phenyl-1,9-dihydro-purin-6-one; 1-(4-Chloro-phenyl)-2-(2,4-dimethyl-phenyl)-9-phenyl-1,9-dihydro-purin-6-one; 2-(4-Chloro-2-fluoro-phenyl) 1-(4-chloro-phenyl)-9-phenyl-1,9-dihydropurin-6-one; 1-(4-Chloro-phenyl)-9-phenyl-2-(4-trifluoromethyl-phenyl)-1,9-dihydro-purin-6-one; 1-(4-Chloro-phenyl)-9-phenyl-2-p-tolyl-1,9-dihydro-purin-6-one; 1-(4-Chloro-phenyl)-9-phenyl-2-(4-propy 1-phenyl)-1,9-dihydro-purin-6-one; 1-(4-Chloro-phenyl)-2-(4-ethyl-phenyl)-9-phenyl-1,9-dihydro-purin-6-one; 4-[1-(4-Chloro-phenyl)-6-oxo-9-phenyl-6,9-dihydro-1H-purin-2-yl]-benzoic acid methyl ester; 2-Biphenyl-4-yl-1-(4-chloro-phenyl)-8-ethyl-9-phenyl-1,9-dihydro-purin-6-one; 1-(4-Chloro-phenyl)-2-(4-isobutyl-phenyl)-9-phenyl-1,9-dihydro-purin-6-one; 1-(4-Chloro-phenyl)-9-phenyl-2-(4-pyridin-3-yl-phenyl)-1,9-dihydro-purin-6-one; 5-(4-Chloro-phenyl)-6-(2,4-dichloro-phenyl)-1-(2-nitro-phenyl)-1,5-dihydro-pyrazolo[3,4-d]pyrimidin-4-one; 1-(4-Amino-phenyl)-5-(4-chloro-phenyl)-6-(2,4-dichloro-phenyl)-1,5-dihydro-pyrazolo[3,4-d]pyrimidin-4-one; 5,6-Bis-(4-chlorophenyl)-1-(4-nitro-phenyl)-1,5-dihydro-pyrazolo[3,4-d]pyrimidin-4-one; 5,6-Bis-(4-chloro-phenyl)-1-(2-nitro-phenyl)-1,5-dihydro-pyrazolo[3,4-d]pyrimidin-4-one; 1-(4-Amino-phenyl)-5,6-bis(4-chloro-phenyl)-1,5-dihydro-pyrazolo[3,4-d]pyrimidin-4-one; 5-(4-Chloro-phenyl)-6-(2,4-dichloro-phenyl)-1-(4-fluoro-phenyl)-1,5-dihydro-pyrazolo[3,4-d]pyrimidin-4-one; 5-(4-Chloro-phenyl)-6-(2,4-dichloro-phenyl)-3-(4-methyl-piperazin-1-yl)-1-phenyl-1,5-dihydro-pyrazolo[3,4-d]pyrimidin-4-one; 5-(4-Bromo-phenyl)-6-(2,4-dichloro-phenyl)-3-methylsulfanyl-1-phenyl-1,5-dihydro-pyrazolo[3,4-d]pyrimidin-4-one; 5-(4-Bromo-phenyl)-6-(2,4-dichloro-phenyl)-3-methanesulfonyl-1-phenyl-1,5-dihydro-pyrazolo[3,4-d]pyrimidin-4-one; 4-[5-(4-Chloro-phenyl)-6-(2,4-dichloro-phenyl)-4-oxo-4,5-dihydro-pyrazolo[3,4-d]pyrimidin-1-yl]-benzoic acid; 5-(4-Chloro-phenyl)-6-(2,4-dichloro-phenyl)-1-(4-hydroxymethyl-phenyl)-1,5-dihydro-pyrazolo[3,4-d]pyrimidin-4-one; 5-(4-Chloro-phenyl)-6-(2,4-dichloro-phenyl)-1-[4-(4-methyl-piperazine-1-carbonyl)-phenyl]-1,5-dihydro-pyrazolo[3,4-d]pyrimidin-4-one; 5-(4-Chloro-phenyl)-6-(2,4-dichloro-phenyl)-1-[4-(morpholine-4-carbonyl)-phenyl]-1,5-dihydro-pyrazolo[3,4-d]pyrimidin-4-one; 5-(4-Chloro-phenyl)-6-(2,4-dichloro-phenyl)-1-[4-(piperidine-1-carbonyl)-phenyl]-1,5-dihydro-pyrazolo[3,4-d]pyrimidin-4-one; 5-(4-Chloro-phenyl)-6-(2,4-dichloro-phenyl)-1-[4-(4-methyl-piperazin-1-ylmethyl)-phenyl]-1,5-dihydro-pyrazolo[3,4-d]pyrimidin-4-one; 5-(4-Chloro-phenyl)-6-(2,4-dichloro-phenyl)-3-methylsulfanyl-1-phenyl-1,5-dihydro-pyrazolo[3,4-d]pyrimidin-4-one; 5-(4-Chloro-phenyl)-6-(2,4-dichloro-phenyl)-3-methanesulfonyl-1-phenyl-1,5-dihydro-pyrazolo[3,4-d]pyrimidin-4-one; 1-(4-Chloro-phenyl)-8-(ethyl-methyl-amino)-9-phenyl-2-(4-tiifluoromethyl-phenyl)-1,9-dihydro-purin-6-one; 1-(4-Chloro-phenyl)-8-dimethylamino-9-phenyl-2-(4-trifluoromethyl-phenyl)-1,9-dihydro-purin-6-one; 1-(4-Chloro-phenyl)-6-oxo-9-phenyl-2-(4-trifluoromethyl-phenyl)-6,9-dihydro-1H-purine-8-carbonitrile; 8-Bromo-1-(4-chloro-phenyl)-2-(2,4-dichloro-phenyl)-9-phenyl-1,9-dihydro-purin-6-one; 1-(4-Chloro-phenyl)-2-(2,4-dichloro-phenyl)-8-(ethyl-methyl-amino)-9-phenyl-1,9-dihydro-purin-6-one; 1-(4-Chloro-pheny f)-2-(2,4-dichloro-phenyl)-8-morphoIin-4-yl-9-phenyl-1,9-dihydro-purin-6-one; 1-(4-Chloro-phenyl)-2-(2,4-dicliloro-phenyl)-8-(4-methyl piperazin-1-yl)-9-phenyl-1,9-dihydro-purin-6-one; 1-(4-Chloro-phenyl)-2-(2,4-dichloro-phenyl)-8-(2-dimethylamino-ethoxy)-9-phenyl-1,9-dihydro-purin-6-one; 1-(4-Chloro-phenyl)-2-(2,4-dichloro-phenyl)-8-(N'-methyl-hydrazino)-9-phenyl-1,9-diliydro-purin-6-one; 1-(4-Chloro-phenyl)-2-(2,4-dichloro-phenyl)-8-[(2-hydroxy-ethyl)-methyl-amino]-9-phenyl-1,9-dihydro-purin-6-one; 1-(4-Chloro-phenyl)-2-(2,4-dichloro-phenyl)-8-methoxy-9-phenyl-1,9-dihydro-purin-6-one; 8-Bromo-2-(4-bromo-phenyl)-1-(4-chloro-phenyl)-9-phenyl-1,9-dihydro-purin-6-one; 5-(4-chloro-phenyl)-1-phenyl-6-(4-pyridin-2-yl-piperazin-1-yl)-1,5-dihydro-pyrazolo[3,4-d]pyrimidin-4-one; 5-(4-chloro-plienyl)-1-phenyl-6-(4-pyridin-4-yl-piperazin-1-yl)-1,5-dihydro-pyrazolo[3,4-d]pyrimidin-4-one; 5-biphenyl-4-yl-6-(4-chloro-phenyl)-3-phenyl-1,6-dihydro-pyrazolo[4,3-d]pyrimidin-7-one; 6-(4-chloro-phenyl)-5-(4-isopropyl-phenyl)-3-phenyl-1,6-dihydro-pyrazolo[4,3-d]pyrimidin-7-one; 6-(4-bromo-phenyl)-2-methyl-3-phenyl-5-p-tolyl-2,6-dihydro-pyrazolo[4,3-d]pyrimidin-7-one; 6-(4-bromo-phenyl)-1-methyl-3-phenyl-5-p-tolyl-1,6-dihydro-pyrazolo[4,3-d]pyrimidin-7-one; 6-(4-chloro-phenyl)-5-(4-isopropyl-phenyl)-1-methanesulfonyl-3-phenyl-1,6-dihydro-pyrazolo[4,3-d]pyrimidin-7-one; 6-(4-chloro-phenyl)-5-(4-isopropyl-phenyl)-7-oxo-3-phenyl-6,7-dihydro-pyrazolo[4,3-d]pyrimidine-1-carboxylic acid dimethylamide; 6-(4-chloro-phenyl)-5-(4-isopropyl-phenyl)-2-methyl-3-phenyl-2,6-dihydro-pyrazolo[4,3-d]pyrimidin-7-one; 6-(4-chloro-phenyl)-5-(4-isopropyl-phenyl)-1-methyl-3-phenyl-1,6-dihydro-pyrazolo[4,3-d]pyrimidin-7-one; [6-(4-chloro-phenyl)-5-(4-isopropyl-phenyl)-7-oxo-3-phenyl-6,7-dihydro-pyrazolo[4,3-d]pyrimidin-2-yl]-acetic acid tert-butyl ester; [6-(4-chloro-phenyl)-5-(4-isopropyl-phenyl)-7-oxo-3-phenyl-6,7-dihydro-pyrazolo[4,3-d]pyrimidin-1 yl]-acetic acid tert-butyl ester; 5-(4-chloro-phenyl)-6-[4-(1-oxy-pyridin-4-yl)-phenyl]-1-phenyl-1,5-dihydro-pyrazolo[3,4-d]pyrimidin-4-one; 5-(4-bromo-phenyl)-6-(4-chloro-phenyl)-3-phenyl-1,6-dihydro-pyrazolo[4,3-d]pyrimidin-7-one; 5-(4-bromo-phenyl)-6-(4-chloro-phenyl)-1-methanesulfonyl-3-phenyl-1,6-dihydro-pyrazolo[4])-3-d]pyrimidin-7-one; 6-(4-chloro-phenyl)-5-(4-isopropyl-phenyl)-3-phenyl-6H-isoxazolo[4,3-d]pyrimidin-7-one; 5-(4-chloro-phenyl)-6-[4-(2-methyl-imidazol-1-yl)-phenyl]-1-phenyl-1,5-dihydro-pyrazolo[3,4-d]pyrimidin-4-one; 5-(4-chloro-phenyl)-6-[4-(4-methyl-imidazol-1-yl)-phenyl]-1-phenyl-1,5-dihydro-pyrazolo[3,4-d]pyrimidin-4-one; 5-biphenyl-4-yl-6-(4-chloro-phenyl)-3-phenyl-6H-isoxazolo[4,3-d]pyrimidin-7-one; 2-[6-(4-chloro-phenyl)-5-(4-isopropyl-phenyl)-7-oxo-3-phenyl-6,7-dihydro-pyrazolo[4,3-d]pyrimidin-1-yl]-acetamide; 5-(4-chloro-phenyl)-3-(3-methyl-[1,2,4]oxadiazol-5-yl)-1-phenyl-6-(4-pyridin-2-yl-phenyl)-1,5-dihydro-pyrazolo[3,4-d]pyrimidin-4-one; [6-(4-chloro-phenyl)-5-(4-isopropyl-phenyl)-7-oxo-3-phenyl-6,7-diliydro-pyrazolo[4,3-d]pyrimidin-1-yl]-acetonitrile; (1-{4-[5-(4-chloro-phenyl)-4-oxo-1-phenyl-4,5-dihydro-1H-pyrazolo[3,4-d]pyrimidin-6-yl]-phenyl}-1H-imidazol-4-yl)- acetonitrile; 5-(4-chloro-phenyl)-6-[4-(1-oxy-pyridin-2-yl)-phenyl]-1-phenyl-1,5-dihydro-pyrazolo[3,4-d]pyrimidin-4-one; 5-(4-chloro-phenyl)-6-[4-(2-ethyl-imidazol-1-yl)-phenyl]-1-phenyl-1,5-dihydro-pyrazolo[3,4-d]pyrimidin-4-one; 5-(4-chloro-phenyl)-6-[4-(2,4-dimethyl-imidazol-1-yl)-phenyl]-1-phenyl-1,5-dihydro-pyrazolo[3,4-d]pyrimidin-4-one; 5-(4-chloro-phenyl)-6-[4-(4-fluoro-phenyl)-piperazin-1-yl]-1-phenyl-1,5-dihydro-pyrazolo[3,4-d]pyrimidin-4-one; 5-(4-bromo-phenyl)-6-(4-chloro-phenyl)-1-methyl-3-phenyl-1,6-dihydro-pyrazolo[4,3-d]pyrimidin-7-one; 6-(4-chloro-phenyl)-5-(4-isopropyl-phenyl)-3-phenyl-6H-isoxazolo[4,5-d]pyrimidin-7-one; 6-(4-chloro-phenyl)-1-methyl-3-phenyl-5-(4-pyridin-2-yl-phenyl)-1,6-dihydro-pyrazolo[4,3-d]pyrimidin-7-one; 6-(4-chloro-phenyl)-2-methyl-3-phenyl-5-(4-pyridin-2-yl-phenyl)-2,6-dihydro-pyrazolo[4,3-d]pyrimidin-7-one; 6-[4-(6-amino-pyridin-3-yl)-phenyl]-5-(4-chloro-phenyl)-1-phenyl-1,5-dihydro-pyrazolo[3,4-d]pyrimidin-4-one; 5-(4-chloro-phenyl)-6-[4-(1-oxy-pyridin-3-yl)-phenyl]-1-phenyl-1,5-dihydro-pyrazolo[3,4-d]pyrimidin-4-one; 5-(4-chloro-phenyl)-6-[4-(1H-imidazol-2-yl)-phenyl]-1-phenyl-1,5-dihydro-pyrazolo[3,4-d]pyrimidin-4-one; 5-(4-chloro-phenyl)-3-methanesulfonyl-1-phenyl-6-(4-pyridin-4-yl-phenyl)-1,5-dihydro-pyrazolo[3,4-d]pyrimidin-4-one; 5-(4-chloro-phenyl)-6-[4-(2-methyl-1-oxy-pyridin-4-yl)-phenyl]-1-phenyl-1,5-dihydro-pyrazolo[3,4-d]pyrimidin-4-one; 5-(4-chloro-phenyl)-6-[4-(3-methyl-1-oxy-pyridin-4-yl)-phenyl]-1-phenyl-1,5-dihydro-pyrazolo[3,4-d]pyrimidin-4-one; 5-(4-chloro-phenyl)-3-methanesulfonyl-6-[4-(1-oxy-pyridin-4-yl)-phenyl]-1-phenyl-1,5-dihydro-pyrazolo[3,4-d]pyrimidin-4-one; 5-(4-chloro-phenyl)-6-[4-(6-oxo-1,6-dihydro-pyridin-3-yl)-phenyl]-1-phenyl-1,5-dihydro-pyrazolo[3,4-d]pyrimidin-4-one; 6-[4-(4-amino-pyridin-2-yl)-phenyl]-5-(4-chloro-phenyl)-1-phenyl-1,5-dihydro-pyrazolo[3,4-d]pyrimidin-4-one; 6-[4-(6-amino-pyridin-2-yl)-phenyl]-5-(4-chloro-phenyl)-1-phenyl-1,5-dihydro-pyrazolo[3,4-d]pyrimidin-4-one; 6-(4-Bromo-phenyl)-5-(4-chloro-phenyl)-4-oxo-1-phenyl-4,5-dihydro-1H-pyrazolo[3,4-d]pyrimidine-3-carboxylic acid; 6-(4-Bromo-phenyl)-5-(4-chloro-phenyl)-4-oxo-1-phenyl-4,5-dihydro-1H-pyrazolo[3,4-d]pyrimidine-3-carboxylic acid ethyl ester; 6-(4-Bromo-phenyl)-5-(4-chloro-phenyl)-4-oxo-1-phenyl-4,5-dihydro-1H-pyrazolo[3,4-d]pyrimidine-3-carboxy lie acid Diethylamide; 6-(4-Bromo-phenyl)-5-(4-chloro-phenyl)-4-oxo-1-phenyl-4,5-dihydro-1H-pyrazolo[3,4-d]pyrimidine-3-carboxylic acid dimethylamide; 6-(4-Bromo-phenyl)-5-(4-chloro-phenyl)-3-(morpholine-4-carbonyl)-1-phenyl-1,5-dihydro-pyrazolo[3,4-d]pyrimidin-4-one; 6-(4-Bromo-phenyl)-5-(4-chloro-phenyl)-4-oxo-1-phenyl-4,5-dihydro-1H-pyrazolo[3,4-d]pyrimidine-3-carboxylic acid piperidin-1-ylamide; 6-(4-Bromo-phenyl)-5-(4-chloro-phenyl)-1-phenyl-3-(piperidine-1-carbonyl)-1,5-dihydro-pyrazolo[3,4-d]pyrimidin-4-one; 6-(4-Bromo-phenyl)-5-(4-chloro-phenyl)-4-oxo-1-phenyl-4,5-dihydro-1H-pyrazolo[3,4-d]pyrimidine-3-carboxylic acid isopropyl ester; 6-(4-Bromo-phenyl)-5-(4-chloro-phenyl)-4-oxo-1-phenyl-4,5-dihydro-1H-pyrazolo[3,4-d]pyrimidine-3-carboxylic acid tert-butyl ester; 5-(4-Chloro-phenyl)-6-(4-isopropyl-phenyl)-4-oxo-1-phenyl-4,5-dihydro-1H-pyrazolo[3,4-d]pyrimidine-3-carboxylic acid amide; 5-(4-Chloro-phenyl)-6-(4-isopropyl-phenyl)-4-oxo-1-phenyl-4,5-dihydro-1H-pyrazolo[3,4-d]pyrimidine-3-carboxylic acid ethyl ester; 5-(4-Chloro-phenyl)-6-(4-isopropyl-phenyl)-3-(3-methyl-[1,2,4]oxadiazol-5-yl)-1-phenyl-1,5-dihydro-pyrazolo[3,4-d]pyrimidin-4-one; 5-(4-Chloro-phenyl)-6-[4-(2-chloro-pyrimidin-4-yl)-phenyl]-3-methylsulfanyl-1-phenyl-1,5-dihydro-pyrazolo[3,4-d]pyrimidin-4-one; 6-[4-(2-Amino-pyrimidin-4-yl)-phenyl]-5-(4-chloro-phenyl)-3-methylsulfanyl-1-phenyl-1,5-dihydro-pyrazolo[3,4-d]pyrimidin-4-one; 5-(4-Chloro-phenyl)-6-(4-isopropyl-phenyl)-4-oxo-1-phenyl-4,5-dihydro-1H-pyrazolo[3,4-d]pyrimidine-3-carboxylic acid methylamide; 5-(4-Chloro-phenyl)-6-(4-isopropyl-phenyl)-4-oxo-1-phenyl-4,5-dihydro-1H-pyrazolo[3,4-d]pyrimidine-3-carbonitrile; 5-(4-Chloro-phenyl)-6-[4-(2-chloro-pyrimidin-4-yl)-phenyl]-3-methanesulfonyl-1-phenyl-1,5-dihydro-pyrazolo[3,4-d]pyrimidin-4-one; 6-[4-(2-Amino-pyrimidin-4-yl)-phenyl]-5-(4-chloro-phenyl)-3-methanesulfonyl-1-phenyl-1,5-dihydro-pyrazolo[3,4-d]pyrimidin-4-one; 6-(4-Bromo-phenyl)-5-(4-chloro-phenyl)-3-(3-methyl-[1,2,4]oxadiazol-5-yl)-1-phenyl-1,5-dihydro-pyrazolo[3,4-d]pyrimidin-4-one; 6-[4-(2-Amino-pyrimidin-4-yl)-phenyl]-5-(4-chloro-phenyl)-4-oxo-1-phenyl-4,5-dihydro-1H-pyrazolo[3,4-d]pyrimidine-3-carboxylic acid amide; 6-[4-(2-Butoxy-vinyl)-phenyl]-5-(4-chloro-phenyl)-1-phenyl-1,5-dihydro-pyrazolo[3,4-d]pyrimidin-4-one; 6-[4-(2-Butoxy-ethyl)-phenyl]-5-(4-chloro-phenyl)-1-phenyl-1,5-dihydro-pyrazolo[3,4-d]pyrimidin-4-one; 5-(4-Chloro-phenyl)-6-[4-(1-methyl-1H-pyrazol-3-yl)-phenyl]-1-phenyl-1,5-dihydro-pyrazolo[3,4-d]pyrimidin-4-one; 5-(4-Chloro-phenyl)-1-phenyl-6-(4-pyridazin-3-yl-phenyl)-1,5-dihydro-pyrazolo[3,4-d]pyrimidin-4-one; 5-(4-Chloro-phenyl)-6-[4-(2-methyl-2H-pyrazol-3-yl)-phenyl]-1-phenyl-1,5-dihydro-pyrazolo[3,4-d]pyrimidin-4-one; 5-(4-Chloro-phenyl)-1-phenyl-6-(4-pyrimidin-2-yl-phenyl)-1,5-dihydro-pyrazolo[3,4-d]pyrimidin-4-one; 6-[4-(6-Amino-pyrazin-2-yl)-phenyl]-5-(4-chloro-phenyl)-1-phenyl-1,5-dihydro-pyrazolo[3,4-d]pyrimidin-4-one; 3-{4-[5-(4-Chlorophenyl)-4-oxo-1-phenyl-4,5-dihydro-1H-pyrazolo[3,4-d]pyrimidin-6-yl]-phenyl}-pyrazine-2-carbonitrile; 5-(4-Chloro-phenyl)-6-[4-(3,6-dimethyl-pyrazin-2-yl)-phenyl]-1-phenyl-1,5-dihydro-pyrazolo[3,4-d]pyrimidin-4-one; 5-(4-Chloro-phenyl)-6-(4-isoxazol-4-yl-phenyl)-1-phenyl-1,5-dihydro-pyrazolo[3,4-d]pyrimidin-4-one; 5-(4-Chloro-phenyl)-6-[4-(1-methyl-1H-imidazol-2-yl)-phenyl]-1-phenyl-1,5-dihydro-pyrazolo[3,4-d]pyrimidin-4-one; 5-(4-Chloro-phenyl)-5-phenyl-6-(4-pyrazin-2-yl-phenyl)-1,5-dihydro-pyrazolo[3,4-d]pyrimidin-4-one; 6-(4-isopropyl-phenyl)-1-phenyl-5-m-tolyl-1,5-dihydro-pyrazolo[3,4-d]pyrimidin-4-one; 6-(4-Isopropyl-phenyl)-1-phenyl-5-(3-trifluoromethyl-phenyl)-1,5-dihydro-pyrazolo[3,4-d]pyrimidin-4-one; 5-(4-Chloro-3-methyl-phenyl)-6-(4-isopropyl-phenyl)-1-phenyl-1,5-dihydro-pyrazolo[3,4-d]pyrimidin-4-one; 5-(3,5-Difluoro-phenyl)-6-(4-isopropyl-phenyl)-1-phenyl-1,5-dihydro-pyrazolo[3,4-d]pyrimidin-4-one; 5-(3,4-Dichloro-phenyl)-6-(4-isopropyl-phenyl)-1-phenyl-1,5-dihydro-pyrazolo[3,4-d]pyrimidin-4-one; 5-(4-Bromo-phenyl)-6-(4-chloro-phenyl)-3-phenyl-3,6-dihydro-[1,2,3]triazolo[4,5-d]pyrimidin-7-one; 5-(3-Fluoro-phenyl)-6-(4-isopropyl-phenyl)-1-phenyl-1,5-dihydro-pyrazolo[3,4-d]pyrimidin-4-one; 5-(3-Chloro-phenyl)-6-(4-isopropyl-phenyl)-1-phenyl-1,5-dihydro-pyrazolo[3,4-d]pyrimidin-4-one; 5-(3-Bromo-phenyl)-6-(4-isopropyl-phenyl) 1-phenyl-1,5-dihydro-pyrazolo[3,4-d]pyrimidin-4-one; 6-(4-Chloro-phenyl)-5-(4-isopropyl-phenyl)-3-phenyl-3,6-dihydro-[1,2,3]triazolo[4,5-d]pyrimidin-7-one; 3-[2-Biphenyl-4-yl-1-(4-chloro-phenyl)-6-oxo-1,6-dihydro-purin-9-yl]-benzoic acid; 3-[2-Biphenyl-4-yl-1-(4-chloro-phenyl)-6-oxo-1,6-dihydro-purin-9-yl]-benzamide; N-[2-Biphenyl-4-yl-1-(4-chloro-phenyl)-6-oxo-9-phenyl-6,9-dihydro-1H-purin-8-ylmethyl]-methanesulfonamide; 3-[2-Biphenyl-4-yl-1-(4-chloro-phenyl)-6-oxo-1,6-dihydro-purin-9-yl]-benzoic acid ethyl ester; 2-Biphenyl-4-yl-1-(4-chloro-phenyl)-8-methanesulfonylmethyl-9-phenyl-6,9-dihydro-purin-6-one; 2-Biphenyl- 4-yl-8-bromomethyl-1-(4-chloro-phenyl)-9-phenyl-3,9-dihydro-purin-6-one; 3-[2-Biphenyl-4-yl-1-(4-chloro-phenyl)-6-oxo-1,6-dihydro-purin-9-yl]-N-cyclopropyl-benzamide; 3-[2-Biphenyl-4-yl-1-(4-chloro-phenyl)-6-oxo-1,6-dihydro-purin-9-yl]-N-pyridin-3-yl-benzamide; 3-[2-Biphenyl-4-yl-1-(4-chloro-phenyl)-6-oxo-1,6-dihydro-purin-9-yl]-N-cyclohexyl-benzamide; 3-[2-Biphenyl-4-yl-1-(4-chloro-phenyl)-6-oxo-1,6-dihydro-purin-9-yl]-N-isoxazol-3-yl-benzamide; 3-[2-Biphenyl-4-yl-1-(4-chloro-phenyl)-6-oxo-1,6-dihydro-purin-9-yl]-N-(2-dimethylamino-ethyl)-benzamide; 3-[2-Biphenyl-4-yl-1-(4-chloro-phenyl)-6-oxo-1,6-dihydro-purin-9-yl]-N-(2-methoxy-ethyl)-benzamide; 1-(4-Bromo-phenyl)-2-(4-methoxy-phenyl)-9-phenyl-1,9-dihydro-purin-6-one; 1-(4-Chloro-phenyl)-2-(4-methoxymethyl-phenyl)-9-phenyl-1,9-dihydro-purin-6-one; 4-[1-(4-Chloro-phenyl)-6-oxo-9-phenyl-6,9-dihydro-1H-purin-2-yl]-benzoic acid; 2-(4-Bromo-phenyl) 1-(4-chloro-phenyl)-9-phenyl-1,9-dihydro-purin-6-one; 1-(4-Chlorophenyl)-9-phenyl-2-(4-pyrazol-1-yl-phenyl)-1,9-dihydro-purin-6-one; 1-(4-Chloro-phenyl)-2-(4-imidazol-1-yl-phenyl)-9-phenyl-1,9-dihydro-purin-6-one; 1-(4-Chloro-phenyl)-2,9-diphenyl-1,9-dihydro-purin-6-one; 1-(4-Chloro-phenyl)-2-(4-[1,2,4]oxadiazol-5-yl-phenyl)-9-phenyl-1,9-dihydro-purin-6-one; 1-(4-Chloro-phenyl)-2-(4-methoxy-phenyl)-9-phenyl-1,9-dihydro-purin-6-one; 1-(4-Chloro-phenyl)-2-[4-(2-oxo-piperidin-1-yl)-phenyl]-9-phenyl-1,9-dihydro-purin-6-one; 1-(4-Chloro-phenyl)-2-[4-(2-oxo-pyrrolidin-1-yl)-phenyl]-9-phenyl-1,9-dihydro-purin-6-one; 1-(4-Chloro-phenyl)-9-phenyl-2-[4-(2H-[1,2,4]triazol-3-yl)-phenyl]-1,9-dihydro-purin-6-one; 1-(4-Chloro-phenyl)-2-[4-(2-methyl-2H-[1,2,4]triazol-3-yl)-phenyl]-9-phenyl-1,9-dihydro-purin-6-one; 1-(4-Chloro-phenyl)-2-[4-(1-methyl-1H-[1,2,4]triazol-3-yl)-phenyl]-9-phenyl-1,9-dihydro-purin-6-one; 1-(4-Chloro-phenyl)-2-(4-hydroxy-phenyl)-9-phenyl-1,9-dihydro-purin-6-one; 2-(4-Chloromethyl-phenyl)-1-(4-chloro-phenyl)-9-phenyl-1,9-dihydro-purin-6-one; 1-(4-Chloro-phenyl)-9-phenyl-2-(4-piperidin-1-ylmethyl-phenyl)-1,9-dihydro-purin-6-one; 1-(4-Chloro-phenyl)-2-(4-morpholin-4-ylmethyl-phenyl)-9-phenyl-1,9-dihydro-purin-6-one; 1-(4-Chloro-phenyl)-2-(4-diethylaminomethyl-phenyl)-9-phenyl-1,9-dihydro-purin-6-one; 1-(4-Chloro-phenyl)-2-[4-(isobutylamino-methyl)-phenyl]-9-phenyl-1,9-dihydro-purin-6-one; 1-(4-Chloro-phenyl)-2-{4-[(cyclopropylmethyl-amino)-methyl]-phenyl}-9-phenyl-1,9-dihydro-purin-6-one; 1-(4-Chloro-phenyl)-2-(4-isopropoxymethyl-phenyl)-9-phenyl-1,9-dihydro-purin-6-one; 1-(4-Chloro-phenyl)-9-phenyl-2-(4-vinyl-phenyl)-1,9-dihydro-purin-6-one; 1-(4-Chloro-phenyl)-2-(4-cyclopropyl-phenyl)-9-phenyl-1,9-dihydro-purin-6-one; 2-(4-Butoxy-phenyl)-1-(4-chlorophenyl)-9-phenyl-1,9-dihydro-purin-6-one; 1-(4-Chloro-phenyl)-8-ethyl-9-phenyl-2-(4-trifluoromethyl-phenyl)-1,9-dihydro-purin-6-one; 1-(4-Chloro-phenyl)-2-[4-(2-chloro-pyrimidin-4-yl)-phenyl]-9-phenyl-1,9-dihydro-purin-6-one; 2-Biphenyl-4-yl-1-(4-chloro-phenyl)-8-methyl-9-phenyl-1,9-dihydro-purin-6-one; 1-(4-Bromo-phenyl)-8-methyl-9-phenyl-2-(4-trifluoromethyl-phenyl)-1,9-dihydro-purin-6-one; 1-(4-Chloro-phenyl)-2-(4-cyclohexyl-phenyl)-9-phenyl-1,9-dihydro-purin-6-one; 1-(4-Chloro-phenyl)-2-(4-oxazol-5-yl-phenyl)-9-phenyl-1,9-dihydro-purin-6-one; 2-(4-Chloro-phenyl)-7-phenyl-1-p-tolyl-1,7-dihydro-purin-6-one; 2-(4-Chloro-phenyl)-1-(4-methoxy-phenyl)-7-phenyl-1,7-dihydro-purin-6-one; 2-(4-Chloro-phenyl)-1-(4-isopropyl-phenyl)-7-phenyl-1,7-dihydro-purin-6-one; 8-Bromo-1-(4-bromo-phenyl)-9-phenyl-2-p-tolyl-1,9-dihydro-purin-6-one; 1-(4-Bromo-phenyl)-8-methoxy-9-phenyl-2-p-tolyl-1,9-dihydro-purin-6-one; 1-(4-Bromo-phenyl)-6-oxo-9-phenyl-2-p-tolyl-6,9-dihydro-1H-purine-8-carbonitrile; 1-(4-Bromo-phenyl)-2-(4-chlorophenyl)-7-phenyl-1,7-dihydro-purin-6-one; 7-Benzyl-2-biphenyl-4-yl-1-(4-chloro-phenyl)-1,7-dihydro-purin-6-one; 3-[2-Biphenyl-4-yl-1-(4-chloro-phenyl)-6-oxo-1,6-dihydro-purin-9-yl]-benzonitrile; 4-[2-Biphenyl-4-yl-1-(4-chloro-phenyl)-6-oxo-1,6-dihydro-purin-9-yl]-benzonitrile; 2-Biphenyl-4-yl-1-(4-chloro-phenyl)-9-(3-trifluoromethoxy-phenyl)-1,9-dihydro-purin-6-one; 2-Biphenyl-4-yl-1-(4-chloro-phenyl)-9-p-tolyl-1,9-dihydro-purin-6-one; 2-Biphenyl-4-yl-1-(4-chloro-phenyl)-9-(2-methoxy-5-methyl-phenyl)-1,9-dihydro-purin-6-one; 2-Biphenyl-4-yl-1-(4-chloro-phenyl)-9-cyclopropyl-1,9-dihydro-purin-6-one; 7-Benzyl-1-biphenyl-4-yl-2-(4-chloro-phenyl)-1,7-dihydro-purin-6-one; 2-(4-Chloro-phenyl)-1-(4'-fluoro-biphenyl-4-yl)-7-phenyl-1,7-dihydro-purin-6-one; 2-(4-Chloro-phenyl)-1-(3'-fluoro-biphenyl-4-yl)-7-phenyl-1,7-dihydro-purin-6-one; 1-(4-Chloro-phenyl)-2-[4-(1-oxy-pyridin-4-yl)-phenyl]-9-phenyl-1,9-dihydro-purin-6-one; 2-(4-Chloro-phenyl)-1-(2'-fluoro-biphenyl-4-yl)-7-phenyl-1,7-dihydro-purin-6-one; 1-(4-Bromo-phenyl)-8-ethyl-9-phenyl-2-(4-trichloromethyl-phenyl)-1,9-dihydro-purin-6-one; 4-[1-(4-Bromo-phenyl)-8-ethyl-6-oxo-9-phenyl-6,9-dihydro-1H-purin-2-yl]-benzoic acid methyl ester; 2-[4-(6-Amino-pyridin-3-yl)phenyl]-1-(4-chloro-phenyl)-9-phenyl-1,9-dihydro-purin-6-one; 1-(4-Chloro-phenyl)-2-[4-(6-oxo-1,6-dihydro-pyridin-3-yl)-phenyl]-9-phenyl-1,9-dihydro-purin-6-one; and 1-(4-Chloro-phenyl)-2-(4-methanesulfonyl-phenyl)-9-phenyl-1,9-dihydro-purin-6-one.

A further embodiment provides for a method of treating a disease mediated by the Cannabinoid-1 receptor (for example, an eating disorder associated with excessive food intake like obesity, bulimia nervosa, and compulsive eating disorders) comprising administration of to a patient in need of such treatment of a therapeutically effective amount of a compound selected from Formula Ia, Ib, Ic, Id, Ie, If, Ig, Ih, Ii, Ij and Ik:

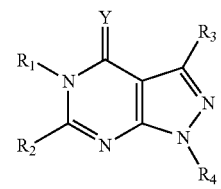

Ia

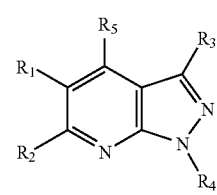

Ib

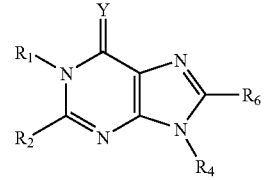

Ic

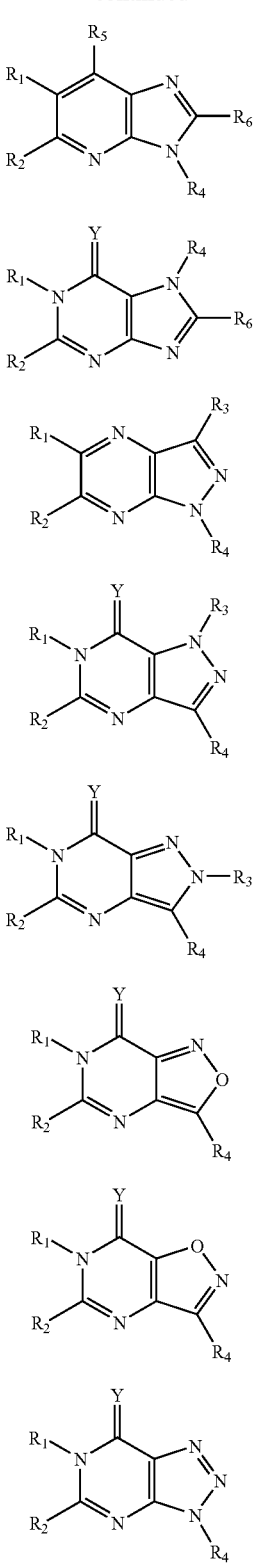

in which:

Y is selected from O, NR$_7$ and S; wherein R$_7$ is selected from hydrogen, hydroxy and C$_{1-6}$alkyl;

R$_1$ is selected from C$_{5-10}$heteroaryl, C$_{3-12}$cycloalkyl, phenyl and benzyl; wherein said heteroaryl, cycloalkyl, phenyl and benzyl of R$_1$ is optionally substituted with 1 to 3 radicals independently selected from halo, hydroxy, cyano, nitro, C$_{1-6}$alkyl, C$_{1-6}$alkoxy, halo-substituted C$_{1-6}$alkyl, halo-substituted C$_{1-6}$alkoxy, —NR$_8$R$_9$, —S(O)$_{0-2}$R$_8$, —C(O)OR$_8$ and R$_{10}$;

R$_2$ is selected from C$_{3-8}$heterocycloalkyl, C$_{5-10}$heteroaryl, phenyl and phenoxy; wherein said heterocycloalkyl, heteroaryl, phenyl or phenoxy of R$_2$ is optionally substituted with 1 to 3 radicals independently selected from halo, hydroxy, cyano, nitro, C$_{1-6}$alkyl, C$_{1-6}$alkoxy, halo-substituted C$_{1-6}$alkyl, C$_{1-6}$alkenyl, halo-substituted C$_{1-6}$alkoxy, XNR$_8$R$_9$, —XOR$_8$, —XC(O)R$_8$, —XS(O)$_{0-2}$R$_8$, —XC(O)NR$_8$R$_9$, —XC(O)OR$_8$, —XOR$_{10}$, —XNR$_8$XR$_{10}$ and —XR$_{10}$; wherein each X is independently selected from a bond, C$_{1-4}$alkylene and C$_{2-4}$alkenylene;

R$_3$ is selected from hydrogen, halo, hydroxy, cyano, cyano-C$_{1-6}$alkyl, nitro, C$_{1-6}$alkyl, C$_{1-6}$alkoxy, halo-substituted-C$_{1-6}$alkyl, halo-substituted C$_{1-6}$alkoxy, —XNR$_8$R$_9$, —XR$_{10}$, —XS(O)$_{0-2}$R$_9$, —XC(O)R$_{10}$, —XC(O)NR$_8$R$_9$, XC(O)NR$_8$R$_{10}$ and —XC(O)OR$_8$;

R$_4$ is selected from C$_{1-6}$alkyl, halo-substituted C$_{1-6}$alkyl, C$_{6-10}$aryl-C$_{0-4}$alkyl, C$_{5-10}$heteroaryl, C$_{3-12}$cycloalkyl, C$_{3-8}$heterocycloalkyl and C(O)R$_{11}$; wherein R$_{11}$ is selected from C$_{3-8}$heterocycloalkyl and C$_{3-8}$heteroaryl; wherein any alkyl of R$_4$ can optionally have a methylene replaced with O, S(O)$_{0-2}$ and NR$_8$; wherein any cycloalkyl, heterocycloalkyl, aryl or heteroaryl of R$_4$ can optionally be substituted with 1 to 3 radicals independently selected from halo, hydroxy, cyano, nitro, C$_{1-6}$alkyl, C$_{1-6}$alkoxy, halo-substituted-C$_{1-6}$alkyl, halo-substituted-C$_{1-6}$alkoxy, —XOR$_8$, —XR$_{10}$, —XC(O)R$_{10}$, XS(O)$_{0-2}$R$_8$, —XNR$_8$R$_9$, —XC(O)NR$_8$R$_9$, —XC(O)NR$_8$R$_{10}$, —XC(O)NR$_8$XNR$_8$R$_9$, —XC(O)NR$_8$XOR$_9$ and —XC(O)OR$_8$;

R$_5$ is selected from hydrogen, halo, hydroxy, C$_{1-6}$alkyl, C$_{1-6}$alkoxy, halo-substituted-C$_{1-6}$alkyl, halo-substituted-C$_{1-6}$alkoxy, hydroxy-substituted-C$_{1-6}$alkyl, hydroxy-substituted-C$_{1-6}$alkoxy, —NR$_8$R$_9$, —OXOR$_9$, —OXR$_{10}$, —NR$_8$XOR$_9$, —OXNR$_8$R$_9$ and —C(O)OR$_8$; wherein X is independently selected from a bond, C$_{1-4}$alkylene and C$_{2-4}$alkenylene;

R$_6$ is selected from hydrogen, halo, hydroxy, cyano, nitro, C$_{1-6}$alkyl, C$_{1-6}$alkoxy, halo-substituted C$_{1-6}$alkyl, halo-substituted C$_{1-6}$alkoxy, —XNR$_8$R$_9$, —XNR$_8$XOR$_9$, —XNR$_8$NR$_8$R$_9$, —XOXNR$_8$R$_9$, —XNR$_8$S(O)$_2$R$_9$, —XS(O)$_2$R$_9$, and XC(O)OR$_9$;

R$_8$ and R$_9$ are independently selected from hydrogen, C$_{1-6}$alkyl and C$_{2-6}$alkenyl; or R$_8$ and R$_9$ together with the nitrogen atom to which both are attached form C$_{3-8}$heterocycloalkyl or C$_{5-10}$heteroaryl; and R$_{10}$ is selected from C$_{5-10}$heteroaryl, C$_{3-8}$heterocycloalkyl, C$_{3-12}$cycloalkyl and phenyl; wherein said heteroaryl or heterocycloalkyl of R$_{10}$ or the combination of R$_8$ and R$_9$ and additionally the cycloalkyl or phenyl of R$_{10}$ is optionally substituted with 1 to 3 radicals independently selected from halo, hydroxy, cyano, cyano-C$_{1-6}$ alkyl, nitro, C$_{1-6}$alkyl, C$_{1-6}$alkoxy, halo-substituted-C$_{1-6}$alkyl, halo-substituted-C$_{1-6}$alkoxy, hydroxy-substituted-C$_{1-6}$alkyl, hydroxy-substituted-C$_{1-6}$alkoxy, phenyl, —NR$_8$R$_8$, —S(O)$_{0-2}$R$_8$ and —C(O)OR$_8$; wherein each R$_8$ is independently selected from hydrogen, C$_{1-6}$alkyl and C$_{2-6}$alkenyl; and the pharmaceutically acceptable salts, hydrates, solvates and isomers thereof.

Another embodiment provides for a method of preventing obesity in a person at risk for obesity comprising administration to said person of about 0.001 mg to about 100 mg per kg of a compound selected from Formula Ia, Ib, Ic, Id, Ie, If, Ig, Ih, Ii, Ij and Ik:

Ia 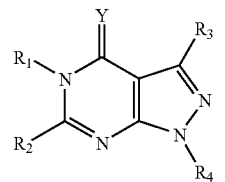

Ib 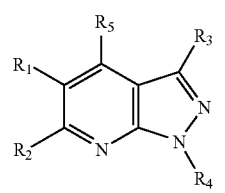

Ic 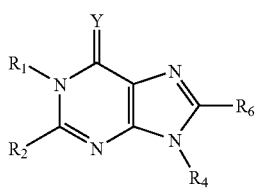

Id 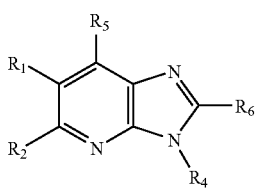

Ie 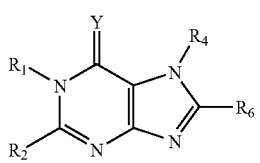

If 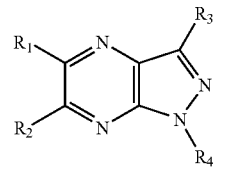

Ig 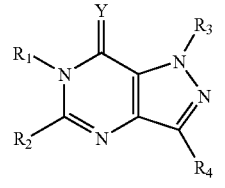

Ih 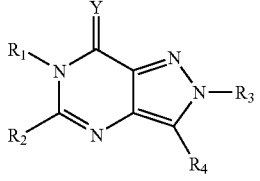

Ii 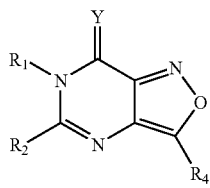

Ij 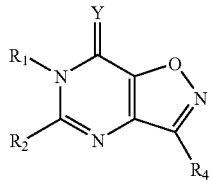

Ik 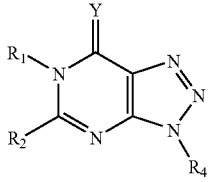

in which:

Y is selected from O, NR$_7$ and S; wherein R$_7$ is selected from hydrogen, hydroxy and C$_{1-4}$alkyl;

R$_1$ is selected from C$_{5-10}$heteroaryl, C$_{3-10}$cyclolalkyl, phenyl and benzyl; wherein said heteroaryl, cycloalkyl, phenyl and benzyl of R$_1$ is optionally substituted with 1 to 3 radicals independently selected from halo, hydroxy, cyano, nitro, C$_{1-6}$alkyl, C$_{1-6}$alkoxy, halo-substituted C$_{1-6}$alkyl, halo-substituted C$_{1-6}$alkoxy, —NR$_8$R$_9$, —S(O)$_{0-2}$R$_8$, —C(O)OR$_8$ and R$_{10}$;

R$_2$ is selected from C$_{3-8}$heterocycloalkyl, C$_{5-10}$heteroaryl, phenyl and phenoxy; wherein said heterocycloalkyl, heteroaryl, phenyl or phenoxy of R$_2$ is optionally substituted with 1 to 3 radicals independently selected from halo, hydroxy, cyano, nitro, C$_{1-6}$alkyl, C$_{1-6}$alkoxy, halo-substituted C$_{1-6}$alkyl, C$_{1-6}$alkenyl, halo-substituted C$_{1-6}$alkoxy, —XNR$_8$R$_9$, —XOR$_8$, —XC(O)R$_8$, —XS(O)$_{0-2}$R$_8$, —XC(O)NR$_8$R$_9$, —XC(O)OR$_9$, —XOR$_{10}$, —XNR$_8$XR$_{10}$ and —XR$_{10}$; wherein each X is independently selected from a bond, C$_{1-4}$alkylene and C$_{2-4}$alkenylene;

R$_3$ is selected from hydrogen, halo, hydroxy, cyano, cyano-C$_{1-6}$alkyl, nitro, C$_{1-6}$alkyl, C$_{1-6}$alkoxy, halo-substituted-C$_{1-6}$alkyl, halo-substituted C$_{1-6}$alkoxy, —XNR$_8$R$_9$, —XR$_{10}$, —XS(O)$_{0-2}$R$_9$, —XC(O)R$_{10}$, —XC(O)NR$_8$R$_9$, —XC(O)NR$_8$R$_{10}$ and —XC(O)OR$_8$;

R$_4$ is selected from C$_{1-6}$alkyl, halo-substituted C$_{1-6}$alkyl, C$_{6-10}$aryl-C$_{0-4}$alkyl, C$_{5-10}$heteroaryl, C$_{3-12}$cycloalkyl, C$_{3-8}$heterocycloalkyl and C(O)R$_{11}$; wherein R$_{11}$ is selected from C$_{3-8}$heterocycloalkyl and C$_{3-8}$heteroaryl; wherein any alkyl of R$_4$ can optionally have a methylene replaced with O, S(O)$_{0-2}$ and NR$_8$; wherein any cycloalkyl, heterocycloalkyl, aryl or heteroaryl of R$_4$ can optionally be substituted with 1 to 3 radicals independently selected from halo, hydroxy, cyano, nitro, C$_{1-6}$alkyl, C$_{1-6}$alkoxy, halo-substituted-C$_{1-6}$alkyl, halo-substituted-C$_{1-6}$alkoxy, —XOR$_9$, —XR$_{10}$, —XC(O)R$_{10}$, —XS(O)$_{0-2}$R$_8$, —XNR$_8$R$_9$, —XC(O)NR$_8$R$_9$, —XC(O)NR$_8$R$_{10}$, —XC(O)NR$_8$XNR$_8$R$_9$, —XC(O)NR$_8$XOR$_9$ and —XC(O)OR$_8$;

R$_5$ is selected from hydrogen, halo, hydroxy, C$_{1-6}$alkyl, C$_{1-6}$alkoxy, halo-substituted-C$_{1-6}$alkyl, halo-substituted-C$_{1-6}$alkoxy, hydroxy-substituted-C$_{1-6}$alkyl, hydroxy-substituted- $C_{1-6}$alkoxy, —$NR_8R_9$, —$OXOR_8$, —$OXR_{10}$, —$NR_8XOR_9$, —$OXNR_8R_9$ and —$C(O)OR_8$; wherein X is independently selected from a bond, $C_{1-4}$alkylene and $C_{2-4}$alkenylene;

$R_6$ is selected from hydrogen, halo, hydroxy, cyano, nitro, $C_{1-6}$alkyl, $C_{1-6}$alkoxy, halo-substituted $C_{1-6}$alkyl, halo-substituted $C_{1-6}$alkoxy, —$XNR_8R_9$, —$XNR_8XOR_9$, —$XNR_8NR_8R_9$, —$XOXNR_8R_9$, —$XNR_8S(O)_2R_9$, —$XS(O)_2R_9$, and —$XC(O)OR_8$;

$R_8$ and $R_9$ are independently selected from hydrogen, $C_{1-6}$alkyl and $C_{2-6}$alkenyl; or $R_8$ and $R_9$ together with the nitrogen atom to which both are attached form $C_{3-8}$heterocycloalkyl or $C_{5-10}$heteroaryl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, cyano-$C_{1-6}$ alkyl, nitro, $C_{1-6}$alkyl, $C_{1-6}$alkoxy, halo-substituted-$C_{1-6}$alkyl, halo-substituted-$C_{1-6}$alkoxy, hydroxy-substituted-$C_{1-6}$alkyl, hydroxy-substituted-$C_{1-6}$alkoxy, phenyl, —$NR_8R_8$, —$S(O)_{0-2}R_8$ and —$C(O)OR_8$; wherein each $R_9$ is independently selected from hydrogen, $C_{1-6}$alkyl and $C_{2-6}$alkenyl; and the pharmaceutically acceptable salts, hydrates, solvates and isomers thereof.

Preferred compounds of Formula I are detailed in the Examples and Table I, infra.

Pharmacology and Utility

Compounds of the invention inhibit the activity of CB1 and, as such, are useful for treating diseases or disorders in which the activity of CB1 contributes to the pathology and/or symptomology of the disease. This invention further provides compounds of this invention for use in the preparation of medicaments for the treatment of diseases or disorders in which CB1 activity contributes to the pathology and/or symptomology of the disease. CB1 mediated diseases or conditions include, but are not limited to, metabolic disorders as well as conditions associated with metabolic disorders including obesity, bulimia nervosa, compulsive eating disorders, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, and hyperlipidemic conditions; or psychiatric disorders such as substance abuse, psychosis, depression, anxiety, stress, epilepsy, mania and schizophrenia; or cognitive disorders such as dementia including Alzheimer's disease, memory deficits, short term memory loss and attention deficit disorders; or neurodegenerative disorders such as Parkinson's Disease, cerebral apoplexy and craniocerebral trauma, hypotension, catabolism in connection with pulmonary dysfunction and ventilator dependency; or cardiac dysfunction including valvular disease, myocardial infarction, cardiac hypertrophy and congestive heart failure); or the overall pulmonary dysfunction, transplant rejection, rheumatoid arthritis, migraine, neuropathy, multiple sclerosis, Guillain-Barre syndrome, the inflammatory sequelae of viral encephalitis, cerebral vascular accidents, inflammatory bowel disease, lupus, graft vs. host disease, T-cell mediated hypersensitivity disease, psoriasis, asthma, Hashimoto's thyroiditis, Guillain-Barre syndrome, cancer, contact dermatitis, allergic rhinitis, ischemic or reperfusion injury, head trauma and movement disorders. The compounds are also useful for the treatment of substance abuse disorders, particularly to opiates, alcohol, marijuana, and nicotine including smoking cessation. The compounds are also useful for the treatment of eating disorders by inhibiting excessive food intake and the resulting obesity and complications associated therewith, including left ventricular hypertrophy. The compounds are also useful for the treatment of constipation and chronic intestinal pseudo-obstruction, as well as for the treatment of asthma, osteoporsis, and cirrhosis of the liver.

Marijuana and its derivatives have been used for centuries for medicinal and recreational purposes. A major active ingredient in marijuana and hashish has been determined to be Δ9-Tetrahydrocannabinol (Δ9-THC). The biological action of Δ9-THC and other members of the cannabinoid family occurs through two G-protein coupled receptors termed CB1 and CB2. The CB1 receptor is primarily found in the central and peripheral nervous systems and to a lesser extent in several peripheral organs.

The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to Δ9-THC, including sedation, hypothermia, intestinal immobility, antinociception, analgesia, catalepsy, anti-emesis, and appetite stimulation.

The genes for the respective cannabinoid receptors have each been disrupted in mice. The CB1 receptor knockout mice appeared normal and fertile. They were resistant to the effects of Δ9-THC and demonstrated a strong reduction in the reinforcing properties of morphine and the severity of withdrawal syndrome. They also demonstrated reduced motor activity and hypoalgesia. The CB2 receptor knockout mice were also healthy and fertile. They were not resistant to the central nervous system mediated effects of administered Δ9-THC. There were some effects on immune cell activation, reinforcing the role for the CB2 receptor in immune system functions.

Excessive exposure to Δ9-THC can lead to overeating, psychosis, hypothermia, memory loss, and sedation.

Treatment of asthma with CB1 receptor modulators (such as CB1 inverse agonists) is supported by the finding that presynaptic cannabinoid CB1 receptors mediate the inhibition of noradrenalin release.

Treatment of cirrhosis of the liver with CB1 receptor modulators is supported by the finding that a CB1 receptor modulator will reverse the low blood pressure observed in rats with carbon tetrachloride-induced liver cirrhosis and will lower the elevated mesenteric blood flow and portal vein pressure.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other substances used in the treatment of diseases or disorders, such as, psychosis, memory deficit, cognitive disorders, migraine, neuropathy, neuroinflammatory disorders, cerebral vascular accidents, head trauma, anxiety disorders, stress, epilepsy, Parkinson's disease, schizophrenia, substance abuse disorders such as smoking cessation, osteoporosis, constipation, chronic intestinal pseudo-obstruction, cirrhosis of the liver, asthma, obesity, and other eating disorders associated with excessive food intake, obesity, etc. (see "Pharmacology and Utility", supra). Where the compounds of the invention are administered in conjunction with other therapies, dosages of the co-administered compounds will of course vary depending on the type of co-drug employed, on the specific drug employed, on the condition being treated and so forth.

A combined preparation or pharmaceutical composition can comprise a compound of the invention as defined above or a pharmaceutical acceptable salt thereof and at least one active ingredient selected from:

a) anti-diabetic agents such as insulin, insulin derivatives and mimetics; insulin secretogogues such as the sulfonylureas, e.g., Glipizide, glyburide and Aryl; insulinotropic sulfonylurea receptor ligands such as megiitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, TMN-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPAR gamma agonist e.g. GI-262570; Diacylglycerol acetyltransferase (DGAT) inhibitors such as those disclosed in WO 2005044250, WO 2005013907, WO 2004094618 and WO 2004047755;

b) hypolipidemic agents such as 3-hydroxy-3-methylglutaryl coenzyme A (HMG-CoA) reductase inhibitors, e.g., lovastatin and related compounds such as those disclosed in U.S. Pat. No. 4,231,938, pravastatin, simvastatin and related compounds such as those disclosed in U.S. Pat. Nos. 4,448,784 and 4,450,171, pravastatin and related compounds such as those disclosed in U.S. Pat. No. 4,346,227, cerivastatin, mevastatin and related compounds such as those disclosed in U.S. Pat. No. 3,983,140, velostatin, fluvastatin, dalvastatin, atorvastatin, rosuvastatin and related statin compounds disclosed in U.S. Pat. No. 5,753,675, rivastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837; squaiene synthase inhibitors; FXR (farnesoid X receptor) and LXR (liver X receptor) ligands; cholestyramine; fibrates; nicotinic acid and aspirin;

c) an anti-obesity agent or appetite regulating agent such as melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta δ agonists as disclosed in U.S. Pat. Nos. 5,541,204, 5,770,615, 5, 491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a SCD-1 inhibitor as disclosed in $WO_{2005011655}$, a lipase inhibitor, such as orlistat or ATL-962 (Aiizyme), serotonin receptor agonists, (e.g., BVT-933 (Biovitrum)), monoamine reuptake inhibitors or releasing agents, such as fenfluramine, dexfenfiuramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, phentermine, leptin, bromocriptine, dexamphetamine, amphetamine, fenfluramine, dexfenfiuramine, sibutramine, orlistat, dexfenfiuramine, mazindol, phentermine, phendimetrazine, diethylpropion, fluoxetine, bupropion, topiramate, diethylpropion, benzphetamine, phenylpropanolamine or ecopipam, ephedrine, pseudoephedrine;

d) anti-hypertensive agents such as loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; beta-adrenergic receptor blockers such as acebutolol, atenolol, betaxolol, bisoprolol, metoprolo), nadolol, propranolol, sotalol and timolol; inotropic agents such as digoxin, dobutamine and milrinone; calcium channel blockers such as amiodipine, bepridil, diltiazem, felodipine, nicardipine, nimodipine, nifedipine, nisoldipine and verapamil; aldosterone receptor antagonists; aldosterone synthase inhibitors; and dual ET/AII antagonist such as those disclosed in WO 00/01389.

e) a HDL increasing compound;

f) Cholesterol absorption modulator such as Zetia® and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazinomethyl)-benzoytamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92; and m) an agent interacting with a $5-HT_3$ receptor and/or an agent interacting with $5-HT_4$ receptor such as tegaserod described in the U.S. Pat. No. 5,510,353 as example 13, tegaserod hydrogen maleate, cisapride, cilansetron;

n) an agent for treating tobacco abuse, e.g., nicotine receptor partial agonists, bupropion hypochloride (also known under the tradename Zyban®) and nicotine replacement therapies;

o) an agent for treating erectile dysfunction, e.g., dopaminergic agents, such as apomorphine), ADD/ADHD agents (e.g., Ritalin®, Strattera®, Concerta® and Adderall®);

p) an agent for treating alcoholism, such as opioid antagonists (e.g., naltrexone (also known under the tradename ReVia®) and nalmefene), disulfuram (also known under the tradename Antabuse®), and acamprosate (also known under the tradename Campral®)). In addition, agents for reducing alcohol withdrawal symptoms may also be co-administered, such as benzodiazepines, beta-blockers, clonidine, carbamazepine, pregabalin, and gabapentin (Neurontin®);

q) other agents that are useful including anti-inflammatory agents (e.g., COX-2 inhibitors); antidepressants (e.g., fluoxetine hydrochloride (Prozac®)); cognitive improvement agents (e.g., donepezil hydrochloride (Aircept®) and other acetylcholinesterase inhibitors); neuroprotective agents (e.g., memantine); antipsychotic medications (e.g., ziprasidone (Geodon®), risperidone (Risperdal®), and olanzapine (Zyprexa®));

or, in each case a pharmaceutically acceptable salt thereof; and optionally a pharmaceutically acceptable carrier.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

In the following schemes, several methods of preparing the compounds of the present invention are illustrative. One of skill in the art will appreciate that these methods are representative, and in no way inclusive of all methods for preparing the compounds of the present invention. The radicals in the schemes are as described in Formula I.

An illustration of the synthesis of the compounds in the present invention of Formula Ib, in which $R_1$ and $R_2$ are selected from optionally substituted phenyl (e.g. $Ar^1$ and $Ar^2$), is given in Scheme 1. 1,2-diarylethanone 1-a can be synthesized using methods reported by M. Wilsterman et al. WO 03051850 and G. M. Anstead, et al., *J. Med, Chem.*, 1990, 33, 2726. Diarylethanone 1-a is heated with 5-amino-pyrazole-4-carbonitrile in dichloromethane in the presence of $TiCl_4$ at high temperature (100° C. to 160° C., preferably 160° C.) to provide the pyrazolo[3,4-b]pyridin-4-ylamine 1-b. The 4-amino group of compound 1-b is converted to $R_5$ ($R_5$ can be halo, alkoxy and etc.) by transformations such as diazotization with tert-butyl nitrite or sodium nitrite under acidic condition followed by treatment with appropriate nucleophiles to provide 1-c.

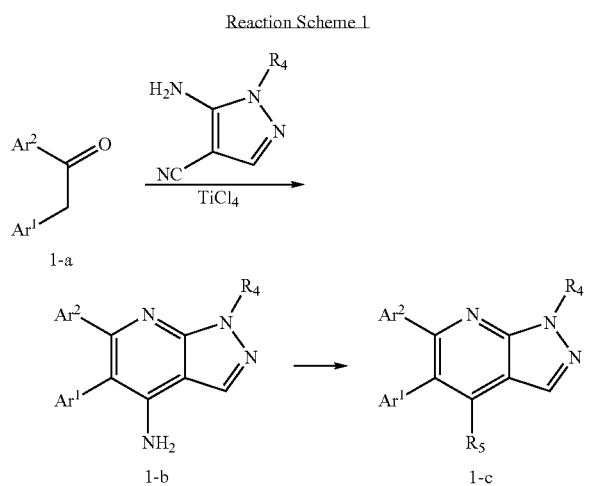

5-amino-pyrazole-4-carbonitriles used in this invention are prepared as described in (a) Peat, A. J. et al Bioorg. & Med. Chem. Lett. (2004), 14(9), 2127-2130; (b) Meegalla, S. K. et al Bioorg. & Med. Chem. Lett. (2003), 13(22), 4035-4037; (c) Dooley, M. J. et al Australian J. Chem. (1989), 42(5), 747-50; (d) Reid, W. et al Tetrahedron (1988), 44(23), 7155-62.

An illustration of the synthesis of the compounds in the present invention of Formula Ia is given in Reaction Scheme 2. An amine 2-a is reacted with an acid chloride 2-b (or its corresponding carboxylic acid) under standard amide formation conditions to provide 2-c. The amide 2-c is treated with chlorination reagents, such as thionyl chloride, oxalyl chloride, oxyphosphorus trichloride and etc., to provide 2-d. The imidoyl chloride 2-d is condensed with 5-amino-4-pyrazole-carboxylate 2-e ($R^a$ is methyl or ethyl) upon heating in the presence of a strong Lewis acid (e.g. $TiCl_4$) to provide an amidine intermediate, which is cyclized in situ to 1,5-dihydro-pyrazolo[3,4-d]pyrimidin-4-one 2-f. Amide coupling reactions were carried out under standard conditions, such as those described in (1) M. Bodanszky et al "The Practice of Peptide Synthesis", Springer-Verlay 2nd ed. 1994; (2) A. R. Chamberlin, *Chem. Rev.* 1997, 97, 2243-66.

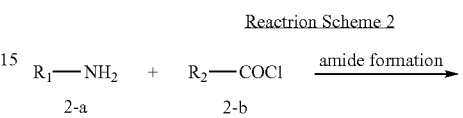

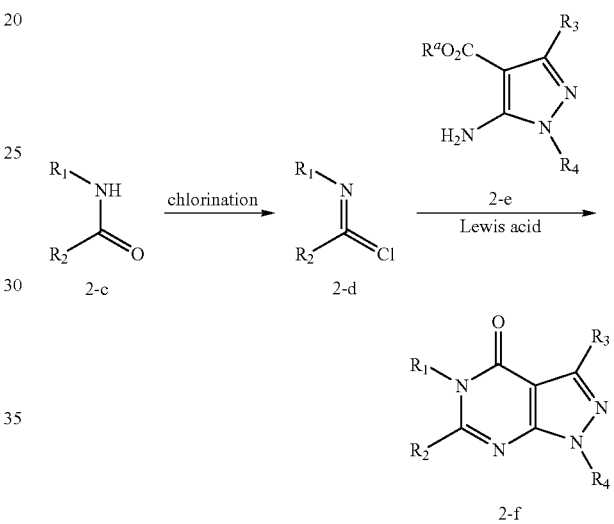

5-amino-4-pyrazole-carboxylates 2-e used in this invention are synthesized as described in (a) Abass, M. Phosphorus, Sulfur and Silicon and the Related Elements (2003), 178(7), 1413-1432; (b) Beck, James R. et al J. Heterocyclic Chem. (1987), 24(3), 693-5; (c) Sunder, S. et al J. Heterocyclic Chem. (1980), 17(7), 1527-9; (d) Beck, James R. et al J. Heterocyclic Chem. (1988), 25(3), 955-8; (e) Ryckmans, T. et al Tetrahedron (1997), 53(5), 1729-1734; (f) Organ, Michael G. et al J. Combi. Chem. (2003), 5(2), 118-124; (g) Kopp, M. et al J. Heterocyclic Chem. (2001), 38(5), 1045-1050.

An illustration of the synthesis of the compounds in the present invention of Formula Ic is given in Reaction Scheme 3. Ethyl cyanoglycoxylate-2-oxime 3-a is reduced according to literature precedent (De Meester et al *Heterocycl Chem.* 1987, 24, 441) to 2-cyanglycine ethyl ester 3-b. Amine 3-b is then condensed with triethyl orthoformate. Without purification, the resulting cyano[(1-ethoxymethylene)amino]acetate 3-c is treated directly with amine $R_4NH2$ to provide 5-amino-1H-imidazole-4-carboxylate 3-d. Syntheses of compound 3-d are also described in (a) Collins. M. et al *Inorg. Chem. Commun.* 2000, 3, 453; (b) Herr, R. el al *J. Org. Chem.* 2002, 67(1), 188-193; (c) Suwinski, J. et al *Eur. J. Org. Chem.* 2003, (6), 1080-1084. 5-Amino-1H-imidazole-4-carboxylate 3-d is converted to 1,9-dihydro-purin-6-one 3-e by the procedures described in Scheme 2.

Reaction Scheme 3

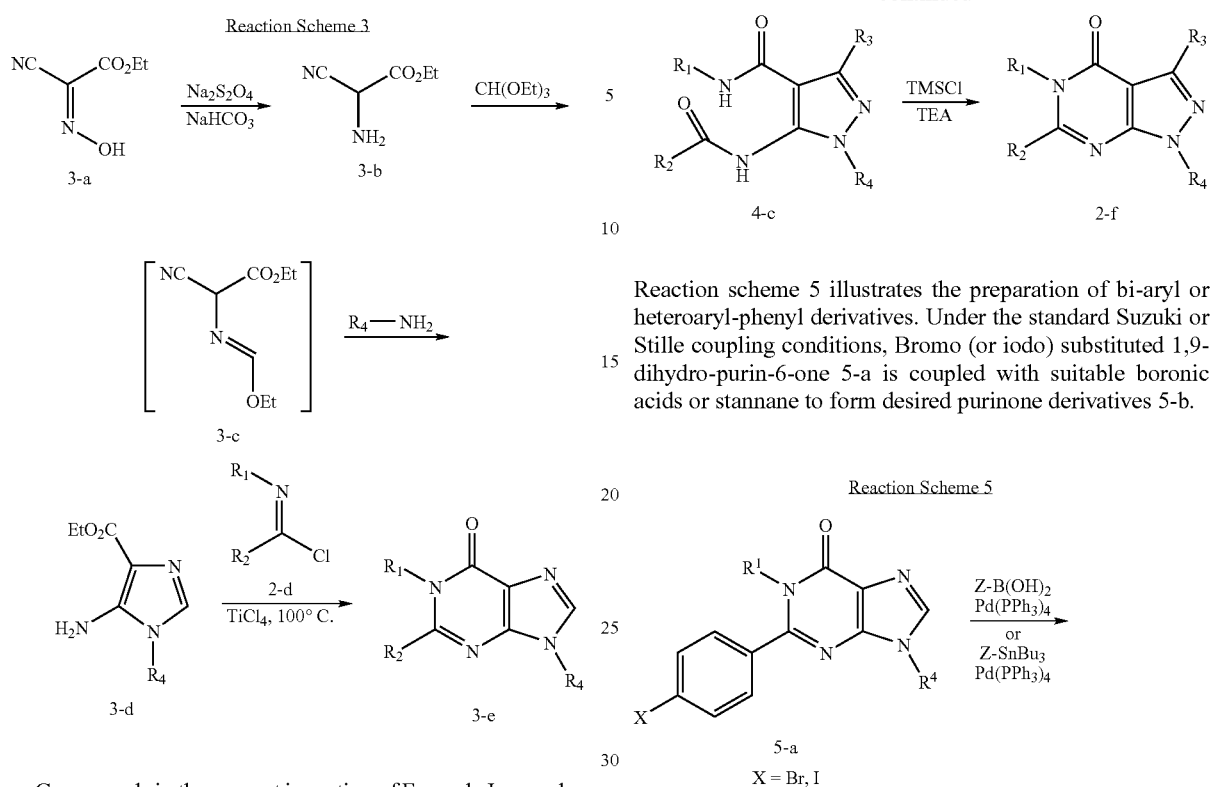

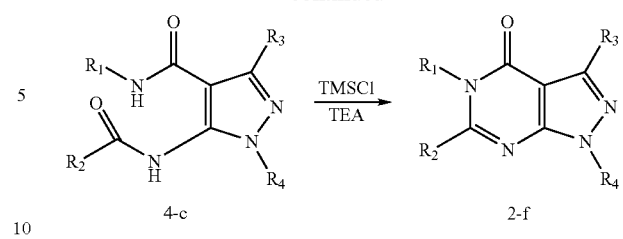

Reaction scheme 5 illustrates the preparation of bi-aryl or heteroaryl-phenyl derivatives. Under the standard Suzuki or Stille coupling conditions, Bromo (or iodo) substituted 1,9-dihydro-purin-6-one 5-a is coupled with suitable boronic acids or stannane to form desired purinone derivatives 5-b.

Compounds in the present invention of Formula Ia can also be made by the procedures given in Reaction Scheme 4. 5-Amino-pyrazole-4-carboxylate 2-e reacts with acid chloride $R_2(C{=}O)Cl$ giving the N,N-diacylated intermediate 4-b which is then treated with an excess amount of lithium amide $R_1NHLi$ to form intermediate 4-c ($R^a$ is methyl or ethyl). Ring closure of 4-c upon treatment with trimethylsilyl chloride and triethylamine gives 1,5-dihydro-pyrazolo[3,4-d]pyrimidin-4-one 2-f. A procedure similar to the annulation step used here is described by Miyata, K. et al U.S. Pat. No. 5,922,866. Other procedures to effect the conversion of compound 4-c to compound 2-f are described in (a) Brzozowski Z. et al J. Med. Chem. (2002), 45(2), 430-37; (b) Zaher, H. A. et al Indian J. Chem. (3974), 12(11), 1212-15.

Reaction Scheme 5

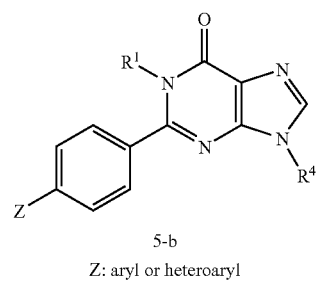

Reaction Scheme 4

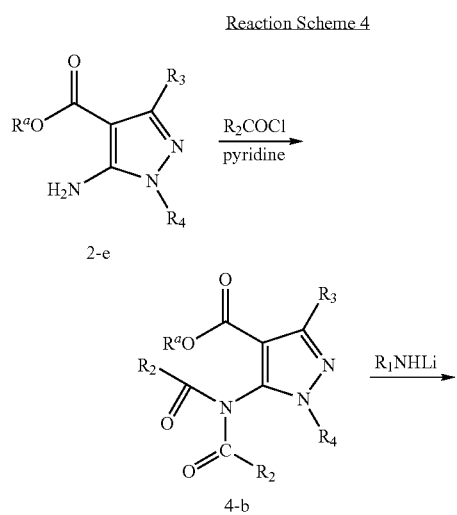

Reaction scheme 6 describes the synthesis of the compounds with various aryl or heteroaryl $R_4$ by a modified cupper complex-catalyzed cross coupling reaction of arylboronic acids with imidazoles developed from J. Collman's labolatory (ref. Org. Lett. 2000, 2, 1233.) The starting material required for this synthesis, ethyl 4-amino-1-benzylimidazole carboxylate, is readily prepared in a large scale from commercially available N-benzylglycine ethyl ester (ref. Synthesis 1995, 855).

Reaction Scheme 6

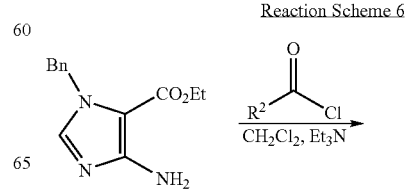

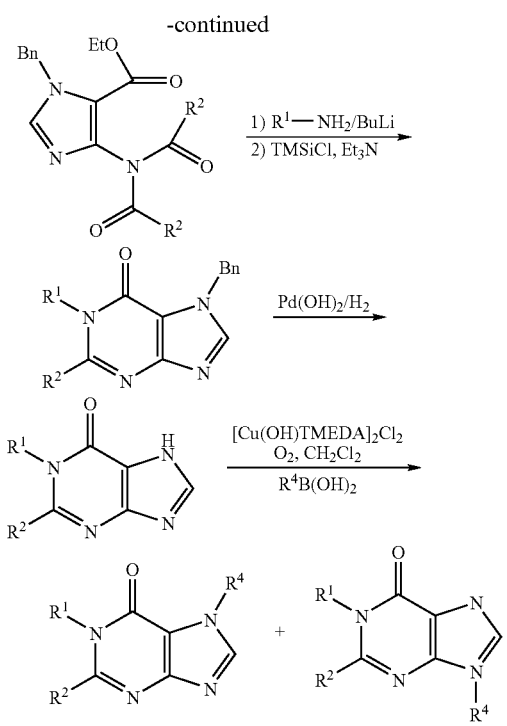

Detailed descriptions of the synthesis of compounds of the Invention are given in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme 1, 2, 3, 4, 5 or 6; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following intermediates (Reference Examples) and Examples that illustrate the preparation of compounds of the invention.

Reference 1

Preparation of 5-Amino-1-cyclohexyl-1H-pyrazole-4-carboxylic acid ethyl ester

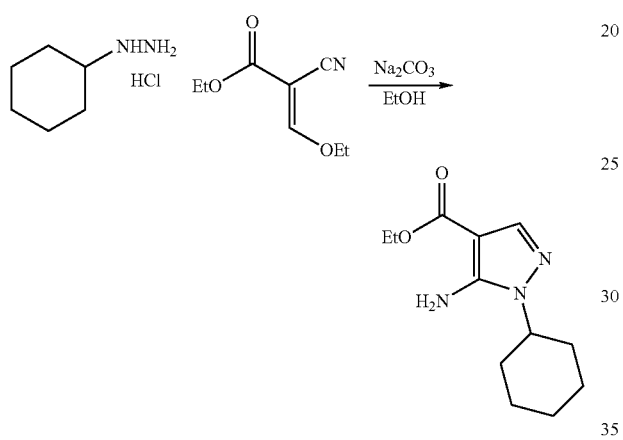

To a round bottom flask is added cyclohexyl-hydrazine hydrochloride (4.5 g, 30 mmol), 2-cyano-3-ethoxy-acrylic acid ethyl ester (5.1 g, 30 mmol), sodium bicarbonate (2.6 g, 30.9 mmol) and 40 mL of ethanol. The mixture is heated to 80° C. for 1 hour, cooled down to room temperature and concentrated. The residue is dissolved in chloroform and washed with water, dried over sodium sulfate. After removal of the solvent, the solid is recrystallized from ethyl acetate: $^1$HNMR (CDCl$_3$): δ 7.40 (1 H, s), 4.77 (2 H, brs), 4.05 (2 H, q, J=7.2 Hz), 3.50 (1 H, m), 1.61-1.71 (6 H, m), 1.50 (1 H, m), 1.02-1.21 (3 H, m), 1.13 (3 H, t, J=7.2 Hz).

Example 1

5-(4-Chloro-phenyl)-6-(2,4-dichloro-phenyl)-1-phenyl-1,5-dihydro-pyrazolo-[3,4-d]pyrimidin-4-one

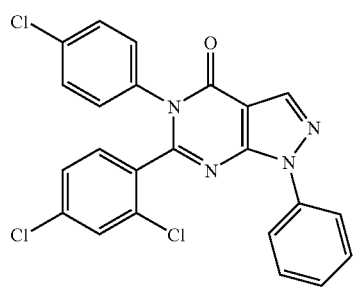

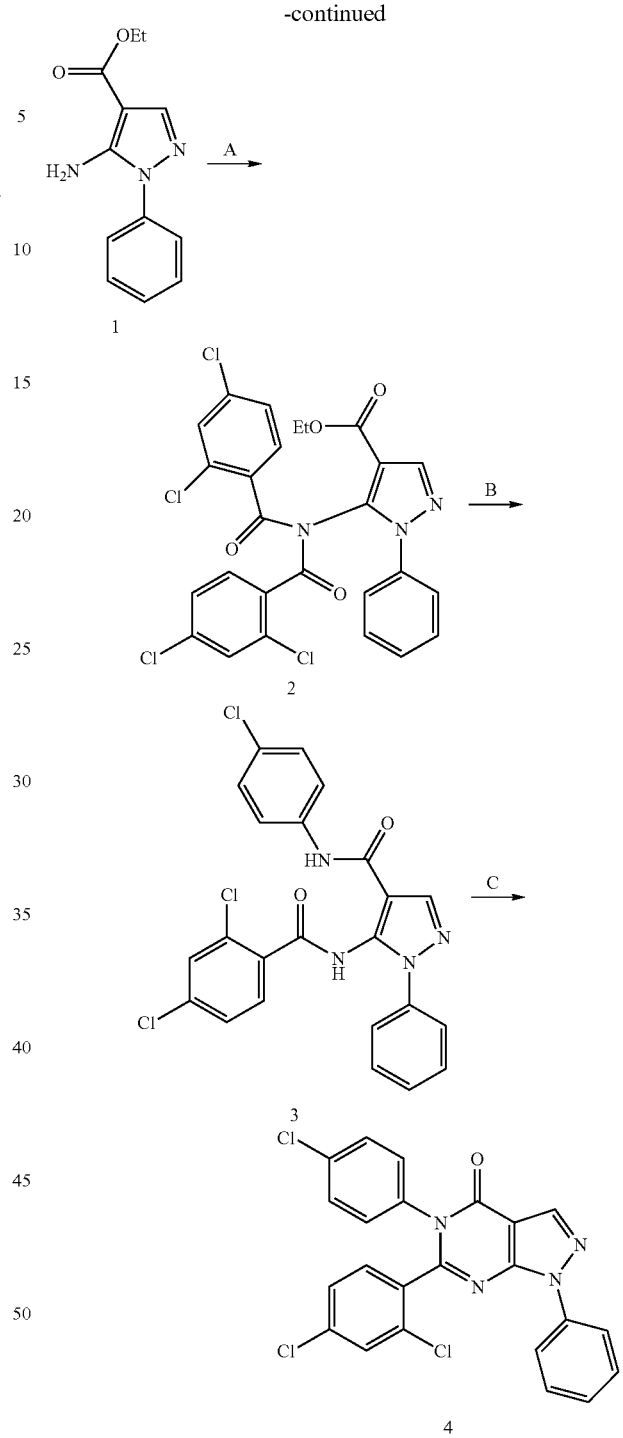

Step A: Commercially available 5-amino-1-phenyl-1H-pyrazole-4-carboxylic acid ethyl ester (1, 2.31 g, 10 mmol) is added to a flask and 10 mL of dry pyridine is added. 2,4-Dichloro-benzoyl chloride (4.18 g, 20.0 mmol) is added via syringe to the stirring reaction mixture. The reaction is heated to reflux for 3 hours. The resulting slurry is poured into 500 mL of 1M HCl and the crude product is extracted out in 2×200 mL of DCM. The organic layer is washed with 100 mL of 1M HCl, followed by 300 mL saturated aqueous sodium bicarbonate and brine. The organic layer is dried over MgSO$_4$, filtered and concentrated. The crude product is recrystallized from hot hexanes with a minimal amount of dichloromethane added to give 2: LC/MS found: 578.1 (M+H⁺).

Step B: 4-Chloro-aniline (663 mg, 5.2 mmol) is added to a three neck flask which is sealed with septa, equipped with an oil bubbler and purged with dry nitrogen. Anhydrous THF (20 mL) is added via syringe under an inert atmosphere. The amine is deprotonated with n-Bu-Li (2.5 M, 2.07 mL, 5.2 mmol) at room temperature. The reaction is stirred for 10 minutes and of 5-[bis-(2,4-dichloro-benzoyl)-amino]-1-phenyl-1H-pyrazole-4-carboxylic acid ethyl ester (2, 500 mg, 0.866 mmol) is added as a solid under a positive purge of nitrogen. The resulting reaction mixture is stirred for 30 minutes and quenched by pouring into saturated aqueous ammonium chloride. The crude product is extracted in 100 mL of ethyl acetate, washed with 1 M HCl, brine, and dried over MgSO₄. The organic layer is filtered and concentrated to dryness. The dark crude material is recrystallized from hot DCM yielding yellow crystals of 3: ¹H NMR (DMSO-d6, 400 MHz) δ 10.7 (s, 1H), 10.1 (s, 1H), 8.4 (s, 1H), 7.75 (d, J=8.9 Hz, 2H), 7.73 (s, br, 1H), 7.66-7.53 (m, 6H), 7.5-7.46 (m, 1H), 7.41 (d, J=8.9 Hz, 2H). LC/MS found: 485.0 (M+H⁺).

Step C. 5-(2,4-Dichloro-benzoylamino)-1-phenyl-1H-pyrazole-4-carboxylic acid (4-chloro-phenyl)-amide (3, 1.1 g, 2.26 mmol) is placed in a large microwave tube with 12 mL of dry TEA and 5 mL of freshly distilled TMSCl. The tube is sealed and the resulting slurry is heated to 100° C. in an oil bath overnight. The reaction mixture is quenched with 500 mL of 1 M HCL and the product is extracted in 2×200 mL of DCM. The organic layer is washed with 100 mL of HQ, 300 mL of saturated aqueous sodium bicarbonate, and 300 mL of brine. The organic layer is dried over MgSO₄, filtered and concentrated. The crude material is purified by flash chromatography to yield 1.0 g of 4 as a white solid: ¹H NMR (CDCl₃, 400 MHz) δ 8.35 (s, 1H), 8.09 (d, J=7.58 Hz, 2H), 7.51-7.47 (m, 2H), 7.39 (d, J=7.5 Hz, 1H), 7.33 (d, J=1.6 Hz, 1H), 7.3-7.28 (m, 2H), 7.21-7.16 (m, 2H), 7.04-7.0 (m, 1H); LC/MS found: 469.0 (M+1/z).

Example 2

5-(4-bromo-phenyl)-1-phenyl-6-p-tolyl-1,5-dihydro-pyrazolo[3,4-d]pyrimidin-4-one

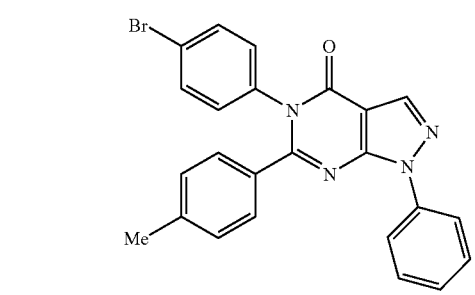

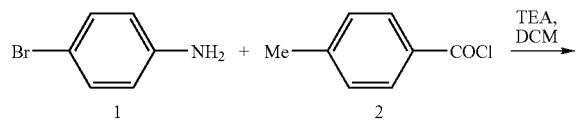

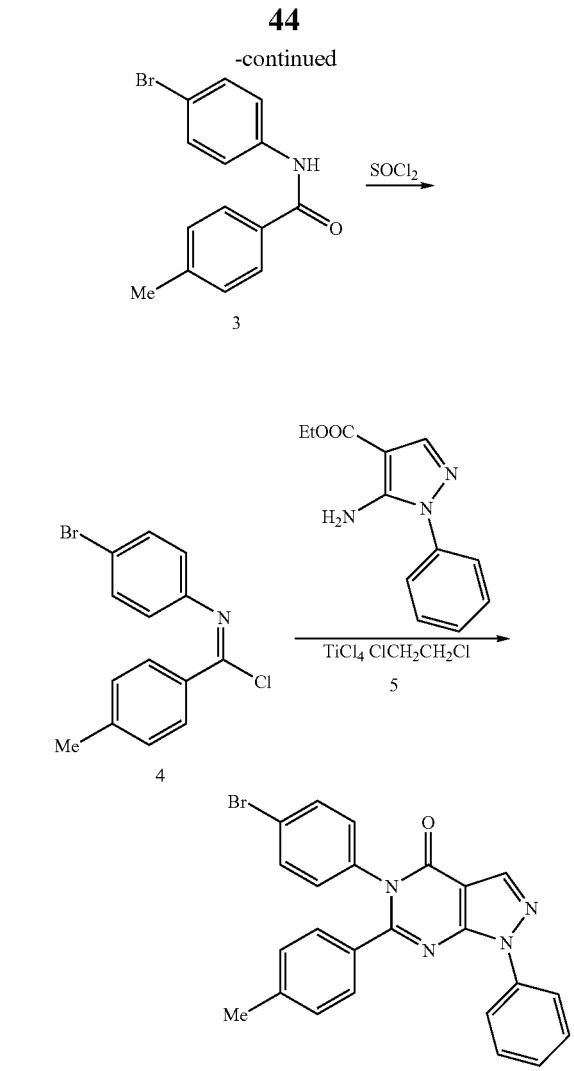

To a solution of 4-bromoaniline (1, 60.0 mg, 0.35 mmol) in dichloromethane (1.5 mL) is added p-toluoyl chloride (2, 46.1 μL, 0.35 mmol) and TEA (97.2 μL, 0.70 mmol). The reaction mixture is stirred at room temperature for 30 minutes to provide N-(4-bromo-phenyl)-4-methylbenzamide (3). After removal of the solvent, without further purification, 3 is taken by thionyl chloride (0.5 mL) and the mixture is heated at 80° C. for 1 hour before thionyl chloride is removed in vacuo to provide imidoyl chloride 4. Without further purification, the crude 4 is dissolved in dichloroethane (1.0 mL), and ethyl 5-amino-1-phenyl-4-pyrazole-carboxylate (5, 96.8 mg, 0.42 mmol) and TiCl₄ (153.0 μL, 1.40 mmol) are added. The reaction mixture is heated at 160° C. in a microwave for 20 minutes, cooled down, diluted with dichloroethane (5 mL), and quenched with H₂O (5 mL). The two layers are separated. The aqueous layer is extracted with dichloroethane. The combined dichloroethane layer is washed with brine, dried over MgSO₄, concentrated, and purified by silica gel chromatography followed by reverse phase HPLC to provide 5-(4-bromo-phenyl)-1-phenyl-6-p-tolyl-1,5-dihydro-pyrazolo[3,4-d]pyrimidin-4-one as a white solid product: ¹H NMR (CDCl₃, 400 MHz) δ 8.31 (s, 1H), 8.16 (d, 2H), 7.50 (t, 2H), 7.47 (d, 2H), 7.34 (t, 1H), 7.22 (d, 2H), 7.06 (d, 2H), 7.02 (d, 2H), 2.32 (s, 3H); HPLC-MS calculated for C₂₄H₁₇BrN₄O (M+H⁺) 457.1. Found: 457.1.

Example 3

5-(4-chloro-phenyl)-6-(2,4-dichloro-phenyl)-1-phenyl-1H-pyrazolo[3,4-b]pyridin-4-ylamine

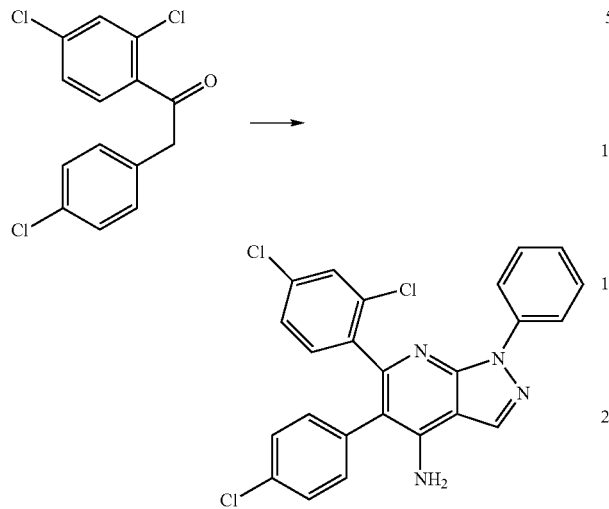

A solution of 2-(4-chloro-phenyl)-1-(2,4-dichloro-phenyl)-ethanone (300 mg, 0.99 mmol) in dichloroethane (3 mL) is stirred at room temperature while TiCl$_4$ (311 mg, 1.64 mmol) is added dropwise. After the addition, the mixture is stirred at room temperature for 5 minutes and a solution of 5-amino-1-phenyl-1H-pyrazole-4-carbonitrile (150 mg, 0.815 mmol) in dichloroethane (3 mL) is added dropwise. After the addition, the mixture is heated to 125° C. for 5 hours. After cooling, the mixture is poured into a mixture of ice cold saturated aqueous NaHCO$_3$ solution (30 mL) and EtOAc (30 mL). The resultant precipitate is filtered through celite and washed with EtOAc (2×10 mL). The filtrate is extracted by EtOAc (3×15 mL). The organic layers are combined and washed with brine and dried (MgSO$_4$). After filtering off the drying agent, the filtrate is concentrated and purified by column chromatography (silica gel, 0%~40% EtOAc/hexane) to provide the titled compound 5-(4-chloro-phenyl)-6-(2,4-dichloro-phenyl)-1-phenyl-1H-pyrazolo[3,4-b]pyridin-4-ylamine as light yellow solid:

$^1$H NMR (MeOD) δ(ppm) 8.38(s, 1H), 8.13(d, 2H), 7.48(t, 2H), 7.34(d, 1H), 7.27-7.31(m, 3H), 7.12-7.25(m, 4H); HPLC-MS calculated for C$_{24}$H$_{15}$C$_{13}$N$_4$ (M+H$^+$): 465.0. Found: 465.2.

Examples 4 and 5

5-(4-Chloro-phenyl)-6-(2,4-dichloro-phenyl)-1-phenyl-1H-pyrazolo[3,4-b]pyridine; and 5-(4-chlorophenyl-6-(2,4-dichloro-phenyl)-4-ethoxy-1-phenyl-1H-pyrazolo-[3,4-b]pyridine

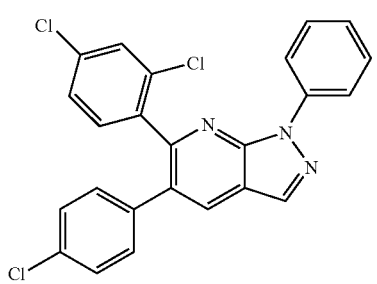

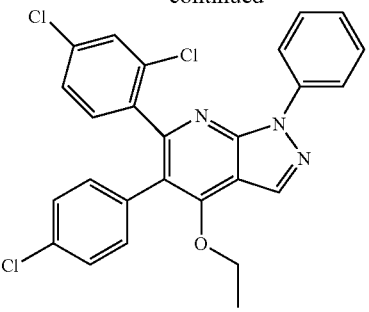

A solution of 5-(4-chloro-phenyl)-6-(2,4-dichloro-phenyl)-1-phenyl-1H-pyrazolo[3,4-b]pyridin-4-ylamine (10 mg, 0.022 mol) in EtOH (1 mL) is treated with tert-butyl nitrite (23 mg, 0.22 mol) and heated to 80° C. for 16 hours. After cooling down to room temperature, the mixture is concentrated and purified by preparative thin layer chromatography to provide 5-(4-Chloro-phenyl)-6-(2,4-dichloro-phenyl)-1-phenyl-1H-pyrazolo[3,4-b]pyridine (Example 4) and 5-(4-chlorophenyl)-6-(2,4-dichloro-phenyl)-4-ethoxy-1-phenyl-1H-pyrazolo[3,4-b]pyridine is also obtained as side product (Example 5). Example 4: $^1$H NMR (CDCl$_3$) δ(ppm) 8.35 (d, 2H), 8.29 (s, 1H), 8.14 (s, 1H), 7.48(t, 2H), 7.37(d, 1H), 7.28 (t, 1H), 7.23-7.17(m, 4H), 7.11(d, 2H); HPLC-MS calculated for C$_{24}$H$_{14}$C$_{13}$N$_3$ (M+H$^+$): 450.0. Found: 450.2. Example 5: $^1$H NMR (CDCl$_3$) δ(ppm) 8.36(s, 1H), 8.30 (d, 2H), 7.48 (t, 2H), 7.32 (d, 1H), 7.29 (d, 1H), 7.18 (d, 2H), 7.05-7.14(m, 4H), 4.68 (q, 2H), 1.42 (t, 3H); HPLC-MS calculated for C$_{26}$H$_{18}$C$_{13}$N$_3$O (M+H$^+$): 494.1, Found: 494.2.

Examples 6 and 7

5-(4-Chloro-phenyl)-6-(2,4-dichloro-phenyl)-1-(4-nitro-phenyl)-1,5-dihydro-pyrazolo[3,4-d]pyrimidin-4-one; and 5-(4-Chloro-phenyl)-6-(2,4-dichloro-phenyl)-1-(2-nitro-phenyl)-1,5-dihydro-pyrazolo-[3,4-d]pyrimidin-4-one

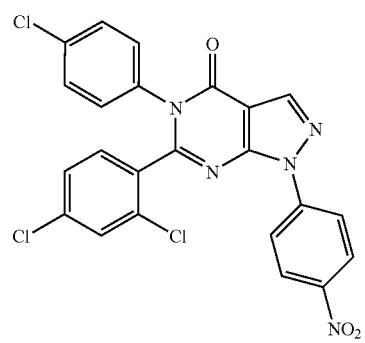

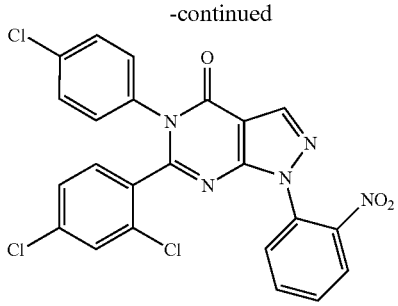

5-(4-Chloro-phenyl)-6-(2,4-dichloro-phenyl)-1-phenyl-1,5-dihydro-pyrazolo[3,4-d]pyrimidin-4-one (50 mg, 0.104 mmol) is dissolved in 5 mL of acetic anhydride. Concentrated nitric acid (300 μL) is added dropwise over 2 minutes. After the reaction mixture is stirred for 15 minutes, the voiatiles are stripped off and the resulting crude material is purified by column chromatography to give 5-(4-Chloro-phenyl)-6-(2,4-dichloro-phenyl)-1-(2-nitro-phenyl)-1,5-dihydro-pyrazolo[3,4-d]pyrimidin-4-one and 5-(4-Chloro-phenyl)-6-(2,4-dichloro-phenyl)-1-(4-nitro-phenyl)-1,5-dihydro-pyrazolo[3,4-d]pyrimidin-4-one.

5-(4-Chloro-phenyl)-6-(2,4-dichloro-phenyl)-1-(2-nitro-phenyl)-1,5-dihydro-pyrazolo[3,4-d]pyrimidin-4-one: $^1$H NMR (CDCl$_3$, 400 MHz) δ 8.34 (s, 1H), 8.02 (d, J=8.1 Hz, 1H), 7.8 (d, J=8.0 Hz, 1H), 7.76-7.71 (m, 1H), 7.58-7.52 (m, 1H), 7.33-7.19 (m, 4H), 7.16-7.08 (m, 2H), 6.96-6.89 (m, 1H); LC/MS found: 512.0 (M+1/z);

5-(4-Chloro-phenyl)-6-(2,4-dichloro-phenyl)-1-(4-nitro-phenyl)-1,5-dihydro-pyrazolo[3,4-d]pyrimidin-4-one: $^1$H NMR (CDCl$_3$, 400 MHz) δ 8.42 (d, J=9.1 Hz, 2H), 8.34 (s, 1H), 8.29 (d, J=9.1 Hz, 2H), 7.3-7.11 (m, 6H), 7.01-6.95 (m, 1H); LC/MS found: 512.1 (M+1/z).

Example 8

1-(4-Amino-phenyl)-5-(4-chloro-phenyl)-6-(2,4-dichloro-phenyl)-1,5-dihydro-pyrazolo-[3,4-d]pyrimidin-4-one

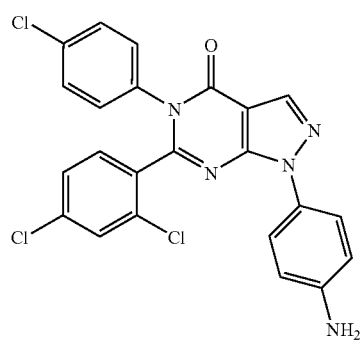

1-(4-Amino-phenyl)-5-(4-chloro-phenyl)-6-(2,4-dichloro-phenyl)-1,5-dihydro-pyrazolo[3,4-d]pyrimidin-4-one is prepared by dissolving 5-(4-Chloro-phenyl)-6-(2,4-dichloro-phenyl)-3-nitro-1-phenyl-1,5-dihydro-pyrazolo[3,4-d]pyrimidin-4-one (100 mg, 0.194 mmol) in 20 mL of 9:1 dioxane/water. The solution is degassed and 11 mg of PtO$_2$ is added under nitrogen. The slurry is degassed again and placed under balloon pressure hydrogen. The reaction mixture is stirred for 4 hours, degassed, filtered, and concentrated. The crude product is purified by reverse phase HPLC to give the title compound: $^1$H NMR (CDCl$_3$, 400 MHz) δ 8.08 (s, 1H), 7.44 (d, J=8.8 Hz, 2H), 7.27-7.24 (m, 2H), 7.19-7.17 (m, 3H), 7.13 (dd, J=8.36, 2 Hz, 1H), 7.1-7.05 (m, 1H), 6.6 (d, J=8.8 Hz, 2H); LC/MS found: 482.0 (M+1/z).

Example 9

5-(4-Bromo-phenyl)-6-(2-fluoro-phenyl)-1-quinolin-2-yl-1,5-dihydro-pyrazolo-[3,4-d]pyrimidin-4-one

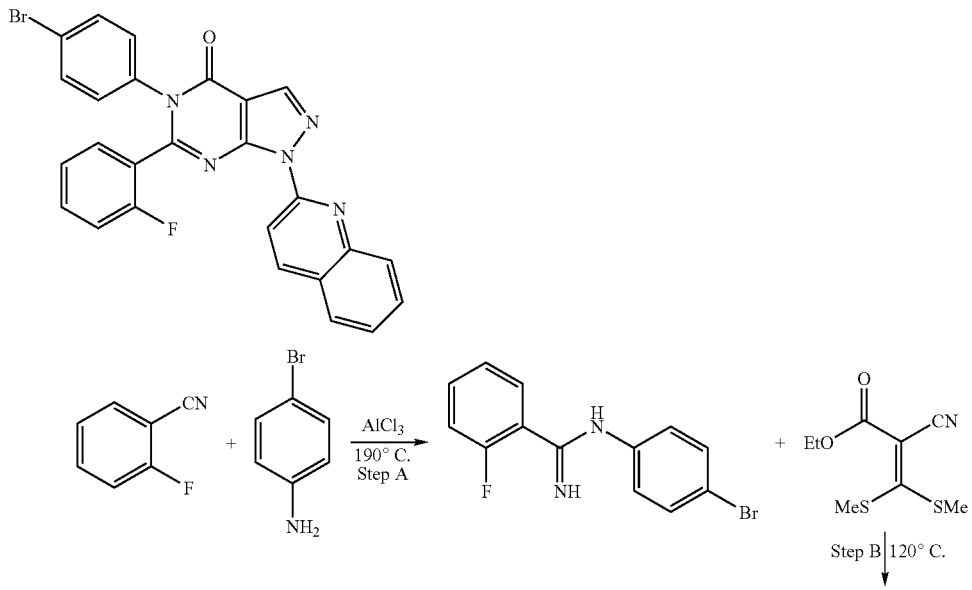

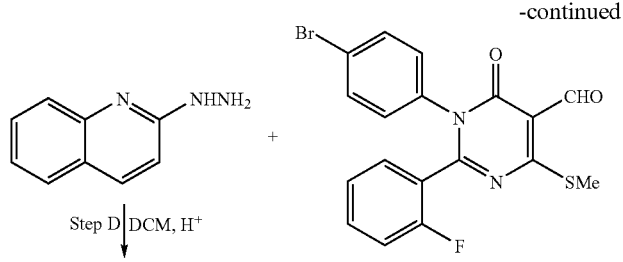 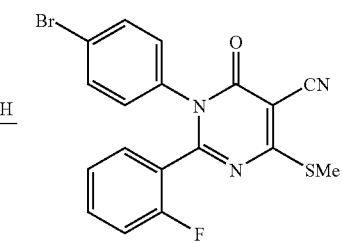

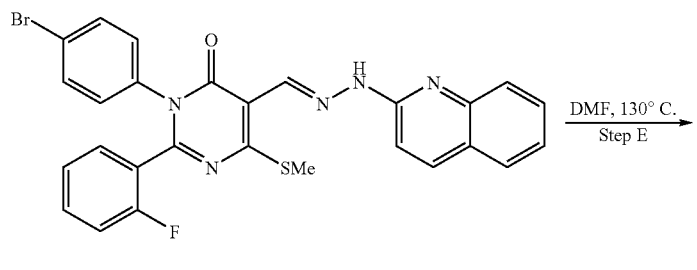 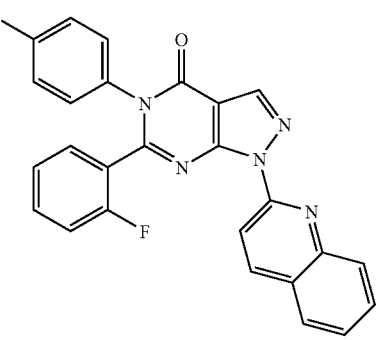

Step A. synthesis of N-(4-Bromo-phenyl)-2-fluoro-benzamidine. 2-fluorobezonitrile (5.00 g, 41.3 mmol) and 4-bromo-aniline (7.20 g, 41.8 mmol) are placed in a 150 mL of round bottom flask. To this stirring mixture is added AlCl₃ (5.6 g, 41.5 mmol). The mixture is heated to 190° C. for 4 hours and cooled to 50° C. EtOAc (100 mL) is added and the mixture is neutralized with 20% NaOH solution to pH~8. The organic layer is separated and washed with water and brine and dried over sodium sulfate. Removal of the solvent gives the crude product, which is recrystallized from ethyl acetate: ¹HNMR (CDCl₃): δ 7.98 (1 H, br), 7.33 (4 H, m), 7.15 (1 H, t, J=6.8 Hz), 7.04 (1H, dd, J=8.4, 12.0 Hz), 6.76 (1 H, d, J=8.0 Hz), 5.06 (1H, br).

Step B. synthesis of 1-(4-Bromo-phenyl)-2-(2-fluoro-phenyl)-4-methylsulfanyl-6-oxo-1,6-dihydro-pyrimidine-5-carbonitrile. N-(4-bromo-phenyl)-2-fluoro-benzamidine (4.00 g, 13.7 mmol) and 2-cyano-3,3-bis-methylsulfanyl-acrylic acid ethyl ester (2.50 g, 12.3 mmol) are mixed in a reaction tube. The mixture is heated to 130° C. for 2.5 hours and cooled to room temperature. Ethyl acetate (50 mL) is added and the mixture is stirred for 5 minutes. After filtration, pure product (4.1 g) is obtained. The solvent is concentrated, and the residue is purified on silica gel: ¹HNMR(CDCl₃): δ 7.34 (2H, d, J=8.8 Hz), 7.28-732 (1H, m), 7.26 (1H, dt, J=1.6, 6.8 Hz), 7.08 (1H, dt, J=0.8, 6.8 Hz), 6.91 (2 H, dd, J=1.2, 8.4 Hz), 6.85 (1H, dt, J=0.8, 8.8 Hz), 2.56 (3 H, s).

Step C. synthesis of 3-(4-Bromo-phenyl)-2-(2-fluoro-phenyl)-6-methylsulfanyl-5-(quinolin-2-yl-hydrazonomethyl)-3H-pyrimidin-4-one. To a dry round bottom flask is added 1-(4-Bromo-phenyl)-2-(2-fluoro-phenyl)-4-methylsulfanyl-6-oxo-1,6-dihydro-pyrimidine-5-carbonitrile (2.0 g, 4.8 mmol). This flask is charged with 15 mL of dichloromethane. The solution is cooled to −20° C. A solution of DIBAL-H (6.5 mL, 1 M in dichloromethane) is added slowly over 5 minutes. The resulting solution is stirred at this temperature for 2 hours and allowed to warm to room temperature and stirred for additional 1 hour. The reaction mixture is cooled in an ice bath and quenched with water. The mixture is extracted with dichloromethane and the extracts are combined, washed with water and dried over sodium sulfate. After removal of the solvent, the residue is purified on silica gel.

Steps D and E. Synthesis of 5-(4-Bromo-phenyl)-6-(2-fluoro-phenyl)-1-quinolin-2-yl-1,5-dihydro-pyrazolo[3,4-d]pyrimidin-4-one. To a reaction tube is added 3-(4-Bromo-phenyl)-2-(2-fluoro-phenyl)-6-methylsulfanyl-5-(quinolin-2-yl-hydrazonomethyl)-3H-pyrimidin-4-one (20 mg, 0.05 mmol), quinolin-2-yl-hydrazine (7.5 mg, 0.05 mmol), dichloromethane (1 mL) and catalytic p-toluenesulfonic acid. The solution is stirred at room temperature for 1 hour. Solvent is removed and DMF (0.5 mL) is added. The mixture is heated at 130° C. for 6 hours and purified by preparative LC-MS: ¹HNMR (CDCl₃): δ 8.41 (1 H, s), 8.32 (1 H, d, J=8.8 Hz), 8.25 (1 H, d, J=8.8 Hz), 8.16 (1 H, d, J=8.8 Hz), 7.79 (1 H, d, J=8.4 Hz), 7.68 (1 H, dt, J=1.2, 8.4 Hz), 7.51 (1 H, t, J=8.0 Hz), 7.66 (2 H, d, J=8.8 Hz), 7.25-7.32 (2 H, m), 7.08 (1 H, dt, J=0.8, 6.8 Hz), 6.99 (2 H, d, J=6.8 Hz), 6.85 (1 H, t, J=9.2 Hz).

Example 68

4-Chloro-5-(4-chloro-phenyl)-6-(2,4-dichloro-phenyl)-1-phenyl-1H-pyrazolo[3,4-b]pyridine

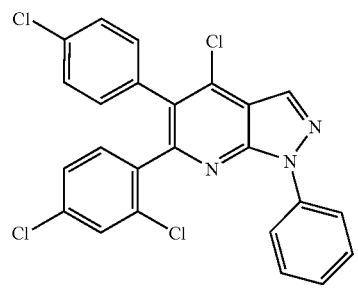

To a solution of 5-(4-chloro-phenyl)-6-(2,4-dichlorophenyl)-1-phenyl-1H-pyrazolo[3,4-b]pyridin-4-ylamine (16 mg, 0.034 mmol) in CH₃CN (0.4 mL) is added cone. HCl (0.8 mL). NaNO₂ (20 mg, 0.29 mmol) is added into the mixture at 0° C. After the addition, the mixture is warmed up to room temperature and stirred for 24 h. The mixture is then neutralized to pH~7 by adding saturated aqueous NaHCO₃ and extracted with EtOAc (3×3 mL). The combined organic layers are concentrated and purified by preparative thin layer chromatography to provide the titled compound as a white solid (4 mg, 24%). $^1$H NMR (CDCl$_3$) δ(ppm) 8.35(s, 1H), 8.28 (d, 2H), 7.50 (t, 2H), 7.27-7.37(m, 2H), 7.24-7.26 (m, 2H), 7.07-7.16 (m, 4H); HPLC-MS calculated for C$_{24}$H$_{13}$Cl$_4$N$_3$ (M+1$^+$): 484.0. Found: 484.1.

Example 69

5,6-Bis-(4-chloro-phenyl)-1-phenyl-1H-pyrazolo[3,4-b]pyridin-4-ol

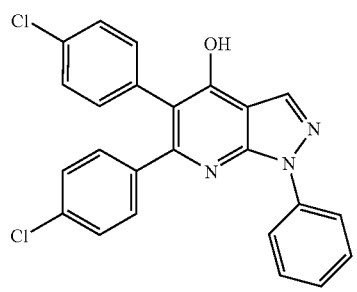

A solution of 1,2-bis-(4-chloro-phenyl)-ethanone (100 mg, 0.38 mmol) in dichloroethane (1 mL) is stirred at room temperature while TiCL$_4$ (143 mg, 0.75 mmol) is added in dropwise. After the addition, the mixture is stirred at room temperature for 5 min and a solution of 5-amino-1-phenyl-1H-pyrazole-4-carboxilic acid ethyl ester (97 mg, 0.42 mmol) in dichloroethane (1 mL) is added dropwise. After the addition, the mixture is heated to 125° C. for 5 h. After cooling down the mixture, it is poured into a mixture of ice cold saturated aqueous NaHCO$_3$ solution (15 mL) and EtOAc (15 mL). The resulted mixture is filtered through celite to remove the precipitate and washed with EtOAc (2×5 mL). The filtrate is extracted by EtOAc (3×5 mL). The organic layers are combined and washed with brine and dried (MgSO$_4$). After filtering off the drying agent, the filtrate is concentrated and purified by preparative LC/MS to provide the titled compound 5,6-bis-(4-chloro-phenyl)-1-phenyl-1H-pyrazolo[3,4-b]pyridin-4-ol as light yellow solid. (55 mg, 31%). $^1$H NMR (MeOD) δ(ppm) 8.37 (s, 1H), 8.23 (d, 2H), 7.53 (t, 2H), 7.34 (t, 1H), 7.31 (d, 2H), 7.29 (d, 2H), 7.23 (d, 2H), 7.15 (d, 2H); HPLC-MS calculated for C$_{24}$H$_{15}$C$_{12}$N$_3$O (M+1$^+$): 432.1. Found: 432.2.

Example 74

1-(4-Bromo-phenyl)-2-(2,4-dichloro-phenyl)-9-phenyl-1,9-dihydro-purin-6-one

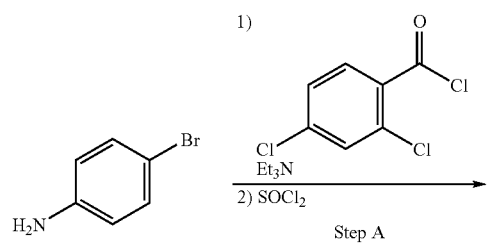

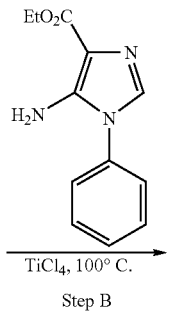

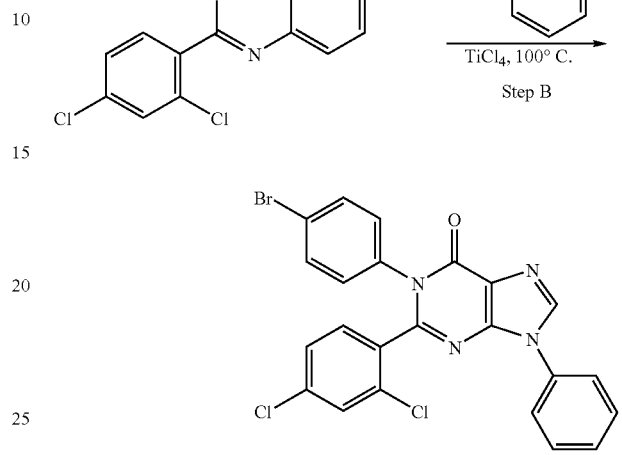

Step A. synthesis of N-(4-Bromo-phenyl)-2,4-dichloro-benzimidoyl Chloride.

To a solution of 4-bromoaniline (0.50 g, 2.9 mmol) and 2,4-dichloro benzoyl chloride (0.41 mL, 2.9 mmol) in dichloromethane is added triethylamine (0.49 mL, 3.49 mmol). After being stirred at room temperature for 30 minutes, the solvent is removed and the residue is dissolved in 2 mL of thionyl chloride. The reaction mixture is heated at 80° C. for 1 hour and concentrated. The product is used for the next step without purification.

Synthesis 5-Amino-1-phenyl-1H-imidazole-4-carboxylic acid ethyl ester.

A solution of amino-cyano-acetic acid ethyl ester (1.64 g, 12.8 mmol) and triethyl orthoformate (2.13 mL, 12.8 mmol) in acetonitrile is heated at reflux for 45 minutes. After the reaction mixture is cooled down to room temperature, aniline (1.17 mL, 12.8 mmol) is added. Solid is precipitated out after the mixture has been stirred for overnight at room temperature. Filtration gave a product as a white solid (two steps yield 59%). $^1$H NMR (CDCl$_3$) δ 7.59 (m, 3H), 7.53 (d, 2H), 7.21 (s, 1H), 5.04 (b, 2H), 4.41 (q, 2H), 1.45 (t, 3H); m/z 232.1 (M+1).

Step B. synthesis of 1-(4-Bromo-phenyl)-2-(2,4-dichloro-phenyl)-9-phenyl-1,9-dihydro-purin-6-one.

To a solution of N-(4-bromo-phenyl)-2,4-dichloro-benzimidoyl chloride (0.22 mmol) and 5-amino-1-phenyl-1H-imidazole-4-carboxylic acid ethyl ester (65 mg, 0.27 mmol) in 1,2-dichloroethane is added titanium tetrachloride (98 μL, 0.89 mmol) dropwise at room temperature. After addition is completed, the reaction mixture is heated at 120° C. for 18 hours. After the reaction is quenched with water and the aqueous layer is extracted with ethyl acetate. The organic solvents are combined and dried over magnesium sulfate. Filtration and concentration provide a crude product which is purified by column chromatography gave a white solid as product (41 mg, three steps yield 36%). $^1$H NMR (CDCl$_3$) δ(ppm) 8.04 (s, 1H), 7.58 (d, 2H), 7.47 (t, 2H), 7.38 (m, 3H), 7.22 (d, 1H), 7.15 (b, 1H), 7.07 (m, 2H), 6.91 (b, 1H); HPLC-MS calculated for $C_{23}H_{13}BrCl_2N4O$ (M+H$^+$): 511.0. Found: 511.0.

Example 77

1-(4-Bromo-phenyl)-2-(4-methyl-phenyl)-9-phenyl-1,9-dihydro-purin-6-one

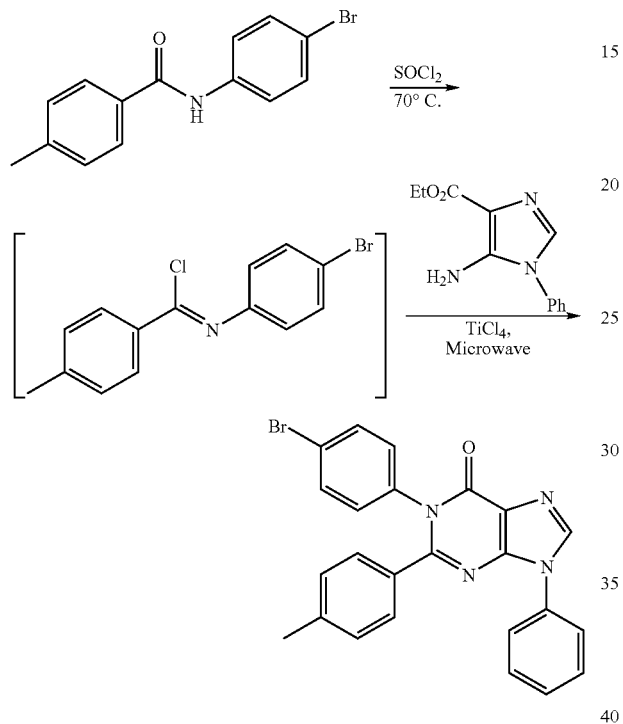

To a solution of N-(4-bromo-phenyl)-4-methyl-benzimidoyl chloride which is prepared from 4-bromoaniline (29.2 mg, 0.17 mmol) and 4-methyl benzoyl chloride (22.5 µL, 0.17 mmol), and 5-amino-1-phenyl-1H-imidazole-4-carboxylic acid ethyl ester (50 mg, 0.20 mmol) in 1,2-dichloroethane is added titanium tetrachloride (75 µL, 0.68 mmol) dropwise at room temperature. After addition, the reaction mixture is heated at 170° C. for 30 min on microwave reactor. Quenching with water is followed by extracting with ethyl acetate. The organic solvents are combined and dried over magnesium sulfate. Filtration and concentration followed by purification with chromatography give a white solid as product.

$^1$H NMR (400 MHz, CDCl$_3$) δ(ppm) 8.12 (s, 1H), 7.70 (d, 2H), 7.55 (t, 2H), 7.45 (m, 3H), 7.15 (d, 2H), 7.03 (m, 4H); HPLC-MS calculated for $C_{24}H_{17}BrN_4O$ (M+H$^+$): 457.0. Found: 457.0.

5-amino-1-phenyl-1H-imidazole-4-carboxylic acid ethyl ester used above is prepared as described below.

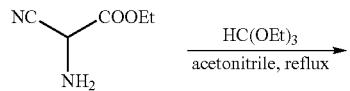

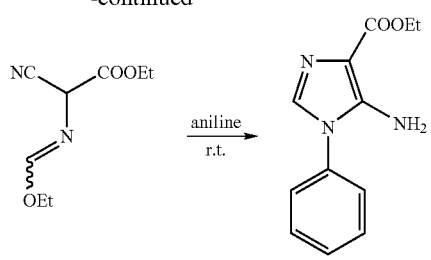

A solution of amino-cyano-acetic acid ethyl ester (1.64 g, 12.8 mmol) and triethyl orthoformate (2.13 mL, 12.8 mmol) in acetonitrile was heated at reflux for 45 min. After cooled down to room temperature, aniline (1.17 mL, 12.8 mmol) was added. Stirred at room temperature for overnight, solid precipitated out. Filtration gave a white solid as product (two steps yield 59%). $^1$H NMR (CDCl$_3$) δ 7.59 (m, 3H), 7.53 (d, 2H), 7.21 (s, 1H), 5.04 (b, 2H), 4.41 (q, 2H), 1.45 (t, 3H); m/z 232.1 (M+1).

N-(4-bromo-phenyl)-4-methyl-benzimidoyl chloride used is prepared by the following procedure. To a solution of 4-bromoaniline (29.2 mg, 0.17 mmol) and 4-methyl benzoyl chloride (22.5 µL, 0.17 mmol) in dichloromethane was added triethylamine (28 µL, 0.20 mmol). After stirred at room temperature for 30 minutes, the solvent was removed. The residue was added 0.5 mL of thionyl chloride. The reaction mixture was heated at 80° C. for 1 h, concentrated. The product was used in the next step reaction.

Example 79

5-(4-Bromo-phenyl)-6-(2-fluoro-phenyl)-1-(morpholine-4-carbonyl)-1,5-dihydro-pyrazolo[3,4-d]pyrimidin-4-one

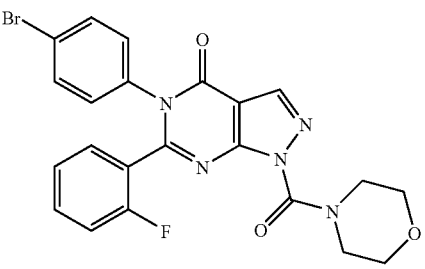

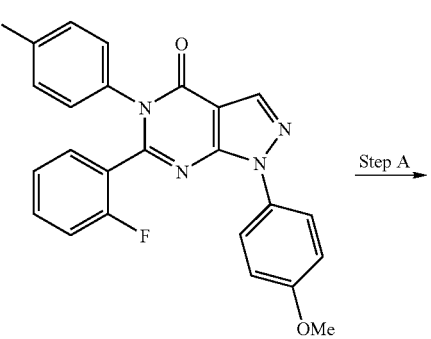

-continued

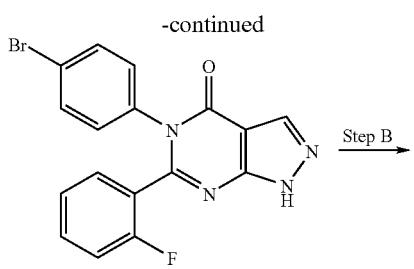

Step B →

Step A: To a solution of 5-(4-bromo-phenyl)-6-(2-fluoro-phenyl)-1-(4-methoxy-phenyl)-1,5-dihydro-pyrazolo[3,4-d]pyrimidin-4-one (208 mg, 0.423 mmol) in aceonitrile (5 mL) is added CAN (1M aqueous solution, 1.7 mL) at 0° C. After the addition, the mixture is allowed to warm up to room temperature and then heated to 80° C. for 5 h. After cooling down to room temperature, the mixture is treated with water (10 mL) and extracted with EtOAc (3×10 mL). The organic layers are combined and washed with water, saturated aqueous $NaHCO_3$, $NaHSO_3$ (10% aqueous solution), brine and dried ($MgSO_4$). After removing the drying agent by filtration, the solvent is removed under vacuum and the residue is purified by flash column chromatography (silica gel, 0%~80% EtOAc/hex) to provide the desired product 5-(4-bromo-phenyl)-6-(2-fluoro-phenyl)-1,5-dihydro-pyrazolo[3,4-d]pyrimidin-4-one as white solid. (51 mg, 31%). $^1$H NMR ($CDCl_3$, 400 MHz) δ 8.26 (s, 1H), 7.41 (d, 2H), 7.29-7.35 (m, 2H), 7.13 (t, 1H), 7.03 (b, 2H), 6.92 (t, 1H); HPLC-MS calculated for $C_{17}H_{10}BrFN_4O$ (M+H$^+$) 385.0. Found: 385.0.

Step B: To a solution of 5-(4-bromo-phenyl)-6-(2-fluoro-phenyl)-1,5-dihydro-pyrazolo[3,4-d]pyrimidin-4-one (20.0 mg, 0.052 mmol) in anhydrous pyridine (0.5 mL) is added 4-morpholinecarbonyl chloride (7.27 μL, 0.062 mmol). The mixture is stirred at room temperature for 2 h before removal of the solvent. The residue is purified by preparative LCMS followed by preparative TLC to provide the title compound (9.1 mg, 35% yield) as a white solid product; $^1$H NMR ($CDCl_3$, 400 MHz) δ 8.91 (s, 1H), 7.42-7.28 (m, 4H), 7.11 (t, 1H), 7.02 (d, 2H), 6.88 (t, 1H), 4.15-3.84 (m, 8H); HPLC-MS calculated for $C_{22}H_{17}BrFN_5O_3$ (M+H$^+$) 498.0. Found: 498.0.

Example 80

5,6-Bis-(4-chloro-phenyl)-1-phenyl-1H-pyrazolo[3,4-b]pyrazine

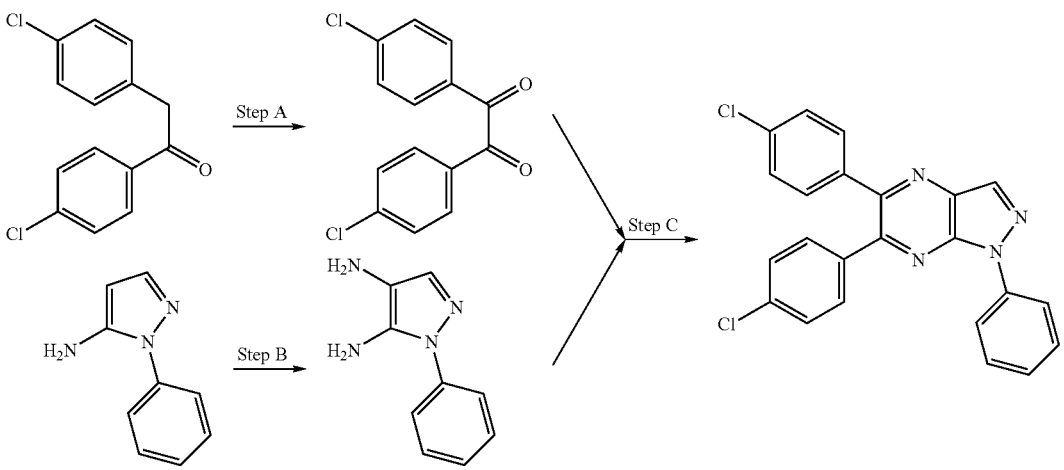

Step A: 1,2-Bis-(4-chloro-phenyl)-ethane-1,2-dione is prepared by following the procedures described in M. Wilsterman et al. WO 03051850. The reaction crude product is used directly for next step without purification.

Step B: To a solution of 2-phenyl-2H-pyrazol-3-ylamine (250 mg, 1.57 mmol) in EtOH (3 mL) is added HCl (4N in dioxane, 1.15 mL, 4.6 mmol). The mixture is then cooled down to −10° C., tert-butyl nitrite (178 mg, 1.73 mmol) is added drop wise. After addition, the mixture is stirred at 0° C. for 1 h. The precipitate is collected by filtration to provide 4-nitroso-2-phenyl-2H-pyrazol-3-ylamine (180 mg, 60%) as yellow solid.

To a suspension of 4-nitroso-2-phenyl-2H-pyrazol-3-ylamine (100 mg, 0.53 mmol) in EtOH (1 mL) is added SnCl$_3$-2H$_2$O (240 mg, 1.06 mmol). The mixture is then heated to 60° C. for 30 min. After cooling down the mixture, it is poured into a mixture of EtOAc (20 mL) and saturated aqueous NaHCO$_3$ solution (20 mL). The solid is removed by filtration through Celite. The filtrate is put into separatory funnel to collect the organic layer, which is washed with brine and dried over MgSO$_4$. After filtering off the drying agent, the filtrate is concentrated to provide the crude 2-phenyl-2H-pyrazole-3,4-diamine (~25 mg) and used immediately for next step.

Step C: A mixture of 1,2-bis-(4-chloro-phenyl)-ethane-1,2-dione from Step A (~20 mg), 2-phenyl-2H-pyrazole-3,4-diamine from Step B (25 mg) and p-TSA in MeOH (1 mL) is heated to 80° C. for 2 h. After cooling down to room temperature, the mixture is treated with saturated aqueous NaHCO$_3$ solution (3 mL) and extracted with EtOAc (3×2 mL). The organic layers are combined and concentrated. The residue is purified by Preparative LC/MS to provide the title compound 5,6-bis-(4-chloro-phenyl)-1-phenyl-1H-pyrazolo[3,4-b]pyrazine. $^1$H NMR (CDCl$_3$) δ(ppm) 8.51(s, 1H), 8.34 (d, 2H), 7.56(t, 2H), 7.46(d, 2H), 7.32~7.43 (m, 7H); HPLC-MS calculated for C$_{23}$H$_{14}$Cl$_2$N$_4$ (M+H$^+$): 417.1. Found: 417.1.

Example 82

5-(4-Bromo-phenyl)-6-(2-fluoro-phenyl)-1-(tetrahydro-thiopyran-4-yl)-1,5-dihydro-pyrazolo[3,4-d]pyrimidin-4-one Step A: A mixture of tetrahydro-thiopyran-4-one (226 mg, 2.0 mmol) and hydrazine hydrate (120 mg, 2.4 mmol) in EtOH (3 mL) is stirred at room temperature for 2 h when NaBH$_4$ (148 mg, 4.0 mmol) is added as one portion. The mixture is then stirred at room temperature for 14 h. After quenching the reaction by treating with saturated aqueous NH$_4$Cl solution (1 mL) at room temperature for 30 min, ethyl(ethoxymethylene)cyano-acetate (677 mg, 4.0 mmol) is added as one portion. The mixture is then heated to 80° C. for 2 h. After cooling down to room temperature, the mixture is poured into water (20 mL) and extracted with EtOAc (3×20 mL). The organic layers are combined and washed with brine and dried (MgSO$_4$). After filtering off the drying agent, the solvent is removed under vacuum and the residue is purified by flash column chromatography (silica gel, 30%~80% EtOAc/hexane) to provide the desired product 5-amino-1-(tetrahydro-thiopyran-4-yl)-4,5-dihydro-1H-pyrazole-4-carboxylic acid ethyl ester as white solid (300 mg, 59%).

Step B: 5-(4-Bromo-phenyl)-6-(2-fluoro-phenyl)-1-(tetrahydro-thiopyran-4-yl)-1,5-dihydro-pyrazolo[3,4-d]pyrimidin-4-one is prepared from 5-amino-1-(tetrahydro-thiopyran-4-yl)-4,5-dihydro-1H-pyrazole-4-carboxylic acid ethyl ester and N-(4-bromo-phenyl)-2-fluoro-benzimidoyl chloride by following the procedure described in example 2. The crude is purified by preparative LC/MS to provide the titled compound 5-(4-bromo-phenyl)-6-(2-fluoro-phenyl)-1-(tetrahydro-thiopyran-4-yl)-1,5-dihydro-pyrazolo[3,4-d]pyrimidin-4-one as white solid. HPLC-MS calculated for C$_{22}$H$_{18}$BrFN$_4$OS (M+H$^+$): 485.0. Found: 485.0.

Example 83

[5,6-Bis-(4-chloro-phenyl)-1-phenyl-1H-pyrazolo[3,4-b]pyridin-4-yl]-dimethyl-amine

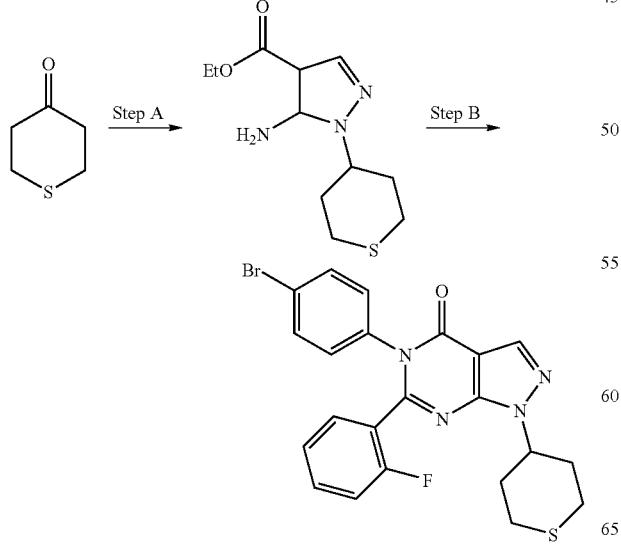

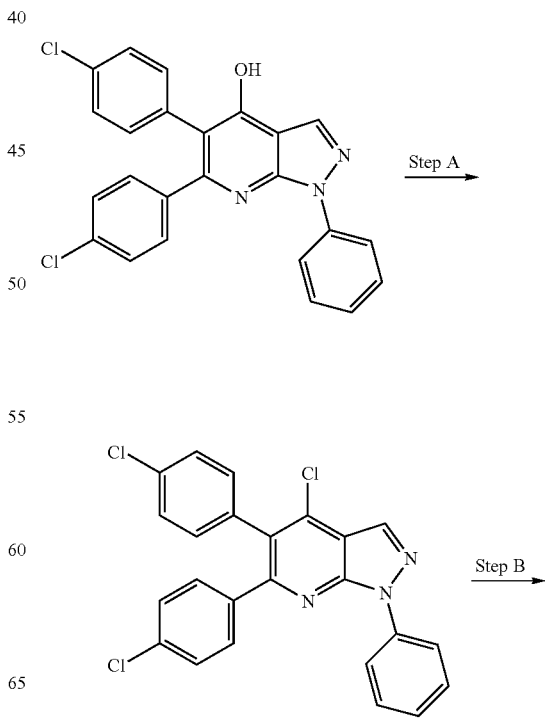

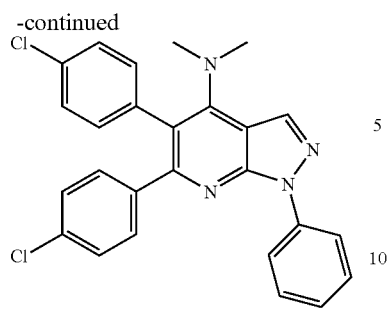

Step A: A mixture a 5,6-bis-(4-chloro-phenyl)-1-phenyl-1H-pyrazolo[3,4-b]pyridin-4-ol from example 69 (40 mg, 0.09 mmol) in POCl₃ (0.5 mL) is heated to 80° C. for 2 h. The reaction mixture is then cooled down to room temperature and concentrated. The residue is used directly for next step without purification.

Step B: 4-Chloro-5,6-bis-(4-chloro-phenyl)-1-phenyl-1H-pyrazolo[3,4-b]pyridine from step A (15 mg, 0.033 mmol) is treated with dimethylamine (2 M in THF, 1 mL, 2 mmol) in a sealed tube at 100° C. for 14 h. After cooling down to room temperature, the mixture is concentrated and the residue is purified by flash column chromatography (silica gel, 0%~15% EtOAc/hex) to provide the titled compound [5,6-Bis-(4-chloro-phenyl)-1-phenyl-1H-pyrazolo[3,4-b]pyridin-4-yl]-dimethyl-amine (11 mg, 73%). ¹H NMR (CDCl₃) δ(ppm) 8.35 (s, 1H), 8.32 (d, 2H), 7.47(t, 2H), 7.27(t, 1H), 7.23(d, 2H), 7.16(d, 2H), 7.11(d, 2H), 7.03(d, 2H), 2.91(s, 6H); HPLC-MS calculated for C₂₆H₂₀Cl₂N₄ (M+H⁺): 459.1. Found: 459.1.

Example 84

5-(4-Bromo-phenyl)-1-(1,1-dioxo-hexahydro-1λ⁶-thiopyran-4-yl)-6-(2-fluoro-phenyl)-1,5-dihydro-pyrazolo[3,4-d]pyrimidin-4-one

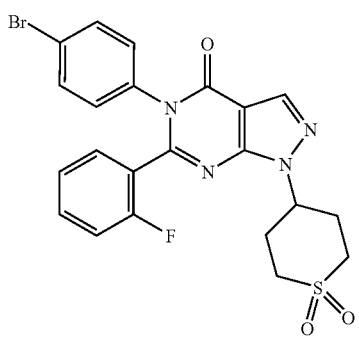

5-(4-bromo-phenyl)-6-(2-fluoro-phenyl)-1-(tetrahydro-thiopyran-4-yl)-1,5-dihydro-pyrazolo[3,4-d]pyrimidin-4-one (5 mg, 0.01 mmol) in CHCl₃ (0.5 mL) is added m-CPBA (9 mg) at 0° C. After the mixture is stirred at 0° C. for 1 h, it is treated with saturated aqueous NaHCO₃ solution (1 mL) and extracted with EtOAc (3×2 mL). The organic layers are combined and concentrated. The residue is purified by preparative thin layer chromatography (silica gel, 40% EtOAc/hex) to provide the titled compound 5-(4-bromo-phenyl)-1-(1,1-dioxo-hexahydro-1λ⁶-thiopyran-4-yl)-6-(2-fluoro-phenyl)-1,5-dihydro-pyrazolo[3,4-d]pyrimidin-4-one as white solid (3.5 mg, 68%). ¹H NMR (CDCl₃) δ(ppm) 8.18(s, 1H), 7.40(d, 2H), 7.34(qd, 1H), 7.28(d, 1H), 7.12(t, 1H), 7.00(bd, 2H), 6.92(t, 1H), 5.07(m, 1H), 3.58(td, 2H), 3.13(td, 2H), 2.75-2.82(m, 2H), 2.53-2.59(m, 2H); HPLC-MS calculated for C₂₂H₁₈BrFN₄OS (M+H⁺): 517.0. Found: 517.0.

Example 85

5-(4-Chloro-phenyl)-6-[4-(3-methyl-[1,2,4]oxadiazol-5-yl)-phenyl]-1-phenyl-1,5-dihydro-pyrazolo[3,4-d]pyrimidin-4-one

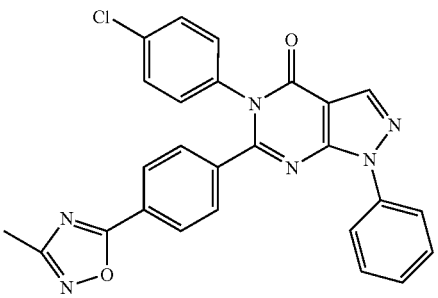

A solution of 4-[5-(4-chloro-phenyl)-4-oxo-1-phenyl-4,5-dihydro-1H-pyrazolo[3,4-d]pyrimidin-6-yl]-benzoic acid methyl ester (50 mg, 0.11 mmol) in dioxane is added NaOH (1N, 400 μL, 0.4 mmol) and stirred at room temperature for 14 h. The mixture is then neutralized by adding HCl (1N, 400 μL, 0.4 mmol) and concentrated. The resulted residue is treated with SOCl₂ (1 mL) at room temperature for 1 h and excess SOCl₂ is removed under vacuum. The residue is dissolved in CH₂Cl₂ and added N-hydroxy-acetamidine (12 mg, 0.16 mmol) followed by Et₃N (17 mg, 0.16 mmol). After stirring at room temperature for 1 h, the mixture is treated with water (2 mL) and extracted with EtOAc (3×2 mL). The organic layers are combined and concentrated, the residue is dissolved in EtOH (4 mL), NaOAc (40 mg) is added and the mixture is heated to 80° C. for 5 h. After cooling down to room temperature, the solvent is removed and the residue is purified by preparative LC/MS to provide the titled compound 5-(4-chloro-phenyl)-6-[4-(3-methyl-[1,2,4]oxadiazol-5-yl)-phenyl]-1-phenyl-1,5-dihydro-pyrazolo[3,4-d]pyrimidin-4-one. ¹H NMR (CDCl₃) δ(ppm) 8.35(s, 1H), 8.12(d, 2H), 8.01(d, 2H), 7.48-7.54(m, 4H), 7.37 (t, 1H), 7.32(d, 2H), 7.10(d, 2H), 2.47(s, 3H); HPLC-MS calculated for C₂₆H₁₇ClN₆O₂ (M+H⁺): 481.1. Found: 481.1.

Example 86

5-Chloro-phenyl)-6-(4-isoxazol-5-yl-phenyl)-1-phenyl-1,5-dihydro-pyrazolo[3,4-d]pyrimidin-4-one

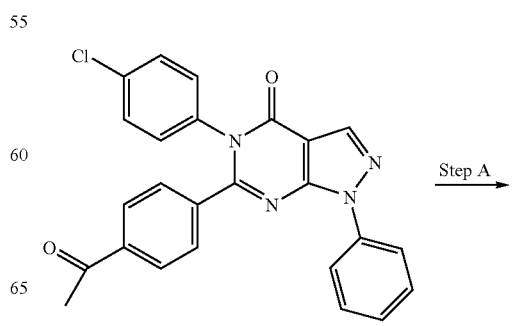

-continued

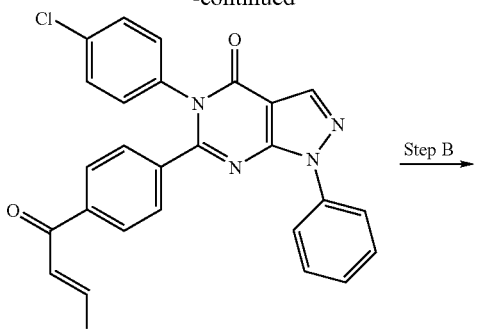

Step B →

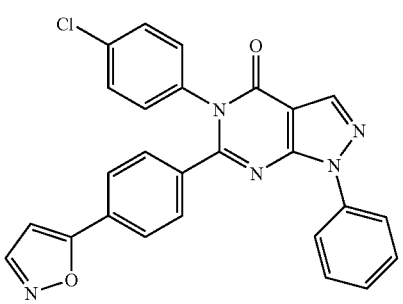

Step A: A mixture of 6-(4-acetyl-phenyl)-5-(4-chloro-phenyl)-1-phenyl-1,5-dihydro-pyrazolo[3,4-d]pyrimidin-4-one (50 mg, 0.11 mmol) and N,N-dimethylformamide dimethyl acetal (1 mL) is heated at 80° C. for 14 h. After cooling down to room temperature, excess N,N-dimethylformamide dimethyl acetal is removed under vacuum to provide 5-(4-chloro-phenyl)-6-[4-(3-dimethylamino-acryloyl)-phenyl]-1-phenyl-1,5-dihydro-pyrazolo[3,4-d]pyrimidin-4-one as yellow solid (56 mg, 100%). HPLC-MS calculated for $C_{28}H_{22}ClN_5O_2$ (M+H$^+$): 496.2. Found: 496.2.

Step B: To a slurry of 5-(4-chloro-phenyl)-6-[4-(3-dimethylamino-acryloyl)-phenyl]-1-phenyl-1,5-dihydro-pyrazolo[3,4-d]pyrimidin-4-one (8.0 mg, 0.016 mmol) in MeOH (0.5 mL) is added NH$_2$OH.HCl (1.5 mg, 0.022 mmol). The mixture is heated to 80° C. for 2 h and cooled down to room temperature. After concentration under vacuum, the residue is purified by preparative LC/MS to provide the titled compound 5-(4-Chloro-phenyl)-6-(4-isoxazol-5-yl-phenyl)-1-phenyl-1,5-dihydro-pyrazolo[3,4-d]pyrimidin-4-one as white solid.

HPLC-MS calculated for $C_{26}H_{16}ClN_5O_2$ (M+H$^+$); 466.1. Found: 466.1.

Example 87

5-(4-Chloro-phenyl)-1-phenyl-6-[4-(2H-pyrazol-3-yl)-phenyl]-1,5-dihydro-pyrazolo[3,4-d]pyrimidin-4-one

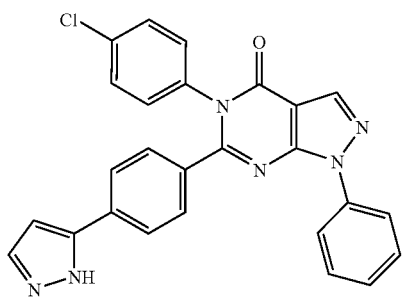

To a suspension of 5-(4-chloro-phenyl)-6-[4-(3-dimethylamino-acryloyl)-phenyl]-1-phenyl-1,5-dihydro-pyrazolo[3,4-d]pyrimidin-4-one (11 mg, 0.022 mmol) in MeOH (0.5 mL) is added hydrazine hydrate (2.0 mg, 0.04 mmol) and HCl (4 M in dioxane, 10 μL, 0.04 mmol), The mixture is heated to 80° C. for 2 h and cooled down to room temperature. The mixture is concentrated and purified by preparative LC/MS to provide the titled compound 5-(4-chloro-phenyl)-1-phenyl-6-[4-(2H-pyrazol-3-yl)-phenyl]-1,5-dihydro-pyrazolo[3,4-d]pyrimidin-4-one as white solid. HPLC-MS calculated for $C_{26}H_{17}ClN_6O$ (M+H$^1$): 465.1. Found: 465.1.

Example 88

6-(4-Acetyl-phenyl)-5-(4-chloro-phenyl)-1-phenyl-1,5-dihydro-pyrazolo[3,4-d]pyrimidin-4-one

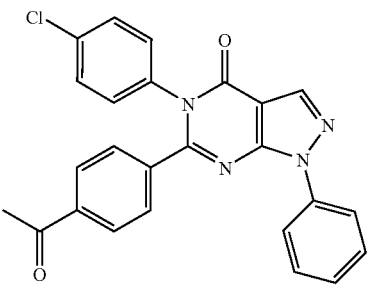

Method 1: A solution of 4-[5-(4-chloro-phenyl)-4-oxo-1-phenyl-4,5-dihydro-1H-pyrazolo[3,4-d]pyrimidin-6-yl]-benzoic acid methyl ester (450 mg, 0.98 mmol) in dioxane (6 mL) is added NaOH (2 N, 1.5 mL, 3 mmol) and stirred at room temperature for 14 h. The mixture is then concentrated and treated with SOCl$_2$ (4 mL) at room temperature for 1 h. The excess SOCl$_2$ is removed under vacuum and flushed with toluene (2×2 mL). The resulted residue is dissolved in CH$_2$Cl$_2$ (3 mL) and slowly dropped into a solution of freshly prepared Me$_2$CuLi (2.0 mmol) in Et$_2$O (4 mL) at −78° C. The mixture is kept at the same temperature for 1 h. when MeOH (1 mL) is added to quench the reaction. The mixture is then allowed to warm up to room temperature and treated with saturated aqueous NH$_4$Cl solution (20 mL). After extraction with EtOAc(3×15 mL), the organic layers are combined, washed with brine and dried (MgSO$_4$). After filtering off the drying agent, the solvent is removed under vacuum and the residue is purified by flash column chromatography (silica gel, 0%~50% EtOAc/hexane) to provide the titled compound 6-(4-acetyl-phenyl)-5-(4-chloro-phenyl)-1-phenyl-1,5-dihydro-pyrazolo[3,4-d]pyrimidin-4-one. HPLC-MS calculated for $C_{25}H_{17}ClN_4O_2$ (M+H$^+$): 441.1. Found: 441.1.

Method 2: To a reaction tube charged with 6-(4-bromo-phenyl)-5-(4-chloro-phenyl)-1-phenyl-1,5-dihydro-pyrazolo[3,4-d]pyrimidin-4-one (20 mg, 0.042 mmol), butylvinyl ether (21 mg, 0.21 mmol), Pd(OAc)$_2$ (1.0 mg, 0.004 mmol), 1,3-bis(diphenylphosphino)propane (3.5 mg, 0.008 mmol) and K$_2$CO$_3$ (7 mg, 0.05 mmol) is added water (0.05 mL) in DMF (0.5 mL). The system is purged with N$_2$, sealed and heated to 100° C. for 14 h. After cooling down to room temperature, the mixture is hydrolyzed by adding 1 mL of 1 N HCl for 30 min. The mixture is then treated with H$_2$O (5 mL) and extracted with EtOAc (3×2 mL). The combined extracts is concentrated and purified by preparative LC/MS to provide the title compound 6-(4-acetyl-phenyl)-5-(4-chloro-phenyl)-1-phenyl-1,5-dihydro-pyrazolo[3,4-d]pyrimidin-4-one and 6-[4-(2-butoxy-vinyl)-phenyl]-5-(4-chloro-phenyl)-1-phenyl-1,5-dihydro-pyrazolo[3,4-d]pyrimidin-4-one (example 360) as a by product (ratio about 1:2). Example 86: HPLC- MS calculated for $C_{25}H_{17}ClNO_2$ (M+1$^+$): 441.1. Found: 441.1. Example 360: HPLC-MS calculated $C_{29}H_{25}ClN_4O_2$ (M+1$^+$): 497.2. Found: 497.2.

Method 3: To a reaction vessel charged with 6-(4-bromo-phenyl)-5-(4-chloro-phenyl)-1-phenyl-1,5-dihydro-pyrazolo[3,4-d]pyrimidin-4-one (0.5 g, 1.05 mmol), tributyl-(1-ethoxy-vinyl)-stannane (0.49 g, 1.36 mmol), Pd (PPh$_3$)$_4$ (0.061 g, 0.053 mmol) and toluene (5 mL) is purged with N2 and heated to 100° C. for 2 h. After cooling down to room temperature, the solvent is removed under vacuum and the residue is treated with acetonitrile (10 mL) and 1 N HCl (40 mL) for 1 h. The mixture is then extracted with EtOAc (3×30 mL) and the combined organic layer is washed with saturated aqueous KF solution (20 mL). The resulted precipitate is removed by filtration and washed with EtOAc (2×10 mL). The organic layer is washed with brine and dried (MgSO$_4$). After filtering off the drying agent, the solvent is removed under vacuum and the residue is purified by flash column chromatography (silica gel, 0%~50% EtOAc/hexane) to provide the titled compound 6-(4-acetyl-phenyl)-5-(4-chloro-phenyl)-1-phenyl-1,5-dihydro-pyrazolo[3,4-d]pyrimidin-4-one (450 mg, 95%). HPLC-MS calculated for $C_{25}H_{17}ClN_4O_2$ (M+1$^+$): 441.1. Found: 441.1.

Example 89

4-[5-(4-Chloro-phenyl)-4-oxo-1-phenyl-4,5-dihydro-1H-pyrazolo[3,4-d]pyrimidin-6-yl]-benzamide

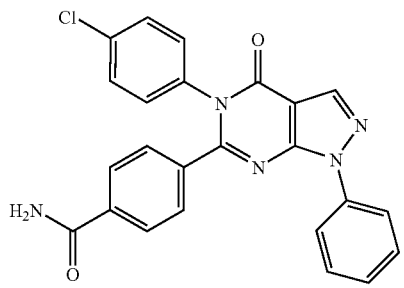

A solution of 4-[5-(4-chloro-phenyl)-4-oxo-1-phenyl-4,5-dihydro-1H-pyrazolo[3,4-d]pyrimidin-6-yl]-benzoic acid methyl ester (70 mg, 0.153 mmol) in dioxane (1 mL) is added NaOH (2 M, 0.25 mL, 0.5 mmol) and stirred at room temperature for 14 h. The mixture is then concentrated and treated with SOCl$_2$ (1 mL) at room temperature for 1 h. The excess SOCl$_2$ is removed under vacuum and flushed with toluene (2×1 mL). The resulted residue is dissolved in CH$_2$Cl$_2$ (1 mL) and dropped into a vigorously stirred ice-cold aqueous NH$_4$OH solution (30%, 4 mL). After the addition, the mixture is extracted with EtOAc (3×4 mL). The organic layers are combined and concentrated. The residue is purified by preparative LC/MS to provide the titled compound 4-[5-(4-chloro-phenyl)-4-oxo-1-phenyl-4,5-dihydro-1H-pyrazolo[3,4-d]pyrimidin-6-yl]-benzamide as white solid. $^1$H NMR (CDCl$_3$) δ(ppm) 8.34(s, 1H), 8.12 (d, 2H), 7.70(d, 2H), 7.51 (t, 2H), 7.43 (d, 2H), 7.36 (t, 1H), 7.32(d, 2H), 7.09(d, 2H), 5.99(b, 1H), 5.63(b, 1H); HPLC-MS calculated for $C_{24}H_{16}ClN_5O_2$ (M+H$^+$): 442.1. Found: 442.1.

Example 90

6-[4-(2-Amino-pyrimidin-4-yl)-phenyl]-5-(4-chloro-phenyl)-1-phenyl-1,5-dihydro-pyrazolo[3,4-d]pyrimidin-4-one

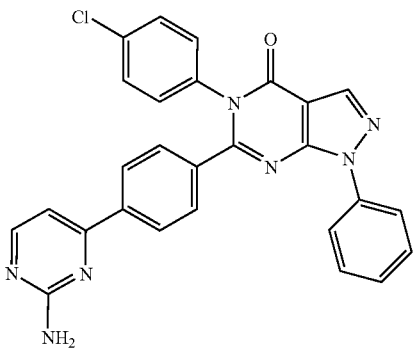

A suspension of 5-(4-chloro-phenyl)-6-[4-(3-dimethylamino-acryloyl)-phenyl]-1-phenyl-1,5-dihydro-pyrazolo[3,4-d]pyrimidin-4-one (24 mg, 0.048 mmol) in MeOH (1 mL) is treated with guanidine hydrochloride (12 mg, 0.13 mmol) and NaOH (4 mg, 0.1 mmol) at 80° C. for 34 h. After cooling down to room temperature, the mixture is treated with saturated aqueus NH$_4$Cl solution (2 mL) and extracted with EtOAc (3×2 mL). The organic layers are concentrated and purified by preparative thin layer chromatography (silica gel, 2.5% MeOH/CH$_2$Cl$_2$) to provide the titled compound 6-[4-(2-amino-pyrimidin-4-yl)-phenyl]-5-(4-chloro-phenyl)-1-phenyl-1,5-dihydro-pyrazolo[3,4-d]pyrimidin-4-one as a white solid. $^1$H NMR (CDCl$_3$) δ(ppm) 8.35(b, 1H), 8.34(s, 1H), 8.14 (d, 2H), 7.92 (d, 2H), 7.51 (t, 2H), 7.46 (d, 2H), 7.35(t, 1H), 7.32(d, 2H), 7.12(d, 2H), 7.03(d, 1H), 5.34(b, 2H); HPLC-MS calculated for $C_{27}H_{18}ClN_7O$ (M+H$^+$): 492.1. Found: 492.2.

Example 93

5-(4-Chloro-phenyl)-1-phenyl-6-[4-(2H-[1,2,4]triazol-3-yl)-phenyl]-1,5-dihydro-pyrazolo[3,4-d]pyrimidin-4-one

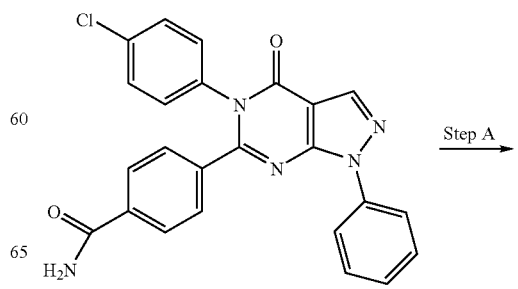

Step A

-continued

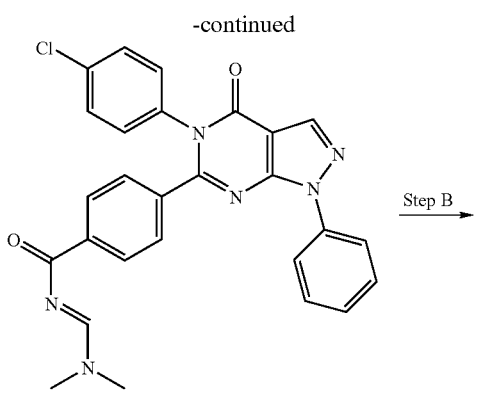

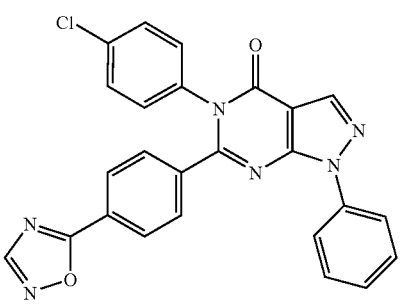

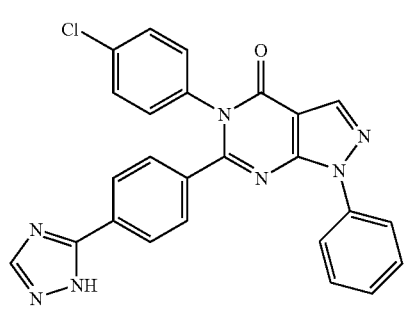

Step A: A mixture of 4-[5-(4-chloro-phenyl)-4-oxo-1-phenyl-4,5-dihydro-1H-pyrazolo[3,4-d]pyrimidin-6-yl]-benzamide (20 mg, 0.045 mmol) in N,N-dimethylformamide dimethyl acetal (0.5 mL) is heated to 120° C. for 1.5 h. and cooled down to room temperature. The excess of N,N-dimethylformamide dimethyl acetal is removed under vacuum to provide the desired product 4-[5-(4-chloro-phenyl)-4-oxo-1-phenyl-4,5-dihydro-1H-pyrazolo[3,4-d]pyrimidin-6-yl]-N-dimethylaminomethylene-benzamide without further purification. HPLC-MS calculated for $C_{27}H_{21}ClN_6O_2$ (M+H$^+$): 497.1. Found: 497.1.

Step B: A mixture of 4-[5-(4-chloro-phenyl)-4-oxo-1-phenyl-4,5-dihydro-1H-pyrazolo[3,4-d]pyrimidin-6-yl]-N-dimethylaminomethylene-benzamide (7.0 mg, 0.014 mmol) and hydrazine hydrate (5 mg, 0.1 mmol) in acetic acid (200 μL) is stirred at 90° C. for 1 h and cooled down to room temperature. The solvent is removed under vacuum and residue is treated with saturated aqueous NaHCO$_3$ solution (1 mL) and extracted with EtOAc (3×2 mL). The organic layers are combined and concentrated. The residue is purified by preparative thin layer chromatography (silica gel, 2% MeOH/CH$_2$Cl$_2$) to provide the titled compound 5-(4-chloro-phenyl)-1-phenyl-6-[4-(2H-[1,2,4]triazol-3-yl)-phenyl]-1,5-dihydro-pyrazolo[3,4-d]pyrimidin-4-one as white solid (4.8 mg, 73%). $^1$H NMR (CDCl$_3$) δ(ppm) 8.40(s, 1H), 8.34(s, 1H), 8.15(d, 2H), 8.03(d, 2H), 7.51(t, 2H), -7.45 (d, 2H), 7.34 (t, 1H), 7.31(d, 2H), 7.11(d, 2H); HPLC-MS calculated for $C_{25}H_{16}ClN_7O$ (M+H$^+$): 466.1. Found: 466.1.

Example 94

5-(4-Chloro-phenyl)-6-(4-[1,2,4]oxadiazol-5-yl-phenyl)-1-phenyl-1,5-dihydro-pyrazolo[3,4-d]pyrimidin-4-one To a solution of 4-[5-(4-chloro-phenyl)-4-oxo-1-phenyl-4,5-dihydro-1H-pyrazolo[3,4-d]pyrimidin-6-yl]-N-dimethylaminomethylene-benzamide (10 mg, 0.02 mmol) in acetic acid (200 μL) is added a mixture of NH$_2$OH.HCl (5 mg, 0.072 mmol) in NaOH (1M, 50 μL, 0.05 mmol)). The mixture is stirred at 90° C. for 1 h. and cooled down to room temperature. Solvent is removed under vacuum and the residue is treated with saturated aqueous NaHCO$_3$ solution (1 mL) and extracted with EtOAc (3×2 mL). The organic layers are combined and concentrated. The residue is purified by preparative thin layer chromatography (silica gel, 30% EtOAc/hex) to provide the titled compound 5-(4-chloro-phenyl)-6-(4-[1,2,4]oxadiazol-5-yl-phenyl)-1-phenyl-1,5-dihydro-pyrazolo[3,4-d]pyrimidin-4-one as white solid (8 mg, 85%). $^1$H NMR (CDCl$_3$) δ(ppm) 8.50(s, 1H), 8.35(s, 1H), 8.12(d, 2H), 8.06 (d, 2H), 7.48-7.54 (m, 4H), 7.37(t, 1H), 7.34(d, 2H), 7.11(d, 2H); HPLC-MS calculated for $C_{25}H_{16}ClN_6O_2$ (M+H$^+$): 467.1. Found: 467.1.

Example 95

6-Biphenyl-4-yl-5-(4-chloro-phenyl)-4-oxo 1-phenyl-4,5-dihydro-1H-pyrazolo[3,4-d']pyrimidine-3-carboxylic acid amide

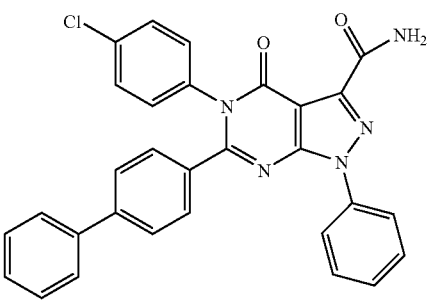

6-Biphenyl-4-yl-5-(4-chloro-phenyl)-4-oxo-1-phenyl-4,5-dihydro-1H-pyrazolo[3,4-d]pyrimidine-3-carboxylic acid ethyl ester (18 mg, 0.033 mmol) in EtOH (1 mL) is treated with LiOH (1M, 50 μL) at room temperature for 14 h. After removing the solvent, the residue is heated with SOCl₂ (0.5 mL) at 80° C. for 3 h. and cooled down to room temperature. After removing the excess SOCl₂ under vacuum, the resulted residue is dissolved in anhydrous CH₂Cl₂ and dropped into a vigorously stirred ice-cold aqueous NH₄OH solution (30%, 2 mL). After the addition, the mixture is extracted with EtOAc (3×2 mL). The organic layers are combined and concentrated. The residue is purified by preparative LC/MS to provide the titled compound 6-Biphenyl-4-yl-5-(4-chloro-phenyl)-4-oxo-1-phenyl-4,5-dihydro-1H-pyrazolo[3,4-d]pyrimidine-3-carboxylic acid amide. ¹H NMR (CDCl₃) δ(ppm) 10.11(b, 1H), 8.19(d, 2H), 7.51~7.57(m, 6H), 7.38~7.47(m, 8H), 7.18 (d, 2H), 6.65(b, 1H); HPLC-MS calculated for C₃₀H₂₀ClN₅O₂ (M+H⁺): 518.1. Found: 518.1.

Example 96

6-Biphenyl-4-yl-5-(4-chloro-phenyl)-4-oxo-1-phenyl-4,5-dihydro-1H-pyrazolo[3,4-d]pyrimidine-3-carboxylic acid ethyl ester

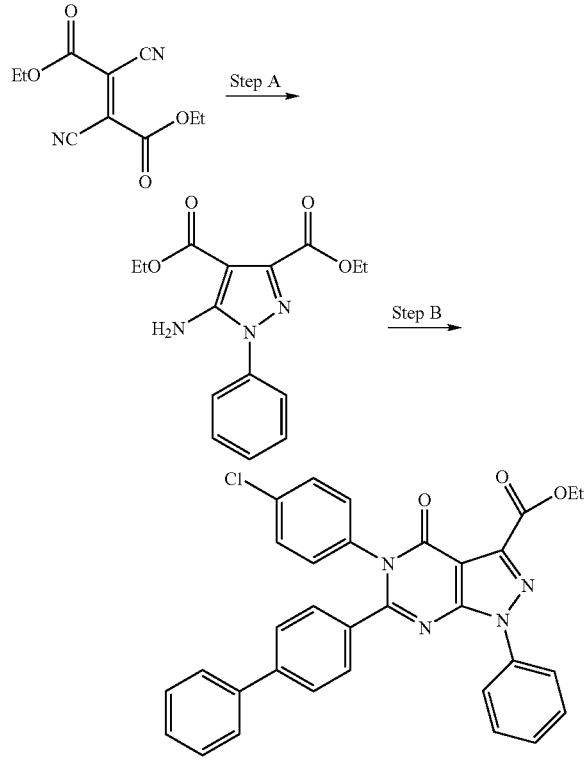

Step A: A mixture of 2,3-dicyano-but-2-enedioic acid diethyl ester (3.9 g, 17.6 mmol, prepared according to the method reported by C. J. Ireland and J. S. Pizey, *J. C.S. Chem., Comm.* 1972, 1, 4), phenyl hydrazine (2.28 g, 21.1 mmol) and NH₄OAc (135.5 mg, 1.76 mmol) in EtOH (30 mL) is heated to 80° C. for 30 min. After cooling down to room temperature, the mixture is poured into water (200 mL) and extracted with EtOAc (3×50 mL). The organic layers are combined and washed with brine and dried (MgSO₄). After filtering off the drying agent, the solvent are removed under vacuum and the residue is purified by flash column chromatography (silica gel, 0%~50% EtOAc/hex) to provide the desired product 3-amino-4-phenyl-cyclopenta-2,5-diene-1,2-dicarboxylic acid diethyl ester as red oil (2.1 g, 38%). ¹H NMR (CDCl₃) δ(ppm) 7.50-7.55 (m, 4H), 7.44(t, 1H), 5.40(b, 2H), 4.41(q, 2H), 4.31(q, 2H), 1.40(t, 3H), 1.35(t, 3H); HPLC-MS calculated for C₁₅H₁₇N₃O₄ (M+H⁺): 304.1. Found: 304.1.

Step B: 6-Biphenyl-4-yl-5-(4-chloro-phenyl)-4-oxo-1-phenyl-4,5-dihydro-1H-pyrazolo[3,4-d]pyrimidine-3-carboxylic acid ethyl ester is prepared from 5-amino-1-phenyl-1H-pyrazole-3,4-dicarboxylic acid diethyl ester and N-(4-chloro-phenyl)-biphenyl-4-carboximidoyl chloride by following a similar procedure as described in example 2 and purified by preparative LC/MS. ¹H NMR (CDCl₃) δ(ppm) 8.14(d, 2H), 7.36~7.57(m, 12H), 7.33(d, 2H), 7.14(d, 2H), 4.53(q, 2H), 1.46(t, 3H); HPLC-MS calculated for C₃₂H₂₃ClN₄O₃ (M+H⁺): 547.2. Found: 547.2.

Example 97

5-(4-chloro-phenyl)-6-(3'-fluoro-biphenyl-4-yl)-1-phenyl-1,5-dihydro-pyrazolo[3,4-d]pyrimidin-4-one

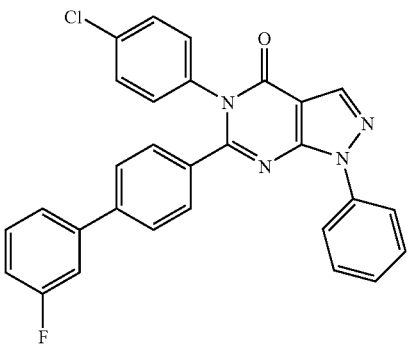

A microwave reaction tube charged with 5-(4-chloro-phenyl)-6-(4-iodo-phenyl)-1-phenyl-1,5-dihydro-pyrazolo[3,4-d]pyrimidin-4-one (74.9 mg, 0.143 mmol), 3-fluorophenyl-boronic acid (39.9 mg, 0.285 mmol), and Pd(PPh₃)₄ (16.5 mg, 0.014 mmol) is purged with nitrogen. Toluene (3.5 mL) and Na₂CO₃ aqueous solution (2.0M, 0.75 mL) are added via syringe. The reaction mixture is heated in a microwave at 170° C. for 20 min, and is partitioned between water and ethyl acetate. The organic phase is washed with brine, dried over MgSC₄, concentrated, and purified by silica gel chromatography to provide the title compound (37.7 mg, 54% yield) as a white solid product; ¹H NMR (CDCl₃, 400 MHz) δ 8.34 (s, 1H), 8.16 (dd, 2H), 7.52 (t, 2H), 7.48 (d, 2H), 7.43-7.33 (m, 7H), 7.25 (dt, 1H), 7.13 (d, 2H), 7.07 (td, 1H); HPLC-MS calculated for C₂₉H₁₈ClFN₄O (M+H⁺) 493.1. Found: 493.1.

Example 98

5-(4-chloro-phenyl)-6-(4-morpholin-4-yl-phenyl)-1-phenyl-1,5-dihydro-pyrazolo[3,4-d]pyrimidin-4-one

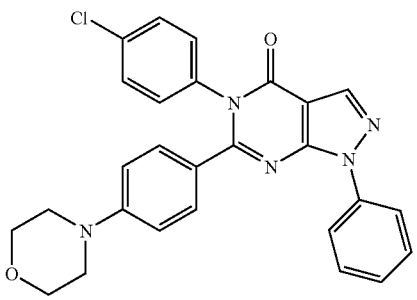

A reaction tube charged with 5-(4-chlorophenyl)-6-(4-iodo-phenyl)-1-phenyl-1,5-dihydro-pyrazolo[3,4-d]pyrimidin-4-one (100.0 mg, 0.191 mmol), Pd$_2$(dba)$_3$ (17.5 mg, 0.019 mmol), BINAP (23.7 mg, 0.038 mmol), and Cs$_2$CO$_3$ (124.2 mg, 0.381 mmol) is purged with nitrogen. Anhydrous toluene (1.0 mL) and morpholine (33.2 µL, 0.381 mmol) are added via syringe. The reaction mixture is heated at 100° C. overnight, and is partitioned between water and ethyl acetate. The organic phase is washed with brine, dried over MgSO$_4$, concentrated, and purified by silica gel chromatography to provide the title compound (64.3 mg, 70% yield) as a yellow solid product; $^1$H NMR (CDCl$_3$, 400 MHz) δ 8.29 (s, 1H), 8.17 (dd, 2H), 7.50 (t, 2H), 7.35 (m, 3H), 7.28 (d, 2H), 7.12 (d, 2H), 6.77 (d, 2H), 3.86 (t, 4H), 3.21 (t, 4H); HPLC-MS calculated for C$_{27}$H$_{22}$ClN$_5$O$_2$ (M+H$^+$) 484.1. Found 484.1.

Example 99

5-(4-chloro-phenyl)-6-(4-imidazol-1-yl-phenyl)-1-phenyl-1,5-dihydro-pyrazolo[3,4-d]pyrimidin-4-one

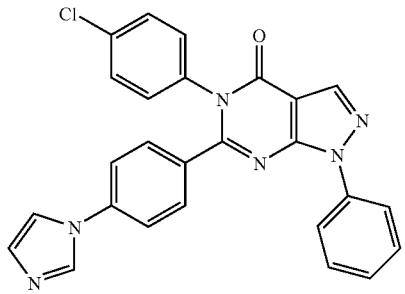

A reaction tube charged with 6-(4-bromo-phenyl)-5-(4-chloro-phenyl)-1-phenyl-1,5-dihydro-pyrazolo[3,4-d]pyrimidin-4-one (100.0 mg, 0.209 mmol), imidazole (85.5 mg, 1.26 mmol), CuI (4.0 mg, 0.021 mmol), (1R, 2R)-diaminomethylcyclohexane (6.0 mg, 0.042 mmol), and K$_3$PO$_4$ (88.9 mg, 0.429 mmol) is purged with nitrogen. Anhydrous 1,4-dioxane (4.0 mL) is added via syringe. The reaction mixture is heated at 100° C. for 5 days, and is partitioned between saturated NH$_4$Cl aqueous solution and ethyl acetate. The organic phase is washed with brine, dried over MgSO$_4$, concentrated, and purified by silica gel chromatography to provide the title compound (78.7 mg, 81% yield) as a white solid product; $^1$HNMR (CDCl$_3$, 400 MHz) δ 8.91 (s, 1H), 8.35 (s, 1H), 8.10 (dd, 2H), 7.59 (d, 2H), 7.52 (m, 3H), 7.44-7.36 (m, 6H), 7.13 (d, 2H); HPLC-MS calculated for C$_{26}$H$_{17}$ClN$_6$O (M+H$^+$) 465.1. Found: 465.1.

If trans-1,2-diaminocyclohexane instead of (1R, 2R)-diaminomethylcyclohexane is used as the ligand, a byproduct 6-[4-(2-amino-cyclohexylamino)-phenyl]-5-(4-chloro-phenyl)-1-phenyl-1,5-dihydro-pyrazolo[3,4-d]pyrimidin-4-one is also obtained as example 144; HPLC-MS calculated for C$_{29}$H$_{27}$ClN$_6$O (M+M$^+$) 511.2. Found 511.1.

Example 100

5-(4-chloro-phenyl)-1-phenyl-6-(4-pyridin-2-yl-phenyl)-1,5-dihydro-pyrazolo[3,4-d]pyrimidin-4-one

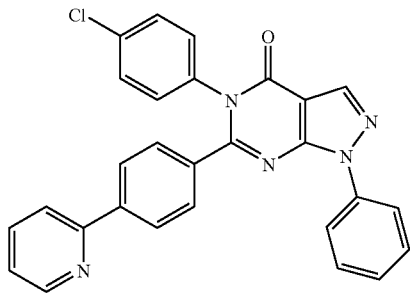

A reaction tube charged with 6-(4-bromophenyl)-5-(4-chloro-phenyl)-1-phenyl-1,5-dihydro-pyrazolo[3,4-d]pyrimidin-4-one (40.0 mg, 0.084 mmol) and Pd(PPh$_3$)$_4$ (9.7 mg, 0.0084 mmol) is purged with nitrogen. A solution of 2-tributylstannanyl-pyridine (61.6 mg, 0.168 mmol) in anhydrous toluene (1.0 mL) is added via syringe. The reaction mixture is heated at 100° C. overnight, and is partitioned between water and ethyl acetate. The organic phase is washed with brine, concentrated, and purified by preparative LCMS followed by silica gel chromatography to provide the title compound (18.4 mg, 46% yield) as a white solid product; HPLC-MS calculated for C$_{28}$H$_{18}$ClN$_5$O (M+H$^+$) 476.1. Found: 476.1.

Example 101

5-(4-chloro-phenyl)-1-phenyl-6-(4-phenyl-piperazin-1-yl)-1,5-dihydro-pyrazolo[3,4-d]pyrimidin-4-one

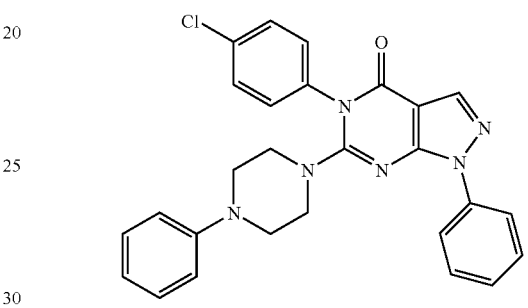

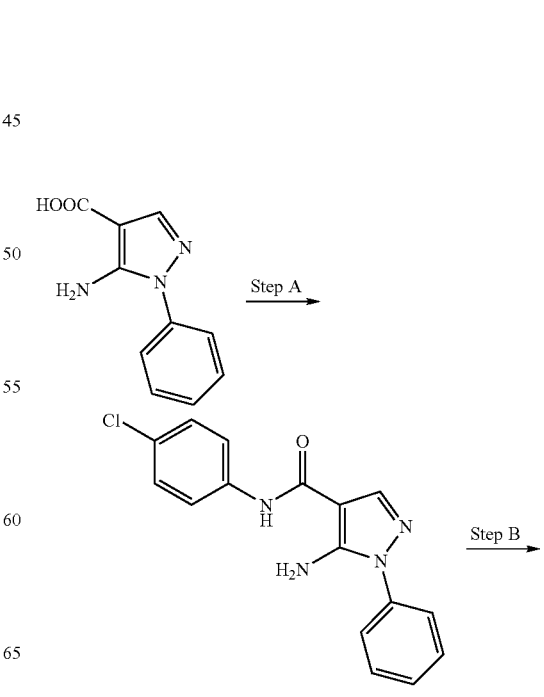

-continued

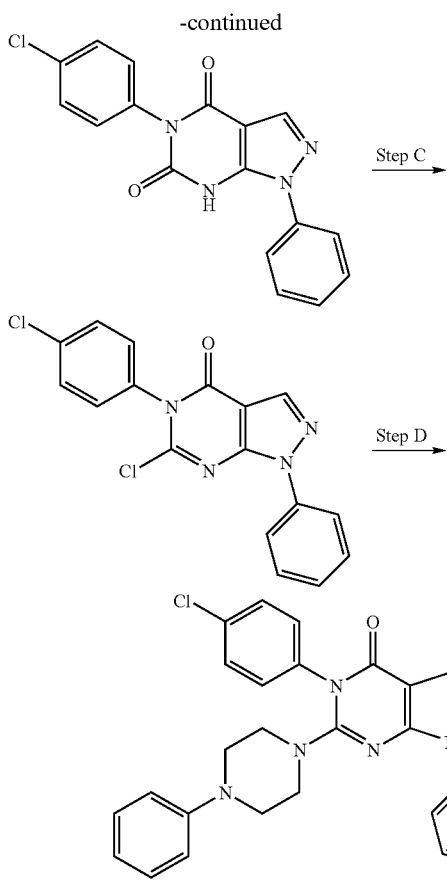

Step A: A suspension of 5-amino-1-phenyl-1H-pyrazole-4-carboxylic acid (500 mg, 2.46 mmol) in thionyl chloride (2.0 mL) is stirred at room temperature for about 15 min before it becomes a clear solution. After removal of the solvent, the crude acid chloride is taken in anhydrous DCM (5.0 mL), and transferred dropwise to a solution of 4-chloroaniline (376.7 mg, 2.95 mmol) and TEA (1.03 mL, 7.38 mmol) in anhydrous DCM (5.0 mL) at 0° C. The reaction mixture is allowed to warm up to room temperature in an hour and lots of precipitate is generated. After filtration, the precipitate is washed with water, followed by small amount of DCM, and air-dried to provide crude 5-amino-1-phenyl-1H-pyrazole-4-carboxylic acid (4-chloro-phenyl)-amide (506.2 mg, 66% yield) as a white solid product; HPLC-MS calculated for $C_{16}H_{13}ClN_4O$ (M+H$^+$) 313.1. Found: 313.0.

Step B and C: The crude product from step A is taken in anhydrous pyridine (5.0 mL) and triphosgen (321.8 mg, 1.08 mmol) is added. The mixture is heated at 100° C. for 1 h before removal of the solvent. The residue is taken in POCl$_3$ (3.0 mL) and heated at 110° C. for 3 h. After removal of POCl$_3$ in vacuo, the residue is taken in cold saturated NaHCO$_3$ aqueous solution and extracted with ethyl acetate. The organic phase is washed with brine, dried over MgSO$_4$, and evaporated to provide crude 6-chloro-5-(4-chloro-phenyl)-1-phenyl-1,5-dihydro-pyrazolo[3,4-d]pyrimidin-4-one (408.8 mg, 71% yield) as a grey solid product; HPLC-MS calculated for $C_{17}H_{10}Cl_2N_4O$ (M+H$^+$) 357.0. Found: 357.0.

Step D: To a solution of crude 6-chloro-5-(4-chloro-phenyl)-1-phenyl-1,5-dihydro-pyrazolo[3,4-d]pyrimidin-4-one from step C (20.0 mg, 0.056 mmol) in DCM (1.0 mL) are added 1-phenylpiperazine (17.1 μL, 0.112 mmol) and TEA (15.6 μL, 0.112 mmol). The mixture is stirred at room temperature overnight. After removal of the solvent, the residue is purified by preparative LCMS to provide the title compound; $^1$H NMR (CDCl$_3$, 400 MHz) δ 8.18 (s, 1H), 8.11 (d, 2H), 7.52 (m, 4H), 7.38-7.29 (m, 5H), 7.00 (m, 3H), 3.44 (t, 4H), 3.07 (t, 4H); HPLC-MS calculated for $C_{27}H_{23}ClN_6O$ (M+H$^+$) 483.2. Found: 483.2.

Example 102

6-benzothiazol-2-yl-5-(4-chloro-phenyl)-1-phenyl-1,5-dihydro-pyrazolo[3,4-d]pyrimidin-4-one

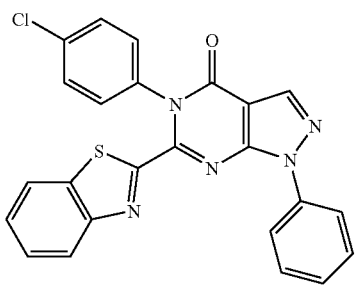

A reaction tube charged with 6-chloro-5-(4-chloro-phenyl)-1-phenyl-1,5-dihydro-pyrazolo[3,4-d]pyrimidin-4-one (20.0 mg, 0.056 mmol) and Pd(PPh$_3$)$_4$ (6.5 mg, 0.0056 mmol) is purged with nitrogen. A solution of 2-tributylstannanyl-benzothiazole (47.6 mg, 0.112 mmol) in anhydrous toluene (1.0 mL) is added via syringe. The reaction mixture is heated at 100° C. for 2 days. After removal of the solvent, the residue is purified by preparative LCMS to provide the title compound; $^1$H NMR (CDCl$_3$, 400 MHz) δ 8.36 (s, 1H), 8.21 (d, 2H), 7.90 (t, 1H), 7.69 (t, 1H), 7.59 (t, 2H), 7.46-7.40 (m, 5H), 7.24 (d, 2H); HPLC-MS calculated for $C_{24}H_{14}ClN_5OS$ (M+H$^+$) 456.1. Found 456.1.

Example 103

5-(4-chloro-phenyl-1-phenyl-6-p-tolyloxy-1,5-dihydro-pyrazolo[3,4-d]pyrimidin-4-one

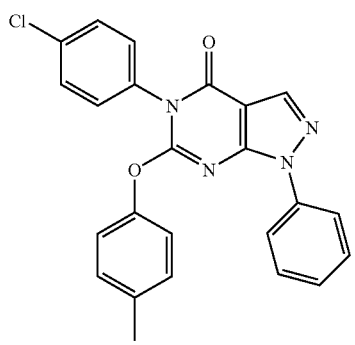

To a solution of 6-chloro-5-(4-chloro-phenyl)-1-phenyl-1,5-dihydro-pyrazolo[3,4-d]pyrimidin-4-one (20.0 mg, 0.056 mmol) in acetonitrile (0.5 mL) are added p-cresol (11.7 μL, 0.112 mmol) and K₂CO₃ (15.5 mg, 0.112 mmol). The mixture is heated at 100° C. overnight. K₂CO₃ is then filtered off. The filtrate is concentrated and purified by preparative LCMS to provide the title compound; $^1$H NMR (CDCl₃, 400 MHz) δ 8.20 (s, 1H), 7.91 (dd, 2H), 7.54 (d, 2H), 7.32 (m, 4H), 7.22 (m, 3H), 7.03 (d, 2H), 2.39 (s, 3H); HPLC-MS calculated for $C_{34}H_{17}ClN_4O_2$ (M+H⁺) 429.1. Found 429.2.

Example 104

6-(4-bromo-phenyl)-3-phenyl-5-p-tolyl-1,6-dihydro-pyrazolo[4,3-d]pyrimidin-7-one

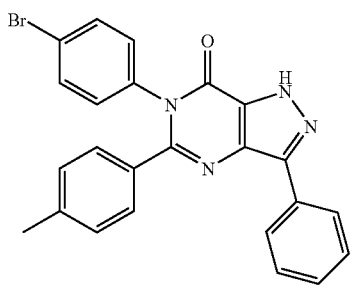

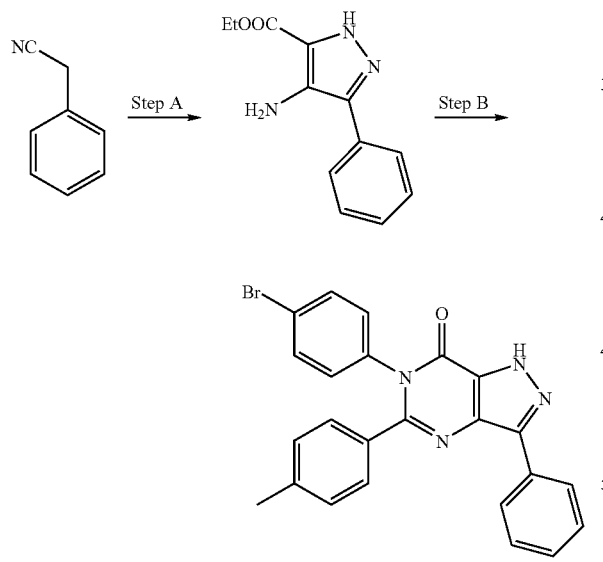

Step A: 4-Amino-5-phenyl-2H-pyrazole-3-carboxylic acid ethyl ester is prepared from benzyl cyanide and ethyl diazoacetate, using the condition described in Rochais, C.; Lisowski, V.; Dellemagne, P.; Rault, S. *Tetrahedron Lett.* 2004, 45, 6353. HPLC-MS calculated for $C_{12}H_{13}N_3O_2$ (M+H⁺) 232.1. Found: 232.2.

Step B: 6-(4-Bromo-phenyl)-3-phenyl-5-tolyl-1,6-dihydro-pyrazolo[4,3-d]pyrimidin-7-one is prepared as described in Example 2, using 4-amino-5-phenyl-2H-pyrazole-3-carboxylic acid ethyl ester from step A instead of ethyl 5-amino-1-phenyl-4-pyrazole-carboxylate. $^1$H NMR (CDCl₃, 400 MHz) δ 8.41 (dd, 2H), 7.48 (m, 4H), 7.39 (t, 1H), 7.21 (d, 2H), 7.05 (m, 4H), 2.32 (s, 3H); HPLC-MS calculated for $C_{24}H_{17}BrN_4O$ (M+H⁺) 457.1. Found 457.1.

Example 121

5-(4-Chloro-phenyl)-6-(2,4-dichloro-phenyl)-4-(2-morpholin-4-yl-ethoxy-1-phenyl-1H-pyrazolo[3,4-b]pyridine

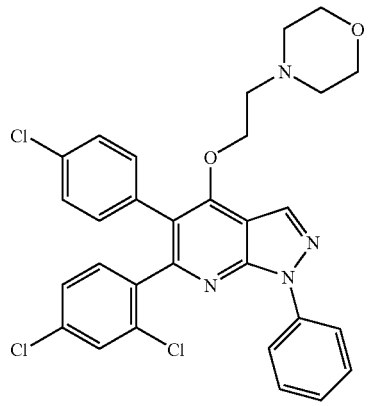

To a solution of 2-[5-(4-chloro-phenyl)-6-(2,4-dichloro-phenyl)-1-phenyl-1H-pyrazolo[3,4-b]pyridin-4-yloxy]-ethanol (13 mg, 0.025 mmol, prepared in 84% yield as described in Example 5 except using ethylene glycol as solvent.) in anhydrous CH₂Cl₂ (0.5 mL) is added CH₃SO₂Cl (5 μL) followed by Et₃N (20 μL). After the addition, the mixture is stirred at room temperature for 2 h. and morpholine (20 μL) is added. After the resulted mixture is stirred at 60° C. for 10 h. it is cooled down to room temperature and treated with water (4 mL) and extracted with EtOAc (3×3 mL). The organic layers are combined and concentrated. The residue is purified by preparative LC/MS to provide the titled compound 5-(4-chloro-phenyl)-6-(2,4-dichloro-phenyl)-4-(2-morpholin-4-yl-ethoxy)-1-phenyl-1H-pyrazolo[3,4-b]pyridine. HPLC-MS calculated for $C_{30}H_{25}Cl_3N_4O_2$ (M+H⁺): 579.1. Found: 579.1.

Example 164

9-Benzyl-1-(4-chloro-phenyl)-2-(2,4-dichloro-phenyl)-1,9-dihydro-purin-6-one

Step 1: Preparation of 5-Amino-1-benzyl-1H-imidazole-4-carboxylic acid ethyl ester:

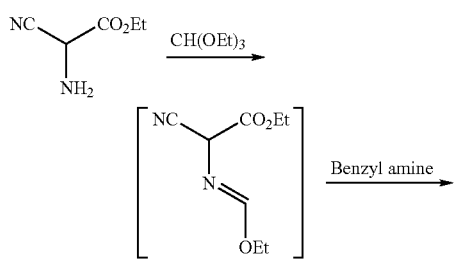

-continued

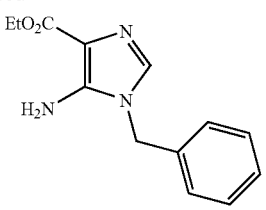

A solution of amino-cyano-acetic acid ethyl ester (1.2 g, 9.38 mmol) and triethyl orthoformate (1.56 mL, 9.38 mmol) in acetonitrile (10 mL) is heated at reflux for 45 min. After cooled down to room temperature, benzylamine (1.1 mL, 9.85 mmol) is added. Stirred at room temperature, solid precipitated out. Filtration gives a white solid as product (two steps yield 51%). 1H NMR (CDCl3) μ 7.37 (m, 3H), 7.15 (d, 3H), 4.99 (s, 2H), 4.68 (b, 2H), 4.34 (q, 2H), 1.39 (t, 3H); m/z 246.1 (M+H$^+$).

Step 2: 1-Benzyl-5-[bis-(2,4-dichloro-benzoyl)amino]-1H-imidazole-4-carboxylic acid ethyl ester:

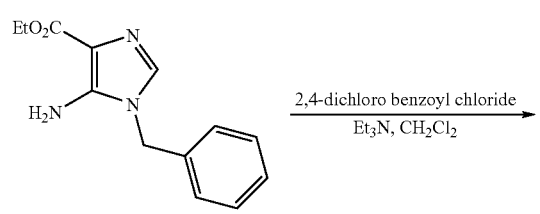

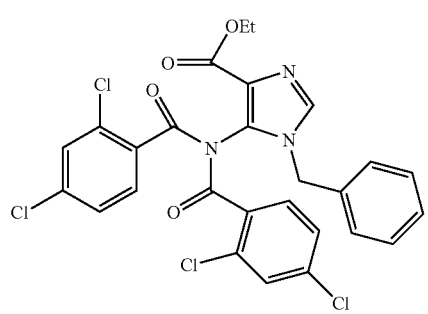

A suspension of 5-amino-1-benzyl-1H-imidazole-4-carboxylic acid ethyl ester (1.15 g, 4.69 mmol) and triethylamine (1.96 mL, 14.1 mmol) in 20 mL of dichloromethane is cooled to 0° C. 2,4-Dichlorobenzoyl chloride solution (1.65 mL, 11.7 mmol in 5 mL of dichloromethane) is then added dropwise. After addition, the reaction mixture is warmed to room temperature for 1 h before quenched with water. The organic phase is separated and the aqueous phase is extracted with dichloromethane. The organic phases are combined and dried over magnesium sulfate. Concentration followed by purification with flash chromatography gives the desired compound as a pale yellow solid (1.5 g, yield 55%). $^1$H NMR (CDCL) δ 7.57 (d, 2H), 7.38 (m, 4H), 7.31 (d, 2H), 7.21 (m, 4H), 5.12 (s, 2H), 4.41 (q, 2H), 1.41 (t, 3H); m/z 590.0 (M+H$^+$).

Step 3: 1-Benzyl-5-(2,4-dichloro-benzoylamino)-1H-imidazole-4-carboxylic acid (4-chloro-phenyl)-amide:

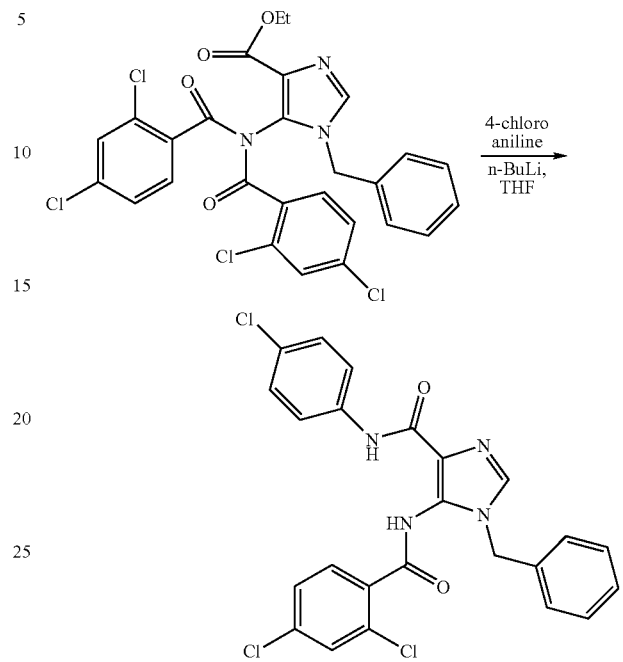

A dry flask charged with 4-chloroanaline (390 mg, 3.05 mmol) and tetrahydrofuran (6 mL) is cooled to 0° C. n-Butyllithium solution (1.6 M in hexanes) is added dropwise. The reaction mixture is warmed to room temperature for 10 min before cooled down again to 0° C. The resulting solution is cannulated a solution of 1-benzyl-5-[bis-(2,4-dichloro-benzoyl)-amino]1H-imidazole-4-carboxylic acid ethyl ester (300 mg, 0.51 mmol) in tetrahydrofuran. After addition, the reaction mixture is stirred at room temperature for 2 h. 1 M HCl is added after the reaction quenched with water. The organic phase is separated and the aqueous phase is extracted with ethyl acetate. The organic phases are combined and dried over magnesium sulfate. Concentration followed by purification with flash chromatography gives the desired product (81 mg, 32% yield). $^1$H NMR (CDCl$_3$) δ 9.01 (s, 1H), 8.86 (s, 1H), 7.59 (m, 3H), 7.47 (d, 1H), 7.35 (m, 4H), 7.27 (m, 3H), 7.18 (m, 2H), 5.35 (s, 2H); m/z 499.0 (M+H$^+$).

Step 4: 9-Benzyl-1-(4-chloro-phenyl)-2-(2-(4-dichloro-phenyl)-1,9-dihydro-purin-6-one:

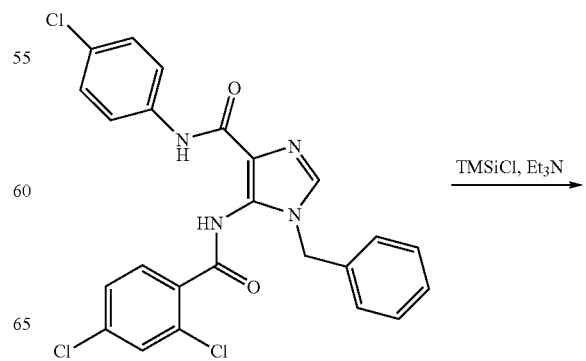

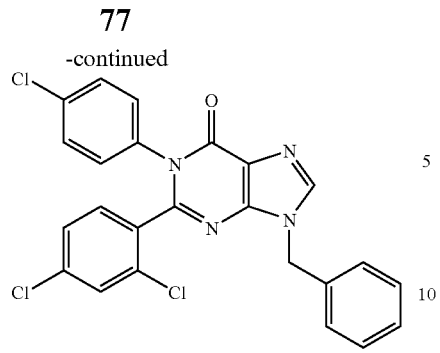

The reaction mixture of 1-benzyl-5-(2,4-dichloro-benzoylamino)-1H-imidazole-4-carboxylic acid (4-chloro-phenyl)-amide (60 mg, 0.12 mmol), triethylamine (670 μL, 4.8 mmol) and trimethylsilyl chloride (303 μL, 2.4 mmol) is heated at 100° C. for 2 days. After cooled to room temperature, the resulting mixture is quenched with 1 N HQ and dichloromethane. The aqueous phase is extracted with dichloromethane. The organic phases is combined, ished with brine and dried over magnesium sulfate. Concentration followed by purification with chromatography gives the desired product (41 mg, 71% yield).

Example 166

1-(4-Bromo-phenyl)-9-cyclopropyl-2-(2,4-dichloro-phenyl)-1,9-dihydro-purin-6-one Step 1: 5-Amino-1-cyclopropyl-1H-imidazole-4-carboxylic acid ethyl ester:

A solution of amino-cyano-acetic acid ethyl ester (333 mg, 2.6 mmol) and triethyl orthoformate (454 μL, 2.73 mmol) in acetonitrile is heated at reflux for 45 min. After cooled down to room temperature, cyclopropylamine (180 μL, 2.6 mmol) is added. After stirred at room temperature overnight, the solution is concentrated and purified with chromatography. The desired product is obtained a white solid as product (290 mg, 57% yield). $^1$H NMR (CDCl$_3$) δ 7.08 (s, 1H), 5.01 (b, 2H), 4.27 (q, 2H), 2.95 (m, 1H), 1.31 (t, 3H), 1.04 (m, 2H), 0.91 (m, 2H); m/z 196.1 (M+H4).

Step 2: N-(4-Bromo-phenyl)-2,4-dichloro-benzimidoyl chloride

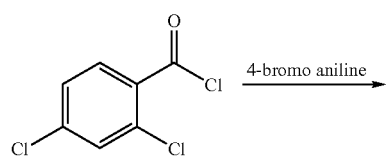

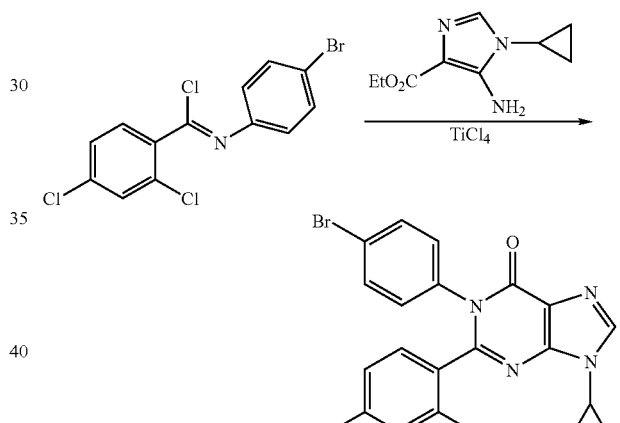

To a solution of 4-bromoaniline (40 mg, 0.12 mmol) and 2,4-dichloro benzoyl chloride (69 μL, 0.12 mmol) in dichloromethane is added triethylamine (20 μL, 0.144 mmol). After stirred at room temperature for 30 min, the solvent is removed. The residue is added 0.5 mL of thionyl chloride. The reaction mixture is heated at 80° C. for 1h, concentrated. The product is used in the next step reaction.

Step 3: 1-(4-Bromo-phenyl)-9-cyclopropyl-2-(2,4-dichloro-phenyl)-1,9-dihydro-purin-6-one:

A similar method as making compound 77 gives the desired product after purification with HPLC. HPLC-MS calculated for C$_{20}$H$_{13}$BrCl$_2$N$_4$O (M+H$^+$): 474.9. Found 474.9.

Example 168

1-(4-Chloro-phenyl)-9-phenyl-2-(4-thiophen-3-yl-phenyl)-1,9-dihydro-purin-6-one

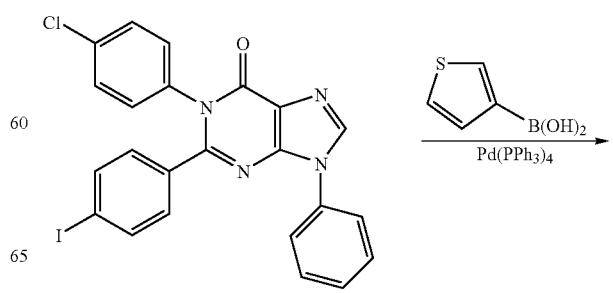

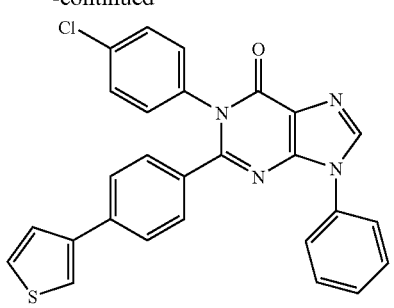

A solution of 1-(4-chloro-phenyl)-2-(4-iodo-phenyl)-9-phenyl-1,9-dihydro-purin-6-one (20 mg, 0.038 mmol), 3-thiophene boronic acid (9.7 mg, 0.076 mmol) and tetrakis(triphenylphosphine) palladium (4.4 mg, 0.0038 mmol) in 1 mL of toluene is added 2.0 M Na$_2$CO$_3$ solution (200 μL). The reaction mixture is heated at 170° C. on the microwave oven for 20 min. After cooled down, the resulting solution is concentrated and purified with HPLC. $^1$H NMR (CDCl$_3$) δ(ppm) 8.12 (s, 1H), 7.71 (d, 2H), 7.57 (t, 2H), 7.47 (m, 4H), 7.38 (m, 1H), 7.33 (m, 5H), 7.14 (d, 2H); HPLC-MS calculated for C$_{27}$H$_{17}$ClN$_4$OS (M+H$^+$): 481.0. Found 481.0.

Example 171

1-(4-Chloro-phenyl)-9-phenyl-2-(4-pyridin-4-yl-phenyl)-1,9-dihydro-purin-6-one

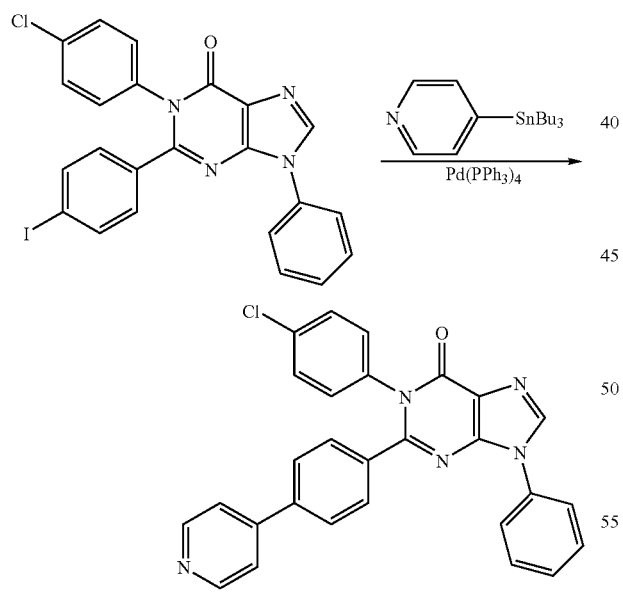

A dry flask charged with 1-(4-chloro-phenyl)-2-(4-iodo-phenyl)-9-phenyl-1,9-dihydro-purin-6-one (20 mg, 0.038 mmol), 4-tributylstannylpyridine (14 mg, 0.038 mmol) and tetrakis(triphenylphosphine) palladium (4.4 mg, 0.0038 mmol) is heated at 100° C. overnight. Filtration and concentration followed by purification gives the desired product. $^1$H NMR (methanol-d$_4$) δ(ppm) 8.69 (d, 2H), 8.49 (s, 1H), 8.04 (d, 2H), 7.81 (m, 4H), 7.60 (m, 4H), 7.51 (m, 1H), 7.35 (m, 4H); HPLC-MS calculated for C$_{28}$H$_{18}$ClN$_5$O (M+H$^+$): 476.2. Found 476.2.

Example 174

1,2-Bis-(4-chloro-phenyl)-7-phenyl-1,7-dihydro-purin-6-one

A mixture of phenylboronic acid (18.7 mg, 0.15 mmol), purinone (30 mg, 0.077 mmol) and [Cu(OH)TMEDA]$_2$Cl$_2$ (17.8 mg, 0.039 mmol) in dry dichloromethane is stirred at room temperature overnight. Celite Alteration to remove copper salt and concentrate the filterate to purify by column chromatography to give N-7 phenyl purinone as a major product. HPLC-MS calculated for C$_{23}$H$_{14}$Cl$_2$N$_4$O (M+H$^+$): 433.1. Found 433.1

Example 255

1-(4-Bromo-phenyl)-8-ethyl-9-phenyl-2-(4-trifluoromethyl-phenyl)-1,9-dihydro-purin-6-one

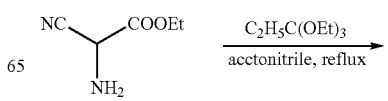

-continued

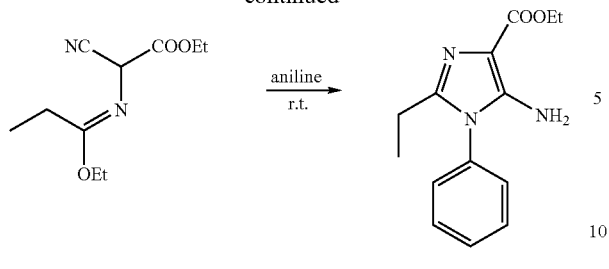

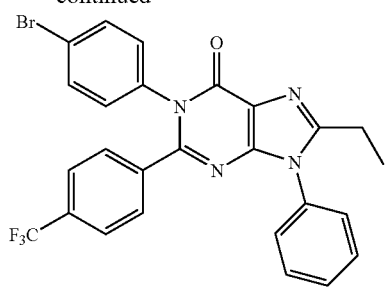

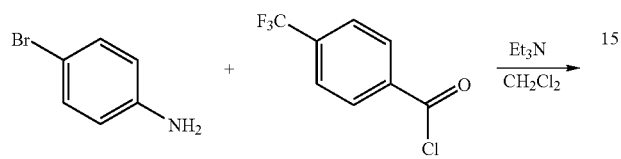

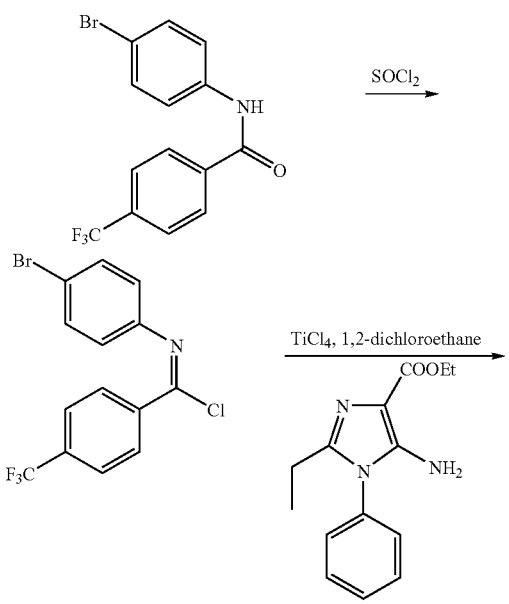

5-Amino-2-ethyl-1-phenyl-1H-imidazole-4-carboxylic acid ethyl ester: A solution of amino-cyano-acetic acid ethyl ester (400 mg, 3.12 mmol) and triethyl orthopropionate (629 μL, 3.12 mmol) in acetonitrile is heated at reflux for 45 minutes. After cooled down to room temperature, aniline (285 μL, 3.12 mmol) is added. After stirred at room temperature overnight, the solution is concentrated and purified with flash chromatography. A pale yellow solid is obtained as the desired product: $^1$H NMR (CDCl$_3$) δ 7.56 (m, 3H), 7.29 (m, 2H), 4.77 (b, 2H), 4.37 (q, 2H), 2.49 (q, 2H), 1.40 (t, 3H), 1.11 (t, 3H); m/z 260.1 (M+1).

1-(4-Bromo-phenyl)-8-ethyl)-9-phenyl-2-(4-trifluoromethyl-phenyl)-1,9-dihydro-purin-6-one: A similar method using in making compound in example 77 is used to make the desired product: $^1$H NMR (CDCl$_3$) δ(ppm) 7.58 (m, 3H), 7.43 (m, 6H), 7.31 (d, 2H), 7.02 (d, 2H), 2.84 (q, 2H), 1.32 (t, 3H); HPLC-MS calculated for C$_{26}$H$_{18}$BrF$_3$N$_4$O (M+H$^+$): 539.1. Found: 539.1.

Example 270

5-(4-Chloro-phenyl-6-(2,4-dichloro-phenyl)-1-(2-nitro-phenyl-1,5-dihydro-pyrazolo[3,4-d]pyrimidin-4-one

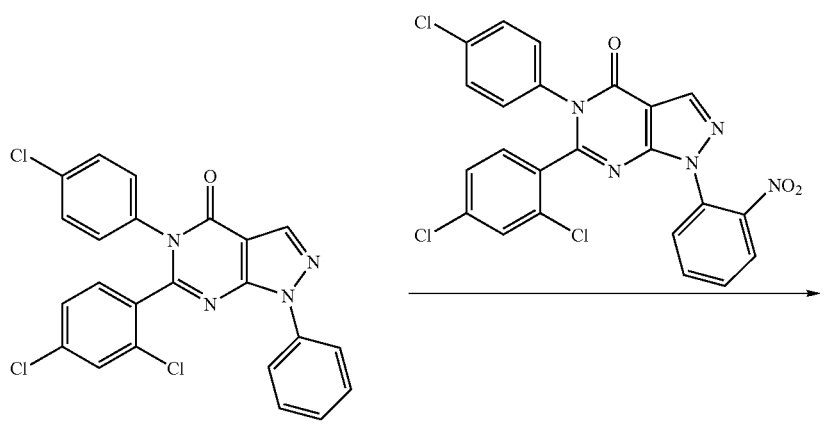

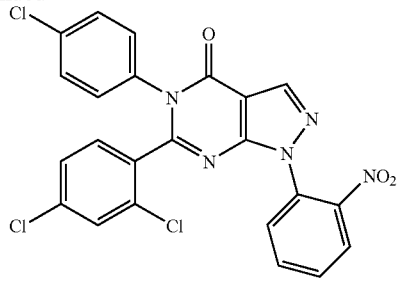

5-(4-Chloro-phenyl)-6-(2,4-dichloro-phenyl)-1-phenyl-1,5-dihydro-pyrazolo[3,4-d]pyrimidin-4-one (50.0 mg, 0.107 mmol) is dissolved in 3 mL of acetic anhydride. Concentrated nitric acid (300 μL, 4.74 mmol) is added dropwise to the reaction mixture at room temperature. A mild temperature increase occurred upon addition of the acid. The reaction mixture is briefly heated just to boil and allowed to cool to room temperature. The reaction mixture is poured onto ice/sodium bicarbonate mixture and extracted with dichloromethane. Ortho and para isomers are separated by column chromatography: $^1$H NMR (CDCl$_3$, 400 MHz) δ 8.40 (s, 1H), 8.07 (d, 1H), 7.87 (d, 1H), 7.79 (t, 1H), 7.61 (t, 1H), 7.33-7.27 (m, 4H), 7.22 (d, 2H), 6.97 (d, 1H). HPLC-MS calculated for $C_{23}H_{12}Cl_3N_5O_3$ (M+H$^+$) 512.0. Found 512.0.

Example 271

1-(4-Amino-phenyl)-5-(4-chloro-phenyl)-6-(2,4-dichloro-phenyl)-1,5-dihydro-pyrazolo[3,4-d]pyrimidin-4-one

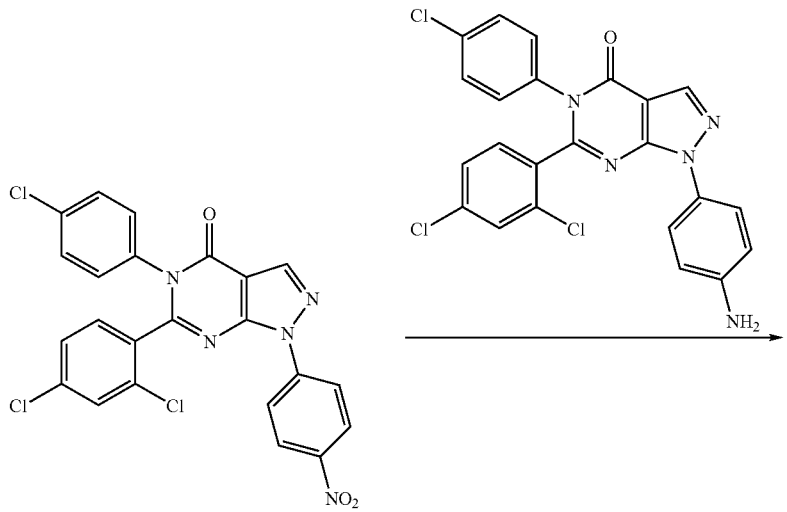

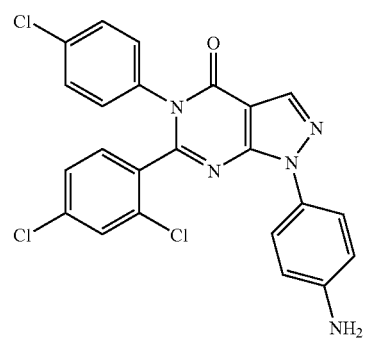

5-(4-Chloro-phenyl)-6-(2,4-dichloro-phenyl)-1-(4-nitro-phenyl)-1,5-dihydro-pyrazolo[3,4-d]pyrimidin-4-one (100 mg, 0.195 mmol) is dissolved in 20 mL of dioxane. Platinumoxide (11.0 mg, 0.0484 mmol) was added as a slurry in 2 mL of water to the reaction mixture under a nitrogen atmosphere. The mixture was placed under balloon pressure of hydrogen and the reaction is completed within 1 h. The solids are filtered off and the solution is concentrated. Purification by reverse phase HPLC affords the title compound. $^1$H NMR (DMSO, 400 MHz) δ 8.78 (s, 1H), 8.15 (d, 2H), 7.97-7.95 (m, 2H), 7.90 (m, 3H), 7.84 (dd, 1H), 7.78 (m, 1H), 7.30 (d, 2H), 6.00 (s, 2H). HPLC-MS calculated for $C_{23}H_{14}Cl_3N_5O$ (M+H$^+$) 482.0. Found: 482.0.

Example 276

5-(4-Chloro-phenyl)-6-(2,4-dichloro-phenyl)-3-(4-methyl-piperazin-1-yl)-1-phenyl-1,5-dihydro-pyrazolo[3,4-d]pyrimidin-4-one

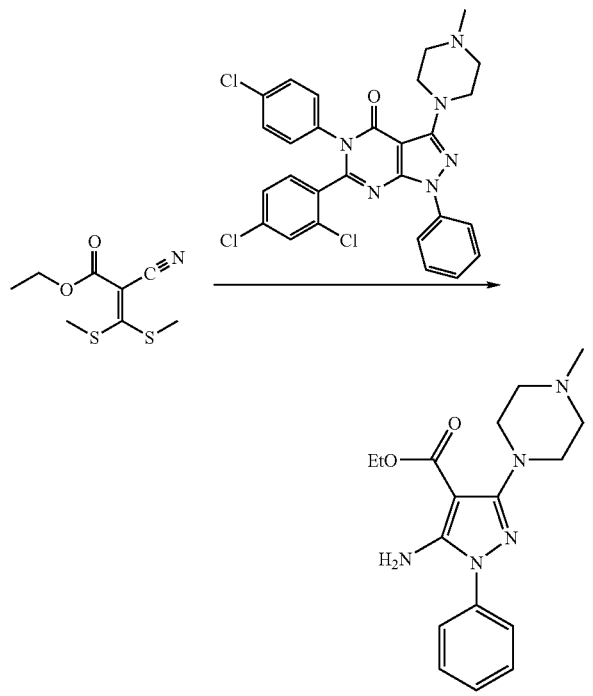

5-Amino-3-(4-methylpiperazin-1-yl)-1-phenyl-1H-pyrazole-4-carboxylic acid ethyl ester is prepared as follow. Commercially available 2-cyano-3,3-bis-methylsulfanyl-acrylic acid ethyl ester (2.18 g, 10.0 mmol) is dissolved in 100 mL of dry ethanol and 1-methyl-piperazine (1.0 g, 10 mmol) is added and the reaction is heated to reflux for 1.5 h. Phenylhydrazine (1.19 g, 10 mmol) is added via syringe and the reaction mixture is heated to reflux overnight. The solvent is evaporated and the resulting solid is purified by flash chromatography to yield 360 mg of the desired product as well as 800 mg of 5-Amino-3-methylsulfanyl-1-phenyl-1H-pyrazole-4-carboxylic acid ethyl ester. $^1$H NMR (CDCl$_3$, 400 MHz) δ 7.50 (m, 4H), 7.35 (m, 1H), 4.35 (q, 2H), 3.38 (m, 4H), 2.65 (m, 4H), 2.39 (s, 3H), 1.39 (t, 3H). HPLC-MS calculated for $C_{17}H_{23}N_5O_2$ (M+H$^+$) 330.18. Found: 330.18.

The title compound of Example 276 was prepared from this material following the procedures described in Example 1. $^1$H NMR CDCl$_3$, 400 MHz) δ 7.94 (d, 2H), 7.33 (t, 3H), 7.20 (d, 2H), 7.06 (m, 2H), 6.90 (m, 1H), 3.74 (m, 4H), 2.67 (m, 4H), 2.37 (broad s, 3H). HPLC-MS calculated for $C_{28}H_{23}Cl_3N_6O$ (M+H$^+$) 565.1. Found: 565.1.

Example 277

5-(4-Bromo-phenyl)-6-(2,4-dichloro-phenyl)-3-methylsulfanyl-1-phenyl-1,5-dihydro-pyrazolo[3,4-d]pyrimidin-4-one

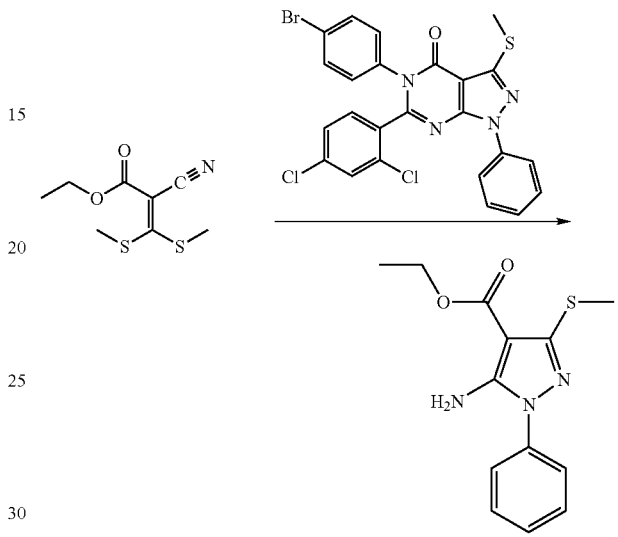

Preparation of 5-Amino-3-methylsulfanyl-1-phenyl-1H-pyrazole-4-carboxylic acid ethyl ester: Commercially available 2-Cyano-3,3-bis-methylsulfanyl-acrylic acid ethyl ester (2.18 grams, 10 mmol) is dissolved in 100 mL of dry ethanol. Phenylhydrazine (1.19 g, 10.0 mmol) is added via a syringe and the reaction mixture is heated to reflux for 3 h. The solvent is then removed and the resulting solid is recrystallized from CH$_2$Cl$_2$ yielding 2.5 g of final product. $^1$H NMR (CDCl$_3$, 400 MHz) δ 7.54 (m, 4H), 7.40 (m, 1H), 4.35 (q, 2H), 2.55 (s, 3H), 1.41 (t, 3H). HPLC-MS calculated for $C_{13}H_{15}N_3O_2S$ (M+H$^+$) 278.1. Found: 278.1.

The title compound of Example 277 is prepared from 5-Amino-3-methylsulfanyl-1-phenyl-1H-pyrazole-4-carboxylic acid ethyl ester following the procedures described Example 1.

$^1$H NMR (CDCl$_3$, 400 MHz) δ 8.08 (d, 2H), 7.47 (m, 4H), 7.33 (m, 2H), 7.18 (m, 3H), 6.95 (m, 1H), 2.73 (s, 3H). HPLC-MS calculated for $C_{24}H_{15}BrCl_2N_4OS$ (M+H$^+$) 557.0. Found 557.0.

Example 278

5-(4-Bromo-phenyl)-6-(2,4-dichloro-phenyl)-3-methanesulfonyl-1-phenyl-1,5-dihydro-pyrazolo[3,4-d]pyrimidin-4-one

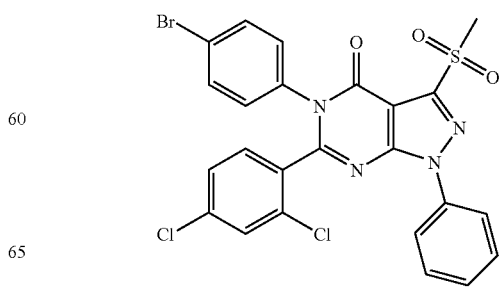

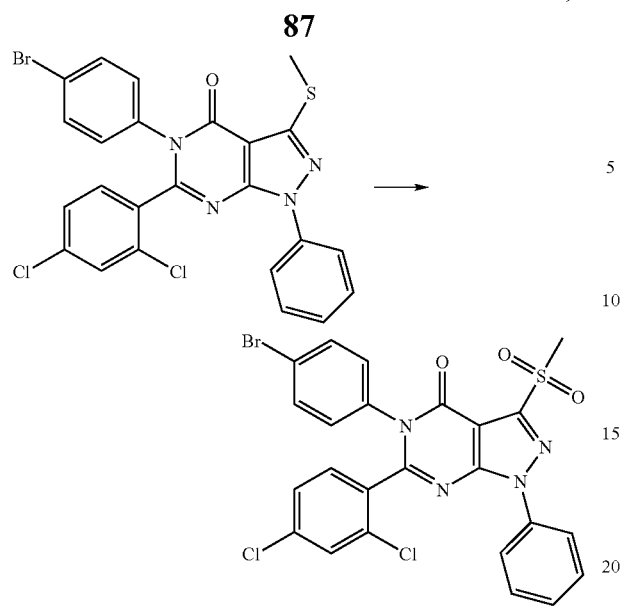

5-(4-Bromo-phenyl)-6-(2,4-dichloro-phenyl)-3-methyl-sulfanyl-1-phenyl-1,5-dihydro-pyrazolo[3,4-d]pyrimidin-4-one (200 mg, 0.358 mmol) is dissolved in 10 mL of dichloromethane. mCPBA (254 mg, 1.07 mmol) is added and the reaction mixture is stirred overnight. The reaction mixture is workuped with aqueous sodium bicarbonate and purified by flash chromatography. $^1$H NMR (CDCl$_3$, 400 MHz) δ 8.05 (d, 2H), 7.59-7.40 (m, 5H), 7.35 (m, 1H), 7.21 (dd, 2H), 7.16 (d, 1H), 6.98 (m, 1H), 3.54 (s, 3H). HPLC-MS calculated for C$_{24}$H$_{15}$BrCl$_2$N$_4$O$_3$S (M+H$^+$) 591.0. Found 591.0.

Example 280

5-(4-Chloro-phenyl)-6-(2,4-dichloro-phenyl)-1-(4-hydroxymethyl-phenyl)-1,5-dihydro-pyrazolo[3,4-d]pyrimidin-4-one

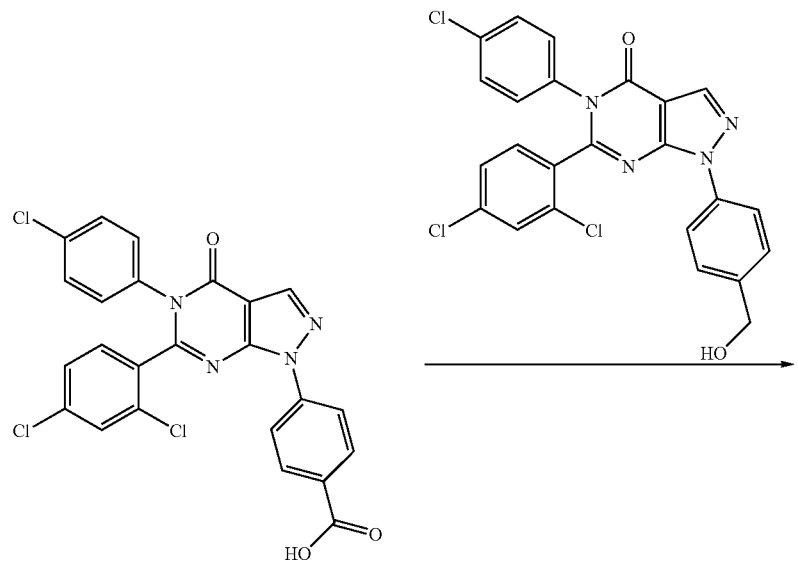

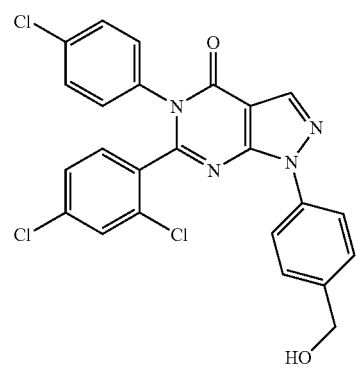

4-[5-(4-Chloro-phenyl)-6-(2,4-dichloro-phenyl)-4-oxo-4,5-dihydro-pyrazolo[3,4-d]pyrimidin-1-yl]-benzoic acid (115 mg, 0.225 mmol) is dissolved in 6 mL of THF. To the solution TEA (68.0 mg, 0.674 mmol) and isobutylchloroformate (46.0 mg, 0.337 mmol) are added and the mixture is stirred for 1.5 h. The resulting mixture is added to a solution of sodium borohydride (33.3 mg, 0.898 mmol) in 3 mL of water and then stirred for 3 h, concentrated, and extracted with water/ethyl acetate and purified by column chromatography. $^1$H NMR (dioxane, 400 MHz) δ 8.33 (s, 1H), 8.00 (d, 2H), 7.45 (s, 1H), 7.39 (d, 2H), 7.16 (d, 1H), 7.29-7.19 (m, 5H), 7.03 (m, 1H), 4.53 (d, 2H), 3.71 (t, 1H). HPLC-MS calculated for $C_{24}H_{15}Cl_3N_4O_2$ (M+H$^+$) 497.0, Found 497.0.

Example 281

5-(4-Chloro-phenyl)-6-(2,4-dichloro-phenyl)-1-[4-(4-methyl-piperazine-1-carbonyl)-phenyl]-1,5-dihydro-pyrazolo[3,4-d]pyrimidin-4-one

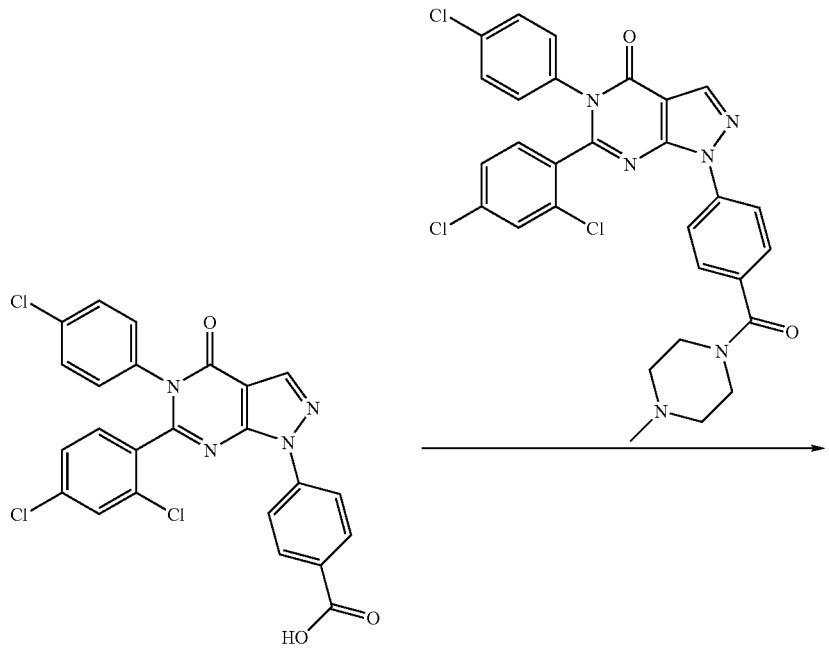

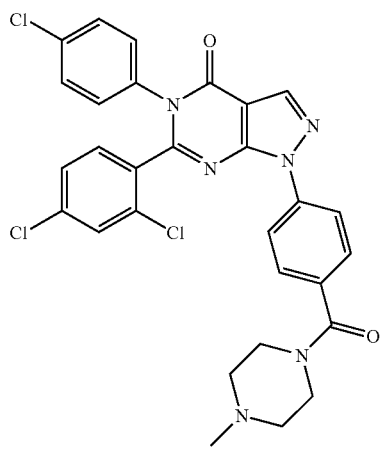

4-[5-(4-Chloro-phenyl)-6-(2,4-dichloro-phenyl)-4-oxo-4,5-dihydro-pyrazolo[3,4-d]pyrimidin-1-yl]-benzoic acid (54.1 mg, 0.106 mmol) is dissolved in 1 mL of thionyl chloride and stirred for 1 h at reflux. The thionyl chloride is then removed under a stream of dry nitrogen and the resulting solid is dissolved in 2 mL of dry dichloromethane. N-methylpiperazine (500 mg, 5.00 mmol) is then added to the solution and the reaction mixture is stirred for 2 h. After the volatiles are evaporated, the resulting residue is dissolved in 1 M NaOH and extracted with ethyl acetate. The crude product is purified by column chromatography. $^1$H NMR (CDCl$_3$, 400 MHz) δ 8.36(s, 1H), 8.28 (d, 2H), 7.57 (d, 2H), 7.36-7.29 (m, 3H), 7.23-7.16 (m, 2H), 7.03 (m, 1H), 3.97 (m, 3H), 3.48 (m, 2H), 2.83 (m, 6H). HPLC-MS calculated for $C_{29}H_{23}Cl_3N_6O_2$ (M+H$^+$) 593.1. Found: 593.1.

Example 284

5-(4-Chloro-phenyl)-6-(2,4-dichloro-phenyl)-1-[4-(4-methyl-piperazin-1-ylmethyl)-phenyl]-1,5-dihydro-pyrazolo[3,4-d]pyrimidin-4-one

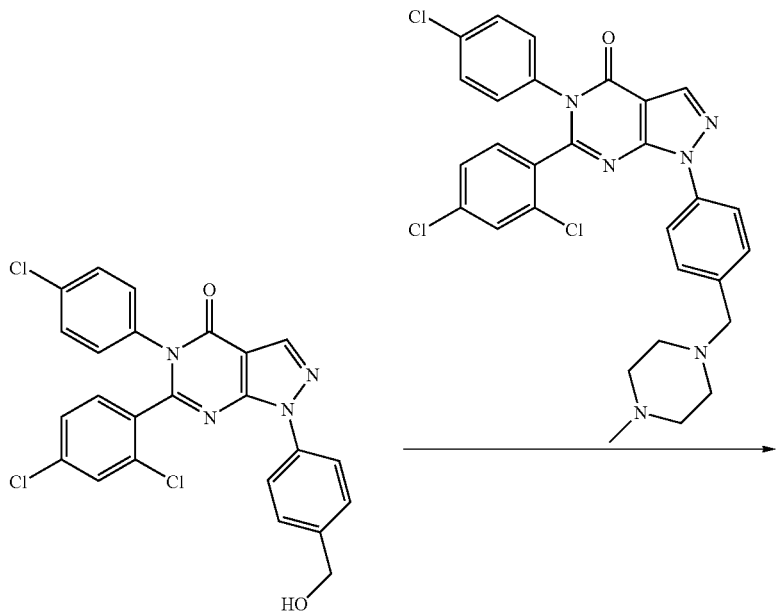

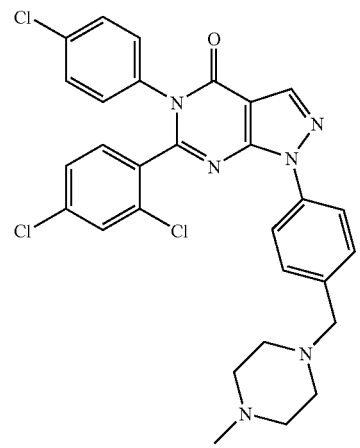

5-(4-Chloro-phenyl)-6-(2,4-dichloro-phenyl)-1-(4-hydroxymethyl-phenyl)-1,5-dihydro-pyrazolo[3,4-d]pyrimidin-4-one (90.0 mg, 0.181 mmol) is dissolved in 10 mL of CH$_2$Cl$_2$. Trichloroisocyanuric acid (42.0 mg, 0.181 mmol) and TEMPO (1 mg) are added sequentially to the reaction mixture. The reaction mixture is allowed to stir for 30 min and the organic layer is washed with sodium bicarbonate and water, thus resulting in pure aldehyde. A portion of the aldehyde (40.0 mg, 0.0807 mmol) is dissolved in 2 mL of dry methanol. 200 µL of acetic acid and 100 µL of N-methylpiperazine are added to the reaction mixture and the mixture is allowed to stir for 10 min at room temp. Sodium cyanoborohydride (15 mg, 0.238 mmol) is added and the reaction mixture is stirred for 10 min and then quenched with ammonium hydroxide. The crude material is purified by column chromatography. $^1$H NMR (CDCl$_3$, 400 MHz) δ 8.34(s, 1H), 8.06 (d, 2H), 7.44 (m, 2H), 7.34-7.28 (m, 3H), 7.18 (m, 2H), 7.03 (m, 1H), 5.31 (s, 2H), 3.66 (m, 2H), 2.89 (m, 6H), 2.71 (s, 3H). HPLC-MS calculated for C$_{29}$H$_{25}$Cl$_3$N$_6$O (M+H$^+$) 579.1. Found: 579.1.

Example 287

1-(4-Chloro-phenyl)-8-(ethyl-methyl-amino)-9-phenyl-2-(4-trifluoromethyl-phenyl)-1,9-dihydro-purin-6-one

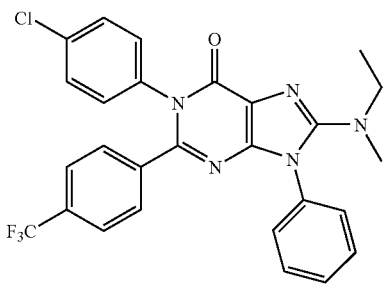

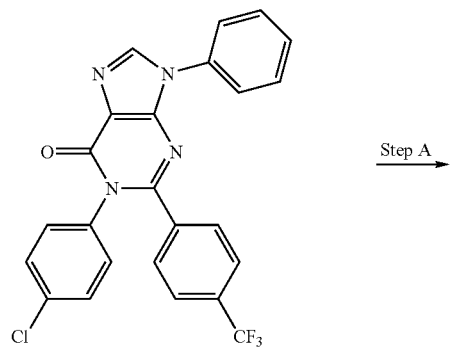 Step A →

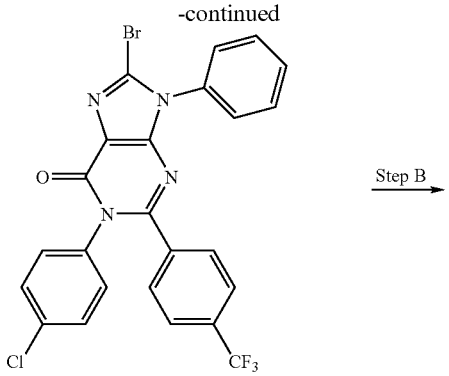 Step B →

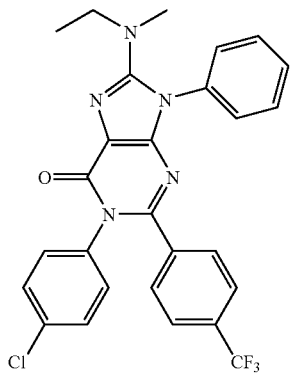

Step A: 1-(4-Chloro-phenyl)-9-phenyl-2-(4-trifluoromethyl-phenyl)-1,9-dihydro-purin-6-one (50.0 mg, 0.107 mmol) and sodium acetate (300 mg) are dissolved in 10 mL of acetic acid. 250 µLs of bromine is added and the reaction mixture is stirred for 3 h. After the volatile is evaporated, the residue is partitioned with DCM and water. The organic layer is collected and evaporated to dryness. The crude material is purified by column chromatography, yielding 78 mg (84%) of 8-Bromo-1-(4-chloro-phenyl)-9-phenyl-2-(4-trifluoromethyl-phenyl)-1,9-dihydro-purin-6-one. $^1$H NMR (DMSO, 400 MHz) δ 7.63 (m, 5H), 7.57 (d, 2H), 7.50 (d, 2H), 7.43 (d, 2H), 7.39 (d, 2H). HPLC-MS calculated for C$_{24}$H$_{13}$BrClF$_3$N$_4$O (M+H$^+$) 545.0. Found 545.0.

Step B: 8-Bromo-1-(4-chloro-phenyl)-9-phenyl-2-(4-trifluoromethyl-phenyl)-1,9-dihydro-purin-6-one (19.0 mg, 0.0348 mmol), potassium carbonate (400 mg, 2.89 mmol), and ethyl-methyl-amine (172 mg, 2.91 mmol) are mixed in a microwave tube with 1 mL of dry acetonitrile. The tube is then capped and heated to 200° C. for 40 min in a microwave reactor. Then the reaction mixture is diluted with CH$_2$Cl$_2$ and filtered. The filtrate is evaporated and the crude product is purified by column chromatography, yielding 9 mg (49%) of the title compound. $^1$H NMR (CDCl$_3$, 400 MHz) δ 7.54 (m, 4H), 7.47 (m, 1H), 7.42 (d, 2H), 7.30 (d, 4H), 7.08 (d, 2H), 3.17 (q, 2H), 2.90 (s, 3H), 1.03 (t, 3H). HPLC-MS calculated for C$_{27}$H$_{21}$ClF$_3$N$_5$O (M+H$^+$) 524.1. Found: 524.1.

Example 289
1-(4-Chloro-phenyl)-6-oxo-9-phenyl-2-(4-trifluoromethyl-phenyl)-6,9-dihydro-1H-purine-8-carbonitrile
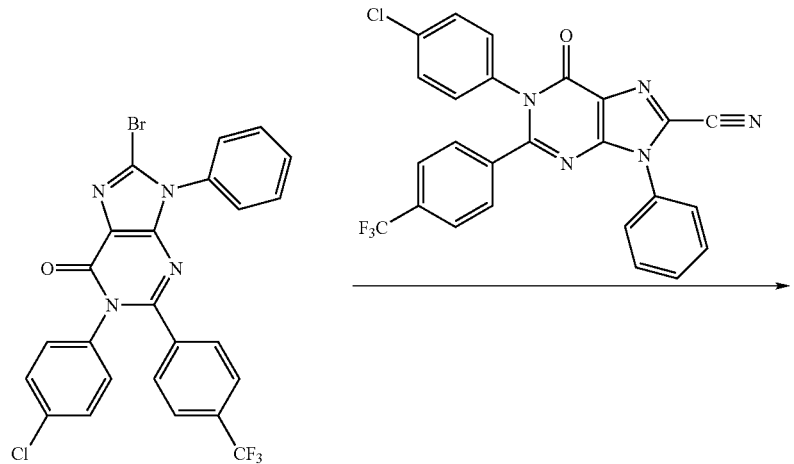
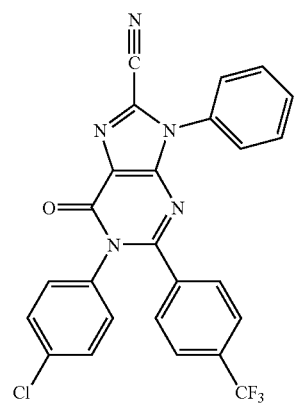

8-Bromo-1-(4-chloro-phenyl)-9-phenyl-2-(4-trifluoromethyl-phenyl)-1,9-dihydro-purin-6-one (10.0 mg, 0.0183 mmol), potassium cyanide (110 mg, 1.68 mmol) and 18-crown-6 (12.0 mg, 0.0454 mmol) are added to a microwave tube with 1 mL of dry acetonitrile. The tube is capped and heated to 200° C. for 45 min in microwave reactor. The reaction mixture is then filtered and the filtrate is evaporated to dryness. The crude material is purified by column chromatography, yielding 6.2 mg (69%) of the title compound. $^1$H NMR (CDCl$_3$, 400 MHz) δ 7.64 (m, 5H), 7.52 (d, 2H), 7.38 (m, 4H), 7.12 (d, 2H). HPLC-MS calculated for C$_{25}$H$_{13}$ClF$_3$N$_5$O (M+H$^+$) 492.1. Found: 492.1.

Example 297

1-(4-Chloro-phenyl)-2-(2,4-dichloro-phenyl)-8-methoxy-9-phenyl-1,9-dihydro-purin-6-one

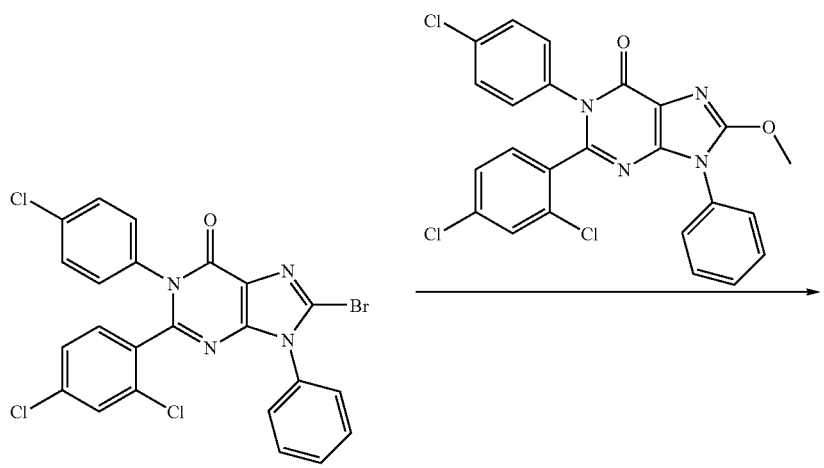

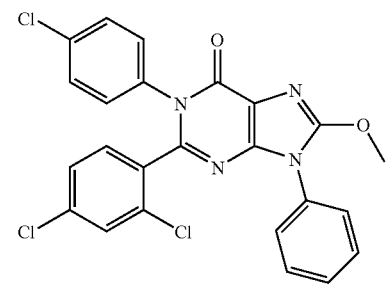

A microwave tube is charged with sodium hydride (24.0 mg, 1.0 mmol) and dry methanol. After the reaction mixture is stirred for 3 min, 8-Bromo-1-(4-chloro-phenyl)-2-(2,4-dichloro-phenyl)-9-phenyl-1,9-dihydro-purin-6-one (8.0 mg, 0.015 mmol) is added. The tube is then capped and the mixture is heated in an oil bath for 3 h at 80° C. The reaction mixture is worked up by evaporating the solvent. The crude material is purified by flash chromatography. 1H NMR (CDCl3, 400 MHz) δ 7.63 (m, 4H), 7.43 (m, 1H), 7.28 (m, 4H), 7.11 (d, 2H), 7.03 (m, 1H), 4.25 (s, 3H). HPLC-MS calculated for $C_{24}H_{15}Cl_3N_4O_2$ (M+H+) 497.0. Found: 497.0.

Example 303

6-(4-bromo-phenyl)-2-methyl-3-phenyl-5-p-tolyl-2,6-dihydro-pyrazolo[4,3-d]pyrimidin-7-one

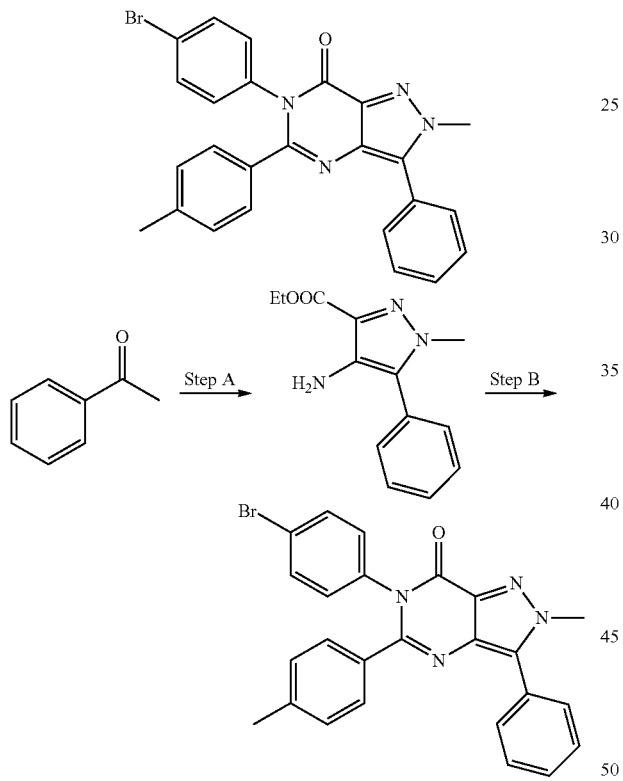

Step A: 4-Amino-1-methyl-5-phenyl-1H-pyrazole-3-carboxylic acid ethyl ester is prepared from acetophenone, using the condition described in Yuan, J.; Gulianello, M.; De Lombaert, S.; Brodbeck, R.; Kieltyka, A.; Hodgetts, K. J. *Bioorg. Med. Chem. Lett.* 2002, 2133; HPLC-MS calculated for $C_{13}H_{15}N_3O_2$ (M+H+) 246.1. Found 246.1.

Step B: 6-(4-Bromo-phenyl)-2-methyl-3-phenyl-5-p-tolyl-2,6-dihydro-pyrazolo[4,3-d]pyrimidin-7-one is prepared as described in Example 2, using 4-amino-1-methyl-5-phenyl-1H-pyrazole-3-carboxylic acid ethyl ester from step A instead of ethyl 5-amino-1-phenyl-4-pyrazole-carboxylate; $^1$H NMR (CDCl$_3$, 400 MHz) δ 7.66 (d, 2H), 7.54 (t, 2H), 7.47 (t, 1H), 7.43 (d, 2H), 7.13 (d, 2H), 7.03 (d, 2H), 6.98 (d, 2H), 4.19 (s, 3H), 2.26 (s, 3H); HPLC-MS calculated for $C_{25}H_{19}BrN_4O$ (M+H+) 471.1. Found 471.1.

Alternatively, 6-(4-Bromo-phenyl)-2-methyl-3-phenyl-5-p-tolyl-2,6-dihydro-pyrazolo[4,3-d]pyrimidin-7-one can also be prepared as a minor by-product as to be described in Example 304.

Example 304

6-(4-bromo-phenyl)-1-methyl-3-phenyl-5-p-tolyl-1,6-dihydro-pyrazolo[4,3-d]pyrimidin-7-one

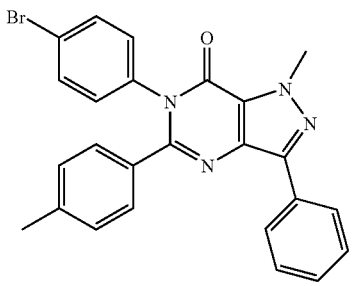

To a solution of 6-(4-bromo-phenyl)-3-phenyl-5-p-tolyl-1,6-dihydro-pyrazolo[4,3-d]pyrimidin-7-one (11.0 mg, 0.024 mmol) in acetonitrile (0.3 mL) are added K$_2$CO$_3$ (6.6 mg, 0.048 mmol) and MeI (5.99 μL, 0.096 mmol). The reaction mixture is stirred at room temperature for overnight before the removal of K$_2$CO$_3$ by filtration. The filtrate is concentrated and purified by preparative LC/MS to provide the title compound; $^1$H NMR (CDCl$_3$, 400 MHz) δ 8.36 (d, 2H), 7.47 (t, 2H), 7.44 (d, 2H), 7.35 (t, 1H), 7.22 (d, 2H), 7.04 (m, 4H), 4.37 (s, 3H), 2.31 (s, 3H); HPLC-MS calculated for $C_{25}H_{19}BrN_4O$ (M+H+) 471.1. found: 471.1.

6-(4-Bromo-phenyl)-2-methyl-3-phenyl-5-p-tolyl-2,6-dihydro-pyrazolo[4,3-d]pyrimidin-7-one in Example 303 is also prepared in this reaction as a minor by-product.

Example 305

6-(4-chloro-phenyl)-5-(4-isopropyl-phenyl)-1-methanesulfonyl-3-phenyl-1,6-dihydro-pyrazolo[4,3-d]pyrimidin-7-one

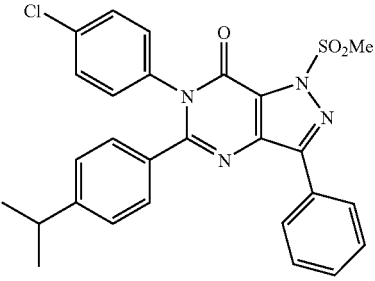

To a solution of 6-(4-chloro-phenyl)-5-(4-isopropyl-phenyl)-3-phenyl-1,6-dihydro-pyrazolo[4,3-d]pyrimidin-7-one (20.0 mg, 0.045 mmol) in DCM (0.5 mL) are added MsCl (7.05 μL, 0.091 mmol) and TEA (12.64 μL, 0.091 mmol). The reaction mixture is stirred at room temperature for overnight before removal of the solvent, The residue is purified by preparative LC/MS to provide the title compound; $^1$H NMR (CDCl$_3$, 400 MHz) δ 8.47 (dd, 2H), 7.48 (m, 3H), 7.34 (d, 2H), 7.28 (d, 2H), 7.14 (m, 4H), 3.77 (s, 3H), 2.87 (m, 1H), 1.22 (s, 3H), 1.21 (s, 3H); HPLC-MS calculated for $C_{27}H_{23}ClN_4O_3S$ (M+H$^+$) 519.1. Found: 519.1.

Example 306

6-(4-chloro-phenyl)-5-(4-isopropyl-phenyl)-7-oxo-3-phenyl-6,7-dihydro-pyrazolo[4,3-d]pyrimidine-1-carboxylie acid dimethylamide

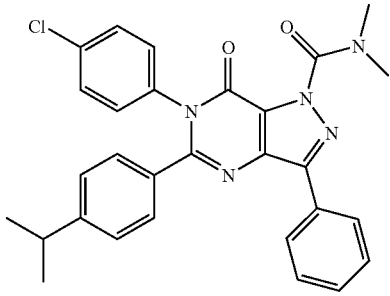

To a solution of 6-(4-chloro-phenyl)-5-(4-isopropyl-phenyl)-3-phenyl-1,6-dihydro-pyrazolo[4,3-d]pyrimidin-7-one (20.0 mg, 0.045 mmol) in anhydrous pyridine (0.3 mL) is added dimethylcarbamyl chloride (41.6 µL, 0.45 mmol). The reaction mixture is stirred at room temperature for overnight before removal of the solvent. The residue is purified by preparative LC/MS to provide the title compound; $^1$H NMR (CDCl$_3$, 400 MHz) δ 8.43 (dd, 2H), 7.48 (t, 2H), 7.41 (t, 1H), 7.30 (d, 2H), 7.27 (d, 2H), 7.11 (m, 4H), 3.24 (s, 3H), 3.12 (s, 3H), 2.86 (m, 1H), 1.22 (s, 3H), 1.20 (s, 3H); HPLC-MS calculated for $C_{79}H26ClN_5O_2$ (M+H$^+$) 512.2. Found 512.2.

Example 311

5-(4-chloro-phenyl)-6-[4-(1-oxy-pyridin-4-yl)-phenyl]-phenyl-1,5-dihydro-pyrazolo[3,4-d]pyrimidin-4-one

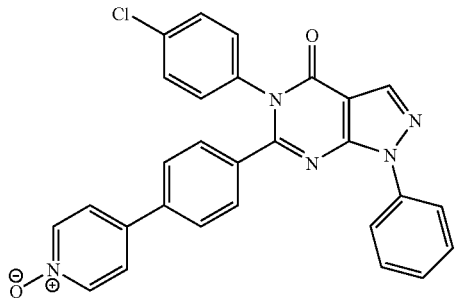

To a solution of 5-(4-chloro-phenyl)-1-phenyl-6-(4-pyridin-4-yl-phenyl)-1,5-dihydro-pyrazolo[3,4-d]pyrimidin-4-one (15.0 mg, 0.032 mmol) in DCM (0.3 mL) are added mCPBA (12.0 mg, 77%, 0.054 mmol) and NaHCO$_3$ (9.0 mg, 0.107 mmol). The reaction mixture is stirred at room temperature for overnight before removal of the solvent. The residue is taken in water (1.5 mL) and extracted with ethyl acetate (3×1 mL). The combined ethyl acetate layer is concentrated and purified by preparative LC/MS to provide the title compound; $^1$H NMR (CDCl$_3$, 400 MHz) δ 8.53 (d, 2H), 8.36 (s, 1H), 8.12 (d, 2H), 7.72 (d, 2H), 7.53 (m, 6H), 7.38 (t, 1H), 7.35 (d, 2H), 7.13 (d, 2H); HPLC-MS calculated for $C_{28}H_{18}ClN_5O_2$ (M+H$^+$) 492.1. Found: 492.1.

Example 314

6-(4-chloro-phenyl)-5-(4-isopropyl-phenyl)-3-phenyl-6H-isoxazolo[4,3-d]pyrimidin-7-one

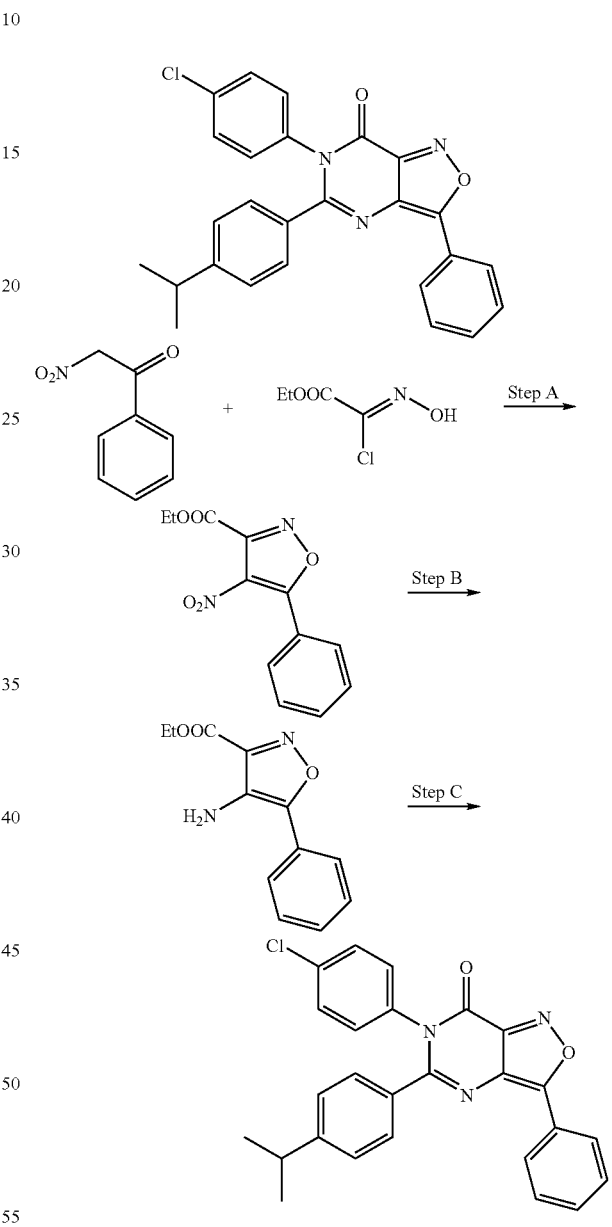

Step A: 4-Nitro-5-phenyl-isoxazole-3-carboxylic acid ethyl ester is prepared from benzoylnitromethane and ethyl chlorooximinoacetate, using the condition described in Dal Piaz, V.; Pinzauti, S.; Lacrimini, P. *Synthesis* 1975, 664; $^1$H NMR (CDCl$_3$, 400 MHz) δ 7.93 (d, 2H), 7.65 (t, 1H), 7.58 (t, 2H), 4.53 (q, 2H), 1.44 (t, 3H); HPLC-MS calculated for $C_{12}H_{10}N_2O_5$ (M+H$^+$) 263.1. Found 263.1.

Step B: To a solution of 4-nitro-5-phenyl-isoxazole-3-carboxylic acid ethyl ester (73.0 mg, 0.278 mmol) in EtOH (2.0 mL) is added Raney Ni and the mixture is stirred under hydrogen (balloon) for overnight. The reaction mixture is then filtered through Celite and evaporated in vacuo to provide crude 4-amino-5-phenyl-isoxazole-3-carboxylic acid ethyl ester (61.7 mg, 95% yield); HPLC-MS calculated for $C_{12}H_{12}N_2O_3$ (M+H⁺) 233.1. Found: 233.1.

Step C: A suspension of N-(4-chloro-phenyl)-4-isopropyl-benzamide (20.0 mg, 0.073 mmol) in thionyl chloride (0.5 mL) is heated at 80° C. for 1.5 h before thionyl chloride is removed in vacuo. The reaction residue is then taken in anhydrous acetonitrile (1.5 mL), followed by the addition of 4-amino-5-phenyl-isoxazole-3-carboxylic acid ethyl ester from step B (18.7 mg, 0.081 mmol) and anhydrous $K_2CO_3$ (25.2 mg, 0.182 mmol). The reaction mixture is heated under nitrogen atmosphere at 180° C. in a microwave for 2 h, then cooled down to room temperature. $K_2CO_3$ is removed by filtration. The filtrate is concentrated and purified by preparative LC/MS to provide the title compound; ¹H NMR (CDCl₃, 400 MHz) δ 8.37 (dd, 2H), 7.53 (m, 3H), 7.31 (d, 2H), 7.25 (d, 2H), 7.11 (m, 4H), 2.87 (m, 1H), 1.22 (s, 3H), 1.20 (s, 3H); HPLC-MS calculated for $C_{26}H_{20}ClN_3O_2$ (M+H⁺) 442.1. Found: 442.2.

Example 318

2-[6-(4-chloro-phenyl)-5-(4-isopropyl-phenyl)-7-oxo-3-phenyl-6,7-dihydro-pyrazolo[4,3-d]pyrimidin-1-yl]-acetamide

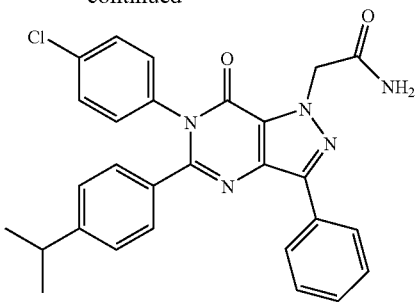

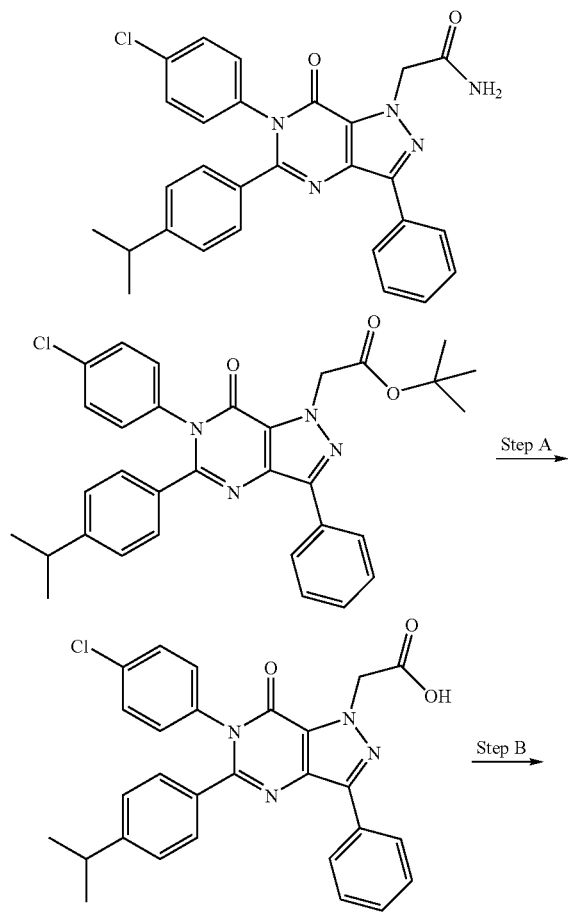

Step A: To [6-(4-chloro-phenyl)-5-(4-isopropyl-phenyl)-7-oxo-3-phenyl-6,7-dihydro-pyrazolo[4,3-d]pyrimidin-1-yl]-acetic acid tert-butyl ester (20.0 mg, 0.036 mmol) are added DCM (0.5 mL) and TFA (0.5 mL), The resultant solution is stirred at room temperature for 4 hours. Removal of the solvent under reduced pressure provides crude [6-(4-chlorophenyl)-5-(4-isopropyl-phenyl)-7-oxo-3-phenyl-6,7-dihydro-pyrazolo[4,3-d]pyrimidin-1-yl]-acetic acid, which is used directly for next reaction without further purification.

Step B: A solution of the crude [6-(4-chloro-phenyl)-5-(4-isopropyl-phenyl)-7-oxo-3-phenyl-6,7-dihydro-pyrazolo[4,3-d]pyrimidin-1-yl]-acetic acid prepared from previous step, HATU (41.1 mg, 0.108 mmol) and ⁱPr₂NEt (37.6 μL, 0.216 mmol) in DMF (0.5 mL) is stirred at room temperature for 1 hour before transferred dropwise into 7 N ammonia in methanol solution (1.0 mL) at 0° C. The resultant reaction mixture is stirred at room temperature for 1 hour before removal of the solvent under reduced pressure. The residue is purified by preparative LC/MS to provide the title compound; HPLC-MS calculated for $C_{28}H_{24}ClN_5O_2$ (M+H⁺) 498.2. Found 498.2.

Example 320

[6-(4-chloro-phenyl)-5-(4-isopropyl-phenyl)-7-oxo-3-phenyl-6,7-dihydro-pyrazolo[4,3-d]pyrimidin-1-yl]-acetonitrile

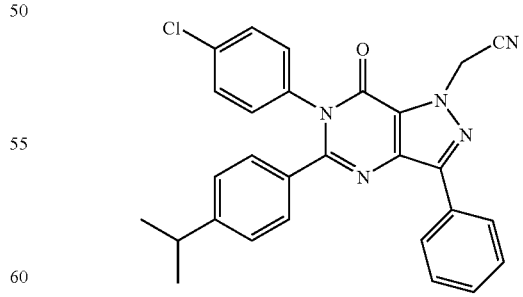

A mixture of 2-[6-(4-chloro-phenyl)-5-(4-isopropyl-phenyl)-7-oxo-3-phenyl-6,7-dihydro-pyrazolo[4,3-d]pyrimidin-1-yl]-acetamide (10.0 mg, 0.020 mmol) and POCl₃ (0.5 mL) is heated at 100° C. for 30 minutes. Upon completion, excess POCl₃ is removed under reduced pressure. The residue is purified by preparative LC/MS to provide the title compound; HPLC-MS calculated for $C_{28}H_{22}ClN_5O$ (M+H$^+$) 480.1. Found 480.1.

Example 327

6-(4-chloro-phenyl)-5-(4-isopropyl-phenyl)-3-phenyl-6H-isoxazolo[4,5-d]pyrimidin-7-one

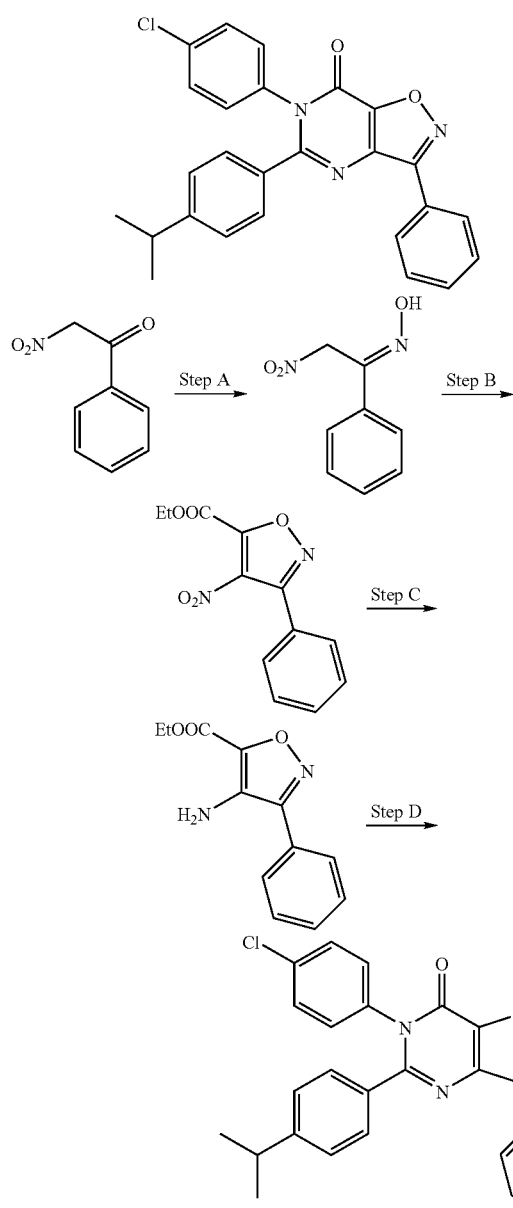

Step A: A solution of benzoylnitromethane (300.0 mg, 1.82 mmol) and NH$_2$OHHCl (126.2 mg, 1.82 mmol) in EtOH (1.5 mL) and acetic acid (0.5 mL) is heated at 100° C. for 7 hours. After cooled down to room temperature, the reaction mixture is taken in H$_2$O (20 mL) and extracted with ethyl acetate (3×10 mL). The combined ethyl acetate layer is dried over MgSO$_4$ and evaporated in vacuo to provide crude 2-nitro-1-phenyl-ethanone oxime, which is used directly in next step without further purification.

Step B: To a solution of the crude 2-nitro-1-phenyl-ethanone oxime from previous step in anhydrous ether (2.0 mL) is added ethyl oxalyl chloride (195.2 μL, 1.74 mmol). The reaction mixture is stirred at room temperature for overnight before the addition of TEA (202.6 μL, 1.45 mmol). The reaction mixture is then stirred at room temperature for another 2 days before removal of the solvents. The residue is purified by reverse phase HPLC to provide 4-nitro-3-phenyl-isoxazole-5-carboxylic acid ethyl ester as an oil-like product (299.0 mg, 63% yield); HPLC-MS calculated for $C_{12}H_{10}N_2O_5$ (M+H$^+$) 263.1. Found: 263.1.

Step C: To a solution of 4-nitro-3-phenyl-isoxazole-5-carboxylic acid ethyl ester (62.3 mg, 0.238 mmol) in EtOH (2.0 mL) is added Raney Ni and the mixture is stirred under hydrogen (balloon) for overnight. The reaction mixture is then filtered through celite and evaporated in vacuo to provide crude 4-amino-3-phenyl-isoxazole-5-carboxylic acid ethyl ester (53.3 mg, 97% yield); HPLC-MS calculated for $C_{12}H_{12}N_2O_3$ (M+H$^+$) 233.1. Found: 233.1.

Step D: 6-(4-Chloro-phenyl)-5-(4-isopropyl-phenyl)-3-phenyl-6H-isoxazolo[4,5-d]pyrimidin-7-one is prepared as described in Example 2, using 4-amino-3-phenyl-isoxazole-5-carboxylic acid ethyl ester from step C instead of ethyl 5-amino-1-phenyl-4-pyrazole-carboxylate, and N-(4-chloro-phenyl)-4-isopropyl-benzamide instead of N-(4 bromo-phenyl)-4-methyl-benzamide; $^1$H NMR (CDCl$_3$, 400 MHz) δ 8.42 (dd, 2H), 7.53 (m, 3H), 7.34 (d, 2H), 7.25 (d, 2H), 7.12 (m, 4H), 2.87 (m, 1H), 1.22 (s, 3H), 1.20 (s, 3H); HPLC-MS calculated for $C_{26}H_{20}ClN_3O_2$ (M+H$^+$) 442.1. Found 442.1.

Example 330

6-[4-(6-amino-pyridin-3-yl)-phenyl]-5-(4-chloro-phenyl)-1-phenyl-1,5-dihydro-pyrazolo[3,4-d]pyrimidin-4-one

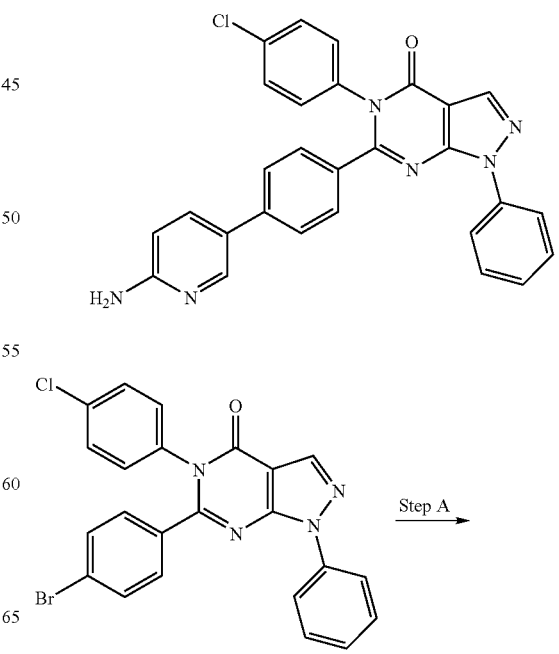

-continued

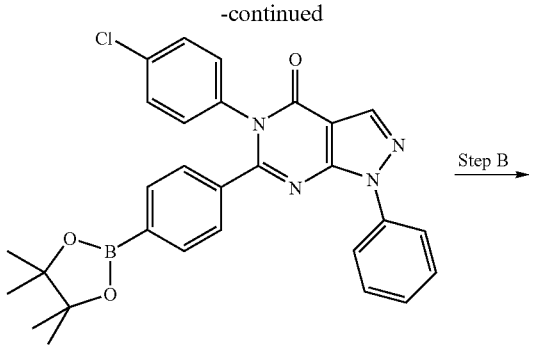

Step B

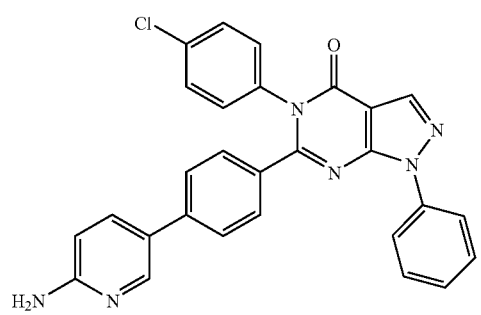

Step A: A reaction tube charged with 6-(4-bromo-phenyl)-5-(4-chloro-phenyl)-1-phenyl-1,5-dihydro-pyrazolo[3,4-d]pyrimidin-4-one (2.85 g, 5.97 mmol), bis(pinacolato)diboron (1.74 g, 6.85 mmol), KOAc(1.76 g, 17.9 mmol), and Pd(dppf)$_2$Cl$_2$ (0.15 g, 0.184 mmol) is purged with nitrogen. Anhydrous DMF (24.0 mL) is added via syringe. The reaction mixture is heated at 100° C. for 2 hours, taken in H$_2$O (300 mL), and extracted with ethyl acetate (3×100 mL). The combined organic phase is washed with brine, dried over MgSO$_4$, concentrated, and purified by silica gel chromatography to provide 5-(4-chloro-phenyl)-1-phenyl-6-[4-(4,4,5,5-tetramethyl-[1,3,2]dioxaborolan-2-yl)-phenyl]-1,5-dihydro-pyrazolo[3,4-d]pyrimidin-4-one (2.50 g, 80% yield) as a white solid product; HPLC-MS calculated for C$_{26}$H$_{17}$ClN$_6$O (M+H$^+$) 525.2. Found 525.2.

Step B: A reaction tube charged with 5-(4-chloro-phenyl)-1-phenyl-6-[4-(4,4,5,5-tetramethyl-[1,3,2]dioxaborolan-2-yl)-phenyl]-1,5-dihydro-pyrazolo[3,4-d]pyrimidin-4-one (500.0 mg, 0.953 mmol), 2-amino-5-bromopyridine (247.3 mg, 1.43 mmol), Cs$_2$CO$_3$ (620.8 mg, 1.91 mmol), and Pd(dppf)$_2$Cl$_2$ (38.9 mg, 0.048 mmol) is purged with nitrogen. Anhydrous DMF (9.5 mL) is added via syringe. The reaction mixture is heated at 100° C. for overnight, cooled down to room temperature, then taken in H$_2$O (100 mL) and ethyl acetate (50 mL). The insoluble solid is filtered off and the two layers of the filtrate are separated. The aqueous layer is extracted with ethyl acetate (2×50 mL). The combined organic phase is washed with brine, dried over MgSO$_4$, concentrated, and purified by reverse phase HPLC to provide 6-[4-(6-amino-pyridin-3-yl)-phenyl]-5-(4-chloro-phenyl)-1-phenyl-1,5-dihydro-pyrazolo[3,4-d]pyrimidin-4-one (244.2 mg, 52% yield) as a light yellow solid product; $^1$H NMR (CDCl$_3$, 400 MHz) δ 8.33 (s, 1H), 8.28 (d, 1H), 8.16 (d, 2H), 7.66 (dd, 1H), 7.51 (t, 2H), 7.40 (m, 4H), 7.35 (m, 3H), 7.13 (d, 2H), 6.59 (d, 1H), 4.72 (br, 2H); HPLC-MS calculated for C$_{28}$H$_{19}$ClN$_6$O (M+H$^+$) 491.1. Found 491.1.

Example 332

5-(4-chloro-phenyl)-6-[4-(1H-imidazol-2-yl)-phenyl]-1-phenyl-1,5-dihydro-pyrazolo[3,4-d']pyrimidin-4-one

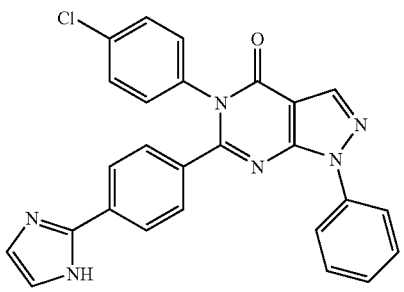

Imidazole (15.6 mg, 0.229 mmol) and MgO (9.2 mg, 0.228 mmol) are suspended in dry 1,4-dioxane (1.0 mL) and stirred at room temperature for 10 minutes to get a homogenous suspension. CuI (14.5 mg, 0.076 mmol), Pd(OAc)$_2$ (0.4 mg, 0.002 mmol) and PPh$_3$ (2.0 mg, 0.008 mmol) are added to the reaction mixture. The reaction tube is then sealed and purged with nitrogen. 5-(4-Chloro-phenyl)-6-(4-iodo-phenyl)-1-phenyl-1,5-dihydro-pyrazolo[3,4-d]pyrimidin-4-one (20.0 mg, 0.038 mmol) is dissolved in dry 1,4-dioxane (0.5 mL), added dropwise to this solution via syringe, and the mixture is heated at 150° C. for overnight. The mixture is then diluted with ethyl acetate (10 mL) and filtered through celite. The solvents are evaporated in vacuo and the residue is purified by preparative TLC followed by preparative LC/MS to provide the title compound; HPLC-MS calculated for C$_{26}$H$_{17}$ClN$_6$O (M+H$^+$) 465.1. Found: 465.1. Detailed conditions of the C-arylation reaction are described in Sezen, B.; Sames, D. *J. Am. Chem. Soc.* 2003, 125, 5274.

Example 334

5-(4-chloro-phenyl)-6-[4-(2-methyl-1-oxy-pyridin-4-yl)-phenyl]-1-phenyl-1,5-dihydro-pyrazolo[3,4-d]pyrimidin-4-one

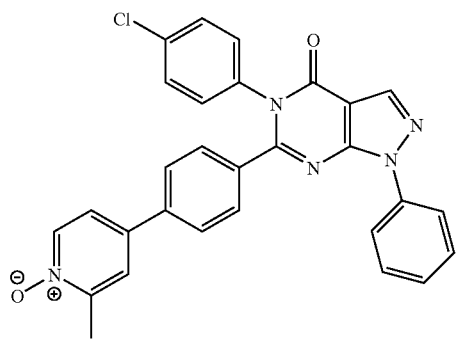

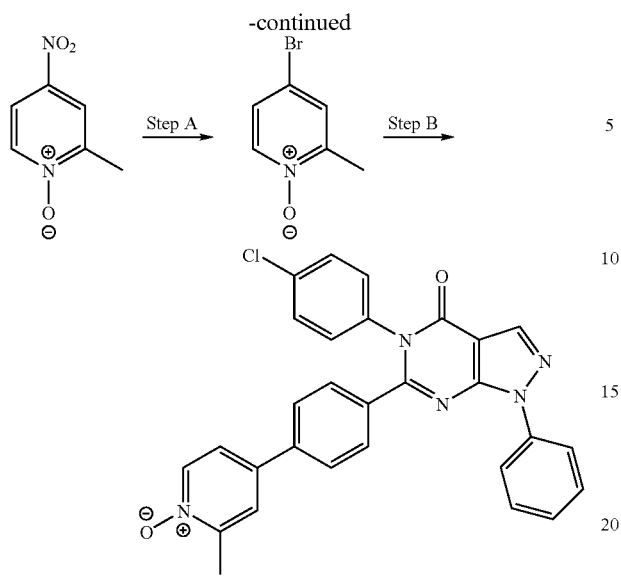

Step A: 4-Bromo-2-methyl-pyridine 1-oxide is prepared from 2-methyl-4-nitro-pyridine 1-oxide, using the condition described in U.S. Pat. No. 5,705,499 (Example 67); HPLC-MS calculated for $C_6H_6BrNO$ (M+H$^+$) 188.0. Found 188.0.

Step B: 5-(4-Chloro-phenyl)-6-[4-(2-methyl-1-oxy-pyridin-4-yl)-phenyl]-1-phenyl-1,5-dihydro-pyrazolo[3,4-d]pyrimidin-4-one is prepared as described in Example 330 (step B), using 4-bromo-2-methyl-pyridine 1-oxide from step A instead of 2-amino-5-bromopyridine; $^1$H NMR (CDCl$_3$, 400 MHz) δ 8.60 (d, 1H), 8.36 (s, 1H), 8.12 (d, 2H), 7.65 (s, 1H), 7.54 (m, 7H), 7.38 (t, 1H), 7.35 (d, 2H), 7.13 (d, 2H), 2.73 (s, 3H); HPLC-MS calculated for $C_{29}H_{20}ClN_5O_2$ (M+H$^+$) 506.1. Found: 506.1.

Example 337

5-(4-chloro-phenyl)-6-[4-(6-oxo-1,6-dihydro-pyridin-3-yl)-phenyl]-1-phenyl-1,5-dihydro-pyrazolo[3,4-d]pyrimidin-4-one

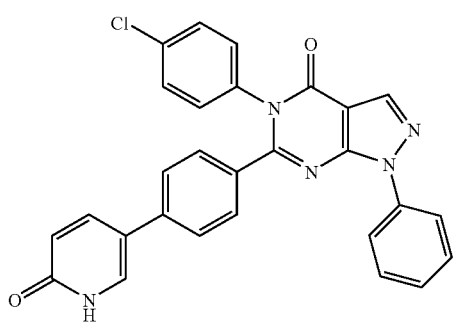

To a solution of 6-[4-(6-amino-pyridin-3-yl)-phenyl]-5-(4-chloro-phenyl)-1-phenyl-1,5-dihydro-pyrazolo[3,4-d]pyrimidin-4-one (28.1 mg, 0.057 mmol) in acetonitrile (0.5 mL) is added a solution of NaNO$_2$ (5.4 mg, 0.078 mmol) in H$_2$O (0.5 mL) followed by addition of one drop of concentrated H$_2$SO$_4$. The reaction mixture is then heated at 100° C. for 30 minutes, cooled down to 0° C., neutralized by saturated NaHCO$_3$ to pH= 4-5, and extracted with ethyl acetate. The organic layer is concentrated and purified by preparative LC/MS to provide the title compound; $^1$H NMR (CDCl$_3$, 400 MHz) δ 8.34 (s, 1H), 8.14 (d, 2H), 7.91 (dd, 1H), 7.75 (d, 1H), 7.52 (t, 2H), 7.44 (d, 2H), 7.36 (m, 5H), 7.13 (d, 2H), 6.88 (d, 1H); HPLC-MS calculated for $C_{28}H_{18}ClN_5O_2$ (M+H$^+$) 492.1. Found: 492.1.

Example 338

6-[4-(4-amino-pyridin-2-yl)-phenyl]-5-(4-chloro-phenyl)-1-phenyl-1,5-dihydro-pyrazolo[3,4-d]pyrimidin-4-one

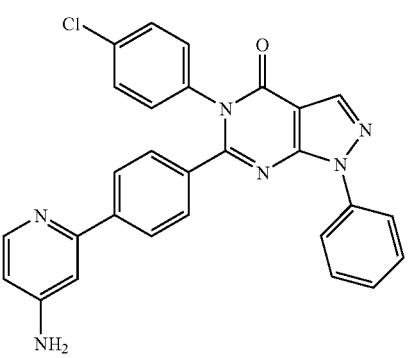

A reaction tube charged with 5-(4-chloro-phenyl)-1-phenyl-6-[4-(4,4,5,5-tetramethyl-[1,3,2]dioxaborolan-2-yl)-phenyl]-1,5-dihydro-pyrazolo[3,4-d]pyrimidin-4-one (20.0 mg, 0.038 mmol), 4-amino-2-chloropyridine (9.8 mg, 0.076 mmol), Cs$_2$CO$_3$ (24.8 mg, 0.076 mmol), Pd$_2$(dba)$_3$ (1.7 mg, 0.002 mmol), and 1,3-bis-(2,6-diisopropyl-phenyl)-3H-imidazol-1-ium chloride (1.6 mg, 0.004 mmol) is purged with nitrogen. Anhydrous 1,4-dioxane (0.5 mL) is added via syringe. The reaction mixture is heated at 120° C. for 3 days, cooled down to room temperature, taken in H$_2$O (5 mL), and extracted by ethyl acetate (3×3 mL). The combined organic phase is concentrated and purified by reverse phase HPLC to provide the title compound; $^1$H NMR (CDCl$_3$, 400 MHz) δ 8.34 (s, 1H), 8.09 (d, 2H), 8.06 (d, 1H), 7.63 (d, 2H), 7.54 (t, 2H), 7.44 (d, 2H), 7.39 (t, 1H), 7.29 (d, 2H), 7.03 (d, 2H), 6.89 (s, 1H), 6.59 (d, 1H); HPLC-MS calculated for $C_{28}H_{19}ClN_6O$ (M+H$^+$) 491.1. Found: 491.1.

Example 340

6-(4-Bromo-phenyl)-5-(4-chloro-phenyl)-4-oxo-1-phenyl-4,5-dihydro-1H-pyrazolo[3,4-d]pyrimidine-3-carboxylic acid

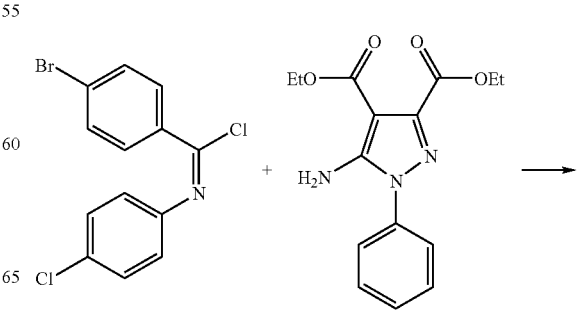

111

-continued

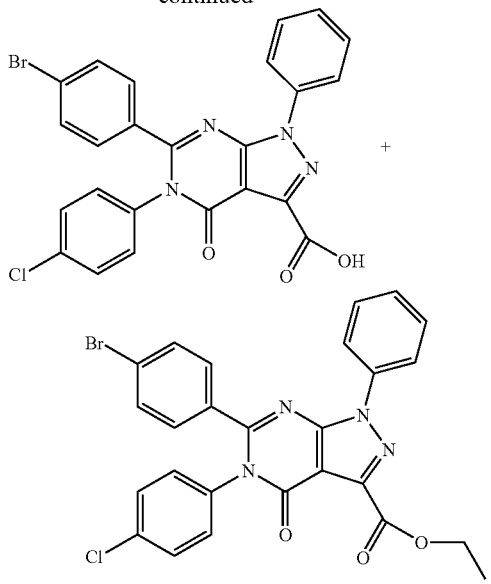

6-(4-Bromo-phenyl)-5-(4-chloro-phenyl)-4-oxo-1-phenyl-4,5-dihydro-1H-pyrazolo[3,4-d]pyrimidine-3-carboxylic acid is prepared from 5-amino-1-phenyl-1H-pyrazole-3,4-dicarboxylic acid diethyl ester and 4-bromo-N-(4-chlorophenyl)-benzimidoyl chloride by following a similar procedure as described in example 2 except that the reaction mixture is heated at 170° C. in a microwave for 45 min instead of 20 min. the crude product is purified by preparative LC/MS to yield 6-(4-bromo-phenyl)-5-(4-chloro-phenyl)-4-oxo-1-phenyl-4,5-dihydro-1H-pyrazolo[3,4-d]pyrimidine-3-carboxylic acid as the major product and 6-(4 bromo-phenyl)-5-(4-chloro-phenyl)-4-oxo-1-phenyl-4,5-dihydro-1H-pyrazolo[3,4-d]pyrimidine-3-carboxylic acid ethyl ester (example 341) as by product. Example 340: HPLC-MS calculated $C_{24}H_{14}BrClN_4O_3$ (M+1$^+$): 520.0. Found: 520.0. Example 341: $^1$H NMR (CDCl$_3$) δ (ppm) 8.10(d, 2H), 7.50(t, 2H), 7.41(m, 3H), 7.34 (d, 2H), 7.20(d, 2H), 7.09 (d, 2H), 4.52(q, 2H), 1.45(t, 3H). HPLC-MS calculated $C_{26}H_{18}BrClN_4O_3$ (M+1$^+$): 549.0. Found: 549.0.

Example 342

6-(4-Bromo-phenyl)-5-(4-chloro-phenyl)-4-oxo-1-phenyl-4,5-dihydro-1H-pyrazolo[3,4-d]pyrimidine-3-carboxylic acid methylamide

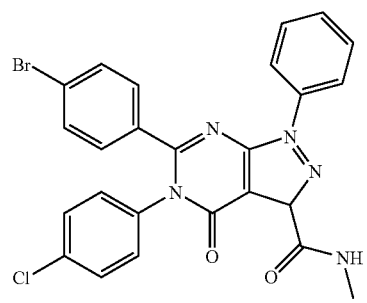

6-(4-bromo-phenyl)-5-(4-chloro-phenyl)-4-oxo-1-phenyl-4,5-dihydro-1H-pyrazolo[3,4-d]pyrimidine-3-carboxy-

112 lic acid (20 mg, 0.038 mmol) is treated with SOCl$_2$ at 50° C. for 1 h. and cooled down to room temperature. SOCl$_2$ is removed under vacuum and the residue is dissolved in anhydrous dichloromethane (0.5 mL), MeNH$_2$ (2N in MeOH, 0.2 mL) is added into the solution and the mixture is stirred at room temperature for 3 h. Solvent is removed under vacuum and the residue is purified by preparative LC/MS to provide the title compound 6-(4-bromo-phenyl)-5-(4-chloro-phenyl)-4-oxo-1-phenyl-4,5-dihydro-1H-pyrazolo[3,4-d]pyrimidine-3-carboxylic acid methylamide. 1H NMR (CDCl3) d (ppm) 9.95(b, 1H), 8.16(d, 2H), 7.51(t, 2H), 7.41(m, 5H), 7.22(d, 2H), 7.13(d, 2H), 3.05(d, 3H). HPLC-MS calculated C25H17BrClN5O2 (M+1+): 534.0. Found: 534.0.

Example 347

6-(4-Bromo-phenyl)-5-(4-chloro-phenyl)-4-oxo-1-phenyl-4,5-dihydro-1H-pyrazolo[3,4-d]pyrimidine-3-carboxylic acid isopropyl ester

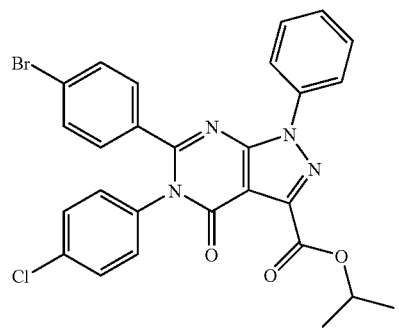

6-(4-bromo-phenyl)-5-(4-chloro-phenyl)-4-oxo-1-phenyl-4,5-dihydro-1H-pyrazolo[3,4-d]pyrimidine-3-carboxylic acid (20 mg, 0.038 mmol) is treated with SOCl$_2$ (0.5 mL) at 80° C. for 1 h and cooled down to room temperature. SOCl2 is removed under vacuum and the residue is dissolved in anhydrous dichloromethane (0.5 mL), isopropanol (0.05 mL) is added followed by Et3N (0.05 mL), The mixture is stirred at room temperature for 3 h. Solvent is removed under vacuum and the residue is purified by preparative LC/MS to provide the title compound 6-(4-bromo-phenyl)-5-(4-chloro-phenyl)-4-oxo-1-phenyl-4,5-dihydro-1H-pyrazolo[3,4-d] pyrimidine-3-carboxylic acid isopropyl ester. 1H NMR (CDCl3) d (ppm) 8.10(d, 2H), 7.51(t, 2H), 7.41(m, 3H), 7.33(d, 2H), 7.19(d, 2H), 7.09(d, 2H), 5.38(m, 1H), 1.44(d, 6H). HPLC-MS calculated C27H20BrClN4O3 (M+1+): 563.0. Found: 563.1.

Example 348

6-(4-Bromo-phenyl)-5-(4-chloro-phenyl)-4-oxo-1-phenyl-4,5-dihydro-1H-pyrazolo[3,4-d]pyrimidine-3-carboxylic acid tert-butyl ester

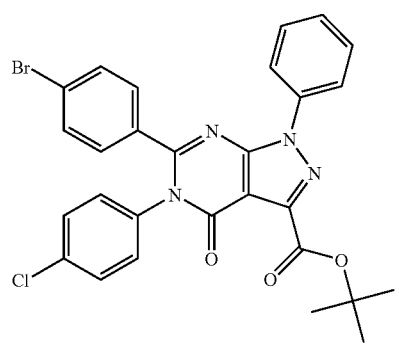

A suspension of 6-(4-bromo-phenyl)-5-(4-chloro-phenyl)-4-oxo-1-phenyl-4,5-dihydro-1H-pyrazolo[3,4-d]pyrimidine-3-carboxylic acid (6 mg, 0.012 mmol) in anhydrous benzene (0.5 mL) is heated to 80° C. when N,N-dimethyl formamide di-tert-butyl acetal (0.02 mL) is added. After the addition, the mixture is stirred at 80° C. for 30 min. After cooling down to room temperature, the solvent is removed under vacuum and the residue is purified by preparative LC/MS to provide the title compound 6-(4-bromo-phenyl)-5-(4-chloro-phenyl)-4-oxo-1-phenyl-4,5-dihydro-1H-pyrazolo[3,4-d]pyrimidine-3-carboxylic acid tert-butyl ester. $^1$H NMR (CDCl$_3$) δ (ppm) 8.12(d, 2H), 7.50(t, 2H), 7.41(m, 3H), 7.33(d, 2H), 7.19(d, 2H), 7.09(d, 2H), 1.67(s, 9H). HPLC-MS calculated C$_{28}$H$_{22}$BrClN$_4$O$_3$ (M+1$^+$): 577.1. Found: 577.1.

Example 351

5-(4-Chloro-phenyl)-6-(4-isopropyl-phenyl)-3-(3-methyl-[1,2,4]oxadiazol-5-yl)-1-phenyl-1,5-dihydro-pyrazolo[3,4-d]pyrimidin-4-one

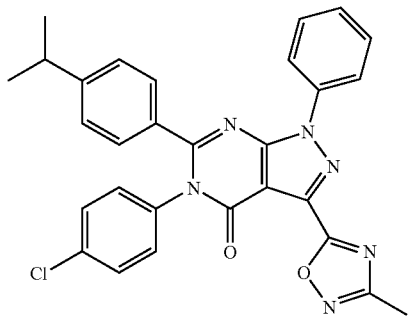

5-(4-Chloro-phenyl)-6-(4-isopropyl-phenyl)-4-oxo-1-phenyl-4,5-dihydro-1H-pyrazolo[3,4-d]pyrimidine-3-carboxylic acid (15 mg, 0.031 mmol) is treated with SOCl$_2$ (0.5 mL) at 80° C. for 1 h. and cooled down to room temperature. SOCl$_2$ is removed under vacuum and the residue is dissolved in anhydrous dichloromethane (0.5 mL). N-hydroxy-acetamidine (9 mg, 0.12 mmol) is added followed by Et$_3$N (0.02 mL). The mixture is stirred at room temperature for 1 h and then poured into water (5 mL). The mixture is extracted with EtOAc(3×3 mL). After the combined extracts is concentrated and dried under vacuum for 5 h., the residue is dissolved in anhydrous dioxane (0.5 mL) followed by the addition of NaOAc (15 mg). The mixture is stirred at 80° C. for 24 h to complete the conversion. After cooling down to room temperature, the mixture is treated with water and extracted with EtOAc. The combined extracts is concentrated and the residue is purified by preparative LC/MS to provide the title compound 5-(4-Chloro-phenyl)-6-(4-isopropyl-phenyl)-3-(3-methyl-[1,2,4]oxadiazol-5-yl)-1-phenyl-1,5-dihydro-pyrazolo[3,4-d]pyrimidin-4-one. $^1$H NMR (CDCl$_3$) δ (ppm) 8.21(d, 2H), 7.54(t, 2H), 7.42(t, 1H), 7.32 (d, 2H), 7.29(d, 2H), 7.12(m, 4H), 2.87(m, 1H), 2.55(s, 3H), 1.20(d, 6H). HPLC-MS calculated C$_{29}$H$_{23}$ClN$_6$O$_2$ (M+1$^+$): 523.2. Found: 523.2.

Example 352

5-(4-Chloro-phenyl)-6-[4-(2-chloro-pyrimidin-4-yl)-phenyl]-3-methylsulfanyl-1-phenyl-1,5-dihydro-pyrazolo[3,4-d]pyrimidin-4-one

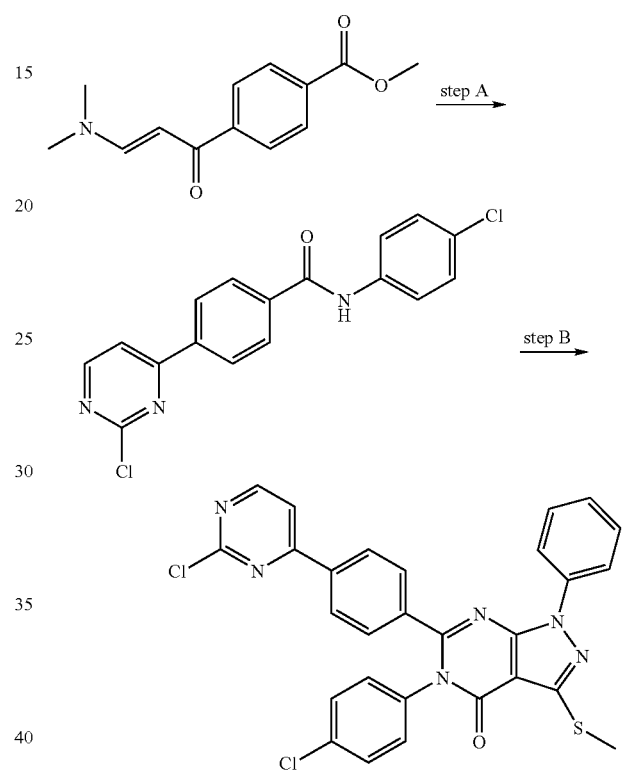

Step A: To a suspension of 4-(3-Dimethylamino-acryloyl)-benzoic acid methyl ester (1 g, 4.29 mmol; Prepared according to the method reported by S. Murahashi et al. *Bulletin of the Chemical Society of Japan,* 1987, 60, 3285) in MeOH (8.5 mL) is added guanidine hydrochloride (1.23 g, 12.86 mmol) and NaOH (412 mg, 10.3 mmol). The mixture is stirred at 80° C. for 24 h and then cooled down to room temperature. The mixture is concentrated and treated with H$_2$SO$_4$/H$_2$O (1:1, 20 mL) and heated to 120° C. for 14 h. After cooling down to room temperature, the mixture is basified by pouring into ice cold NH$_4$OH (50 mL) and acidified to pH= 1 by adding concentrated hydrogen chloride solution. The precipitate is collected by filtration, washed with acetonitrile and dried in a vacuum oven for 24 h to yield 680 mg of crude 4-(2-hydroxy-pyrimidin-4-yl)-benzoic acid.

The crude 4-(2-hydroxy-pyrimidin-4-yl)-benzoic acid is treated with POCl$_3$ (4 mL) at 100° C. for 14 h and cooled down to room temperature. POCl$_3$ is removed under vacuum and the residue is flushed once with toluene (3 mL). The residue is dissolved in anhydrous dichloromethane (4 mL) and put into ice bath. 4-Chloroaniline (790 mg, 6.28 mmol) is added followed by the addition of Et$_3$N (1.2 g, 12 mmol). After stirring at 0° C. for 1 h, the mixture is poured into water (100 mL) and extracted with EtOAc (3×50 mL). The combined extracts is washed with brine, dried (MgSO$_4$) and concentrated. The residue is purified by flash column chromatography (silica gel, 0-80% EtOAc/hexane) to provide the desired N-(4-chloro-phenyl)-4-(2-chloro-pyrimidin-4-yl)-benzamide as yellow solid (650 mg, 44%). HPLC-MS calculated C$_{17}$H$_{11}$Cl$_2$N$_3$O (M+1$^+$): 344.0. Found: 344.0.

Step B: 5-(4-Chloro-phenyl)-6-[4-(2-chloro-pyrimidin-4-yl)-phenyl]-3-methylsulfanyl-1-phenyl-1,5-dihydro-pyrazolo[3,4-d]pyrimidin-4-one is prepared from N-(4-chloro-phenyl)-4-(2-chloro-pyrimidin-4-yl)-benzamide and 5-amino-3-methylsulfanyl-1-phenyl-1H-pyrazole-4-carboxylic acid ethyl ester by following a similar procedure as described in example 2. $^1$H NMR (CDCl$_3$) δ (ppm) 8.68(d, 1H), 8.15(d, 2H), 8.01(d, 2H), 7.63(d, 1H), 7.49(m, 4H), 7.32(m, 3H). 7.11(d, 2H), 2.73(s, 3H). HPLC-MS calculated C$_{28}$H$_{18}$Cl$_2$N$_6$OS (M+1$^+$): 557.1. Found: 557.1.

Example 353

6-[4-(2-Amino-pyrimidin-4-yl)-phenyl]-5-(4-chloro-phenyl)-3-methylsulfanyl-1-phenyl-1,5-dihydro-pyrazolo[3,4-d]pyrimidin-4-one

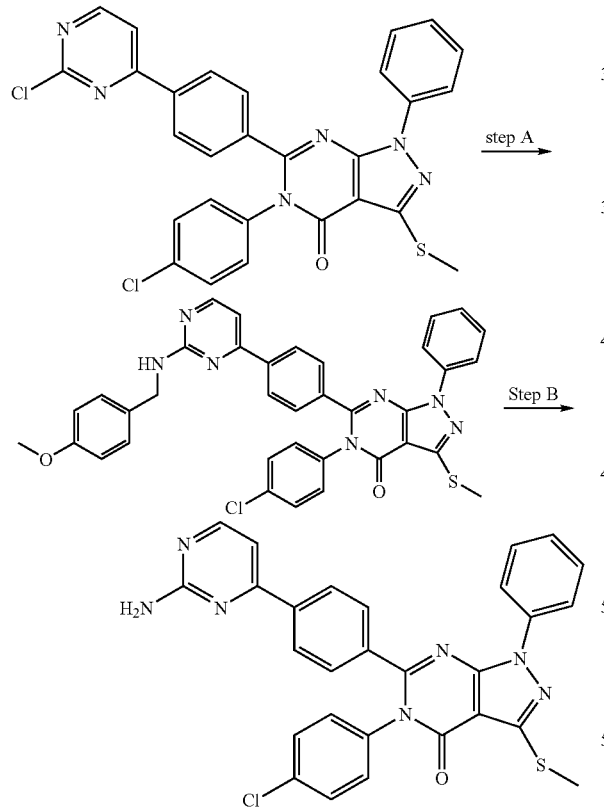

Step A: To a suspension of 5-(4-chloro-phenyl)-6-[4-(2-chloro-pyrimidin-4-yl)-phenyl]-3-methylsulfanyl-1-phenyl-1,5-dihydro-pyrazolo[3,4-d]pyrimidin-4-one (10 mg, 0.018 mmol) in propanol (0.5 mL) is added 4-methoxylbenzylamine (15 μL), The mixture is heated at 100° C. for 14 h and then cooled down to room temperature. Solvent is removed under vacuum, residue is used directly for next step without further purification.

Step B: The residue from previous step is dissolved in TFA (0.5 mL) and heated at 60° C. for 5 h. After cooling down to room temperature, the mixture is concentrated and purified by preparative LC/MS to provide the title compound 6-[4-(2-Amino-pyrimidin-4-yl)-phenyl]-5-(4-chloro-phenyl)-3-methylsulfanyl-1-phenyl-1,5-dihydro-pyrazolo[3,4-d]pyrimidin-4-one. $^1$H NMR (CDCl$_3$) δ (ppm) 8.23(d, 1H), 8.12(d, 2H), 8.01(d, 2H), 7.52(m, 4H), 7.33(m, 3H), 7.23(d, 1H), 7.11(d, 2H), 2.73(s, 3H). HPLC-MS calculated C$_{28}$H$_{20}$ClN$_7$OS (M+1$^+$): 538.1. Found: 538.1.

Example 355

5-(4-Chloro-phenyl)-6-(4-isopropyl-phenyl)-4-oxo-1-phenyl-4,5-dihydro-1H-pyrazolo[3,4-d]pyrimidine-3-carbonitrile

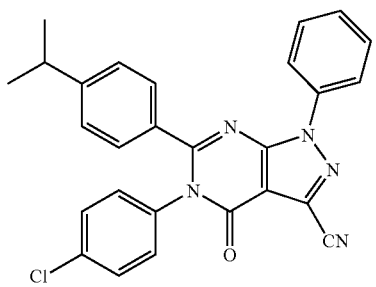

5-(4-Chloro-phenyl)-6-(4-isopropyl-phenyl)-4-oxo-1-phenyl-4,5-dihydro-1H-pyrazolo[3,4-d]pyrimidine-3-carboxylic acid amide (10 mg, 0.021 mmol; prepared from 5-(4-chloro-phenyl)-6-(4-isopropyl-phenyl)-4-oxo-1-phenyl-4,5-dihydro-1H-pyrazolo[3,4-d]pyrimidine-3-carboxylic acid following the procedure as in example 342) is treated with POCl$_3$ at 80° C. for 30 min. The mixture is then cooled down to room temperature and concentrated under vacuum. The residue is treated with sat. aqueous NaHCO$_3$ solution (1 mL) and extrated with EtOAc. The combined extracts is then concentrated and purified by preparative thin layer chromatography (silica gel, 30% EtOAc/hexane) to provide the title compound 5-(4-Chloro phenyl)-6-(4-isopropylphenyl)-4-oxo-1-phenyl-4,5-dihydro-1H-pyrazolo[3,4-d]pyrimidine-3-carbonitrile as white solid. $^1$H NMR (CDCl$_3$) δ (ppm) 8.13(d, 2H), 7.54(t, 2H), 7.44(t, 1H), 7.33(d,2H), 7.25(d, 2H), 7.10 (m, 4H), 2.87(m, 1H), 1.20(d, 6H). HPLC-MS calculated C$_{27}$H$_{20}$ClN$_5$O (M+1$^+$): 466.1. Found: 466.1.

Example 356

5-(4-Chloro-phenyl)-6-[4-(2-chloro-pyrimidin-4-yl)-phenyl]-3-methanesulfonyl-1-phenyl-1,5-dihydro-pyrazolo[3,4-d]pyrimidin-4-one

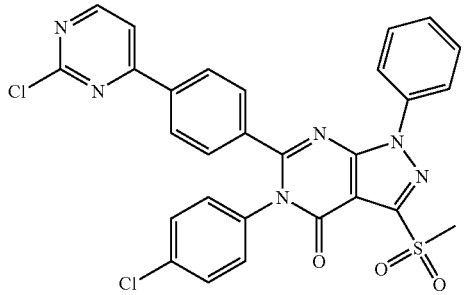

To a solution of 5-(4-chloro-phenyl)-6-[4-(2-chloro-pyrimidin-4-yl)-phenyl]-3-methylsulfanyl-1-phenyl-1,5-dihydro-pyrazolo[3,4-d]pyrimidin-4-one (230 mg, 0.41 mmol) in $CH_2Cl_2$ (6 mL) is added m-CPBA (240 mg, 1.39 mmol) at 0° C. The mixture is stirred at 0° C. for 5 min and then allowed to warm up to room temperature. After stirring at room temperature for 5 h, the mixture is treated with saturated aqueous $NaHCO_3$ solution (10 mL) and extracted with $CH_2Cl_2$ (3×20 mL). The combined extracts is washed with brine, dried ($MgSO_4$) and concentrated. A small portion is purified by preparative LC/MS to provide the title compound 5-(4-chlorophenyl)-6-[4-(2-chloro-pyrimidin-4-yl)-phenyl]-3-methanesulfonyl-1-phenyl-1,5-dihydro-pyrazolo[3,4-d]pyrimidin-4-one. $^1$H NMR ($CDCl_3$) δ (ppm) 8.69(d, 1H), 8.09(d, 2H), 8.03(d, 2H), 7.64(d, 1H), 7.54(t, 3H), 7.50 (d, 2H), 7.44(t, 1H), 7.34(d, 2H), 7.15(d, 1H), 3.53(s, 3H). HPLC-MS calculated $C_{28}H_{18}Cl_2N_6O_3S$ (M+1$^+$): 589.1. Found: 589.1. The rest of residue is used directly for Example 357.

Example 357

6-[4-(2-Ammo-pyrimidin-4-yl)-phenyl]-5-(4-chloro-phenyl)-3-methanesulfonyl-1-phenyl-1,5-dihydro-pyrazolo[3,4-d]pyrimidin-4-one

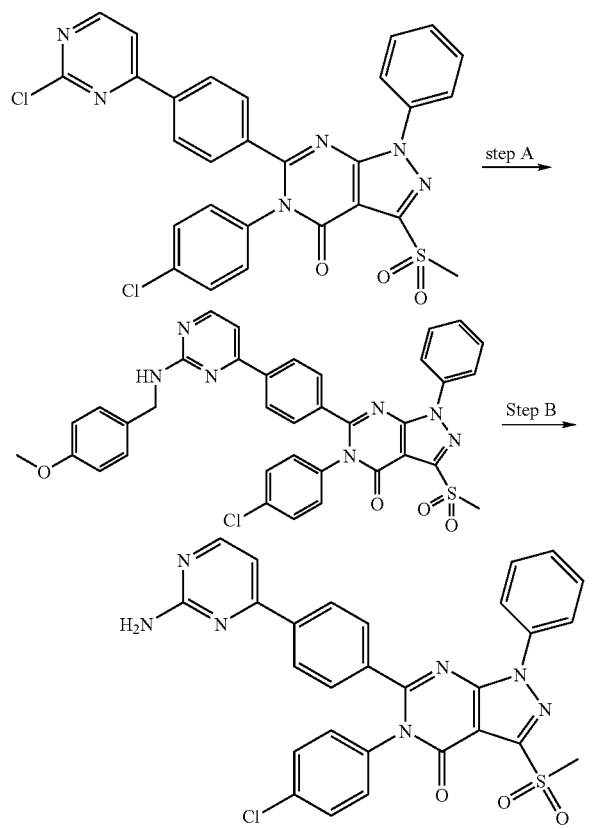

Step A: To a suspension of crude 5-(4-chloro-phenyl)-6-[4-(2-chloro-pyrimidin-4-yl)-phenyl]-3-methanesulfonyl-1-phenyl-1,5-dihydro-pyrazolo[3,4-d]pyrimidin-4-one (from example 356) in EtOH (6 mL) is added 4-methoxylbenzylamine (0.4 mL). The mixture is heated at 100° C. for 24 h and then cooled down to room temperature. The precipitate is collected by filtration and washed with EtOH (2×3 mL). The solid is air dried for 14 h to provide the desired 5-(4-chloro-phenyl)-3-methanesulfonyl-6-{4-[2-(4-methoxy-benzylamino)-pyrimidin-4-yl]-phenyl}-1-phenyl-1,5-dihydro-pyrazolo[3,4-d]pyrimidin-4-one as white solid (230 mg, 80%). HPLC-MS calculated $C_{36}H_{28}ClN_7O_4S$ (M–H$^+$): 690.2. Found: 690.2.

Step B: A solution of 5-(4-chloro-phenyl)-3-methanesulfonyl-6-{4-[2-(4-methoxy-benzylamino)-pyrimidin-4-yl]-phenyl}-1-phenyl-1,5-dihydro-pyrazolo[3,4-d]pyrimidin-4-one (230 mg, 0.33 mmol) in TEA (4 mL) is stirred at 50° C. for 8 h and then cooled down to room temperature. The excess of TFA is removed under vacuum and the residue is treated with saturated aqueous $NaHCO_3$ solution (5 mL). After extracted with $CH_2Cl_2$, The combined extracts is washed with brine, dried ($MgSO_4$) and concentrated. The residue is purified by flash column chromatography (silica gel, 0~2% MeOH/$CH_2Cl_2$) to provide the title compound 6-[4-(2-Amino-pyrimidin-4-yl)-phenyl]-5-(4-chloro-phenyl)-3-methanesulfonyl-1-phenyl-1,5-dihydro-pyrazolo[3,4-d]pyrimidin-4-one. $^1$H NMR ($CDCl_3$) δ (ppm) 8.36(d, 1H), 8.11(d, 2H), 7.94(d, 2H), 7.54(t, 2H), 7.45 (m, 3H), 7.34(d, 2H), 7.15(d, 2H), 7.03(d, 1H), 5.34(b, 2H), 3.55(s, 3H). HPLC-MS calculated $C_{28}H_{20}ClN_7O_3S$ (M+1$^+$): 570.1. Found: 570.1.

Example 361

6-[4-(2-Butoxyethyl)-phenyl]-5-(4-chloro-phenyl)-1-phenyl-1,5-dihydro-pyrazolo[3,4-d]pyrimidin-4-one

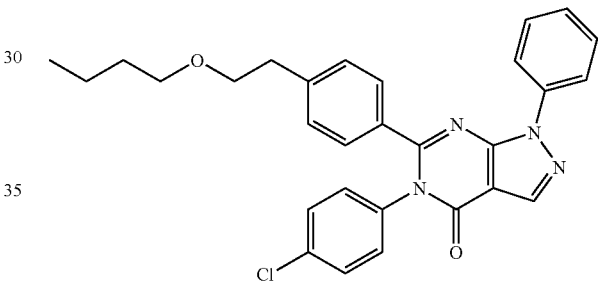

To a solution of 6-[4-(2-butoxy-vinyl)-phenyl]-5-(4-chloro-phenyl)-1-phenyl-1,5-dihydro-pyrazolo[3,4-d]pyrimidin-4-one (5 mg, 0.01 mmol) in EtOH (1 mL) is added Pd/C (2 mg). The system is degassed by alternately applying vacuum and $H_2$ for 3 times. The mixture is then stirred at room temperature under $H_2$ for 24 h. After removing the catalyst by filtration, the filtrate is concentrated and purified by flash column chromatography (silica gel, 0~30% EtOAc/hexane) to provide the title compound as white solid (3.5 mg, 69%). HPLC-MS calculated $C_{29}H_{25}ClN_4O_2$ (M+1$^+$): 497.2. Found: 497.2

Example 362

5-(4-Chloro-phenyl)-6-[4-(1-methyl-1H-pyrazol-3-yl)-phenyl]-1-phenyl-1,5-dihydro-pyrazolo[3,4-d] pyrimidin-4-one

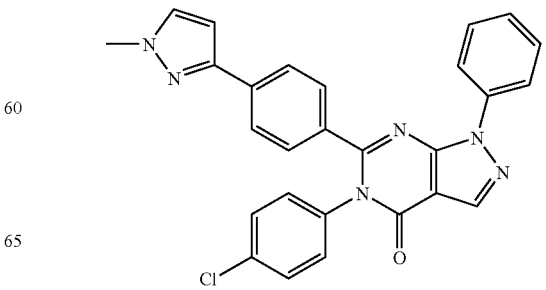

To a solution of 5-(4-chloro-phenyl)-1-phenyl-6-[4-(1H-pyrazol-3-yl)-phenyl]-1,5-dihydro-pyrazolo[3,4-d]pyrimidin-4-one (4 mg, 0.008 mmol) in MeCN (0.5 mL) is added $K_2CO_3$ (5 mg) followed by MeI (0.05 mL). The mixture is heated to 60° C. for 16 h and then cooled down to room temperature. The reaction mixture is then treated with water (3 mL) and extracted with EtOAc. The combined extracts is concentrated and purified by preparative thin layer chromatography (silica gel, 30% EtOA/hexane) to provide the title compound 5-(4-chloro-phenyl)-6-[4-(1-methyl-1H-pyrazol-3-yl)-phenyl]-1-phenyl-1,5-dihydro-pyrazolo[3,4-d]pyrimidin-4-one as white solid (3.8 mg, 92%). $^1$H NMR (CDCl$_3$) δ (ppm) 8.33(s, 1H), 8.17(d, 2H), 7.70(d, 2H), 7.51(t, 2H), 7.38 (m, 4H), 7.11(d, 2H), 6.54(d, 1H), 3.97(s, 3H). HPLC-MS calculated $C_{27}H_{19}ClN_6O$ (M+1$^+$): 479.1. Found: 479.1.

Example 363

5-(4-Chloro-phenyl)-1-phenyl-6-(4-pyridazin-3-yl-phenyl)-1,5-dihydro-pyrazolo[3,4-d]pyrimidin-4-one

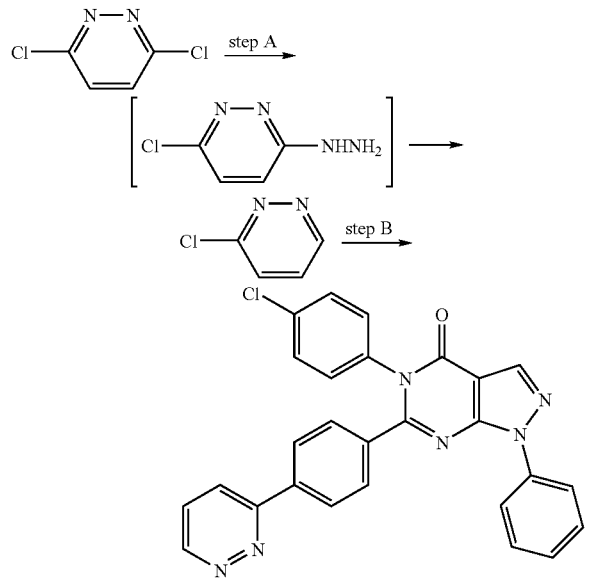

Step A: To a solution of 3,6-dichloro-pyridazine (500 mg, 3.36 mmol) in EtOH (6 mL) is added hydrazine hydrate (840 mg, 16.8 mini). The mixture is heated at 80° C. for 14 h and then cooled downed to room temperature. The solvent is removed under vacuum and the residue is triturated with water (2 mL), filtered off and dried to afford 6-chloro-3-pyridazinyl-hydrazine (280 mg, 58%) as white solid. HPLC-MS calculated $C_4H_5ClN_4$ (M+1$^+$): 145.0. Found: 145.0.

Step B: To a vigorously stirred suspension of yellow mercuric oxide (840 mg, 3.88 mmol) in water (10 mL) is slowly added 6-chloro-3pyridazinyl-hydrazine (280 mg, 1.94 mmol) portion wise. The resulted mixture is then stirred at room temperature for 5 h and extracted with EtOAc (3×15 mL). The combined extracts is washed with brine, dried (MgSO$_4$) and concentrated to provide the desired product 3-chloropyridazine as brownish solid (130 mg, 34%). HPLC-MS calculated $C_4H_3ClN_2$ (M+1$^+$): 115.0. Found: 115.0.

Step C: 5-(4-Chloro-phenyl)-1-phenyl-6-(4-pyridazin-3-yl-phenyl)-1,5-dihydro-pyrazolo[3,4-d]pyrimidin-4-one is prepared from 3-chloropyridazine and 5-(4-chloro-phenyl)-1-phenyl-6-[4-(4,4,5,5-tetramethyl-[1,3,2]dioxaborolan-2-yl)-phenyl]-1,5-dihydro-pyrazolo[3,4-d]pyrimidin-4-one by using the same method described in example 338. The crude product is purified by flash column chromatography (silica gel, 0~70% EtOAc/hexane). $^1$H NMR (CDCl$_3$) δ (ppm) 9.19 (b, 1H), 8.34(s, 1H), 8.15(d, 2H), 8.02(d, 2H), 7.84(d, 1H), 7.51(m, 5H), 7.33 (m, 3H), 7.15(d, 2H). HPLC-MS calculated $C_{27}H_{17}ClN_6O$ (M+1$^+$): 477.1. Found: 477.1.

Example 371

5-(4-Chloro-phenyl)-1-phenyl-6-(4-pyrazin-2-yl-phenyl)-1,5-dihydro-pyrazolo[3,4-d]pyrimidin-4-one

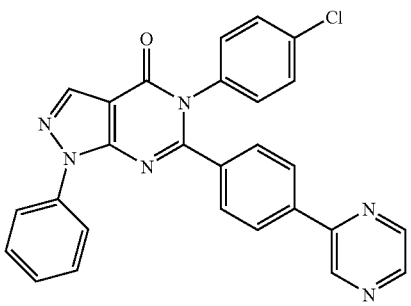

5-(4-Chloro-phenyl)-1-phenyl-6-(4-pyrazin-2-yl-phenyl)-1,5-dihydro-pyrazolo[3,4-d]pyrimidin-4-one is prepared from 5-(4-chloro-phenyl)-1-phenyl-6-[4-(4,4,5,5-tetramethyl [1,3,2]dioxaborolan-2-yl)-phenyl]-1,5-dihydro-pyrazolo[3,4-d]pyrimidin-4-one and 2-chloro-pyrazine by using the method described in example 338 except that the reaction mixture is stirred at 100° C. for 14 hours: $^1$H NMR (CDCl$_3$) δ (ppm) 9.02(d, 1H), 8.67(t, 1H), 8.55(d, 1H), 8.35(s, 1H), 8.15 (d, 2H), 7.95(d, 2H), 7.51(m, 4H), 7.37 (t, 1H), 7.33(d, 2H), 7.14(d, 2H). HPLC-MS calculated $C_{27}H_{17}ClN_6O$ (M+1$^+$): 477.1. Found: 477.1.

Example 377

5-(4-Bromo-phenyl)-6-(4-chloro-phenyl)-3-phenyl-3,6-dihydro-[1,2,3]triazolo[4,5-d]pyrimidin-7-one

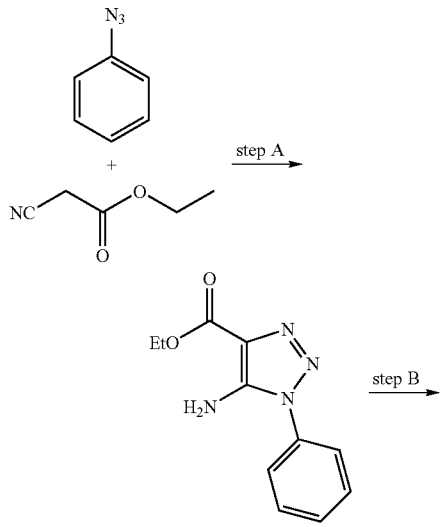

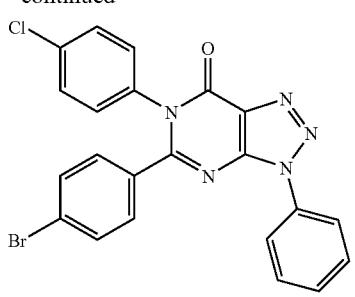

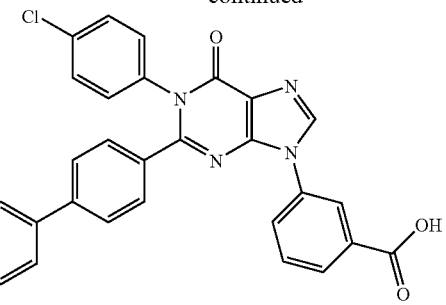

Step A: To a freshly prepared NaOEt (1.18 mmol) solution in EtOH (0.75 mL) is added ethyl cyanoacetate (100 mg, 0.88 mmol) at 0° C. After stirring at 0° C. for 10 min., azidobenzene (100 mg, 0.84 mmol, prepared according to the method reported by M. Kurumi et al. *Heterocycles.* 2000, 53, 2809) is added. After the addition, the mixture is allowed to slowly warm up to room temperature and stirred for 14 h. The mixture is then treated with water (3 mL) and extracted with EtOAc (3×3 mL). The combined extracts is concentrated and purified by flash column chromatography (silica gel, 0%-70% EtOAc/hexane) to provide 5-amino-1-phenyl-1H-[1,2,3]triazole-4-carboxylic acid ethyl ester as a white solid (100 mg, 51%). HPLC-MS calculated $C_{11}H_{12}N_4O_2$ (M+1$^+$): 233.1. Found: 233.1.

Step B: A mixture of 5-amino-1-phenyl-1H-[1,2,3]triazole-4-carboxylic acid ethyl ester (30 mg, 0.33 mmol), 4-bromo-N-(4-chloro-phenyl)-benzimidoyl chloride (51 mg, 0.16 mmol) and TiCl$_4$ (20 μL) in anhydrous dichloroethane (1 mL) is heated in microwave reactor at 170° C. for 1 h and then at 115° C. for 48 h in an oil bath. After cooling down to room temperature, the mixture is worked up as in example 2 and purified by flash column chromatography (silica gel, 0~30% EtOAc/hexane) to provide the title compound 5-(4-Bromo-phenyl)-6-(4-chloro-phenyl)-3-phenyl-3,6-dihydro-[1,2,3]triazolo[4,5-d]pyrimidin-7-one as white solid. (45 mg, 73%). $^1$H NMR (CDCl$_3$) δ (ppm) 8.15(d, 2H), 7.59(t, 2H), 7.49(t, 1H), 7.43 (d, 2H), 7.37(d, 2H), 7.21(d, 2H), 7.10(d, 2H), 2.87(m, 1H). HPLC-MS calculated $C_{22}H_{13}BrClN_5O$ (M+1$^+$): 478.0. Found: 478.0.

Example 383

3-[2-Biphenyl-4-yl-1-(4-chloro-phenyl)-6-oxo-1,6-dihydro-purin-9-yl]-benzamide

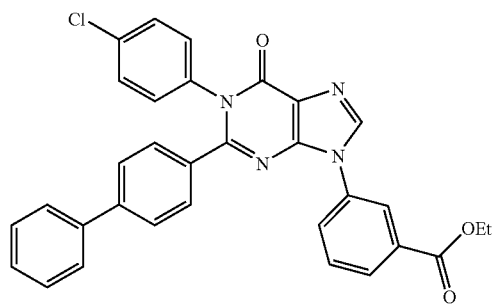

Step A: A solution of 3-[2-biphenyl-4-yl-1-(4-chloro-phenyl)-6-oxo-1,6-dihydro-purin-9-yl]-benzoic acid ethyl ester (200 mg, 0.37 mmol) in THF/MeOH/H$_2$O 3:2:1 (5 mL) was cooled to 0° C. and treated with 3 N aqueous LiOH (183 μL, 0.55 mmol). The reaction mixture was allowed to warm to room temperature and was stirred for 4 h. The reaction was diluted with H$_2$O, extracted with Et$_2$O, and acidified with 1N aqueous HCl. The resulting white precipitate was collected by suction filtration to provide 3-[2-Biphenyl-4-yl-1-(4-chloro-phenyl)-6-oxo-1,6-dihydro-purin-9-yl]-benzoic acid (155 mg, 82%) as a white solid. HPLC-MS calculated for $C_{30}H_{19}ClN_4O_3$ (M+H$^+$): 519.1. Found: 519.1.

Step B: A solution of 3-[2-biphenyl-4-yl-1-(4-chloro-phenyl)-6-oxo-1,6-dihydro-purin-9-yl]-benzoic acid (40 mg, 0.077 mmol) in SOCl$_2$ (1 mL) was heated at 70° C. for 1 h. The reaction mixture was allowed to cool to room temperature and poured into a 50% aqueous solution of NH$_4$OH (15 mL). The resulting mixture was diluted with H$_2$O and extracted with CH$_2$Cl$_2$. The combined organics were dried (MgSO$_4$), filtered, and concentrated. The crude material was purified by flash column chromatography (silica gel, 5% MeOH/CH$_2$Cl$_2$) to give the title compound 3-[2-biphenyl-4-yl-1-(4-chloro-phenyl)-6-oxo-1,6-dihydro-purin-9-yl]-benzamide as a white solid. $^1$H NMR (CDCl$_3$) δ (ppm) 8.67 (s, 1H), 8.29 (t, 1H), 8.15 (br s, 1H), 8.02 (d, 1H), 7.98 (d, 1H), 7.71 (t, 1H), 7.64 (d, 2H), 7.58 (d, 3H), 7.46 (br s, 2H), 7.44

(m, 6H), 7.37 (m, 1H); HPLC-MS calculated for $C_{30}H_{20}ClN_5O_2$ (M+H$^+$): 518.1. Found 518.1.

Example 384

N-[2-Biphenyl-4-yl-1-(4-chloro-phenyl)-6-oxo-9-phenyl-6,9-dihydro-1H-purin-8-ylmethyl]-methanesulfonamide

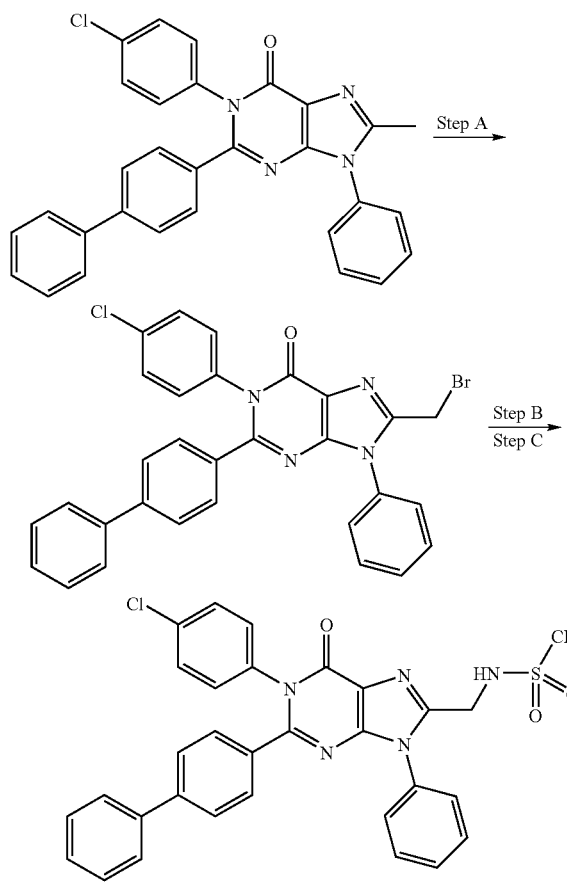

Step A: A solution of 2-biphenyl-4-yl-1-(4-chloro-phenyl)-8-methyl-9-phenyl-1,9-dihydro-purin-6-one (51 mg, 0.104 mmol) in CCl$_4$ (2 mL) was treated sequentially with NBS (24 mg, 0.135 mmol) followed by AIBN (22 mg, 0.135 mmol). The reaction was heated at 80° C. for 3 h, allowed to cool to room temperature, and concentrated in vacuo. The crude oil was purified by flash column chromatography (silica, 0 30% Hex/EtOAc) to provide 2-biphenyl-4-yl-8-bromomethyl-1-(4-chloro-phenyl)-9-phenyl-1,9-dihydro-purin-6-one (46 mg, 78%) as a white solid. HPLC-MS calculated for $C_{30}H_{20}BrClN_4O$ (M+H$^+$): 567.1. Found: 567.1.

Step B: A solution of W-(4-methoxy-benzyl)-methanesulfonamide (7.8 mg, 0.035 mmol) in anhydrous DMF (0.3 mL) was treated with 60% dispersed NaH (1.4 mg, 0.059 mmol). The reaction mixture was stirred until the evolution of hydrogen ceased and added via syringe to a solution of 2-biphenyl-4-yl-8-bromomethyl-1-(4-chloro-phenyl)-9-phenyl-1,9-dihydro-purin-6-one (20 mg, 0.35 mmol) in anhydrous DMF (0.1 mL). The resulting reaction mixture was heated at 50° C. for 2 h, allowed to cool to room temperature, and quenched with 1N aqueous HCl. The resulting white precipitate was collected by suction filtration to provide N-[2-biphenyl-4-yl-1-(4-Chloro-phenyl)-6-oxo-9-phenyl-6,9-dihydro-1H-purin-8-ylmethyl]-A-(4-methoxy-benzyl)-methanesulfonamide (18 mg, 72%) as a white solid. HPLC-MS calculated for $C_{39}H_{32}BrClN_5O_4S$ (M+H$^+$): 702.2. Found: 702.2.

Step C: A solution of N-[2-biphenyl-4-yl-1-(4-chloro-phenyl)-6-oxo-9-phenyl-6,9-dihydro-1H-purin-8-ylmethyl]-N-(4-methoxy-benzyl)-methanesulfonamide (18 mg, 0.026 mmol) in TFA (1 mL) was heated at 90° C. in a sealed tube for 12 h. The reaction mixture was concentrated in vacuo and the resulting crude oil was purified by flash chromatography (silica, 5% MeOH/CH$_2$Cl$_2$) to give the title compound Ar-[2-biphenyl-4-yl-1-(4-chloro-phenyl)-6-oxo-9-phenyl-6,9-dihydro-1H-purin-8-ylmethyl]-methanesulfonamide as a white solid. $^1$H NMR (CDCl$_3$) δ (ppm) 7.64 7.54 (m, 3H), 7.51 7.45 (m, 4H), 7.44 7.38 (m, 4H), 7.37 7.30 (m, 4H), 7.28 (s, 1H), 7.13 (d, 2H), 5.92 (br s, 1H), 4.48 (s, 2H), 2.99 (s, 3H); HPLC-MS calculated for $C_{31}H_{24}ClN_5O_3S$ (M+H$^+$): 582.1. Found 582.1.

Example 386

2-Biphenyl-4-yl-1-(4-chloro-phenyl)-8-methanesulfonylmethyl-9-phenyl-1,9-dihydro-purin-6-one

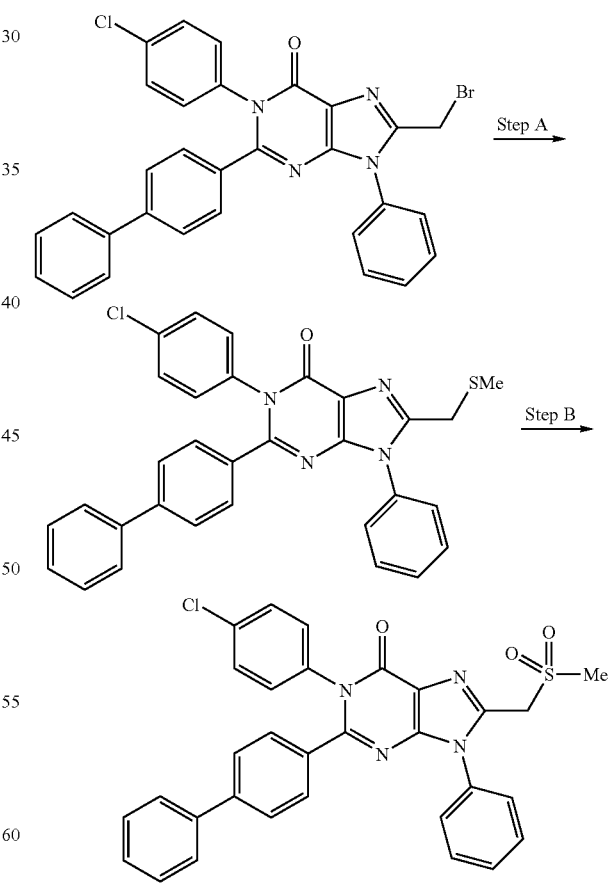

Step A: A solution of 2-biphenyl-4-yl-8-bromomethyl-1-(4-chloro-phenyl)-9-phenyl-1,9-dihydro-purin-6-one (17 mg, 0.030 mmol) in anhydrous DMF (0.2 mL) was treated with sodium thiomethoxide (3 mg, 0.042 mmol). The reaction mixture was stirred for (0 min and acidified with 1N aqueous HCl. The resulting precipitate was collected by filtration to give 2-biphenyl-4-yl-1-(4-chloro-phenyl)-8-methylsulfanyl-methyl-9-phenyl-1,9-dihydro-purin-6-one (14 mg, 86%) as a white solid. HPLC-MS calculated for $C_{31}H_{23}ClN_4OS$ (M+H$^+$): 535.1. Found 535.1.

Step B: A solution of 2-biphenyl-4-yl-1-(4-chloro-phenyl)-8-methylsulfanylmethyl-9-phenyl-1,9-dihydro-purin-6-one (14 mg, 0.026 mmol) in $CH_2Cl_2$ (0.5 mL) was treated with MCPBA (9 mg, 0.052 mmol). The reaction mixture was gently heated at 40° C. for 2 hours, allowed to cool to room temperature, and concentrated in vacuo. The crude amorphous solid was purified by flash chromatography (silica, 0 20% EtOAc/$CH_2Cl_2$) to provide the title compound 2-biphenyl-4-yl-1-(4-chloro-phenyl)-8-methanesulfonylmethyl-9-phenyl-1,9-dihydro-purin-6-one as a white solid. $^1$H NMR (CDCl$_3$δ (ppm) 7.65 7.53 (m, 5H), 7.49 (d, 2H), 7.41 7.39 (m, 4H), 7.37 7.31 (m, 3H), 7.29-7.24 (m, 2H, partially obscured by CHCl$_3$), 7.16 (d, 2H), 4.43 (br s, 2H), 3.35 (br s, 3H); HPLC-MS calculated for $C_{31}H_{23}ClN_4O_3S$ (M+H$^+$): 567.1. Found 567.1.

Example 391

3-[2-Biphenyl-4-yl-1-(4-chloro-phenyl)-6-oxo-1,6-dihydro-purin-9yl]-N-isoxazol-3-yl-benzamide

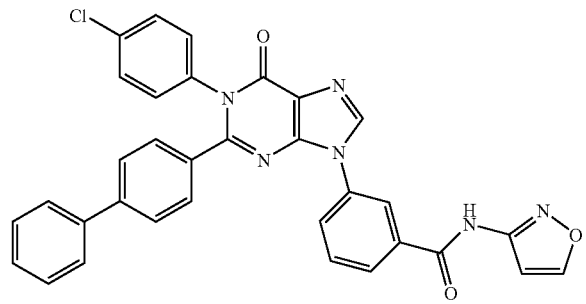

A solution of 3-[2-biphenyl-4-yl-1-(4-chloro-phenyl)-6-oxo-1,6-dihydro-purin-9-yl]-benzoic acid (50 mg, 0.096 mmol) in SOCl$_2$ (1 mL) was heated at 70° C. for 1 h. The reaction mixture was concentrated, dissolved in $CH_2Cl_2$ (2 mL), and treated with 3-aminoisoxazole (2.97 mg, 0.035 mmol). The reaction mixture was stirred at room temperature for 1 h, concentrated, and purified by flash column chromatography (silica gel, 0 30% Hex/EtOAc) to give the title compound 3-[2-biphenyl-4-yl-1-(4-chloro-phenyl)-6-oxo-1,6-dihydro-purin-9-yl]-N-isoxazol-3-yl-benzamide as a white solid. $^1$H NMR (CDCl$_3$ (ppm) 9.94 (s, 1H), 8.46 (s, 1H), 8.32 (s, 1H), 8.29 (s, 1H), 8.08 (d, 1H), 8.02 (d, 1H), 7.72 (t, 1H), 7.49 (d, 2H), 7.45 (d, 2H), 7.39 (t, 2H), 7.35 7.29 (m, 5H), 7.25 (br s, 1H), 7.14 (d, 2H); HPLC-MS calculated for $C_{30}H_{20}ClN_5O_2$ (M+H$^+$): 585.1. Found: 585.1.

Example 447

2-[4-(6-Amino-pyridin-3-yl)-phenyl]-1-(4-chloro-phenyl)-9-phenyl-1,9-dihydro-purin-6-one

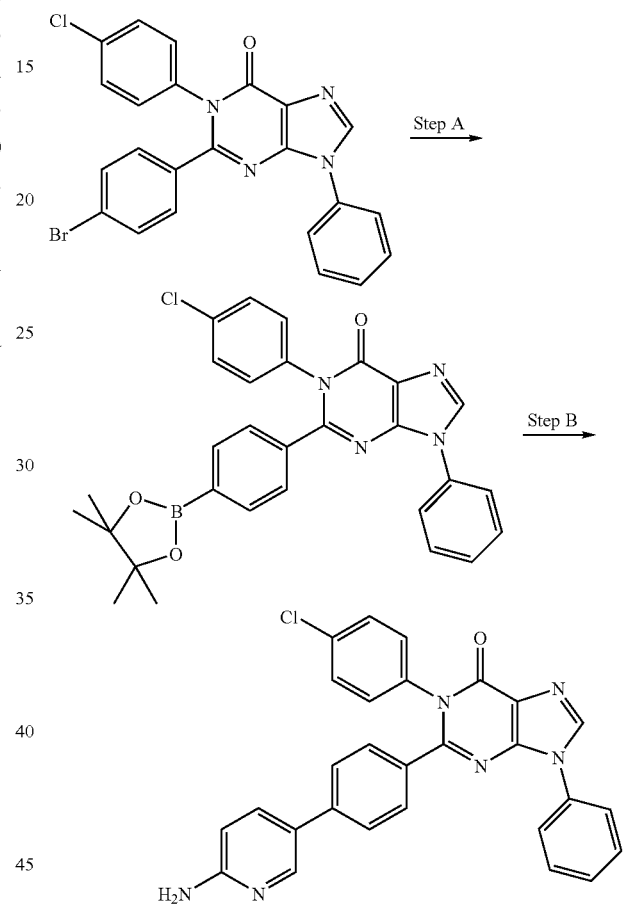

Step A: A solution of 2-(4-Bromo-phenyl)-1-(4-chloro-phenyl)-9-phenyl-1,9-dihydro-purin-6-one (190 mg, 0.40 mmol) in anhydrous DMF (3.5 mL) was treated sequentially with bis(pinacolato)diboron (108 mg, 0.46 mmol), KOAc (117 mg, 1.19 mmol), and Pd(dppf)$_2$Cl$_2$ (16 mg, 0.02 mmol). The resulting suspension was degassed with N$_2$ and heated at 100° C. for 2 h. The reaction mixture was allowed to cool to room temperature, diluted with H$_2$O, and extracted with EtOAc. The combined organics were dried (MgSO$_4$), filtered, and concentrated. The crude material was purified by flash column chromatography (silica, 0 20% EtOAc/$CH_2Cl_2$) to give 1-(4-chloro-phenyl)-9-phenyl-2-[4-(4,4,5,5-tetramethyl-[1,3,2]dioxaborolan-2-yl)-phenyl]-1,9-dihydro-purin-6-one (180 mg, 86%) as a light tan solid. HPLC-MS calculated for $C_{29}H_{26}ClN_4O_3$ (M+H$^+$): 525.2. Found: 525.2.

Step B: A solution of 1-(4-chloro-phenyl)-9-phenyl-2-[4-(4,4,5,5-tetramethyl-[1,3,2]dioxaborolan-2-yl)-phenyl]-1,9-dihydro-purin-6-one (180 mg, 0.34 mmol) and 2-amino-5-bromopyridine (89 mg, 0.51 mmol) in anhydrous DMF (3 mL) was treated sequentially with Cs$_2$CO$_3$ (224 mg, 0.69 mmol) and Pd(dppf)$_2$Cl$_2$ (14 mg, 0.017 mmol). The reaction mixture was degassed with N$_2$ and heated at 100° C. for 24 h. The reaction was cooled to room temperature, diluted with H$_2$O, and extracted with EtOAc. The combined organics were dried (MgSO$_4$), filtered, and concentrated. The crude material was purified by flash column chromatography (silica, 30% EtOAc/CH$_2$Cl$_2$) to provide the title compound 2-[4-(6-amino-pyridin-3-yl)-phenyl]-1-(4-chloro-phenyl)-9-phenyl-1,9-dihydro-purin-6-one as a white solid. $^1$H NMR (CDCl$_3$) δ (ppm) 8.19 (s, 1H), 7.95 (m, 2H), 7.72 (d, 2H), 7.61 (apparent t, 2H), 7.52 (apparent t, 1H), 7.42 (d, 2H), 7.35 (m, 4H), 7.17 (d, 2H), 6.95 (d, 1H); HPLC-MS calculated for C$_{28}$H$_{19}$ClN$_6$O (M+H$^+$): 491.1. Found: 491.1.

Example 448

1-(4-Chloro-phenyl)-2-[4-(6-oxo-1,6-dihydro-pyridin-3-yl)phenyl]-9-phenyl-1,9-dihydro-purin-6-one

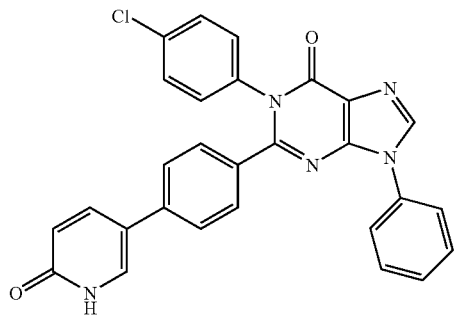

A solution of 2-[4-(6-amino-pyridin-3-yl)-phenyl]-1-(4-chloro-phenyl)-9-phenyl-1,9-dihydro-purin-6-one (10 mg, 0.02 mmol) in acetonitrile (0.4 mL) and H$_2$O (0.4 mL) was treated with NaNO$_2$ and 5 µL of concentrated H$_2$SO$_4$. The reaction mixture was heated at 100° C. for 1 h. The reaction was allowed to cool to room temperature and neutralized with aqueous Na$_2$CO$_3$. The reaction was diluted with H$_2$O and extracted with EtOAc. The combined organics were dried (MgSO$_4$), filtered, and concentrated. The resulting crude material was purified by preparative LCMS to provide the title compound 1-(4-chloro-phenyl)-2-[4-(6-oxo-1,6-dihydro-pyridin-3-yl)-phenyl]-9-phenyl-1,9-dihydro-purin-6-one as a white solid. $^1$H NMR (CDCl$_3$) δ (ppm) 8.21 (s, 1H), 8.01 (dd, 1H), 7.81 (d, 1H), 7.58 (apparent t, 2H), 7.49 (m, 1H), 7.39 (d, 2H), 7.33 (m, 3H), 7.14 (d, 2H), 6.98 (d, 1H); HPLC-MS calculated for C$_{28}$H$_{18}$ClN$_5$O$_2$ (M+H$^+$): 492.1. Found: 492.1.

By repeating the procedures described in the above examples, using appropriate starting materials, the following compounds of Formula I, as identified in Table 1, are obtained.

TABLE 1

| Compound Number | Structure | Physical Data $^1$H NMR 400 MHz (CDCl$_3$) and/or MS (m/z) |
|---|---|---|
| 10 | 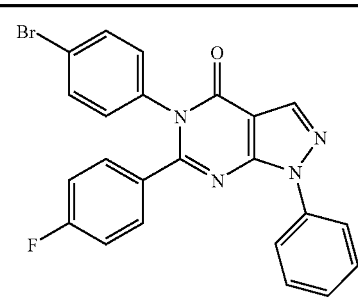 | The title compound is prepared as described in Example 2, using 4-fluorobenzoyl chloride instead of p-toluoyl chloride. $^1$H NMR (CDCl$_3$, 400 MHz) δ 8.33 (s, 1H), 8.12 (d, 2H), 7.50 (m, 4H), 7.35 (m, 3H), 7.02 (d, 2H), 6.96 (t, 2H); HPLC-MS calculated for C$_{23}$H$_{14}$BrFN$_4$O (M + H$^+$) 461.0, found 461.1. |
| 11 | 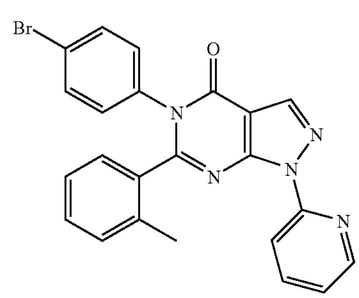 | LCMS: 458.0(M + H$^+$). |

TABLE 1-continued

| Compound Number | Structure | Physical Data $^1$H NMR 400 MHz (CDCl$_3$) and/or MS (m/z) |
|---|---|---|
| 12 | 4-bromophenyl / 2-fluorophenyl / hydroxyethyl pyrazolopyrimidinone | LCMS: 429.0 (M + H$^+$). |
| 13 | 2,4-dichlorophenyl / 2-fluorophenyl / phenyl pyrazolopyrimidinone | The title compound is prepared as described in Example 1. $^1$H NMR (CDCl$_3$, 400 MHz) δ 8.29 (s, 1H), 8.05 (d, J = 7.51 Hz, 2H), 7.48-7.38 (m, 3H), 7.32-7.26 (m, 4H), 7.2-7.17 (m, 1H), 7.05 (t, J = 7.57 Hz, 1H). 6.88 (t, J = 9.3 Hz, 1H). LC/MS found: 451.1 (M + H$^+$). |
| 14 | 4-bromophenyl / 2,4-dichlorophenyl / phenyl pyrazolopyrimidinone | The title compound is prepared as described in Example 1. $^1$H NMR (CDCl$_3$, 400 MHz) δ 8.29 (s, 1H), 8.01 (d, J = 7.62 Hz, 2H), 7.44-7.37 (m, 4H), 7.3 (d, J = 7.41 Hz, 1H), 7.26 (d, J = 1.6 Hz, 1H), 7.19-7.07 (m, 3H). 6.9 (d, J = 7.6 Hz, 1H). LC/MS found: 511.0 (M + H$^+$). |
| 15 | 4-fluorophenyl / 2,4-dichlorophenyl / phenyl pyrazolopyrimidinone | The title compound is prepared as described in Example 1. $^1$H NMR (CDCl$_3$, 400 MHz) δ 8.27 (s, 1H), 8.0 (d, J = 7.62 Hz, 2H), 7.43-7.39 (m, 2H), 7.31-7.2 (m, 3H), 7.12-7.05 (m, 2H), 7.02-6.92 (m, 3H). LC/MS found: 451.0 (M + H$^+$). |
| 16 | 2,4-dichlorophenyl / 4-chlorophenyl / phenyl pyrazolopyrimidinone | The title compound is prepared as described in Example 1. $^1$H NMR (CDCl$_3$, 400 MHz) δ 8.35 (s, 1H), 8.14 (d, J = 7.6 Hz, 2H), 7.53-7.5 (m, 2H), 7.45 (d, J = 2.2 Hz, 1H), 7.41-7.33 (m, 3H), 7.3-6.26 (m, 3H), 7.19 (d, J = 8.45 Hz, 1H). LC/MS found: 467.1 (M + H$^+$). |

TABLE 1-continued

| Compound Number | Structure | Physical Data<br>¹H NMR 400 MHz (CDCl₃)<br>and/or MS (m/z) |
|---|---|---|
| 17 | 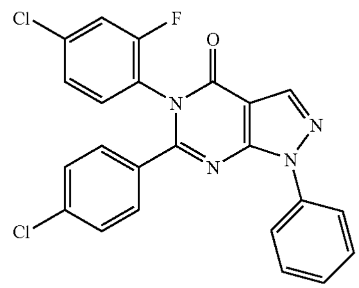 | The title compound is prepared as described in Example 1. ¹H NMR (CDCl₃, 400 MHz) δ 8.31 (s, 1H), 8.09 (d, J = 7.4 Hz, 2H), 7.51-7.47 (m, 2H), 7.37-7.26 (m, 5H), 7.15-7.06 (m, 3H). LC/MS found: 451.1 (M + 1/z). |
| 18 | 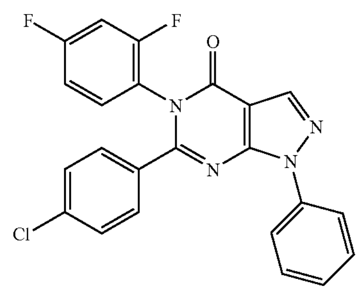 | The title compound is prepared as described in Example 1. ¹H NMR (CDCl₃, 400 MHz) δ 8.34 (s, 1H), 8.12 (d, J = 7.7 Hz, 2H), 7.51-7.49 (m, 2H), 7.41-7.28 (m, 5H), 7.19-7.12 (m, 1H). 6.94-6.84 (m, 1H). LC/MS found: 435.0 (M + 1/z). |
| 19 | 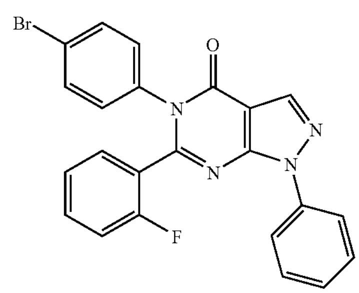 | The title compound is prepared as described in Example 1. ¹H NMR (CDCl₃, 400 MHz) δ 8.32 (s, 1H), 8.07 (d, J = 8.05 Hz, 2H). 7.46 (t, J = 7.9 Hz, 2H), 7.4 (d, J = 8.55 Hz, 2H), 7.34-7.32 (m, 2H). 7.24 (s, 1H). 7.1 (t, J = 7.5 Hz, 1H), 7.01 (t, J = 7.15 Hz, 2H), 6.88 (t, J = 9 Hz, 1H). LC/MS found: 461.0 (M + 1/z). |
| 20 | 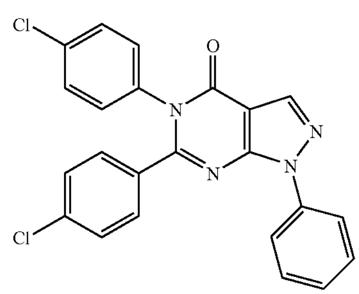 | The title compound is prepared as described in Example 1. ¹H NMR (CDCl₃, 400 MHz) δ 8.32 (s, 1H). 8.12 (d, J = 7.6 Hz, 2H), 7.53-7.49 (m, 2H), 7.38-7.33 (m, 3H), 7.29-7.23 (m, 5H), 7.1-7.05 (m, 3H), 7.08 (d, J = 8.7 Hz, 2H). LC/MS found: 433.1 (M + 1/z). |
| 21 | 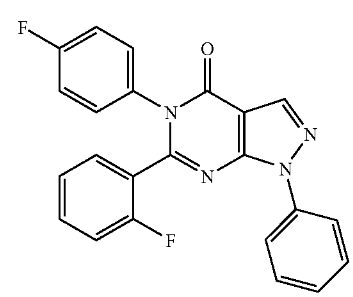 | The title compound is prepared as described in Example 1. ¹H NMR (CDCl₃, 400 MHz) δ 8.37 (s, 1H), 8.12 (d, J = 7.6 Hz, 2H), 7.53-7.49 (m, 2H), 7.38-7.31 (m, 3H), 7.16-7.1 (m, 3H), 7.02-6.98 (m, 2H), 6.94-6.89 (m, 1H). LC/MS found: 401.1 (M + 1/z). |

TABLE 1-continued

| Compound Number | Structure | Physical Data $^1$H NMR 400 MHz (CDCl$_3$) and/or MS (m/z) |
|---|---|---|
| 22 | 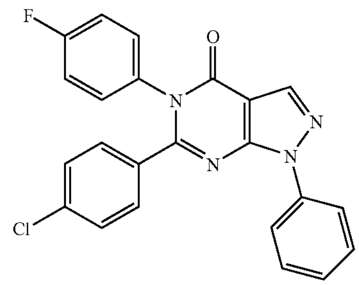 | The title compound is prepared as described in Example 1. $^1$H NMR (CDCl$_3$, 400 MHz) δ 8.32 (s, 1H), 8.13 (d, J = 7.6 Hz, 2H). 7.53-7.49 (m, 2H), 7.36-7.31 (m, 1H), 7.38-7.34 (m, 1H), 7.28-7.23 (m, 5H), 7.14-7.04 (m, 4H). LC/MS found: 417.1 (M + 1/z). |
| 23 | 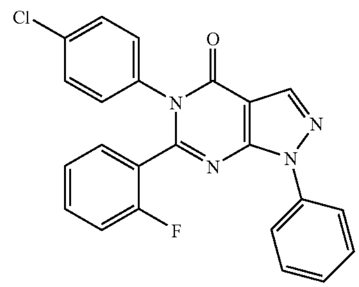 | The title compound is prepared as described in Example 1. $^1$H NMR (CDCl$_3$, 400 MHz) δ 8.29 (s, 1H), 8.05 (d, J = 7.8 Hz, 2H). 7.46-7.42 (m, 2H), 7.32-7.26 (m, 3H), 7.23-7.2 (m. 2H), 7.1-7.05 (m, 3H), 6.88-6.83 (m, 1H). LC/MS found: 417.1 (M + 1/z). |
| 24 | 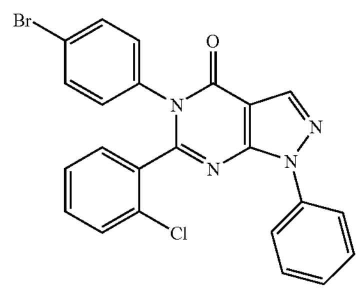 | The title compound is prepared as described in Example 2, using 2-chlorobenzoyl chloride instead of p-toluoyl chloride. HPLC-MS calculated for C$_{23}$H$_{14}$BrClN$_4$O (M + H$^+$) 477.0, found 477.0. |
| 25 | 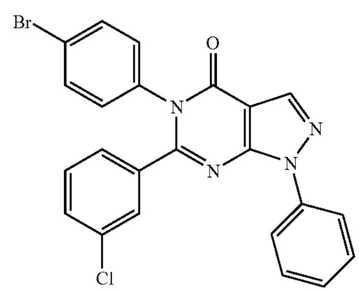 | The title compound is prepared as described in Example 2, using 3-chlorobenzoyl chloride instead of p-toluoyl chloride. HPLC-MS calculated for C$_{23}$H$_{14}$BrClN$_4$O (M + H$^+$) 477.0, found 477.0. |
| 26 | 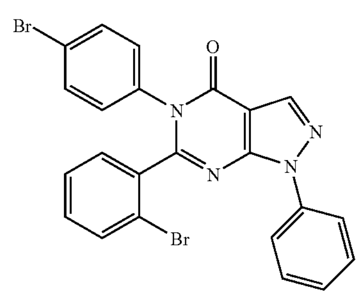 | The title compound is prepared as described in Example 2, using 2-bromobenzoyl chloride instead of p-toluoyl chloride. HPLC-MS calculated for C$_{23}$H$_{14}$Br$_2$N$_4$O (M + H$^+$) 521.0, found 520.9. |

TABLE 1-continued

| Compound Number | Structure | Physical Data<br>¹H NMR 400 MHz (CDCl₃) and/or MS (m/z) |
|---|---|---|
| 27 | 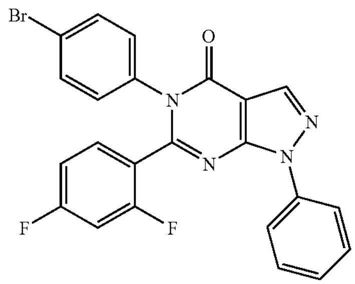 | The title compound is prepared as described in Example 2, using 2,4-difluorobenzoyl chloride instead of p-toluoyl chloride. HPLC-MS calculated for $C_{23}H_{13}BrF_2N_4O$ (M + H⁺) 479.0, found 479.1. |
| 28 | 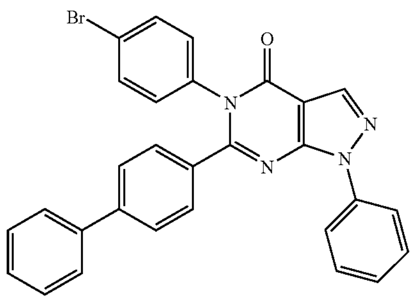 | The title compound is prepared as described in Example 2, using 4-biphenylcarbonyl chloride instead of p-toluoyl chloride. HPLC-MS calculated for $C_{29}H_{19}BrN_4O$ (M + H⁺) 519.1, found 519.1. |
| 29 | 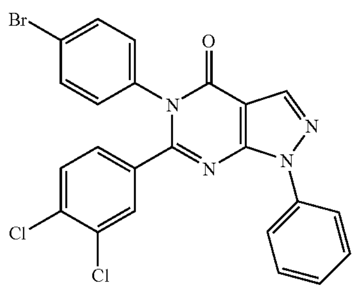 | The title compound is prepared as described in Example 2, using 3,4-dichlorobenzoyl chloride instead of p-toluoyl chloride. HPLC-MS calculated for $C_{23}H_{13}BrCl_2N_4O$ (M + H⁺) 511.0, found 511.0. |
| 30 | 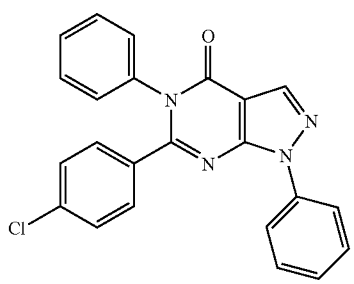 | The title compound is prepared as described in Example 2, using commercially available 4-chlorobenzanilide instead of preparing it from aniline and 4-chlorobenzoyl chloride. ¹H NMR (CDCl₃, 400 MHz) δ 8.34 (s, 1H), 8.13 (d, 2H), 7.51 (t, 2H), 7.36 (m, 4H), 7.28 (d, 2H). 7.20 (d, 2H), 7.14 (dd, 2H); HPLC-MS calculated for $C_{23}H_{15}ClN_4O$ (M + H⁺) 399.1, found 399.1. |
| 31 | 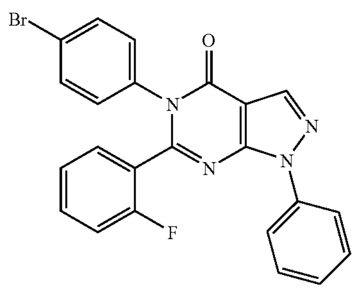 | 5-Amino-1-pyridin-2-yl-1H-pyrazole-4-carboxylic acid ethyl ester is prepared as described in Reference 1. The title compound is prepared as described in Example 2, using 2-fluorobenzoyl chloride instead of p-toluoyl chloride and 5-amino-1-pyridin-2-yl-1H-pyrazole-4-carboxylic acid ethyl ester instead of ethyl 5-amino-1-phenyl-4-pyrazole-carboxylate. HPLC-MS calculated for $C_{22}H_{13}BrFN_5O$ (M + H⁺) 462.0, found 462.0. |

TABLE 1-continued

| Compound Number | Structure | Physical Data<br>¹H NMR 400 MHz (CDCl₃) and/or MS (m/z) |
|---|---|---|
| 32 | 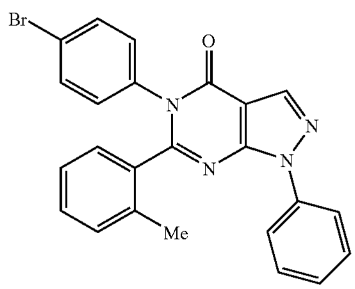 | The title compound is prepared as described in Example 2, using o-toluoyl chloride instead of p-toluoyl chloride. HPLC-MS calculated for $C_{24}H_{17}BrN_4O$ (M + H⁺) 457.1, found 457.0. |
| 33 | 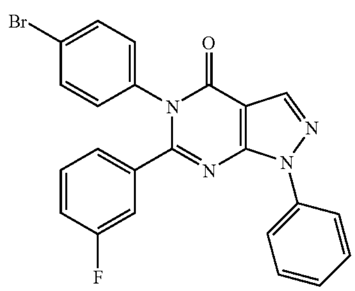 | The title compound is prepared as described in Example 2, using 3-fluorobenzoyl chloride instead of p-toluoyl chloride. ¹H NMR (CDCl₃, 400 MHz) δ 8.34 (s, 1H). 8.11 (d, 2H), 7.52 (t, 2H), 7.49 (d, 2H), 7.37 (t, 1H), 7.22 (m, 1H), 7.11 (d, 1H). 7.03 (m, 4H); HPLC-MS calculated for $C_{23}H_{14}BrFN_4O$ (M + H⁺) 461.0, found 461.0. |
| 34 | 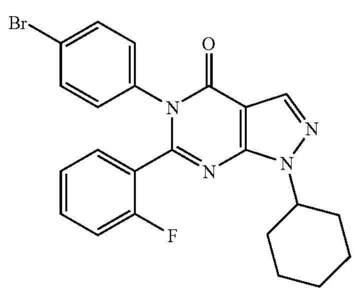 | 5-Amino-1-cyclohexyl-1H-pyrazole-4-carboxylic acid ethyl ester is prepared as described in Reference 1. The title compound is prepared as described in Example 2, using 2-fluorobenzoyl chloride instead of p-toluoyl chloride and 5-amino-1-cyclohexyl-1H-pyrazole-4-carboxylic acid ethyl ester instead of ethyl 5-amino-1-phenyl-4-pyrazole-carboxylate. HPLC-MS calculated for $C_{23}H_{20}BrFN_4O$ (M + H⁺) 467.1, found 467.0 |
| 35 | 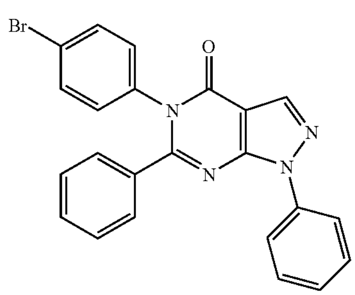 | The title compound is prepared as described in Example 2, using benzoyl chloride instead of p-toluoyl chloride. HPLC-MS calculated for $C_{23}H_{15}BrN_4O$ (M + H⁺) 443.0, found 443.1. |
| 36 | 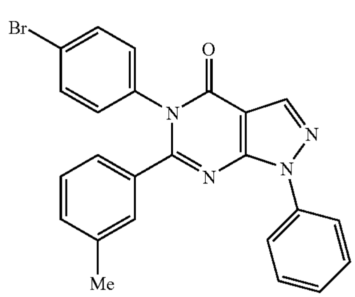 | The title compound is prepared as described in Example 2, using m-toluoyl chloride instead of p-toluoyl chloride. HPLC-MS calculated for $C_{24}H_{17}BrN_4O$ (M + H⁺) 457.1, found 457.0. |

TABLE 1-continued

| Compound Number | Structure | Physical Data<br>$^1$H NMR 400 MHz (CDCl$_3$)<br>and/or MS (m/z) |
|---|---|---|
| 37 | 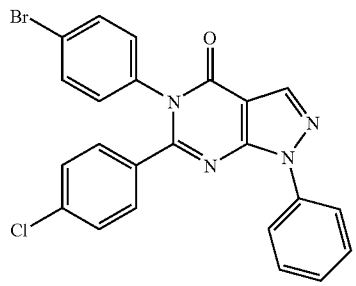 | The title compound is prepared as described in Example 1. $^1$H NMR (CDCl$_3$, 400 MHz) δ 8.29 (s, 1H). 8.10 (d, J = 7.5 Hz, 2H). 7.5-7.45 (m, 4H), 7.36-7.31 (m, 1H), 7.26-7.2 (m, 5H). 6.99 (d, J = 8.66 Hz, 2H). LC/MS found: 477.1 (M + 1/z). |
| 38 | 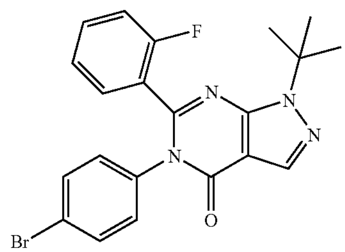 | $^1$H NMR (CDCl$_3$) δ (ppm) 8.11 (s, 1H), 7.39 (d, 2H), 7.26-7.33 (m, 2H), 7.11 (t, 1H), 7.01 (bd, 2H), 6.90 (t, 1H), 1.80 (s, 9H); HPLC-MS calculated for C$_{21}$H$_{18}$BrFN$_4$O (M + H$^+$): 440.1, found 440.2. |
| 39 | 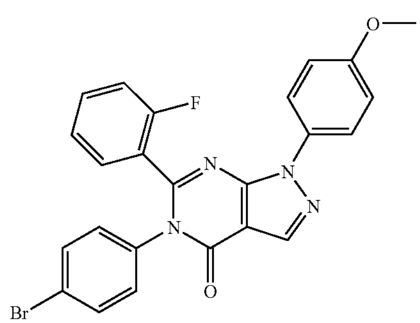 | $^1$H NMR (CDCl$_3$) δ (ppm) 8.32 (s, 1H), 7.95 (d, 2H), 7.41 (d, 2H), 7.28-7.35 (m, 2H), 7.11 (t, 1H), 7.03 (bd, 2H), 7.00 (d, 2H), 6.90 (t, 1H); HPLC-MS calculated for C$_{24}$H$_{16}$BrFN$_4$O$_2$ (M + H$^+$): 491.0, found 491.2. |
| 40 | 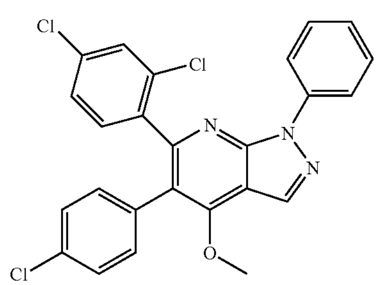 | 5-(4-chloro-phenyl)-6-(2,4-dichlorophenyl)-4-methoxy-1-phenyl-1H-pyrazolo[3,4-b]pyridine is prepared in 78% yield as described in Example 4 except using MeOH as solvent. $^1$H NMR (CDCl$_3$) δ (ppm) 8.44 (s, 1H), 8.30 (d, 2H), 7.49 (t, 2H), 7.24-7.33 (m, 2H), 7.20 (d, 2H), 7.04-7.15 (m, 4H), 4.36 (s, 3H); HPLC-MS calculated for C$_{25}$H$_{16}$Cl$_3$N$_3$O (M + H$^+$): 480.0, found 480.2 |
| 41 | 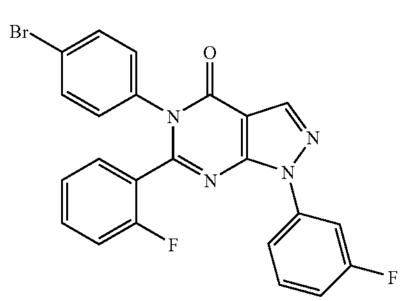 | LCMS: 479.0 (M + H)$^+$. |

TABLE 1-continued

| Compound Number | Structure | Physical Data $^1$H NMR 400 MHz (CDCl$_3$) and/or MS (m/z) |
|---|---|---|
| 42 | 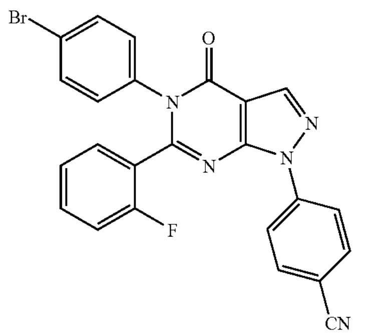 | $^1$H NMR (CDCl$_3$): δ 8.25 (2H, d, J = 8.8 Hz), 8.20 (1H, s), 7.60 (2H, dd, J = 2.0, 8.8 Hz), 7.27 (2H, d, J = 8.8 Hz), 7.15-7.22 (2H, m), 6.99 (1H, t, J = 8.8 Hz), 6.86 (2H, d, J = 6.8 Hz), 6.78 (1H, t, J = 8.8 Hz) ppm; LCMS: 486.0 (M + H)$^+$. |
| 43 | 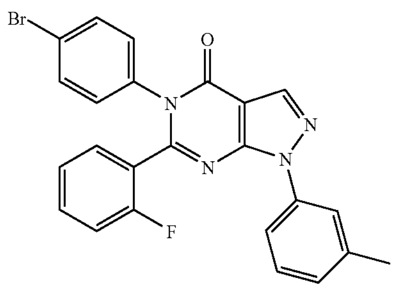 | $^1$H NMR (CDCl$_3$): δ 8.46 (1H, s), 8.02 (1H, d, J = 8.8 Hz), 7.98 (1H, brs), 7.55 (2H, d, J = 8.8 Hz), 7.45-7.49 (3H, m), 7.37 (1H, d, J = 6.8 Hz), 7.30 (1H, dt, J = 2.0, 6.8), 7.18 (2H, d, J = 8.8), 7.03 (1H, dt, J = 2.0, 6.8), 2.56 (3H, s) ppm; LCMS: 475.0 (M + H)$^+$. |
| 44 | 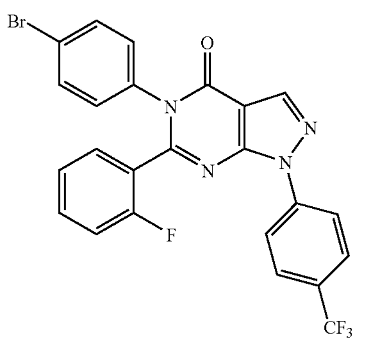 | $^1$H NMR (CDCl$_3$): δ 8.22 (1H, s), 8.20 (2H, d, J = 8.8 Hz), 7.60 (1H, d, J = 8.4 Hz), 7.28 (2H, d, J = 8.4 Hz), 7.19-2.26 (2H, m), 7.10 (1H, dt. J = 0.8, 6.8 Hz), 6.89 (2H, d, J = 6.8 Hz), 6.80 (1H, dt, J = 0.8, 6.8 Hz) ppm. |
| 45 | 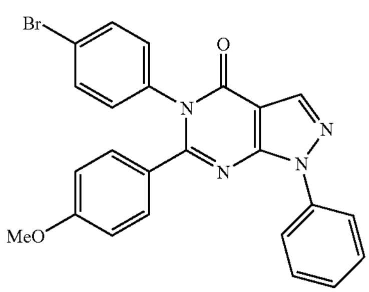 | The title compound is prepared as described in Example 2, using p-anisoyl chloride instead of p-toluoyl chloride. $^1$H NMR (CDCl$_3$, 400 MHz) δ 8.30 (s, 1H), 8.16 (d, 2H), 7.50 (m, 4H), 7.35 (t, 1H), 7.28 (d, 2H), 7.03 (d, 2H), 6.76 (d, 2H), 3.79 (s, 3H); HPLC-MS calculated for C$_{24}$H$_{17}$BrN$_4$O$_2$ (M +H$^+$) 473.0, found 473.0. |
| 46 | 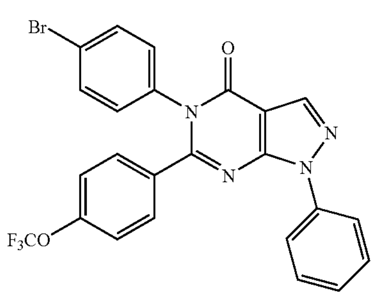 | The title compound is prepared as described in Example 2, using 4-trifluoromethoxy-benzoyl chloride instead of p-toluoyl chloride. HPLC-MS calculated for C$_{24}$H$_{14}$BrF$_3$N$_4$O$_2$ (M + H$^+$) 527.0, Found 527.0. |

TABLE 1-continued

| Compound Number | Structure | Physical Data<br>$^1$H NMR 400 MHz (CDCl$_3$) and/or MS (m/z) |
|---|---|---|
| 47 | 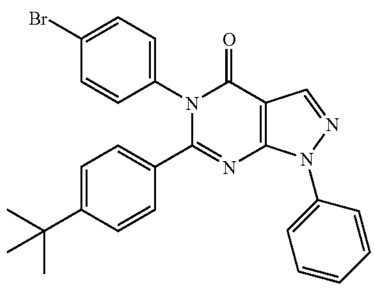 | The title compound is prepared as described in Example 2, using 4-tert-butyl-benzoyl chloride instead of p-toluoyl chloride. HPLC-MS calculated for C$_{27}$H$_{23}$BrN$_4$O (M + H$^+$) 499.1, found 499.1. |
| 48 | 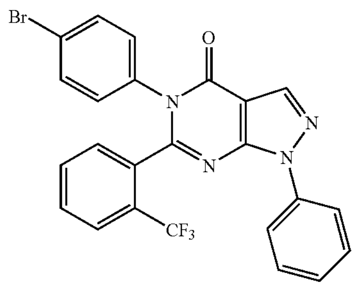 | The title compound is prepared as described in Example 2, using 2-trifluoromethyl-benzoyl chloride instead of p-toluoyl chloride. HPLC-MS calculated for C$_{24}$H$_{14}$BrF$_3$N$_4$O (M + H$^+$) 511.0, round 511.0. |
| 49 | 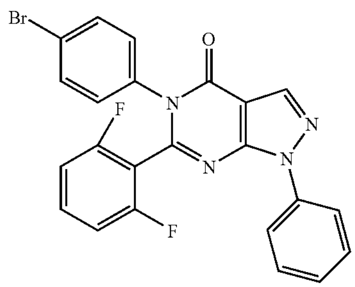 | The title compound is prepared as described in Example 2, using 2,6-difluoro-benzoyl chloride instead of p-toluoyl chloride. $^1$H NMR (CDCl$_3$, 400 MHz) δ 8.35 (s, 1H), 8.07 (d, 2H), 7.49 (t, 2H), 7.45 (d, 2H), 7.35 (t, 1H), 7.30 (t, 1H), 7.12 (d, 2H), 6.81 (t, 2H); HPLC-MS calculated for C$_{23}$H$_{13}$BrF$_2$N$_4$O (M + H$^+$) 479.0, found 479.0. |
| 50 | 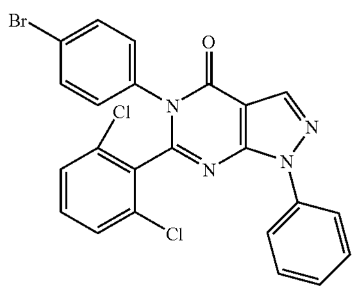 | The title compound is prepared as described in Example 2, using 2,6-dichloro-benzoyl chloride instead of p-toluoyl chloride. HPLC-MS calculated for C$_{23}$H$_{13}$BrCl$_2$N$_4$O (M + H$^+$) 511.0, found 511.0. |
| 51 | 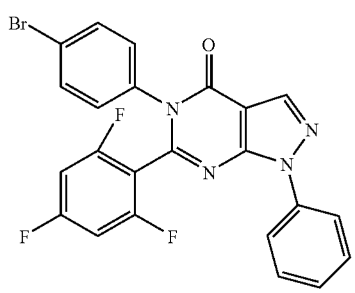 | The title compound is prepared as described in Example 2, using 2,4,6-trifluoro-benzoyl chloride instead of p-toluoyl chloride. HPLC-MS calculated for C$_{23}$H$_{12}$BrF$_3$N$_4$O (M + H$^+$) 497.0, found 497.0. |

TABLE 1-continued

| Compound Number | Structure | Physical Data<br>¹H NMR 400 MHz (CDCl₃)<br>and/or MS (m/z) |
|---|---|---|
| 52 | 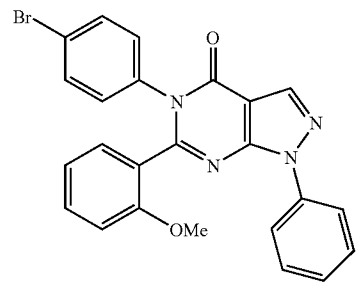 | The title compound is prepared as described in Example 2, using o-anisoyl chloride instead of p-toluoyl chloride. ¹H NMR (CDCl₃, 400 MHz) δ 8.32 (s, 1H), 8.13 (dd, 2H), 7.47 (m, 3H), 7.32 (m, 5H), 6.95 (td, 1H), 6.71 (br, 1H), 6.63 (d, 1H), 3.60 (s, 3H); HPLC-MS calculated for C₂₄H₁₇BrN₄O₂ (M + H⁺) 473.0, found 473.0. |
| 53 | 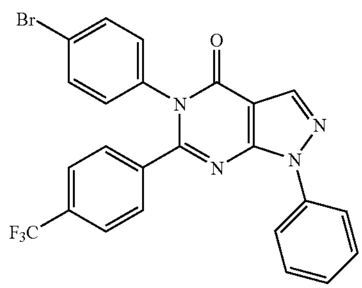 | The title compound is prepared as described in Example 2, using 4-trifluoromethyl-benzoyl chloride instead of p-toluoyl chloride. ¹H NMR (CDCl₃, 400 MHz) δ 8.34 (s, 1H), 8.11 (dd, 2H), 7.50 (m, 8H), 7.37 (t, 1H), 7.03 (d, 2H); HPLC-MS calculated for C₂₄H₁₄BrF₃N₄O (M + H⁺) 511.0, found 511.0. |
| 54 | 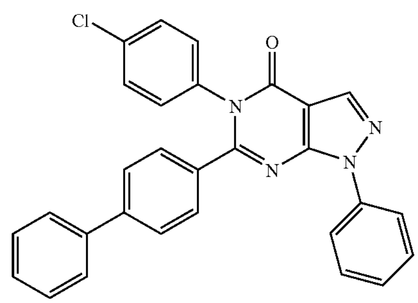 | The title compound is prepared as described in Example 2, using 4-biphenylcarbonyl chloride instead of p-toluoyl chloride and 4-chloroaniline instead of 4-bromoaniline. ¹H NMR (CDCl₃, 400 MHz) δ 8.33 (s, 1H), 8.17 (d, 2H), 7.56-7.33 (m, 14H), 7.13 (d, 2H); HPLC-MS calculated for C₂₉H₁₉ClN₄O (M + H⁺) 475.1, found 475.1. |
| 55 | 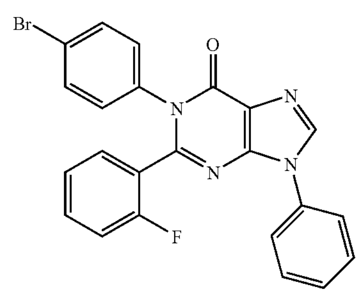 | ¹H NMR (CDCl₃) δ (ppm) 8.11 (s, 1H), 7.67 (d, 2H), 7.54 (t, 2H), 7.43 (m, 3H), 7.27 (m, 2H), 7.07 (m, 3H), 6.88 (t, 1H): HPLC-MS calculated for C₂₃H₁₄BrFN₄O (M + H⁺): 461.0. found 461.0. |
| 56 | 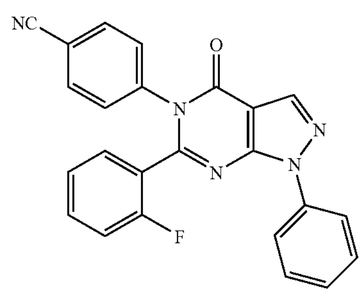 | HPLC-MS calculated for C₂₄H₁₄FN₅O (M + 1⁺): 408.1, found: 408.2 |

TABLE 1-continued

| Compound Number | Structure | Physical Data $^1$H NMR 400 MHz (CDCl$_3$) and/or MS (m/z) |
|---|---|---|
| 57 | 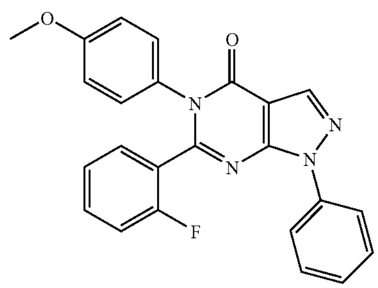 | HPLC-MS calculated for C$_{24}$H$_{17}$FN$_4$O$_2$ (M + 1$^+$): 413.3, found: 413.3 |
| 58 | 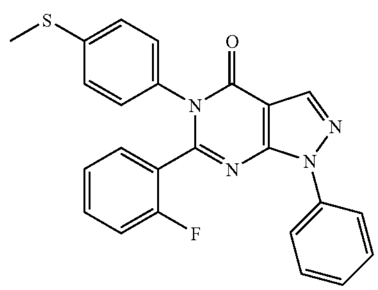 | $^1$H NMR (CDCl$_3$) δ (ppm) 8.34 (s, 1H), 8.11 (d, 2H), 7.49 (t, 2H), 7.26-7.33 (m, 3H), 7.05-7.15 (m, 5H), 6.90 (t, 1H), 4.43 (s, 3H); HPLC-MS calculated for C$_{24}$H$_{17}$FN$_4$OS (M + 1$^+$): 429.1, found: 429.2. |
| 59 | 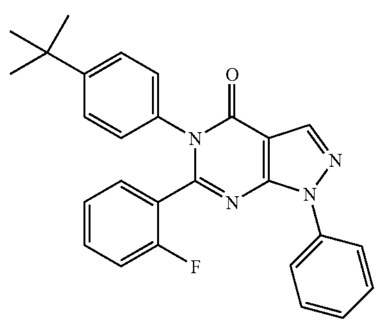 | HPLC-MS calculated for C$_{27}$H$_{23}$FN$_4$O (M + 1$^+$): 439.2, found: 439.2. |
| 60 | 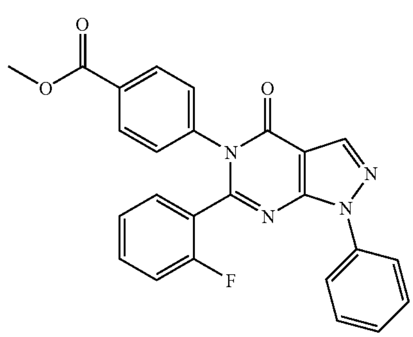 | HPLC-MS calculated for C$_{25}$H$_{17}$FN$_4$O$_3$ (M + 1$^+$): 441.1, found: 441.2. |
| 61 | 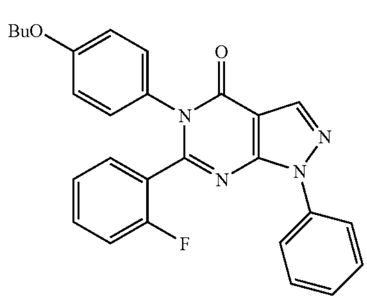 | HPLC-MS calculated for C$_{27}$H$_{23}$FN$_4$O$_2$ (M + 1$^+$): 455.2, found: 455.2 |

TABLE 1-continued

| Compound Number | Structure | Physical Data<br>¹H NMR 400 MHz (CDCl₃) and/or MS (m/z) |
| --- | --- | --- |
| 62 | 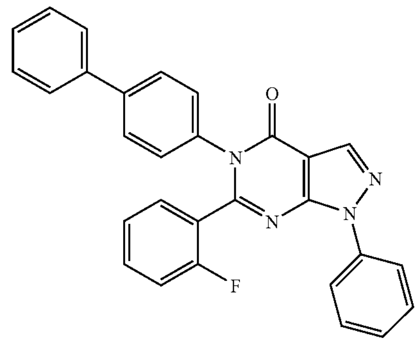 | HPLC-MS calculated for C₂₉H₁₉FN₄O (M + 1⁺): 459.2; found: 459.2. |
| 63 | 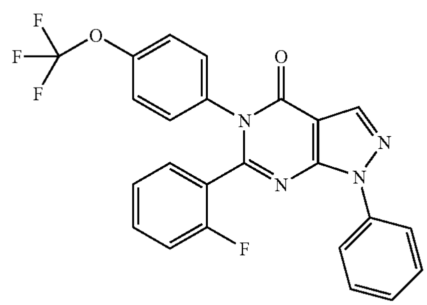 | HPLC-MS calculated for C₂₄H₁₄F₄N₄O₂ (M + 1⁺): 467.1, found: 467.2 |
| 64 | 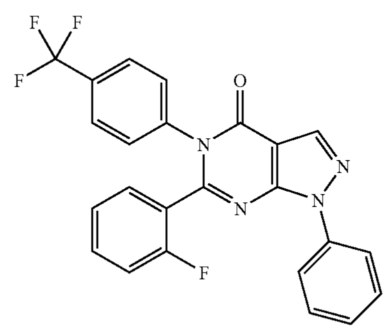 | ¹H NMR (CDCl₃) δ (ppm) 8.36 (s, 1H), 8.10 (d, 2H), 7.56 (d, 2H), 7.50 (t, 2H), 7.26-7.37 (m, 5H), 7.12 (t, 1H), 6.88 (t, 1H); HPLC-MS calculated for C₂₄H₁₄F₄N₄O (M + 1⁺): 451.1, found: 451.1. |
| 65 | 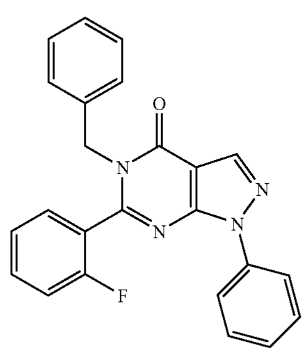 | ¹H NMR (CDCl₃) δ (ppm) 8.34 (s, 1H), 8.05 (d, 2H), 7.42-7.52 (m, 3H), 7.31 (t, 1H), 7.05-7.25 (m, 6H), 6.83 (d, 2H), 5.70 (bd, 1H). 4.85 (bd, 1H); HPLC-MS calculated for C₂₄H₁₇FN₄O (M + 1⁺): 397.1, found: 397.2. |

TABLE 1-continued

| Compound Number | Structure | Physical Data $^1$H NMR 400 MHz (CDCl$_3$) and/or MS (m/z) |
|---|---|---|
| 66 | 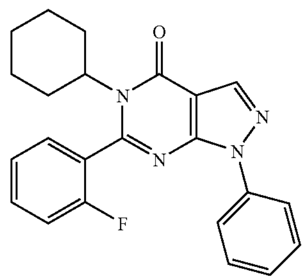 | HPLC-MS calculated for C$_{23}$H$_{21}$FN$_4$O (M + 1$^+$): 389.2, found: 389.2. |
| 67 | 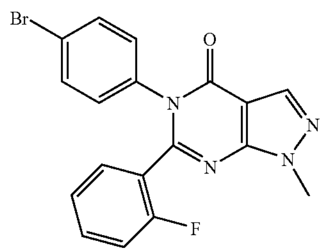 | $^1$H NMR (CDCl$_3$) δ (ppm) 8.15 (s, 1H), 7.39 (d, 2H), 7.29-7.35 (m, 2H), 7.12 (t, 1H), 7.00 (bd, 2H), 6.90 (t, 1H), 4.05 (s, 3H); HPLC-MS calculated for C$_{18}$H$_{12}$BrFN$_4$O (M + 1$^+$): 399.0, found: 399.1. |
| 70 | 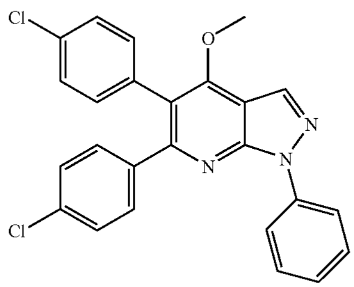 | HPLC-MS calculated for C$_{25}$H$_{17}$Cl$_2$N$_3$O (M + 1$^+$): 446.1, found: 446.2. |
| 71 | 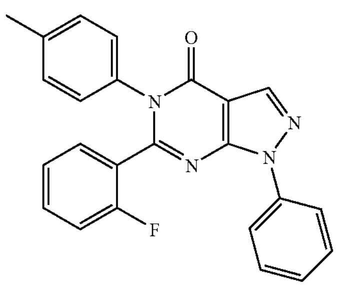 | $^1$H NMR (CDCl$_3$) δ (ppm) 8.34 (s, 1H) 8.12 (d, 2H), 7.48 (t, 2H), 7.26-7.353 (m, 3H), 7.03-7.10 (m, 5H), 6.88 (t, 1H), 2.28 (s, 3H); HPLC-MS calculated for C$_{24}$H$_{17}$FN$_4$O (M + 1$^+$): 397.1, found: 397.2. |
| 72 | 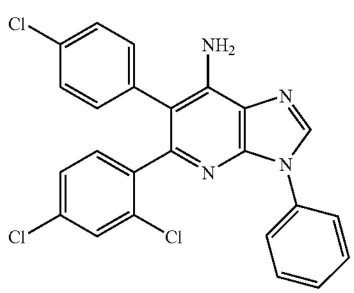 | $^1$H NMR (CDCl$_3$) δ (ppm) 8.19 (s, 1H), 7.61 (d, 2H), 7.46 (t, 1H), 7.29 (m, 2H), 7.26 (d, 1H), 7.19 (d, 2H), 7.06 (d, 2H), 6.72 (dd, 1H), 5.92 (d, 1H); HPLC-MS calculated for C$_{24}$H$_{15}$Cl$_3$N$_4$ (M + H$^+$): 465.0, found 465.0. |

TABLE 1-continued

| Compound Number | Structure | Physical Data $^1$H NMR 400 MHz (CDCl$_3$) and/or MS (m/z) |
|---|---|---|
| 73 | 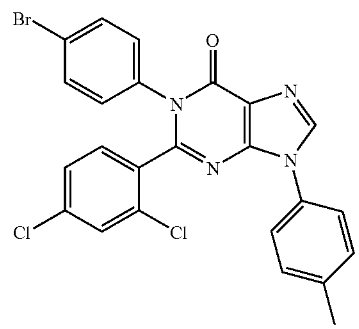 | $^1$H NMR (CDCl$_3$) δ (ppm) 8.07 (s, 1H), 7.51 (d, 2H), 7.44 (d, 2H), 7.32 (d 2H), 7.29 (d, 1H), 7.21 (b, 1H), 7.13 (m, 2H), 6.98 (b, 1H), 2.41 (s, 3H); HPLC-MS calculated for C$_{24}$H$_{15}$BrCl$_2$N$_4$O (M + H$^+$): 525.0, found 525.0. |
| 75 | 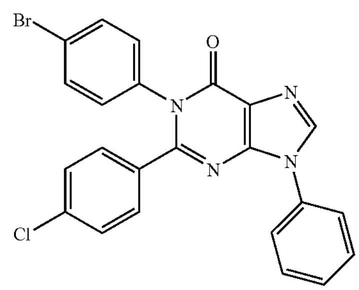 | $^1$H NMR (CDCl$_3$) δ (ppm) 8.13 (s, 1H), 7.67 (d, 2H), 7.56 (t, 3H), 7.48 (m, 3H), 7.21 (m, 3H), 7.03 (d, 2H); HPLC-MS calculated for C$_{23}$H$_{14}$BrClN$_4$O (M + H$^+$): 477.0, found 477.0 |
| 76 | 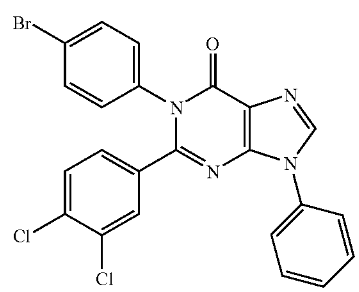 | $^1$H NMR (CDCl$_3$) δ (ppm) 8.16 (s, 1H), 7.67 (d, 2H), 7.59 (t, 2H), 7.50 (m, 4H), 7.27 (s, 1H). 7.03 (m, 3H); HPLC-MS calculated for C$_{23}$H$_{13}$BrC$_{12}$N$_4$O (M + H$^+$): 511.0, found 511.0. |
| 77 | 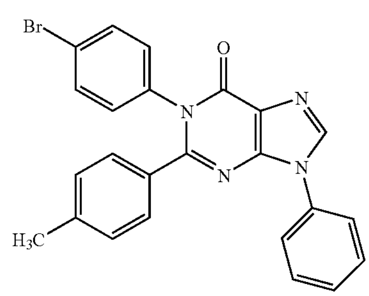 | $^1$H NMR (CDCl$_3$) δ (ppm) 8.12 (s, 1H), 7.70 (d, 2H), 7.55 (t, 2H), 7.45 (m, 3H), 7.15 (d, 2H), 7.03 (m, 4H); HPLC-MS calculated for C$_{24}$H$_{17}$BrN$_4$O (M + H$^+$): 457.0, found 457.0. |
| 78 | 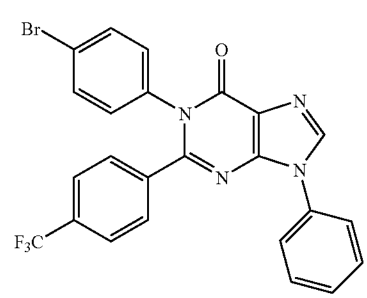 | $^1$H NMR (CDCl$_3$) δ (ppm) 8.16 (s, 1H), 7.67 (d, 2H), 7.57 (t, 2H), 7.49 (m, 5H), 7.41 (d, 2H), 7.04 (d, 2H); HPLC-MS calculated for C$_{24}$H$_{14}$BrF$_3$N$_4$O (M + H$^+$): 511.0, found 511.0. |

TABLE 1-continued

| Compound Number | Structure | Physical Data $^1$H NMR 400 MHz (CDCl$_3$) and/or MS (m/z) |
|---|---|---|
| 80 | 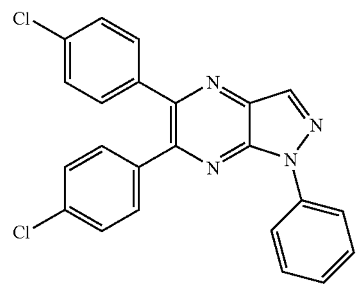 | $^1$H NMR (CDCl$_3$) δ (ppm) 8.51 (s, 1H), 8.34 (d, 2H), 7.56 (t, 2H), 7.46 (d, 2H), 7.32 ~ 7.43 (m, 7H); HPLC-MS calculated for C$_{23}$H$_{14}$Cl$_2$N$_4$ (M + H$^+$): 417.1, found: 417.1. |
| 81 | 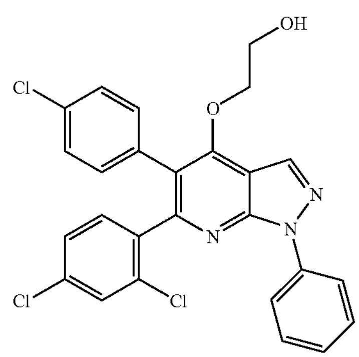 | $^1$H NMR (CDCl$_3$) δ (ppm) 8.37 (s, 1H), 8.29 (d, 2H), 7.49 (t, 2H), 7.26-7.34 (m, 2H), 7.22 (d, 2H), 7.07-7.13 (m, 4H), 4.69 (t, 2H), 3.90 (t, 2H); HPLC-MS calculated for C$_{26}$H$_{18}$Cl$_3$N$_3$O$_2$ (M + H$^+$): 510.1, found: 510.1. |
| 82 | 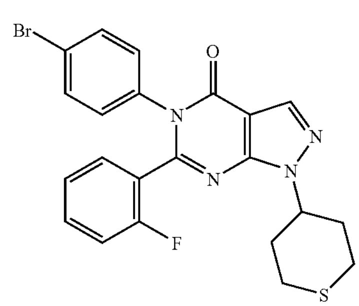 | HPLC-MS calculated for C$_{22}$H$_{18}$BrFN$_4$OS (M + H$^+$): 485.0, found: 485.0. |
| 83 | 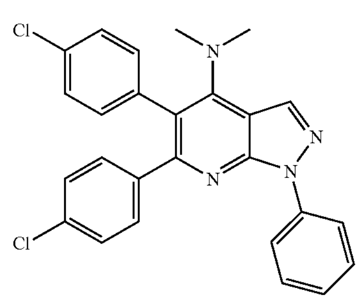 | $^1$H NMR (CDCl$_3$) δ (ppm) 8.35 (s, 1H), 8.32 (d, 2H), 7.47 (t, 2H), 7.27 (t, 1H), 7.23 (d, 2H), 7.16 (d, 2H), 7.11 (d, 2H), 7.03 (d, 2H), 2.91 (s, 6H); HPLC-MS calculated for C$_{26}$H$_{20}$Cl$_2$N$_4$ (M + H$^+$): 459.1, found: 459.1. |

TABLE 1-continued

| Compound Number | Structure | Physical Data<br>¹H NMR 400 MHz (CDCl₃) and/or MS (m/z) |
|---|---|---|
| 84 | 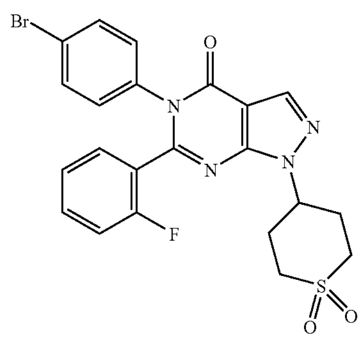 | ¹H NMR (CDCl₃) δ (ppm) 8.18 (s, 1H), 7.40 (d, 2H), 7.34 (qd, 1H), 7.28 (d, 1H), 7.12 (t, 1H), 7.00 (bd, 2H), 6.92 (t, 1H). 5.07 (m, 1H), 3.58 (td, 2H) 3.13 (td, 2H), 2.75 ~ 2.82 (m, 2H), 2.53 ~ 2.59 (m, 2H); HPLC-MS calculated for $C_{22}H_{18}BrFN_4O_3S$ (M + H⁺): 517.0, found: 517.0. |
| 85 | 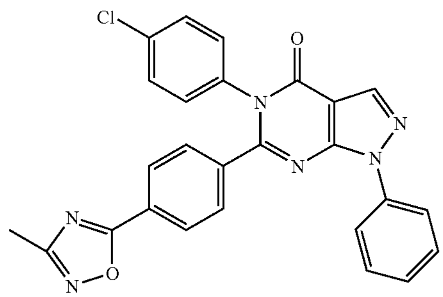 | ¹H NMR (CDCl₃) δ (ppm) 8.35 (s, 1H), 8.12 (d, 2H), 8.01 (d, 2H), 7.48-7.54 (m, 4H), 7.37 (t, 1H), 7.32 (d, 2H), 7.10 (d, 2H), 2.47 (s, 3H); HPLC-MS calculated for $C_{26}H_{17}ClN_6O_2$ (M + H⁺): 481.1, found: 481.1. |
| 86 | 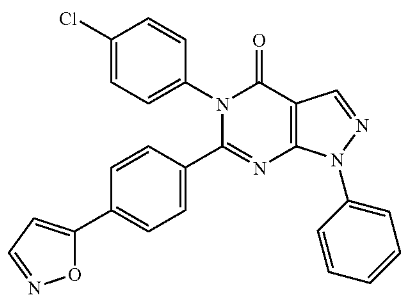 | HPLC-MS calculated for $C_{26}H_{16}ClN_5O_2$ (M + H⁺): 466.1, found: 466.1. |
| 87 | 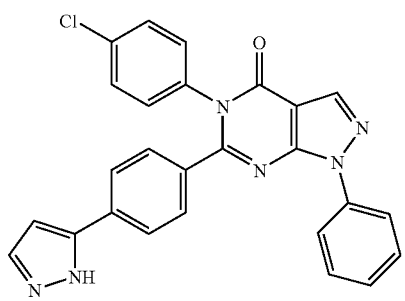 | HPLC-MS calculated for $C_{26}H_{17}ClN_6O$ (M + H⁺): 465.1, found: 465.1. |
| 88 | 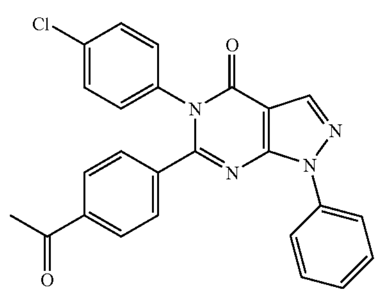 | HPLC-MS calculated for $C_{25}H_{17}ClN_4O_2$ (M + H⁺): 441.1, found: 441.1. |

TABLE 1-continued

| Compound Number | Structure | Physical Data<br>¹H NMR 400 MHz (CDCl₃)<br>and/or MS (m/z) |
|---|---|---|
| 89 | 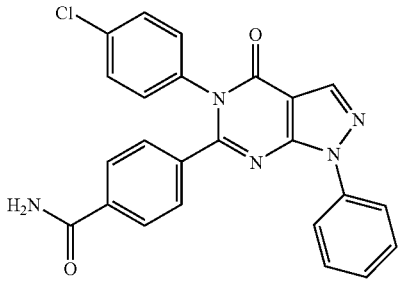 | ¹H NMR (CDCl₃) δ (ppm) 8.34 (s, 1H), 8.12 (d, 2H), 7.70 (d, 2H), 7.51 (t, 2H), 7.43 (d, 2H), 7.36 (t, 1H), 7.32 (d, 2H), 7.09 (d, 2H), 5.99(b, 1H), 5.63 (b, 1H); HPLC-MS calculated for $C_{24}H_{16}ClN_3O_2$ $(M + H^+)$: 442.1, found: 442.1. |
| 90 | 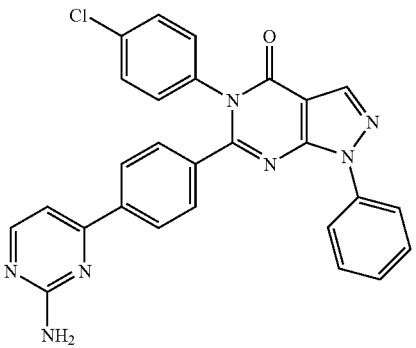 | ¹H NMR (CDCl₃) δ (ppm) 8.35 (b, 1H), 8.34 (s, 1H), 8.14 (d, 2H), 7.92 (d, 2H), 7.51 (t, 2H), 7.46 (d, 2H), 7.35 (t, 1H), 7.32 (d, 2H), 7.12 (d, 2H), 7.03 (d, 1H), 5.34 (b, 2H); HPLC-MS calculated for $C_{27}H_{18}ClN_7O$ $(M + H^+)$: 492.1, found: 492.2. |
| 91 | 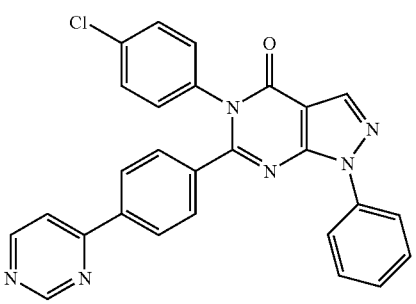 | HPLC-MS calculated for $C_{27}H_{17}ClN_6O$ $(M + H^+)$: 477.1, found: 477.2. |
| 92 | 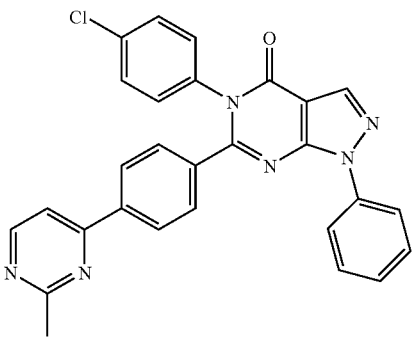 | ¹H NMR (CDCl₃) δ (ppm) 8.71 (d, 1H), 8.34 (s, 1H), 8.15 (d, 2H), 8.00 (d, 2H), 7.47 ~ 7.52 (m, 5H), 7.34 (t, 1H), 7.32 (d, 2H), 7.12 (d, 2H), 2.81 (s, 3H); HPLC-MS calculated for $C_{28}H_{19}ClN_6O$ $(M + H^+)$: 491.1, found: 491.1. |

TABLE 1-continued

| Compound Number | Structure | Physical Data $^1$H NMR 400 MHz (CDCl$_3$) and/or MS (m/z) |
|---|---|---|
| 93 | 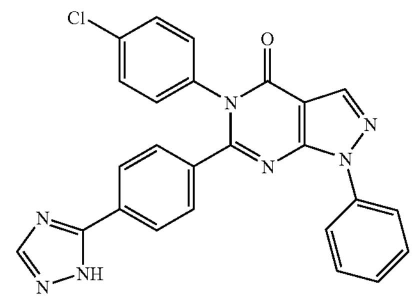 | $^1$H NMR (CDCl$_3$) δ (ppm) 8.40 (s, 1H), 8.34 (s, 1H), 8.15 (d, 2H), 8.03 (d, 2H), 7.51 (t, 2H), ~7.45 (d, 2H), 7.34 (t, 1H), 7.31 (d, 2H), 7.11 (d, 2H); HPLC-MS calculated for C$_{25}$H$_{16}$ClN$_7$O (M + H$^+$): 466.1, found: 466.1. |
| 94 | 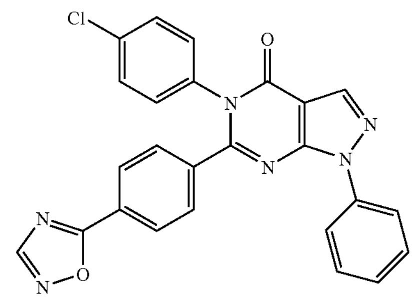 | $^1$H NMR (CDCl$_3$) δ (ppm) 8.50 (s, 1H), 8.35 (s, 1H), 8.12 (d, 2H), 8.06 (d, 2H), 7.48-7.54 (m, 4H), 7.37 (t, 1H), 7.34 (d, 2H), 7.11 (d, 2H); HPLC-MS calculated for C$_{25}$H$_{16}$ClN$_6$O$_2$ (M + H$^+$): 467.1, found: 467.1. |
| 95 | 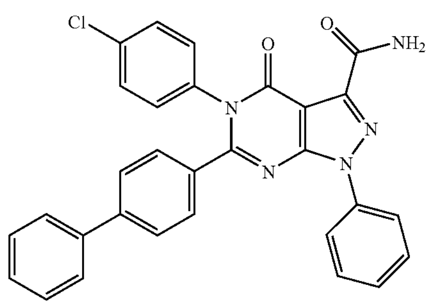 | $^1$H NMR (CDCl$_3$) δ (ppm) 10.11 (b, 1H), 8.19 (d, 2H), 7.51 ~ 7.57 (m, 6H), 7.38 ~ 7.47 (m, 8H), 7.18 (d, 2H), 6.65 (b, 1H); HPLC-MS calculated for C$_{30}$H$_{20}$ClN$_5$O$_2$ (M + H$^+$): 518.1, found: 518.1. |
| 96 | 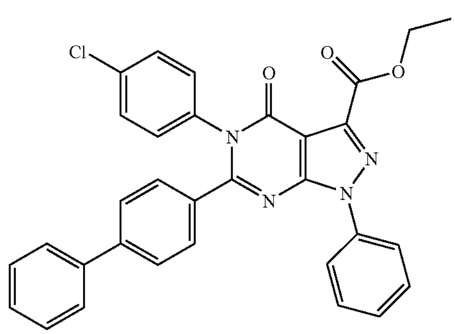 | $^1$H NMR (CDCl$_3$) δ (ppm) 8.14 (d, 2H), 7.36 ~ 7.57 (m, 12H), 7.33 (d, 2H), 7.14 (d, 2H), 4.53 (q, 2H), 1.46 (t, 3H); HPLC-MS calculated for C$_{32}$H$_{23}$ClN$_4$O$_3$ (M + H$^+$): 547.2, found: 547.2 |
| 105 | 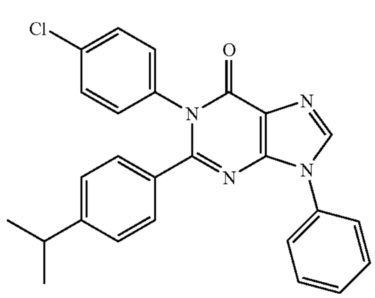 | $^1$H NMR (CDCl$_3$) δ (ppm) 8.15 (s, 1H), 7.70 (d, 2H), 7.56 (t, 2H), 7.29 (t, 1H), 7.13 (d, 2H), 7.02 (d, 2H), 6.91 (m, 4H), 2.66 (m, 1H), 1.00 (d, 6H); HPLC-MS calculated for C$_{26}$H$_{21}$ClN$_4$O (M + H$^+$): 441.1, found 441.1 |

TABLE 1-continued

| Compound Number | Structure | Physical Data<br>$^1$H NMR 400 MHz (CDCl$_3$) and/or MS (m/z) |
|---|---|---|
| 106 | 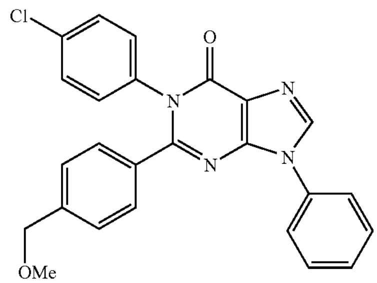 | HPLC-MS calculated for C$_{25}$H$_{19}$ClN$_4$O$_2$ (M + H$^+$): 443.0, found 443.0. |
| 107 | 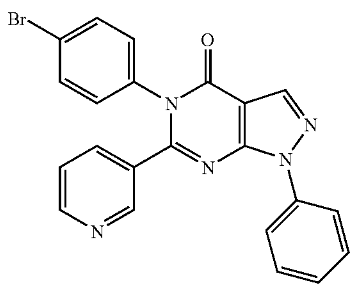 | $^1$H NMR (CDCl$_3$, 400 MHz) δ 8.68 (d, 1H), 8.56 (dd, 1H), 8.34 (s, 1H), 8.12 (d, 2H), 7.57 (dt, 1H), 7.52 (m, 4H), 7.37 (t, 1H), 7.20 (dd, 1H), 7.04 (d, 2H); HPLC-MS calculated for C$_{22}$H$_{14}$BrN$_5$O (M + H$^+$) 444.0, found 441.1. |
| 108 | 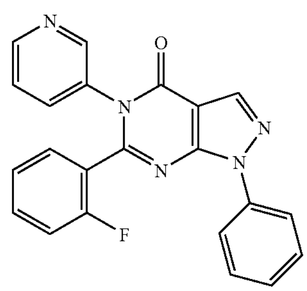 | HPLC-MS calculated for C$_{22}$H$_{14}$FN$_5$O (M + H$^+$): 384.1, found: 384.1. |
| 109 | 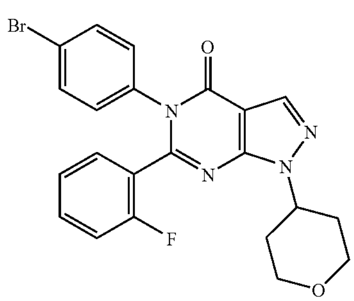 | $^1$H NMR (CDCl$_3$) δ (ppm) 8.18 (s, 1H), 7.40 (d, 2H), 7.27 ~ 7.35 (m, 2H), 7.12 (t, 1H), 7.00 (bd, 2H), 6.91 (t, 1H), 4.92 (m, 1H), 4.13 (dd, 2H), 3.58 (td, 2H), 2.42 (qd, 2H), 1.97 (dd, 2H): HPLC-MS calculated for C$_{22}$H$_{18}$BrFN$_4$O$_2$ (M + H$^+$): 469.1, found: 469.1. |
| 110 | 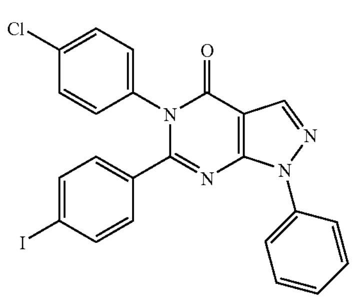 | $^1$H NMR (CDCl$_3$, 400 MHz) δ 8.32 (s, 1H), 8.12 (dd, 2H), 7.61 (d, 2H), 7.50 (t, 2H), 7.36 (m, 3H), 7.07 (m, 4H); HPLC-MS calculated for C$_{23}$H$_{14}$ClIN$_4$O (M + H$^+$) 525.0, found 524.9. |

TABLE 1-continued

| Compound Number | Structure | Physical Data<br>¹H NMR 400 MHz (CDCl₃) and/or MS (m/z) |
|---|---|---|
| 111 | 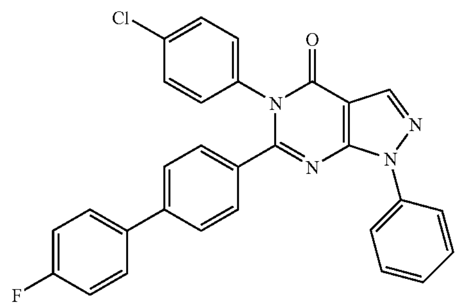 | ¹H NMR (CDCl₃, 400 MHz) δ 8.34 (s, 1H), 8.16 (dd, 2H), 7.51 (m, 4H), 7.46-7.33 (m, 7H), 7.12 (m, 4H): HPLC-MS calculated for C₂₉H₁₈ClFN₄O (M + H⁺) 493.1, found 493.1. |
| 112 | 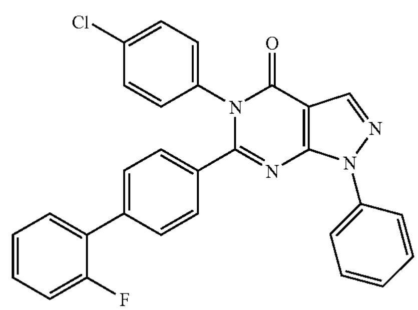 | HPLC-MS calculated for C₂₉H₁₈ClFN₄O (M + H⁺) 493.1, found 493.1. |
| 113 | 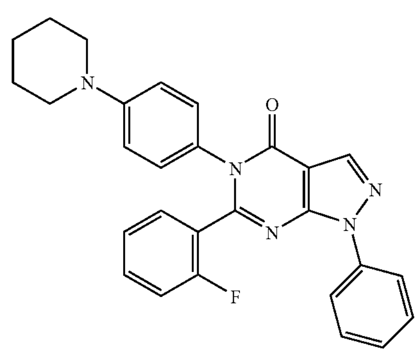 | ¹H NMR (CDCl₃) δ (ppm) 8.33 (s, 1H), 8.12 (d, 2H), 7.47 (t, 2H), 7.24 ~ 7.35 (m, 3H), 7.06 (t, 1H), 6.99 (d, 2H), 6.89 (t, 1H), 6.77 (d, 2H) 3.13 (m, 5H), 1.64 (m, 5H); HPLC-MS calculated for C₂₈H₂₄FN₅O (M + H⁺): 466.2, found: 466.2. |
| 114 | 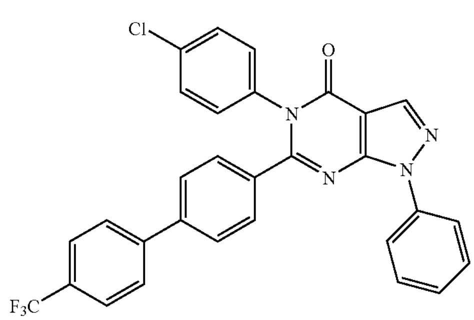 | ¹H NMR (CDCl₃, 400 MHz) δ 8.34 (s, 1H), 8.16 (dd, 2H), 7.67 (m, 4H), 7.54-7.44 (m, 6H), 7.36 (m, 3H), 7.14 (d, 2H); HPLC-MS calculated for C₃₀H₁₈ClF₃N₄O (M + H⁺) 543.1, found 543.1. |

TABLE 1-continued

| Compound Number | Structure | Physical Data<br>¹H NMR 400 MHz (CDCl₃) and/or MS (m/z) |
|---|---|---|
| 115 | 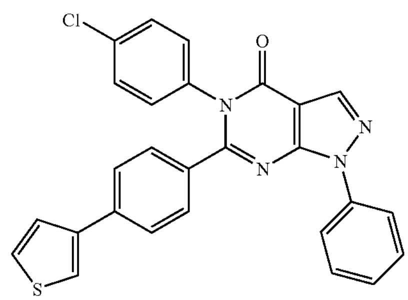 | ¹H NMR (CDCl₃, 400 MHz) δ 8.33 (s, 1H), 8.17 (dd, 2H), 7.53-7.48 (m, 5H), 7.41-7.32 (m, 7H), 7.13 (d, 2H): HPLC-MS calculated for C₂₇H₁₇ClN₄OS (M + H⁺) 481.1, found 481.1. |
| 116 | 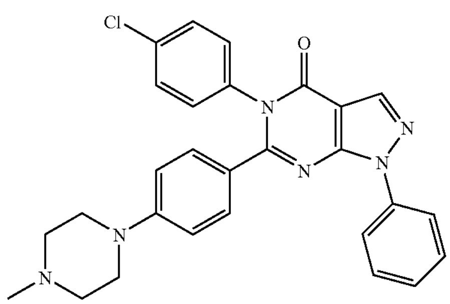 | ¹H NMR (CDCl₃, 400 MHz) δ 8.30 (s, 1H), 8.15 (dd, 2H), 7.50 (t, 2H), 7.34 (m, 3H), 7.28 (d, 2H), 7.11 (d, 2H), 6.73 (d, 2H), 3.52 (t, 4H), 3.12 (t, 4H), 2.78 (s, 3H); HPLC-MS calculated for C₂₈H₂₅ClN₆O (M + H⁺) 497.2, found 497.1. |
| 117 | 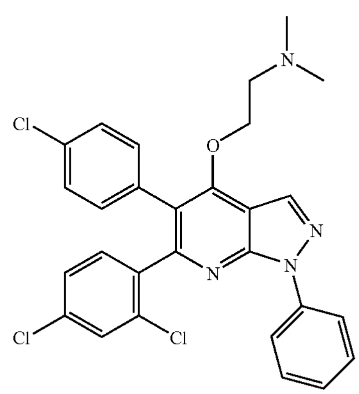 | HPLC-MS calculated for C₂₈H₂₃Cl₃N₄O (M + H⁺): 537.1, found: 537.1. |
| 118 | 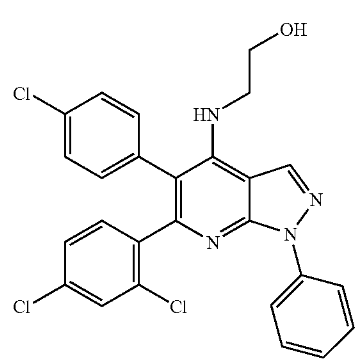 | ¹H NMR (MeOD) δ (ppm) 8.47 (s, 1H), 8.11 (d, 2H), 7.47 (t, 2H). 7.28-7.34 (m, 4H), 7.22 (d, 2H), 7.07-7.13-7.23 (m, 4H), 3.78 (s, 4H): HPLC-MS calculated for C₂₄H₁₉Cl₃N₄O (M + H⁺): 509.1, found: 509.1. |

TABLE 1-continued

| Compound Number | Structure | Physical Data $^1$H NMR 400 MHz (CDCl$_3$) and/or MS (m/z) |
|---|---|---|
| 119 | 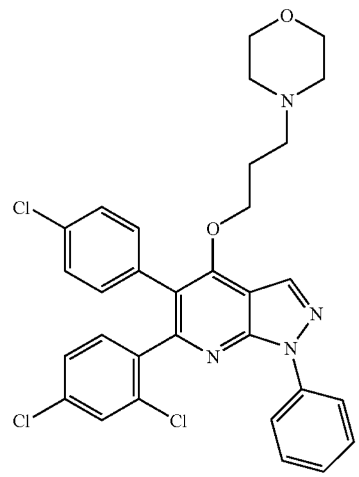 | HPLC-MS calculated for C$_{31}$H$_{27}$Cl$_3$N$_4$O$_2$ (M + H$^+$): 593.1, found: 593.1. |
| 120 | 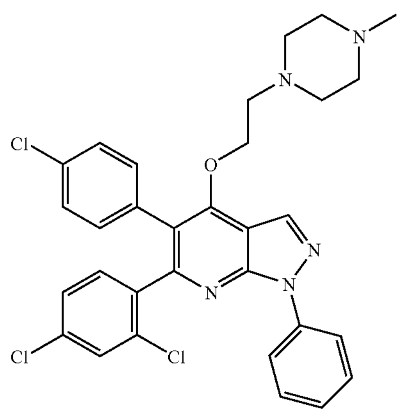 | HPLC-MS calculated for C$_{31}$H$_{28}$Cl$_3$N$_5$O (M + H$^+$): 592.1, found: 592.1. |
| 121 | 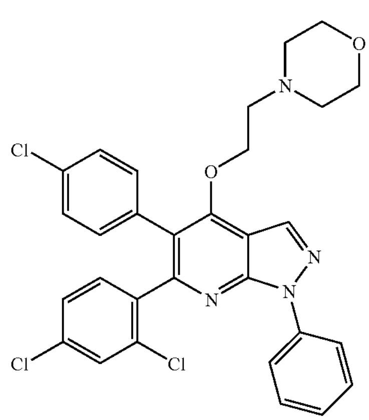 | HPLC-MS calculated for C$_{30}$H$_{25}$Cl$_3$N$_4$O$_2$ (M + H$^+$): 579.1 found: 579.1. |

TABLE 1-continued

| Compound Number | Structure | Physical Data<br>¹H NMR 400 MHz (CDCl₃) and/or MS (m/z) |
|---|---|---|
| 122 | 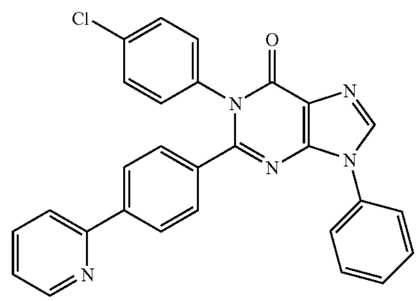 | ¹H NMR (methanol-d₄) δ (ppm) 8.97 (s, 1H), 8.68 (d, 1H), 8.49 (m, 2H), 7.83 (m, 3H), 7.67 (d, 2H), 7.57 (m, 4H), 7.51 (m, 1H), 7.36 (m, 4H); HPLC-MS calculated for C₂₈H₁₈ClN₅O (M + H⁺): 476.1, found 476.1. |
| 123 | 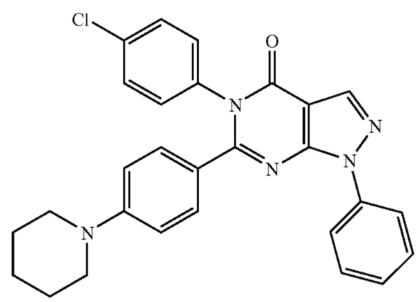 | ¹H NMR (CD₃OD, 400 MHz) δ 8.28 (s, 1H), 8.16 (dd, 2H), 7.54 (t, 2H), 7.39 (m, 3H), 7.25 (m, 4H), 6.77 (d, 2H), 3.22 (t, 4H), 1.63 (m, 6H); HPLC-MS calculated for C₂₈H₂₄ClN₅O (M + H⁺) 482.2, found 482.1. |
| 124 | 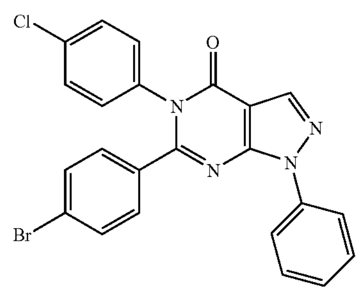 | ¹H NMR (CDCl₃, 400 MHz) δ 8.32 (s, 1H), 8.12 (dd, 2H), 7.51 (t, 2H), 7.42-7.33 (m, 5H), 7.20 (d, 2H), 7.08 (d, 2H); HPLC-MS calculated for C₂₃H₁₄BrClN₄O (M + H⁺) 477.0, found 477.0. |
| 125 | 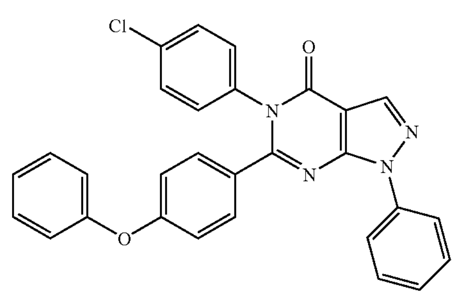 | ¹H NMR (CDCl₃, 400 MHz) δ 8.32 (s, 1H), 8.14 (d, 2H), 7.51 (t, 2H), 7.36 (m, 5H), 7.29 (d, 2H), 7.17 (t, 1H), 7.10 (d, 2H), 7.00 (d, 2H), 6.83 (d, 2H); HPLC-MS calculated for C₂₉H₁₉ClN₄O₂ (M + H⁺) 491.1, found 491.1. |
| 126 | 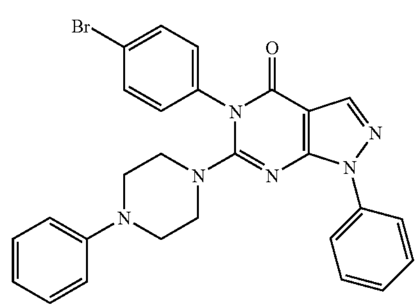 | ¹H NMR (CDCl₃, 400 MHz) δ 8.19 (s, 1H), 8.09 (d, 2H), 7.67 (d, 2H), 7.52 (t, 2H), 7.36 (m, 3H), 7.27 (d, 2H), 7.13 (m, 3H), 3.53 (t, 4H), 3.16 (t, 4H); HPLC-MS calculated for C₂₇H₂₃BrN₆O (M + H⁺) 527.1, found 527.1. |

TABLE 1-continued

| Compound Number | Structure | Physical Data $^1$H NMR 400 MHz (CDCl$_3$) and/or MS (m/z) |
|---|---|---|
| 127 | 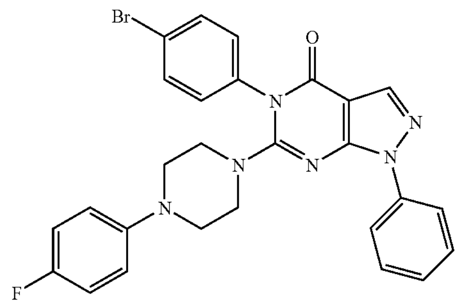 | $^1$H NMR (CDCl$_3$, 400 MHz) δ 8.19 (s, 1H), 8.09 (d, 2H), 7.67 (d, 2H), 7.52 (t, 2H), 7.36 (t, 1H), 7.27 (d, 2H), 7.05 (m, 4H), 3.50 (t, 4H), 3.08 (t, 4H); HPLC-MS calculated for C$_{27}$H$_{22}$BrFN$_6$O (M + H$^+$) 545.1, found 545.0. |
| 128 | 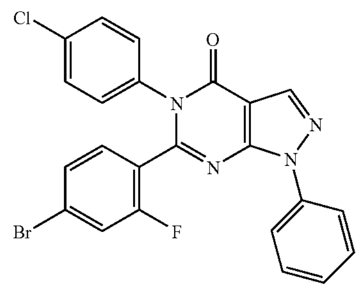 | $^1$H NMR (CDCl$_3$) δ (ppm) 8.34 (s, 1H), 8.08 (d, 2H), 7.49 (t, 2H), 7.36 (t, 1H), 7.22 ~ 7.7.32 (m, 4H), 7.08 ~ 7.12 (m, 3H): HPLC-MS calculated for C$_{23}$H$_{13}$BrClFN$_4$O (M + H$^+$): 495.0, found: 495.0. |
| 129 | 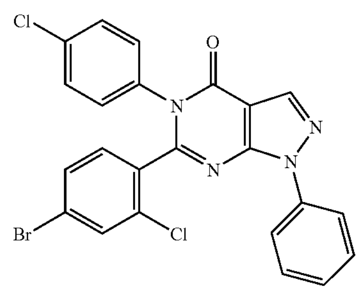 | $^1$H NMR (CDCl$_3$) δ (ppm) 8.34 (s, 1H), 8.08 (d, 2H), 7.48 (t, 3H), 7.26-7.36 (m, 5H), 7.09 (d, 1H), 6.95 (b, 1H); HPLC-MS calculated for C$_{23}$H$_{13}$BrCl$_2$N$_4$O (M + H$^+$): 511.0, found: 511.0. |
| 130 | 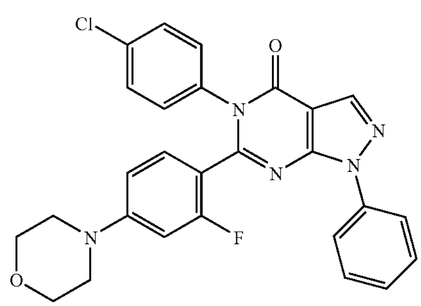 | HPLC-MS calculated for C$_{27}$H$_{21}$ClFN$_5$O$_2$ (M + H$^+$): 502.1, found: 502.1. |
| 131 | 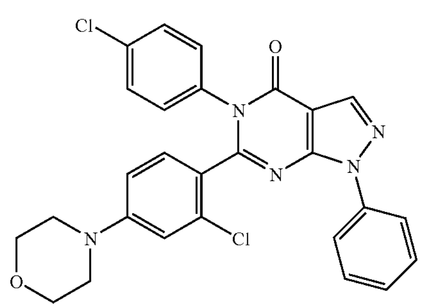 | $^1$H NMR (CDCl$_3$) δ (ppm) 8.33 (s, 1H), 8.11 (d, 2H), 7.48 (t, 2H), 7.34 (t, 1H), 7.26-7.29 (m, 3H), 7.06 (d, 2H), 6.78 (d, 1H), 6.69 (dd, 1H), 3.84 (t, 4H), 3.17 (t, 4H); HPLC-MS calculated for C$_{27}$H$_{21}$Cl$_2$N$_5$O$_2$ (M + H$^+$): 518.1, found: 518.1. |

TABLE 1-continued

| Compound Number | Structure | Physical Data $^1$H NMR 400 MHz (CDCl$_3$) and/or MS (m/z) |
|---|---|---|
| 132 | 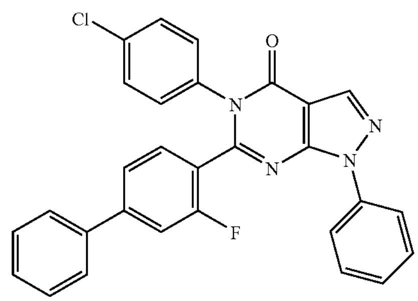 | $^1$H NMR (CDCl$_3$) δ (ppm) 8.35 (s, 1H), 8.12 (d, 2H), 7.52 (t, 2H), 7.33 ~ 7.50 (m, 8H), 7.29 (d, 2H), 7.12 ~ 7.15 (m, 3H); HPLC-MS calculated for C$_{29}$H$_{18}$ClFN$_4$O (M + H$^+$): 492.1, found: 492.1. |
| 133 | 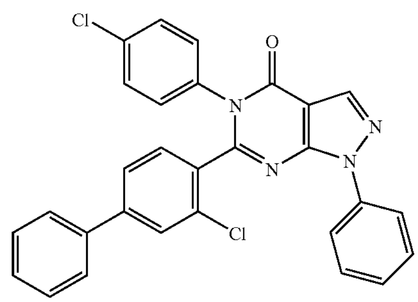 | HPLC-MS calculated for C$_{29}$H$_{18}$Cl$_2$N$_4$O (M + H$^+$): 509.1, found: 509.1. |
| 134 | 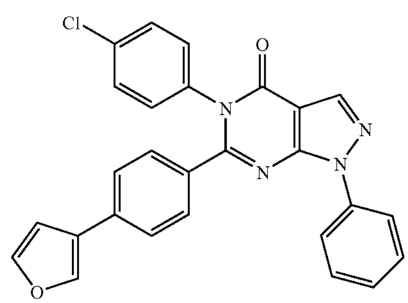 | $^1$H NMR (CDCl$_3$, 400 MHz) δ 8.33 (s, 1H), 8.16 (dd, 2H), 7.74 (s, 1H), 7.51 (t, 2H), 7.48 (t, 1H), 7.39-7.32 (m, 7H), 7.12 (d, 2H), 6.67 (d, 1H); HPLC-MS calculated for C$_{27}$H$_{17}$ClN$_4$O$_2$ (M + H$^+$) 465.1, found 465.0. |
| 135 | 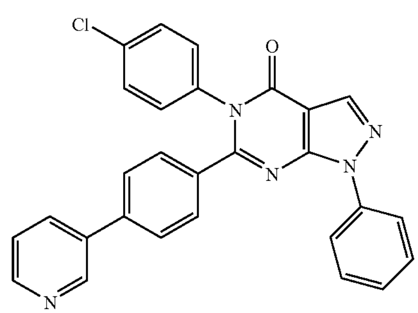 | $^1$H NMR (CDCl$_3$, 400 MHz) δ 8.86 (d, 1H), 8.65 (dd, 1H), 8.34 (s, 1H), 8.15 (dd, 2H), 8.04 (d, 1H), 7.56-7.50 (m, 7H), 7.36 (m, 3H), 7.14 (d, 2H); HPLC-MS calculated for C$_{28}$H$_{18}$ClN$_5$O (M + H$^+$) 476.1, found 476.1. |
| 136 | 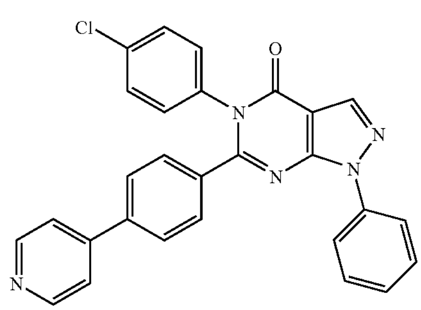 | $^1$H NMR (CDCl$_3$, 400 MHz) δ 8.76 (d, 2H), 8.36 (s, 1H), 8.12 (dd, 2H), 7.94 (d, 2H), 7.65 (d, 2H), 7.58 (d, 2H), 7.52 (t, 2H), 7.38 (t, 1H), 7.35 (d, 2H), 7.14 (d, 2H); HPLC-MS calculated for C$_{28}$H$_{18}$ClN$_5$O (M + H$^+$) 476.1, found 476.1. |

TABLE 1-continued

| Compound Number | Structure | Physical Data $^1$H NMR 400 MHz (CDCl$_3$) and/or MS (m/z) |
|---|---|---|
| 137 | 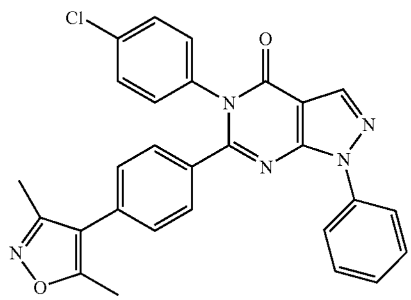 | $^1$H NMR (CDCl$_3$, 400 MHz) δ 8.34 (s, 1H), 8.15 (dd, 2H), 7.52 (t, 2H), 7.39 (m, 3H), 7.34 (d, 2H), 7.16 (d, 2H), 7.12 (d, 2H), 2.38 (s, 3H), 2.23 (s, 3H); HPLC-MS calculated for C$_{28}$H$_{20}$ClN$_5$O$_2$ (M + H$^+$) 494.1, found 494.1. |
| 138 | 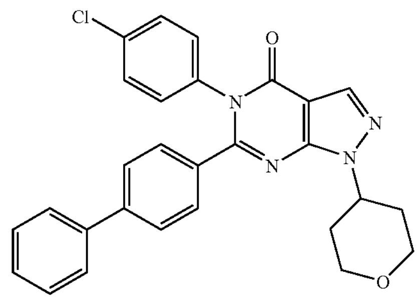 | $^1$H NMR (CDCl$_3$, 400 MHz) δ 8.17 (s, 1H), 7.55 (d, 2H), 7.50 (d, 2H), 7.44 (t, 2H), 7.37 (m, 3H), 7.31 (d, 2H), 7.10 (d, 2H), 4.97 (m, 1H), 4.15 (dd, 2H), 3.61 (td, 2H), 2.45 (ddd, 2H), 1.99 (dd, 2H); HPLC-MS calculated for C$_{28}$H$_{23}$ClN$_4$O$_2$ (M + H$^+$) 483.2, found 483.1. |
| 139 | 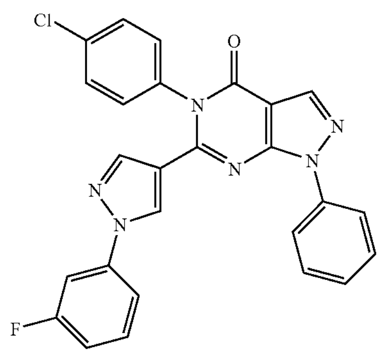 | $^1$H NMR (CDCl$_3$, 400 MHz) δ 8.30 (s, 1H), 8.15 (d, 2H), 7.61 (d, 2H), 7.57 (t, 2H), 7.42 (m, 4H), 7.31 (m, 3H), 7.23 (dd, 1H), 7.04 (td, 1H); HPLC-MS calculated for C$_{26}$H$_{16}$ClFN$_6$O (M + H$^+$) 483.1, found 483.1. |
| 140 | 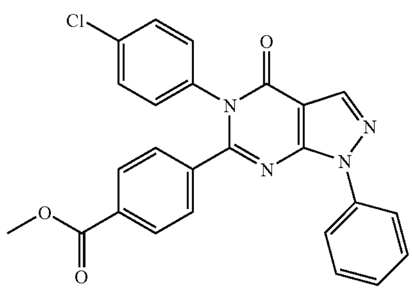 | $^1$H NMR (CDCl$_3$) δ (ppm) 8.34 (s, 1H), 8.13 (d, 2H), 7.93 (d, 2H), 7.51 (t, 2H), 7.40 (d, 2H), 7.36 (t, 1H), 7.31 (d, 2H), 7.08 (d, 2H), 3.91 (s, 3H); HPLC-MS calculated for C$_{25}$H$_{17}$ClN$_4$O$_3$ (M + H$^+$): 457.1, found: 457.1. |
| 141 | 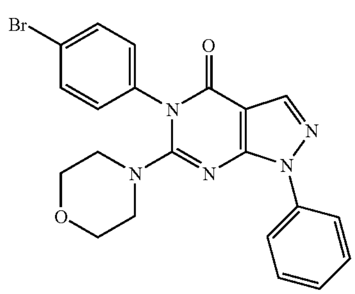 | HPLC-MS calculated for C$_{21}$H$_{18}$BrN$_5$O$_2$ (M + H$^+$) 452.1, found 452.0. |

TABLE 1-continued

| Compound Number | Structure | Physical Data<br>¹H NMR 400 MHz (CDCl₃)<br>and/or MS (m/z) |
|---|---|---|
| 142 | 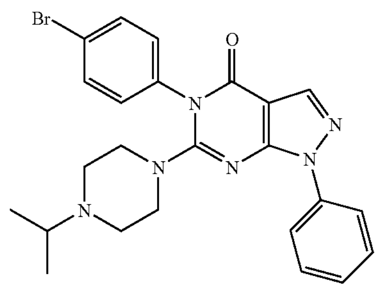 | HPLC-MS calculated for<br>C$_{24}$H$_{25}$BrN$_6$O (M + H⁺) 493.1,<br>found 493.1. |
| 143 | 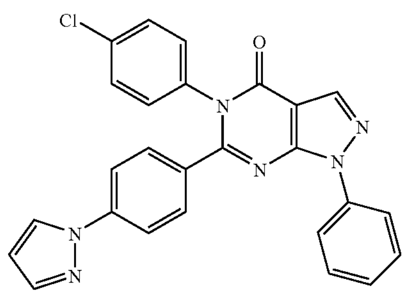 | HPLC-MS calculated for<br>C$_{26}$H$_{17}$ClN$_6$O (M + H⁺) 465.1,<br>found 465.1. |
| 144 | 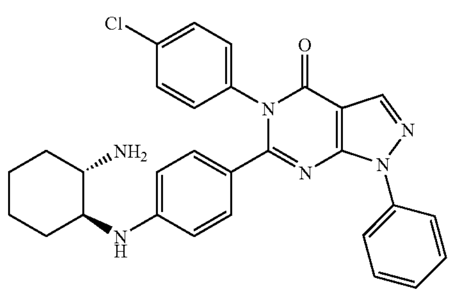 | HPLC-MS calculated for<br>C$_{29}$H$_{27}$ClN$_6$O (M + H⁺) 511.2,<br>found 511.1. |
| 145 | 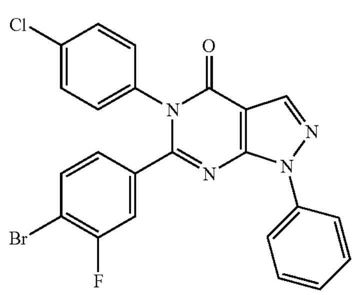 | HPLC-MS calculated for<br>C$_{23}$H$_{13}$BrClFN$_4$O (M + H⁺):<br>495.0, found: 495.0. |
| 146 | 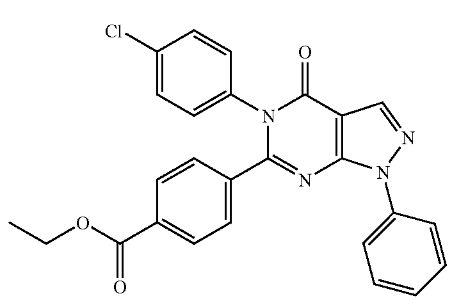 | ¹H NMR (CDCl₃) δ (ppm)<br>8.34 (s, 1H), 8.13 (d, 2H),<br>7.93 (d, 2H), 7.50 (t, 2H), 7.40<br>(d, 2H), 7.36 (t, 1H), 7.31 (d,<br>2H), 7.08 (d, 2H), 4.37 (q, 2H),<br>1.39 (t, 3H); HPLC-MS<br>calculated for C$_{26}$H$_{19}$ClN$_4$O$_3$<br>(M + H⁺): 471.1, found: 470.1. |

TABLE 1-continued

| Compound Number | Structure | Physical Data<br>¹H NMR 400 MHz (CDCl₃) and/or MS (m/z) |
|---|---|---|
| 147 | 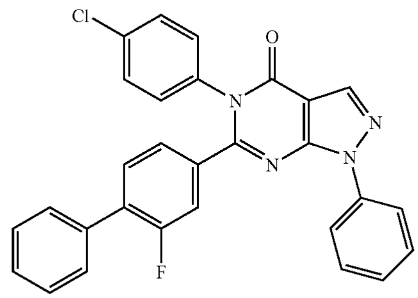 | HPLC-MS calculated for C₂₉H₁₈ClFN₄O (M + H⁺): 493.1, found: 493.1. |
| 148 | 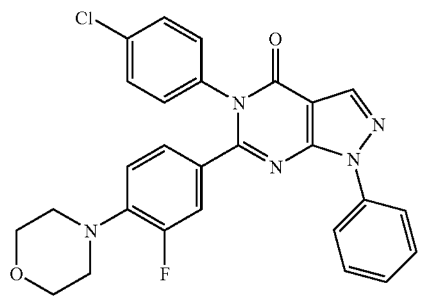 | HPLC-MS calculated for C₂₇H₂₁ClFN₅O₂ (M + H⁺): 502.1.0, found: 502.1, 501.94 |
| 149 | 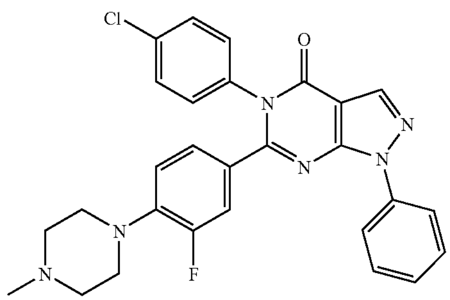 | ¹H NMR (CDCl₃) δ (ppm) 8.32 (s, 1H), 8.11 (d, 2H), 7.52 (t, 2H), 7.39 (t, 1H), 7.36 (d, 2H), 7.11 (d, 2H), 7.07 (d, 2H), 6.79 (t, 1H), 3.69 (d, 2H), 3.53 (d, 2H), 3.33 (t, 2H), 3.05 (t, 2H), 2.89 (s, 3H); HPLC-MS calculated for C₂₈H₂₄ClFN₆O (M + H⁺): 515.2, found: 515.2. |
| 150 | 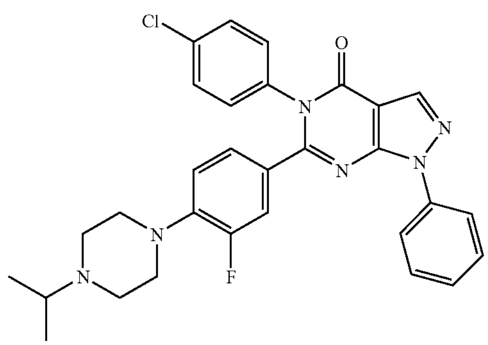 | ¹H NMR (CDCl₃) δ (ppm) 8.31 (s, 1H), 8.11 (d, 2H), 7.52 (t, 2H), 7.39 (t, 1H), 7.36 (d, 2H), 7.11 (d, 2H), 7.07 (d, 2H), 6.79 (t, 1H), 3.53-3.62 (m, 5H), 3.36 (t, 2H), 3.08 (t, 2H), 1.40 (d, 6H); HPLC-MS calculated for C₃₀H₂₈ClFN₆O (M + H⁺): 543.2, found: 543.2. |
| 151 | 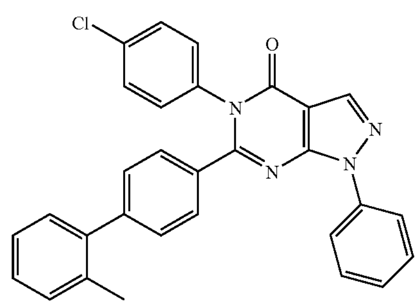 | ¹H NMR (CDCl₃, 400 MHz) δ 8.35 (s, 1H), 8.17 (dd, 2H), 7.53 (t, 2H), 7.39-7.32 (m, 5H), 7.26 (m, 2H), 7.23 (m, 3H), 7.14 (m, 3H), 2.18 (s, 3H); HPLC-MS calculated for C₃₀H₂₁ClN₄O (M + H⁺) 489.1, found 489.1. |

TABLE 1-continued

| Compound Number | Structure | Physical Data $^1$H NMR 400 MHz (CDCl$_3$) and/or MS (m/z) |
|---|---|---|
| 152 | 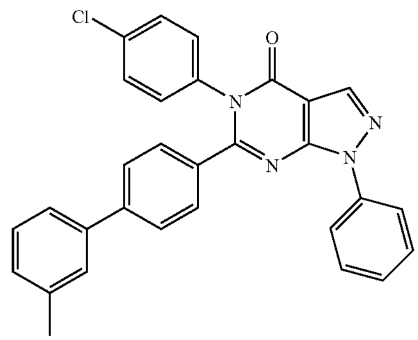 | $^1$H NMR (CDCl$_3$, 400 MHz) δ 8.33 (s, 1H), 8.17 (dd, 2H), 7.52 (t, 2H), 7.48 (d, 2H), 7.41-7.32 (m, 8H), 7.19 (d, 1H), 7.13 (d, 2H), 2.41 (s, 3H); HPLC-MS calculated for C$_{30}$H$_{21}$ClN$_4$O (M + H$^+$) 489.1, found 489.1. |
| 153 | 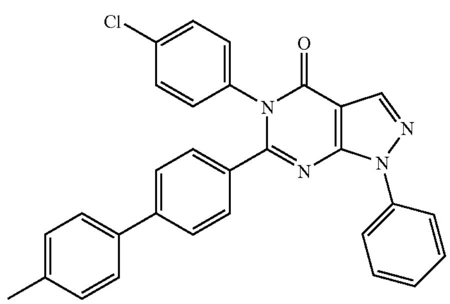 | $^1$H NMR (CDCl$_3$, 400 MHz) δ 8.33 (s, 1H), 8.17 (dd, 2H), 7.51 (t, 2H), 7.47 (d, 2H), 7.45 (d, 2H), 7.39 (d, 2H), 7.35 (m, 3H), 7.24 (d, 2H), 7.13 (d, 2H), 2.39 (s, 3H); HPLC-MS calculated for C$_{30}$H$_{21}$ClN$_4$O (M + H$^+$) 489.1, found 489.1. |
| 154 | 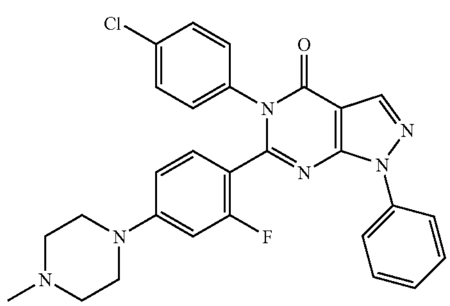 | HPLC-MS calculated for C$_{28}$H$_{24}$ClFN$_6$O (M + H$^+$): 515.2, found: 515.2. |
| 155 | 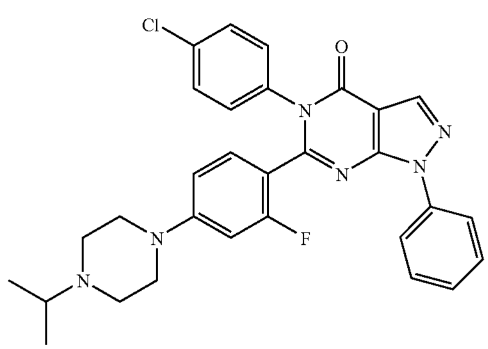 | HPLC-MS calculated for C$_{30}$H$_{28}$ClFN$_6$O (M + H$^+$): 543.2, found: 543.2. |

TABLE 1-continued

| Compound Number | Structure | Physical Data $^1$H NMR 400 MHz (CDCl$_3$) and/or MS (m/z) |
|---|---|---|
| 156 | 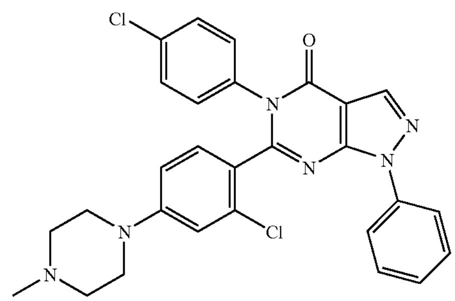 | HPLC-MS calculated for C$_{28}$H$_{24}$Cl$_2$N$_6$O (M + H$^+$): 531.1, found: 531.1. |
| 157 | 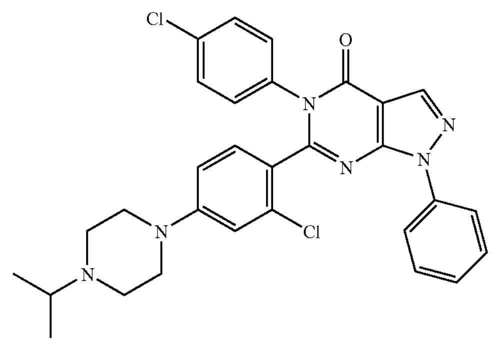 | HPLC-MS calculated for C$_{30}$H$_{28}$Cl$_2$N$_6$O (M + H$^+$): 559.2, found: 559.2. |
| 158 | 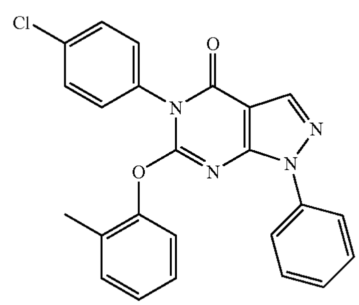 | HPLC-MS calculated for C$_{24}$H$_{17}$ClN$_4$O$_2$ (M + H$^+$) 429.1, found 429.2. |
| 159 | 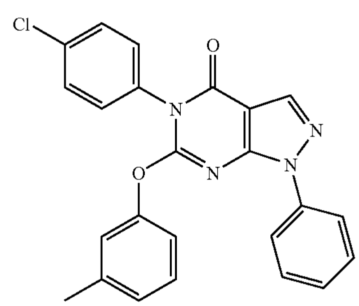 | HPLC-MS calculated for C$_{24}$H$_{17}$ClN$_4$O$_2$ (M + H$^+$) 429.1, found 429.2. |
| 160 | 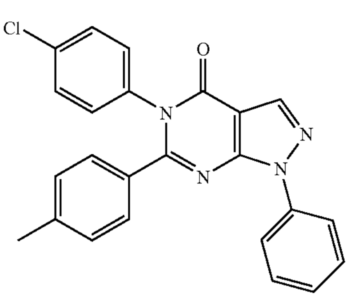 | HPLC-MS calculated for C$_{24}$H$_{17}$ClN$_4$O (M + H$^+$) 413.1, found 413.2. |

TABLE 1-continued

| Compound Number | Structure | Physical Data $^1$H NMR 400 MHz (CDCl$_3$) and/or MS (m/z) |
|---|---|---|
| 161 | 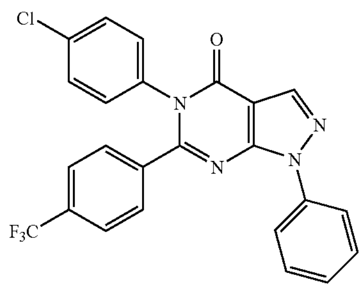 | HPLC-MS calculated for C$_{24}$H$_{14}$ClF$_3$N$_4$O (M + H$^+$) 467.1, found 467.2. |
| 162 | 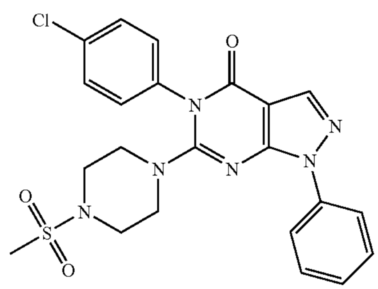 | $^1$H NMR (CDCl$_3$, 400 MHz) δ 8.17 (s, 1H), 8.08 (dd, 2H), 7.52 (m, 4H), 7.36 (t, 1H), 7.30 (d, 2H), 3.30 (t, 4H), 3.06 (t, 4H), 2.76 (s, 3H); HPLC-MS calculated for C$_{22}$H$_{21}$ClN$_6$O$_3$S (M + H$^+$) 485.1, found 485.2. |
| 163 | 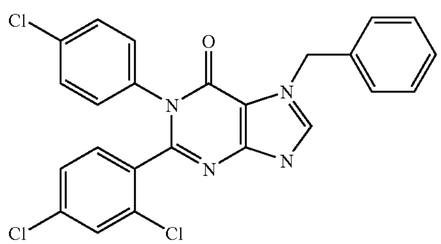 | HPLC-MS calculated for C$_{24}$H$_{15}$Cl$_3$N$_4$O (M + H$^+$): 481.9, found 481.9 |
| 164 | 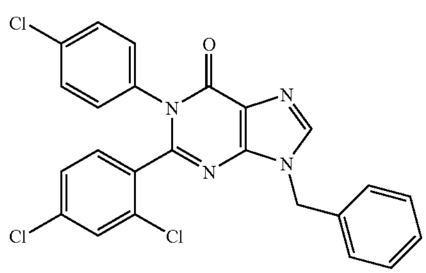 | $^1$H NMR (CDCl$_3$) δ (ppm) 7.72 (s, 1H), 7.28 (m, 6H), 7.19 (m, 3H), 7.08 (m, 2H), 6.97 (b, 1H), 5.27 (d, 2H); HPLC-MS calculated for C$_{24}$H$_{15}$Cl$_3$N$_4$O (M + H$^+$): 481.0, found 481.0. |
| 165 | 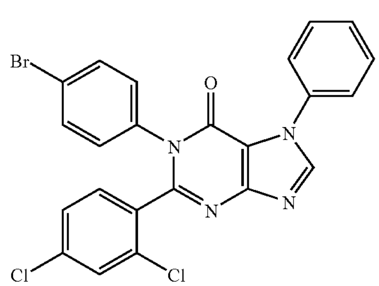 | HPLC-MS calculated for C$_{23}$H$_{13}$BrCl$_2$N$_4$O (M + H$^+$): 510.9, found 510.9. |

TABLE 1-continued

| Compound Number | Structure | Physical Data $^1$H NMR 400 MHz (CDCl$_3$) and/or MS (m/z) |
|---|---|---|
| 166 | 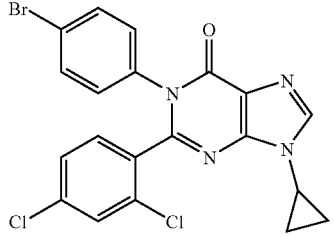 | HPLC-MS calculated for C$_{20}$H$_{13}$BrCl$_2$N$_4$O (M + H$^+$): 474.9, found 474.9. |
| 167 | 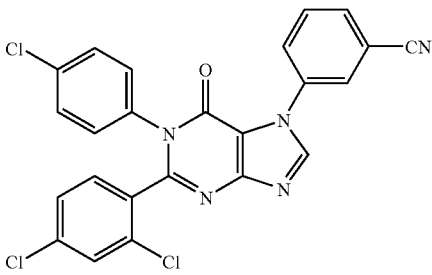 | HPLC-MS calculated for C$_{24}$H$_{12}$Cl$_3$N$_5$O (M + H$^+$): 492.1, found 492.1. |
| 168 | 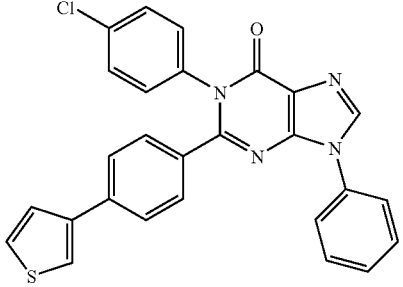 | $^1$H NMR (CDCl$_3$) δ (ppm) 8.12 (s, 1H), 7.71 (d, 2H), 7.57 (t, 2H), 7.47 (m, 4H), 7.38 (m, 1H), 7.33 (m, 5H), 7.14 (d, 2H); HPLC-MS calculated for C$_{27}$H$_{17}$ClN$_4$OS (M + H$^+$): 481.0, found 481.0. |
| 169 | 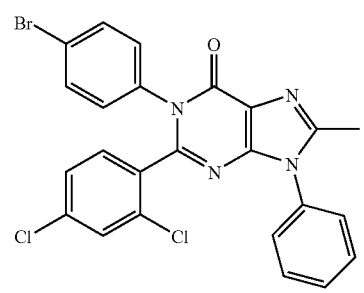 | $^1$H NMR (CDCl$_3$) δ (ppm) 7.54 (m, 3H), 7.42 (m, 4H), 7.45 (b, 1H), 7.10 (m, 4H), 2.56 (s, 3H); HPLC-MS calculated for C$_{24}$H$_{15}$BrCl$_2$N$_4$O (M + H$^+$): 524.9, found 524.9. |
| 170 | 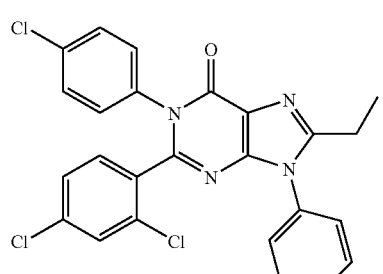 | $^1$H NMR (CDCl$_3$) δ (ppm) 7.56 (m, 3H), 7.40 (m, 2H), 7.24 (m, 4H), 7.06 (m, 3H), 2.85 (q, 2H), 1.32 (t, 3H); HPLC-MS calculated for C$_{25}$H$_{17}$Cl$_3$N$_4$O (M + H$^+$): 495.0, found 495.0. |

TABLE 1-continued

| Compound Number | Structure | Physical Data $^1$H NMR 400 MHz (CDCl$_3$) and/or MS (m/z) |
|---|---|---|
| 171 | 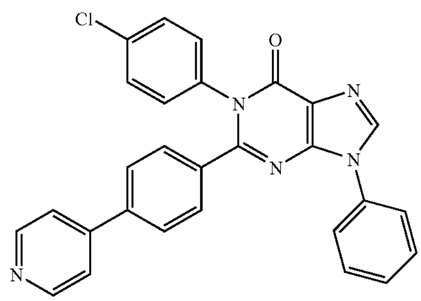 | $^1$H NMR (methanol-d$_4$) δ (ppm) 8.69 (d, 2H), 8.49 (s, 1H), 8.04 (d, 2H), 7.81 (m, 4H), 7.60 (m, 4H), 7.51 (m, 1H), 7.35 (m, 4H): HPLC-MS calculated for C$_{28}$H$_{18}$ClN$_5$O (M + H$^+$): 476.2, found 476.2. |
| 172 | 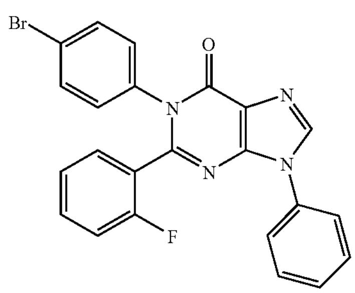 | $^1$H NMR (CDCl$_3$) δ (ppm) 8.11 (s, 1H), 7.67 (d, 2H), 7.54 (t, 2H), 7.43 (m, 3H), 7.29 (t, 2H), 7.07 (m, 3H), 6.88 (t, 1H); HPLC-MS calculated for C$_{23}$H$_{14}$BrFN$_4$O (M + H$^+$): 461.0, found 461.0. |
| 173 | 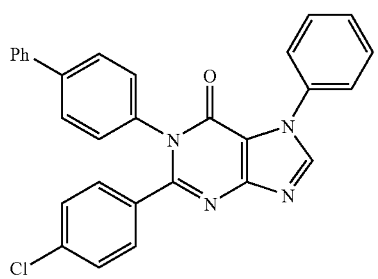 | HPLC-MS calculated for C$_{29}$H$_{19}$ClN$_4$O (M + H$^+$): 475.1, found 475.1. |
| 174 | 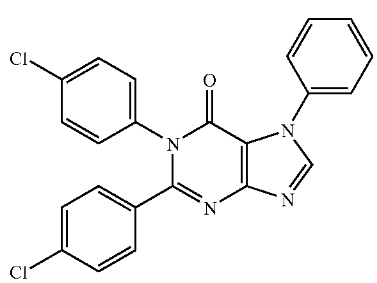 | HPLC-MS calculated for C$_{23}$H$_{14}$Cl$_2$N$_4$O (M + H$^+$): 433.1, found 433.1. |
| 175 | 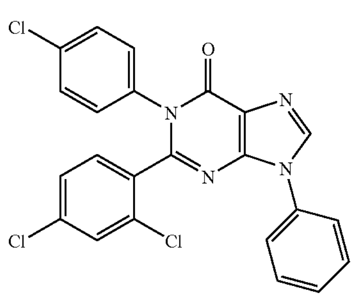 | $^1$H NMR (DMSO-d$_6$) δ (ppm) 8.65 (s, 1H), 7.77 (d, 2H), 7.62 (m, 4H), 7.42 (m, 6H); HPLC-MS calculated for C$_{23}$H$_{13}$C$_{13}$N$_4$O (M + H$^+$): 467.0, found 467.0. |

TABLE 1-continued

| Compound Number | Structure | Physical Data ¹H NMR 400 MHz (CDCl₃) and/or MS (m/z) |
|---|---|---|
| 176 | 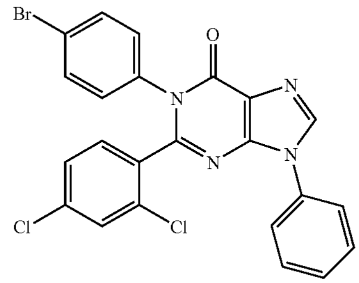 | $^1$H NMR (CDCl$_3$) δ (ppm) 8.04 (s, 1H), 7.58 (d, 2H), 7.47 (t, 2H), 7.38 (m, 3H), 7.22 (d, 1H), 7.15 (b, 1H), 7.07 (m, 2H), 6.91 (b, 1H); HPLC-MS calculated for C$_{23}$H$_{13}$BrCl$_2$N$_4$O (M + H$^+$): 511.0. found 511.0. |
| 177 | 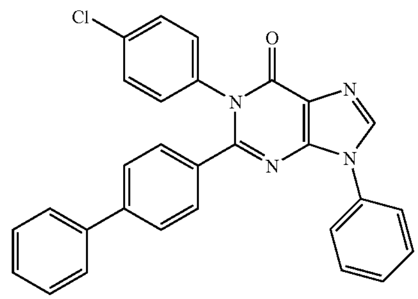 | $^1$H NMR (CDCl$_3$) δ (ppm) 8.10 (s, 1H), 7.72 (d, 2H), 7.55 (m, 4H), 7.44 (m, 5H), 7.34 (m, 5H), 7.15 (d, 2H); HPLC-MS calculated for C$_{23}$H$_{13}$BrCl$_2$N$_4$O (M + H$^+$): 475.1, found 475.1. |
| 178 | 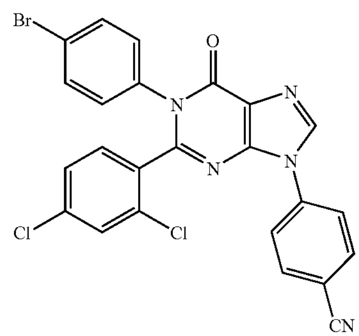 | $^1$H NMR (CDCl$_3$) δ (ppm) 8.19 (s, 1H), 7.86 (m, 4H), 7.45 (d, 2H), 7.33 (d, 1H), 7.17 (m, 3H), 6.97 (b, 1H); HPLC-MS calculated for C$_{24}$H$_{12}$BrCl$_2$N$_5$O (M + H$^+$): 535.8, found 535.8. |
| 179 | 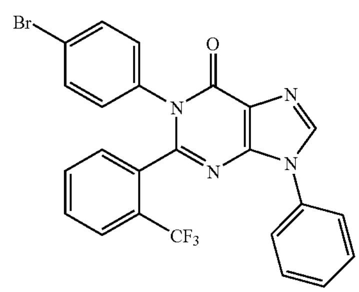 | $^1$H NMR (CDCl$_3$) δ (ppm) 8.13 (s, 1H), 7.66 (m, 3H), 7.50 (m, 3H), 7.42 (m, 2H), 7.22 (m, 1H), 7.12 (d, 1H), 6.88 (dd, 1H); HPLC-MS calculated for C$_{24}$H$_{14}$BrF$_3$N$_4$O (M + H$^+$): 511.0, found 511.0. |
| 180 | 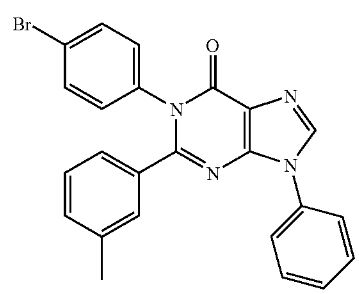 | $^1$H NMR (CDCl$_3$) δ (ppm) 8.10 (s, 1H), 7.70 (d, 2H), 7.55 (t, 2H), 7.45 (m, 3H), 7.08 (m, 6H), 2.24 (s, 3H); HPLC-MS calculated for C$_{24}$H$_{17}$BrN$_4$O (M + H$^+$): 457.0, found 457.0. |

TABLE 1-continued

| Compound Number | Structure | Physical Data<br>$^1$H NMR 400 MHz (CDCl$_3$)<br>and/or MS (m/z) |
|---|---|---|
| 181 | 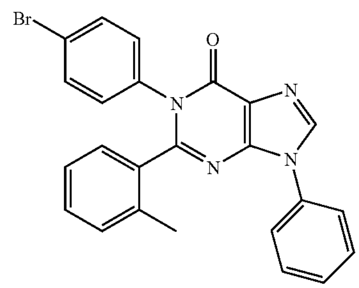 | $^1$H NMR (CDCl$_3$) δ (ppm) 8.09 (s, 1H), 7.65 (d, 2H), 7.46 (m, 6H), 7.16 (m, 1H), 7.02 (m, 4H). 2.26 (s, 3H); HPLC-MS calculated for C$_{24}$H$_{17}$BrN$_4$O (M + H$^+$): 457.0, found 457.0. |
| 182 | 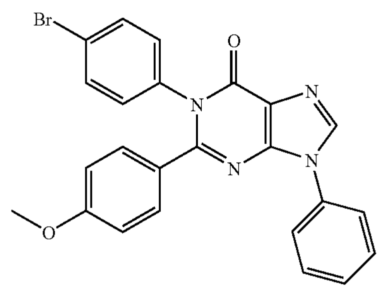 | $^1$H NMR (CDCl$_3$) δ (ppm) 8.09 (s, 1H), 7.69 (d, 2H), 7.55 (t, 2H), 7.46 (m, 3H), 7.22 (m, 2H), 2.05 (d, 2H), 6.72 (d, 2H), 3.76 (s, 3H); HPLC-MS calculated for C$_{24}$H$_{17}$BrN$_4$O$_2$ (M + H$^+$): 473.1, found 473.1. |
| 183 | 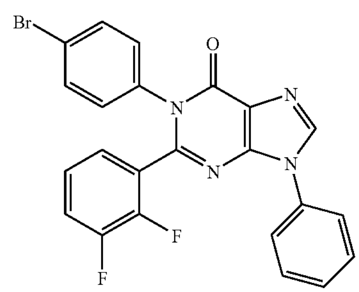 | $^1$H NMR (CDCl$_3$) δ (ppm) 8.13 (s, 1H), 7.66 (d, 2H), 7.55 (t, 2H), 7.46 (m, 3H), 7.06 (m, 5H); HPLC-MS calculated for C$_{23}$H$_{13}$BrF$_2$N$_4$O (M + H$^+$): 479.0, found 479.0. |
| 184 | 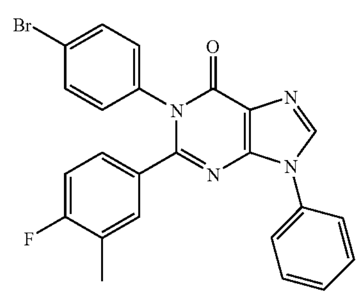 | $^1$H NMR (CDCl$_3$) δ (ppm) 8.13 (s, 1H), 7.68 (d, 2H), 7.56 (t, 2H), 7.47 (m, 3H), 7.15 (dd, 1H), 7.01 (m, 3H), 6.82 (t, 1H), 2.16 (s, 3H); HPLC-MS calculated for C$_{24}$H$_{16}$BrFN$_4$O (M + H$^+$): 475.0, found 475.0. |
| 185 | 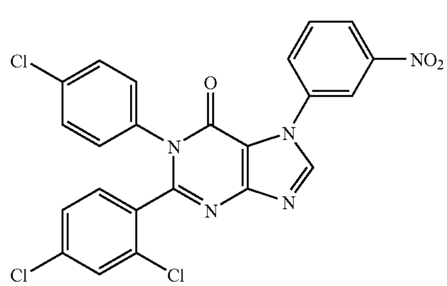 | HPLC-MS calculated for C$_{23}$H$_{12}$Cl$_3$N$_5$O3 (M + H$^+$): 511.9, found 511.9. |

TABLE 1-continued

| Compound Number | Structure | Physical Data $^1$H NMR 400 MHz (CDCl$_3$) and/or MS (m/z) |
|---|---|---|
| 186 | 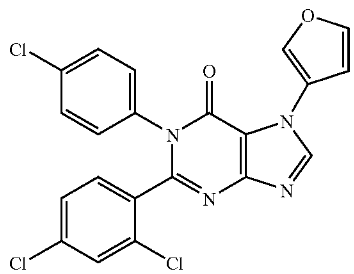 | HPLC-MS calculated for C$_{21}$H$_{11}$Cl$_3$N$_4$O2 (M + H$^+$): 456.9, found 456.9. |
| 187 | 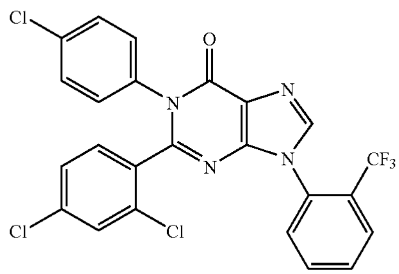 | HPLC-MS calculated for C$_{24}$H$_{12}$F$_3$Cl$_3$N$_4$O (M + H$^+$): 534.9, found 534.9. |
| 188 | 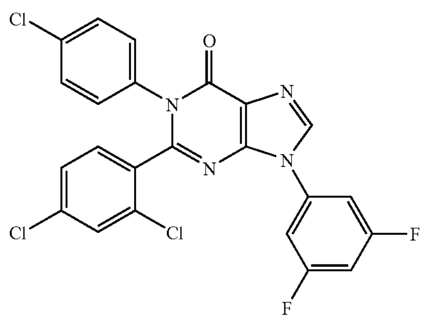 | HPLC-MS calculated for C$_{23}$H$_{11}$Cl$_3$F$_2$N$_4$O (M + H$^+$): 502.9, found 502.9. |
| 189 | 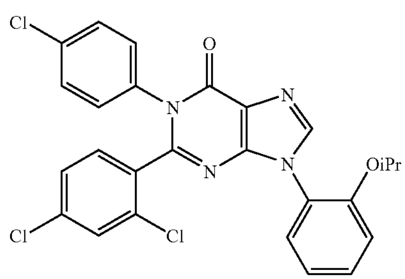 | HPLC-MS calculated for C$_{26}$H$_{19}$Cl$_3$N$_4$O (M + H$^+$): 525.0, found 525.0. |
| 190 | 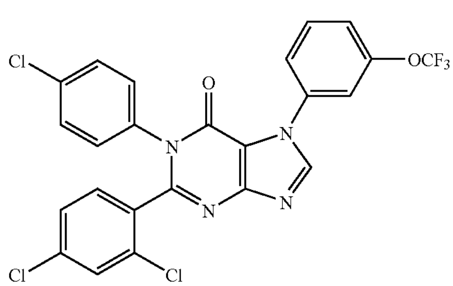 | HPLC-MS calculated for C$_{24}$H$_{11}$Cl$_3$F$_3$N$_4$O2 (M + H$^+$): 550.9, found 550.9. |

TABLE 1-continued

| Compound Number | Structure | Physical Data<br>¹H NMR 400 MHz (CDCl₃) and/or MS (m/z) |
|---|---|---|
| 191 | 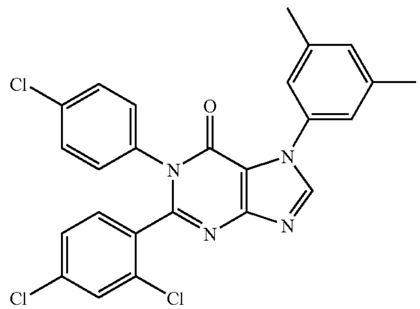 | HPLC-MS calculated for C$_{25}$H$_{17}$Cl$_3$N$_4$O (M + H$^+$): 494.9, found 494.9. |
| 192 | 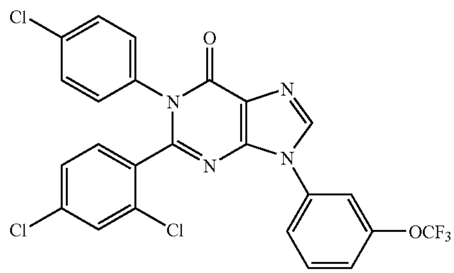 | HPLC-MS calculated for C$_{24}$H$_{11}$Cl$_3$F$_3$N$_4$O2 (M + H$^+$): 550.9, found 550.9. |
| 193 | 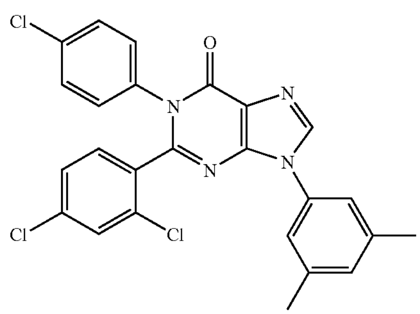 | HPLC-MS calculated for C$_{25}$H$_{17}$Cl$_3$N$_4$O (M + H$^+$): 494.9, found 494.9. |
| 194 | 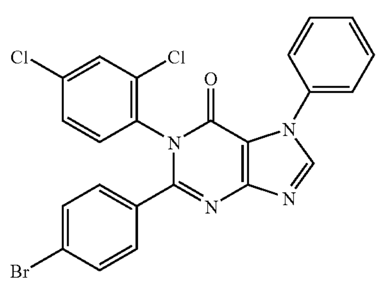 | HPLC-MS calculated for C$_{23}$H$_{13}$BrCl$_2$N$_4$O (M + H$^+$): 510.9, found 510.9. |
| 195 | 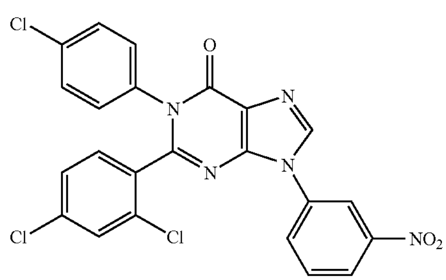 | HPLC-MS calculated for C$_{23}$H$_{12}$Cl$_3$N$_5$O3 (M + H$^+$): 511.9, found 511.9. |

TABLE 1-continued

| Compound Number | Structure | Physical Data<br>$^1$H NMR 400 MHz (CDCl$_3$)<br>and/or MS (m/z) |
|---|---|---|
| 196 | 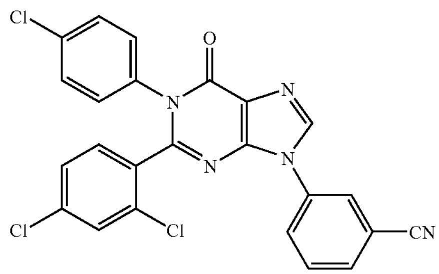 | HPLC-MS calculated for C$_{24}$H$_{12}$Cl$_3$N$_5$O (M + H$^+$): 492.0, found 492.0. |
| 197 | 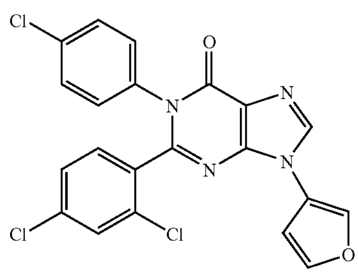 | HPLC-MS calculated for C$_{22}$H$_{11}$Cl$_3$N$_4$O2 (M + H$^+$): 456.9, found 456.9. |
| 198 | 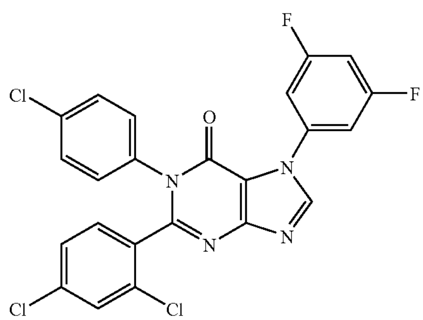 | HPLC-MS calculated for C$_{23}$H$_{11}$Cl$_3$F$_3$N$_4$O (M + H$^+$): 502.9, found 502.9. |
| 199 | 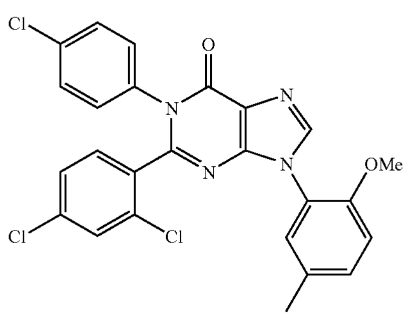 | HPLC-MS calculated for C$_{25}$H$_{17}$Cl$_3$N$_4$O$_2$ (M + H$^+$): 511.0, found 511.9. |
| 200 | 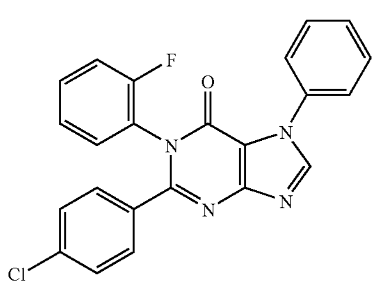 | HPLC-MS calculated for C$_{23}$H$_{14}$ClFN$_4$O (M + H$^+$): 417.0, found 417.0. |

TABLE 1-continued

| Compound Number | Structure | Physical Data<br>$^1$H NMR 400 MHz (CDCl$_3$)<br>and/or MS (m/z) |
|---|---|---|
| 201 | 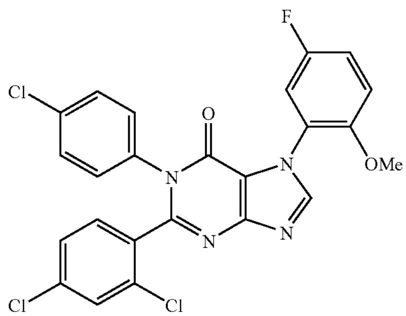 | HPLC-MS calculated for C$_{24}$H$_4$Cl$_3$FN$_4$O2 (M + H$^+$): 514.9, found 514.9. |
| 202 | 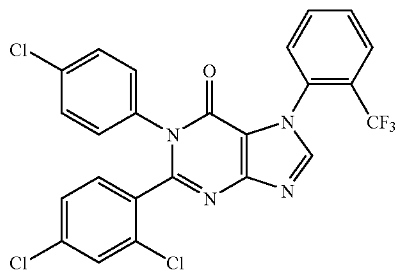 | HPLC-MS calculated for C$_{24}$H$_{12}$F$_3$Cl$_3$N$_4$O (M + H$^+$): 534.9, found 534.9. |
| 203 | 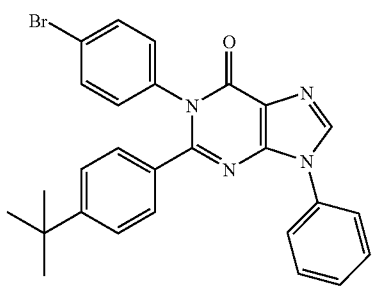 | $^1$H NMR (CDCl$_3$) δ (ppm) 8.21 (s, 1H), 7.71 (d, 2H), 7.57 (t, 2H), 7.48 (m, 3H), 7.22 (m, 4H), 7.05 (d, 2H), 1.25 (s, 9H); HPLC-MS calculated for C$_{27}$H$_{23}$BrN$_4$O (M + H$^+$): 499.0, found 499.0. |
| 204 | 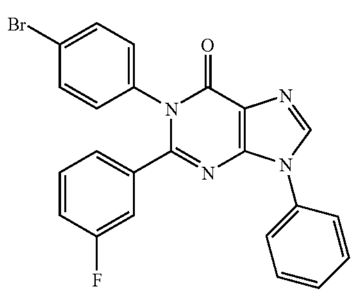 | $^1$H NMR (CDCl$_3$) δ (ppm) 8.12 (s, 1H), 7.68 (d, 2H), 7.57 (m, 3H), 7.48 (m, 3H), 7.17 (m, 1H), 7.05 (m, 3H), 6.99 (m, 1H); HPLC-MS calculated for C$_{23}$H$_{14}$BrFN$_4$O (M + H$^+$): 461.0, found 461.0. |
| 205 | 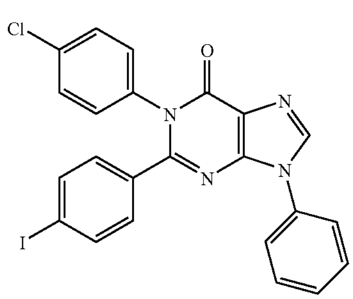 | $^1$H NMR (CDCl$_3$) δ (ppm) 8.11 (s, 1H), 7.68 (d, 2H), 7.56 (m, 4H), 7.48 (t, 1H), 7.33 (d, 2H), 7.10 (d, 2H), 7.01 (d, 2H); HPLC-MS calculated for C$_{23}$H$_{14}$ClIN$_4$O (M + H$^+$): 525.1, found 525.1. |

TABLE 1-continued

| Compound Number | Structure | Physical Data<br>¹H NMR 400 MHz (CDCl₃) and/or MS (m/z) |
|---|---|---|
| 206 | 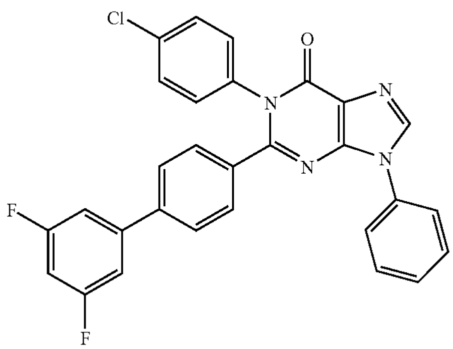 | ¹H NMR (CDCl₃) δ (ppm) 8.15 (s, 1H), 7.70 (d, 2H), 7.57 (t, 2H), 7.48 (t, 1H), 7.38 (m, 6H), 7.14 (d, 2H), 7.04 (m, 2H), 6.80 (m, 1H); HPLC-MS calculated for $C_{29}H_{17}ClF_2N_4O$ (M + H⁺): 511.0, found 511.0. |
| 207 | 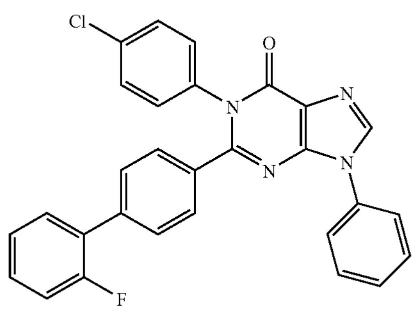 | ¹H NMR (CDCl₃) δ (ppm) 8.11 (s, 1H), 7.72 (d, 2H), 7.57 (t, 2H), 7.48 (t, 1H), 7.43 (m, 2H), 7.35 (m, 6H), 7.20 (m, 1H), 7.14 (m, 3H); HPLC-MS calculated for $C_{29}H_{18}ClFN_4O$ (M + H⁺): 493.0, found 493.0. |
| 208 | 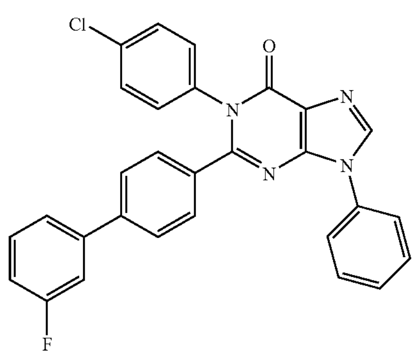 | ¹H NMR (CDCl₃) δ (ppm) 8.14 (s, 1H), 7.72 (d, 2H), 7.57 (t, 2H), 7.45 (m, 3H), 7.35 (m, 6H), 7.22 (m, 1H), 7.15 (d, 2H), 7.05 (m, 1H); HPLC-MS calculated for $C_{29}H_{18}ClFN_4O$ (M + H⁺): 493.0, found 493.0. |
| 209 | 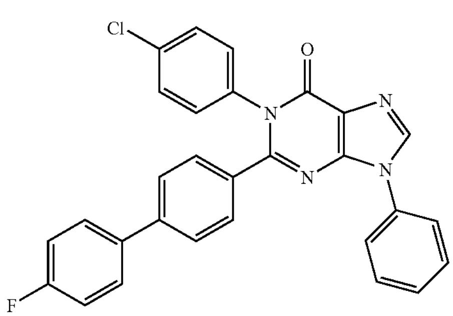 | ¹H NMR (CDCl₃) δ (ppm) 8.14 (s, 1H), 7.72 (d, 2H), 7.57 (t, 2H), 7.48 (m, 3H), 7.40 (m, 2H), 7.34 (m, 4H), 7.13 (m, 4H); HPLC-MS calculated for $C_{29}H_{18}ClFN_4O$ (M + H⁺): 493.0, found 493.0. |

TABLE 1-continued

| Compound Number | Structure | Physical Data<br>¹H NMR 400 MHz (CDCl₃) and/or MS (m/z) |
|---|---|---|
| 210 | 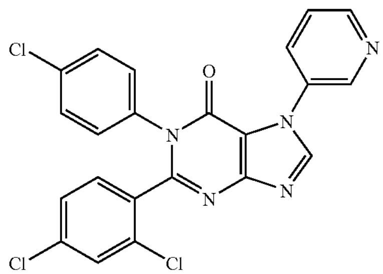 | HPLC-MS calculated for $C_{22}H_{12}Cl_3N_4O$ (M + H⁺): 467.9, found 467.9. |
| 211 | 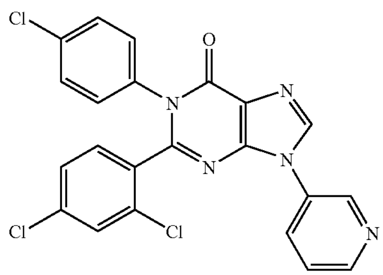 | HPLC-MS calculated for $C_{22}H_{12}Cl_3N_4O$ (M + H⁺): 467.9, found 467.9. |
| 212 | 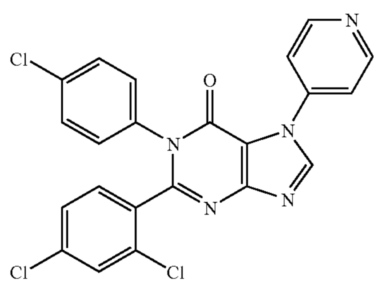 | HPLC-MS calculated for $C_{22}H_{12}Cl_3N_4O$ (M + H⁺): 467.9, found 467.9. |
| 213 | 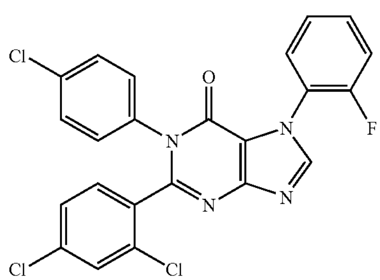 | HPLC-MS calculated for $C_{23}H_{12}Cl_3FN_4O$ (M + H⁺): 484.9, found 484.9. |
| 214 | 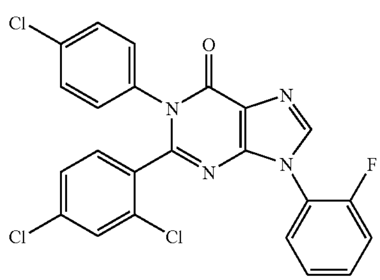 | HPLC-MS calculated for $C_{23}H_{12}Cl_3FN_4O$ (M + H⁺): 484.9, found 484.9 |

TABLE 1-continued

| Compound Number | Structure | Physical Data $^1$H NMR 400 MHz (CDCl$_3$) and/or MS (m/z) |
|---|---|---|
| 215 | 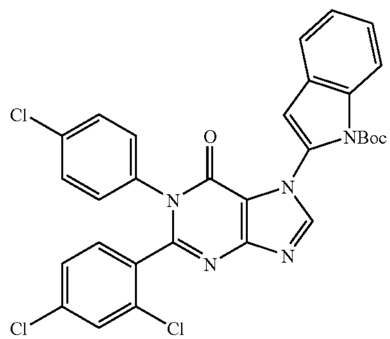 | HPLC-MS calculated for C$_{30}$H$_{22}$Cl$_3$N$_5$O$_3$ (M + H$^+$): 605.9, found 605.9. |
| 216 | 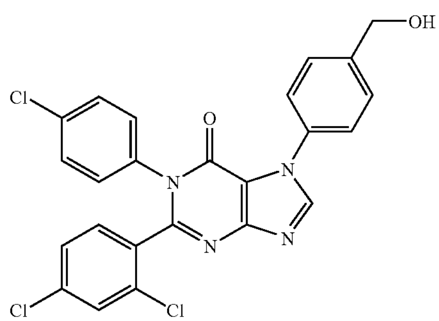 | HPLC-MS calculated For C$_{24}$H$_{15}$Cl$_3$N$_4$O$_2$ (M + H$^+$): 497.1, found 497.1. |
| 217 | 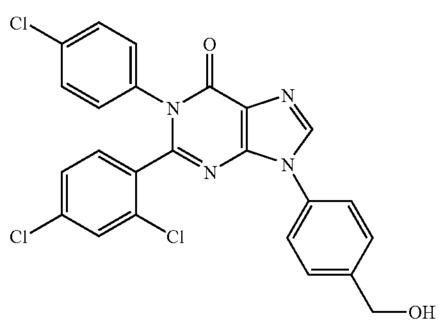 | HPLC-MS calculated for C$_{24}$H$_{15}$Cl$_3$N$_4$O$_2$ (M + H$^+$): 497.1, found 497.1. |
| 218 | 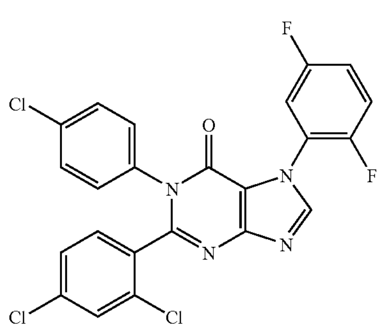 | HPLC-MS calculated for C$_{23}$H$_{11}$Cl$_3$F$_3$N$_4$O (M + H$^+$): 502.9, found 502.9. |

TABLE 1-continued

| Compound Number | Structure | Physical Data<br>$^1$H NMR 400 MHz (CDCl$_3$)<br>and/or MS (m/z) |
|---|---|---|
| 219 | 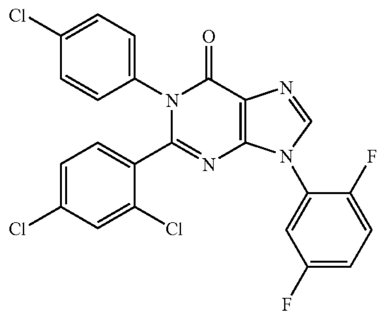 | HPLC-MS calculated for C$_{23}$H$_{11}$Cl$_3$F$_3$N$_4$O (M + H$^+$): 502.9, found 502.9. |
| 220 | 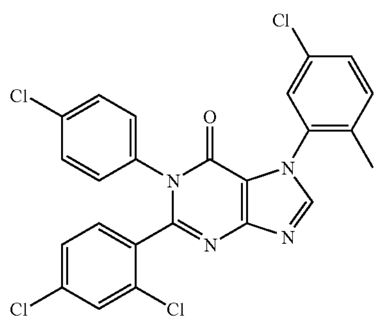 | HPLC-MS calculated for C$_{24}$H$_{14}$Cl$_4$N$_4$O (M + H$^+$): 514.9, found 514.9. |
| 221 | 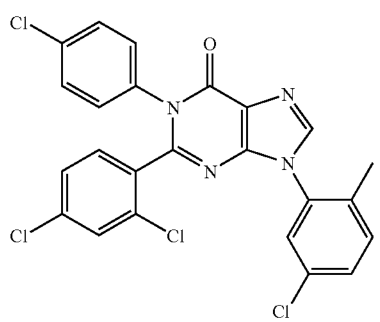 | HPLC-MS calculated for C$_{24}$H$_{14}$Cl$_4$N$_4$O (M + H$^+$): 514.9, found 514.9. |
| 222 | 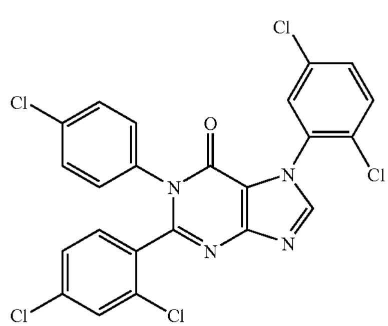 | HPLC-MS calculated for C$_{23}$H$_{11}$Cl$_5$N$_4$O (M + H$^+$): 534.9, found 534.9. |

TABLE 1-continued

| Compound Number | Structure | Physical Data<br>$^1$H NMR 400 MHz (CDCl$_3$)<br>and/or MS (m/z) |
| --- | --- | --- |
| 223 | 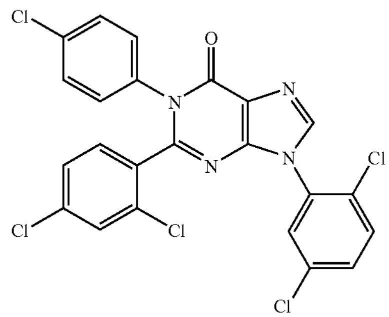 | HPLC-MS calculated for C$_{23}$H$_{11}$Cl$_5$N$_4$O (M + H$^+$): 534.9, found 534.9. |
| 224 | 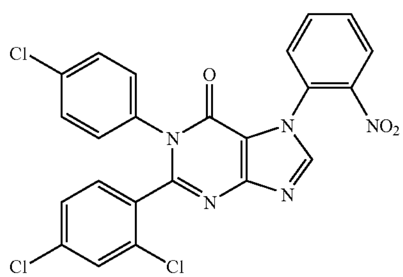 | HPLC-MS calculated for C$_{23}$H$_{12}$Cl$_3$N$_5$O$_3$ (M + H$^+$): 511.9, found 511.9. |
| 225 | 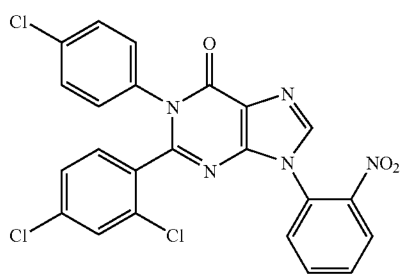 | HPLC-MS calculated for C$_{23}$H$_{12}$Cl$_3$N$_5$O$_3$ (M + H$^+$): 511.9, found 511.9. |
| 226 | 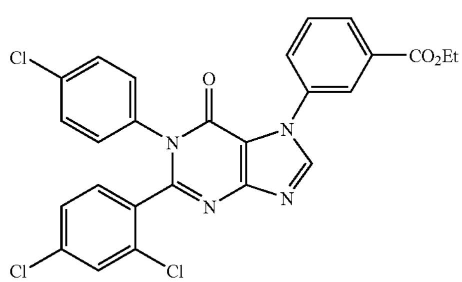 | HPLC-MS calculated for C$_{26}$H$_{17}$Cl$_3$N$_4$O$_3$ (M + H$^+$): 539.0, found 539.0. |
| 227 | 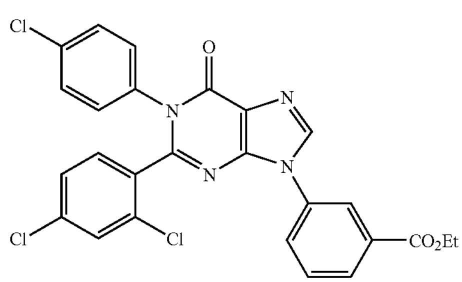 | HPLC-MS calculated for C$_{26}$H$_{17}$Cl$_3$N$_4$O$_3$ (M + H$^+$): 539.0, found 539.0. |

TABLE 1-continued

| Compound Number | Structure | Physical Data $^1$H NMR 400 MHz (CDCl$_3$) and/or MS (m/z) |
|---|---|---|
| 228 | 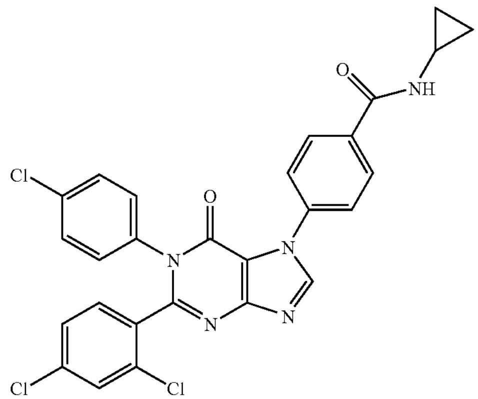 | HPLC-MS calculated for C$_{27}$H$_{18}$Cl$_3$N$_5$O$_2$ (M + H$^+$): 550.0, found 550.0. |
| 229 | 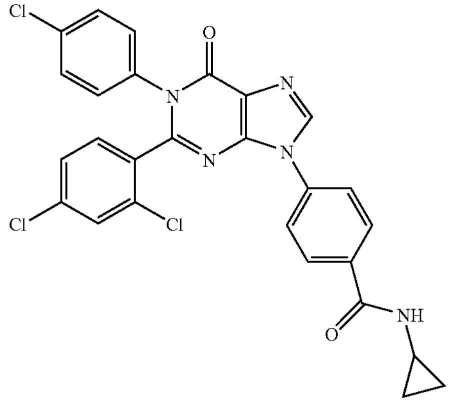 | HPLC-MS calculated for C$_{27}$H$_{18}$Cl$_3$N$_5$O$_2$ (M + H$^+$): 550.0, found 550.0. |
| 230 | 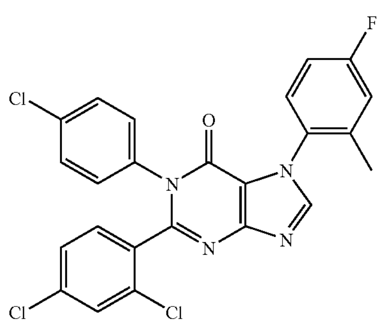 | HPLC-MS calculated for C$_{24}$H$_{14}$Cl$_3$FN$_5$O (M + H$^+$): 498.9, found 498.9. |
| 231 | 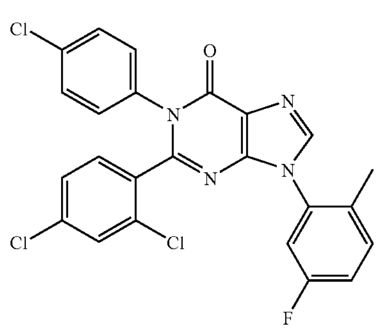 | HPLC-MS calculated for C$_{24}$H$_{14}$Cl$_3$FN$_5$O (M + H$^+$): 498.9, found 498.9. |

TABLE 1-continued

| Compound Number | Structure | Physical Data $^1$H NMR 400 MHz (CDCl$_3$) and/or MS (m/z) |
|---|---|---|
| 232 | 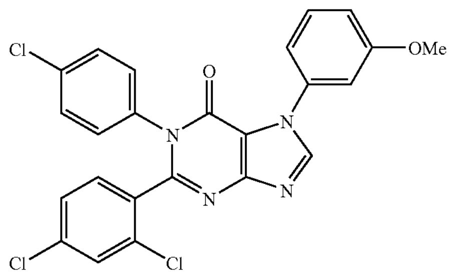 | HPLC-MS calculated for C$_{24}$H$_{15}$Cl$_3$N$_4$O$_2$ (M + H$^+$): 497.0, found 497.0. |
| 233 | 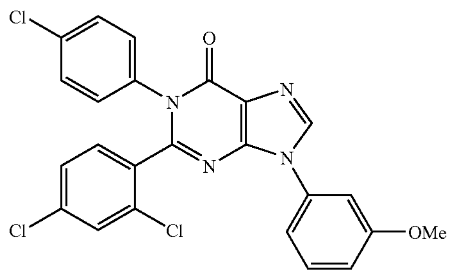 | HPLC-MS calculated for C$_{24}$H$_{15}$Cl$_3$N$_4$O$_2$ (M + H$^+$): 497.0, found 497.0. |
| 234 | 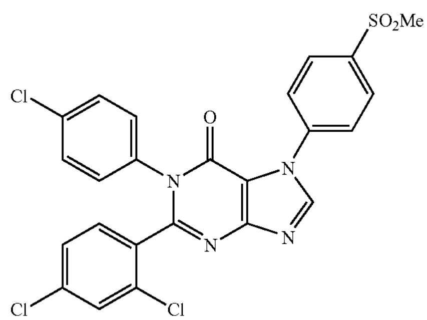 | HPLC-MS calculated for C$_{24}$H$_{15}$Cl$_3$N$_4$O$_3$S (M + H$^+$): 544.9, found 544.9. |
| 235 | 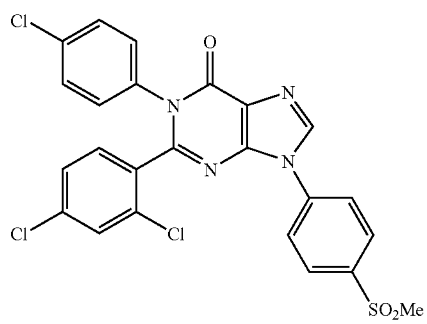 | HPLC-MS calculated for C$_{24}$H$_{15}$Cl$_3$N$_4$O$_3$S (M + H$^+$): 544.9, found 544.9. |
| 236 | 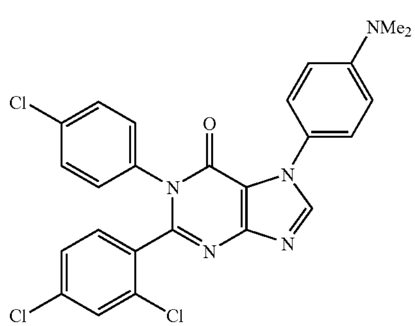 | HPLC-MS calculated for C$_{25}$H$_{18}$Cl$_3$N$_4$O (M + H$^+$): 510.0, found 510.0. |

TABLE 1-continued

| Compound Number | Structure | Physical Data $^1$H NMR 400 MHz (CDCl$_3$) and/or MS (m/z) |
|---|---|---|
| 237 | 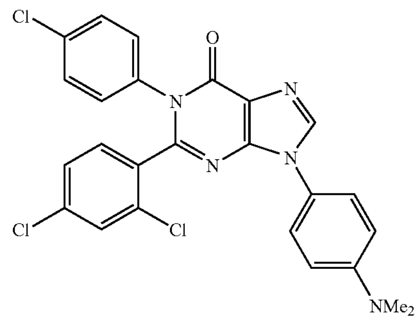 | HPLC-MS calculated for C$_{25}$H$_{18}$Cl$_3$N$_4$O (M + H$^+$): 510.0, found 510.0. |
| 238 | 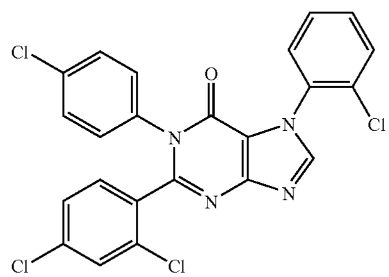 | HPLC-MS calculated for C$_{23}$H$_{12}$Cl$_4$N$_4$O (M + H$^+$): 500.9, found 500.9. |
| 239 | 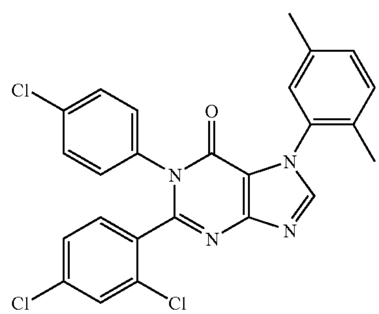 | HPLC-MS calculated for C$_{25}$H$_{17}$Cl$_3$N$_4$O (M + H$^+$): 495.0, found 495.0. |
| 240 | 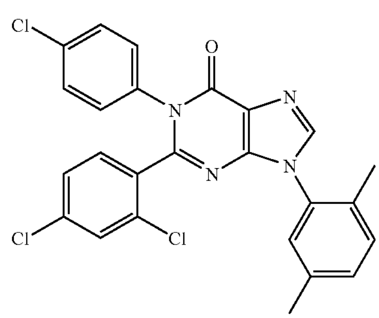 | HPLC-MS calculated for C$_{25}$H$_{17}$Cl$_3$N$_4$O (M + H$^+$): 495.0, found 495.0. |
| 241 | 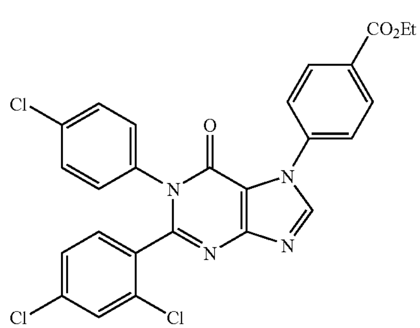 | HPLC-MS calculated for C$_{26}$H$_{17}$Cl$_3$N$_4$O$_3$ (M + H$^+$): 539.0, found 539.0. |

TABLE 1-continued

| Compound Number | Structure | Physical Data<br>¹H NMR 400 MHz (CDCl₃) and/or MS (m/z) |
|---|---|---|
| 242 | 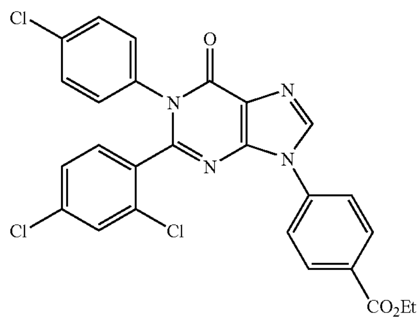 | HPLC-MS calculated for $C_{26}H_{17}Cl_3N_4O_3$ (M + H⁺): 539.0, found 539.0. |
| 243 | 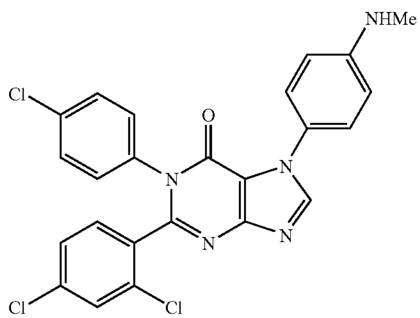 | HPLC-MS calculated for $C_{24}H_{16}Cl_3N_5O$ (M + H⁺): 496.0, found 496.0. |
| 244 | 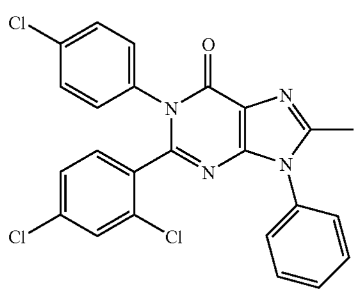 | HPLC-MS calculated for $C_{24}H_{15}Cl_{13}N_4O$ (M + H⁺): 480.9, found 480.9. |
| 245 | 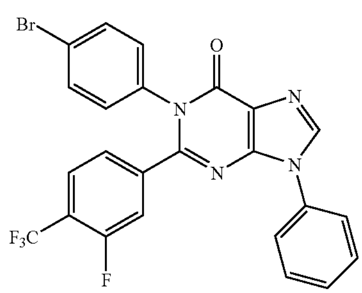 | HPLC-MS calculated for $C_{24}H_{13}BrF_4N_4O$ (M + H⁺): 529.0, found 529.0. |
| 246 | 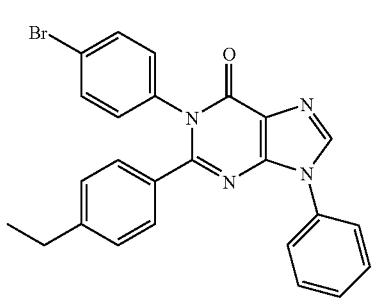 | ¹H NMR (CDCl₃) δ (ppm) 8.10 (s, 1H), 7.70 (d, 2H), 7.55 (t, 2H), 7.45 (m, 3H), 7.18 (d, 2H), 7.04 (d, 4H), 2.58 (q, 2H), 1.17 (t, 3H); HPLC-MS calculated for $C_{25}H_{19}BrN_4O$ (M + H⁺) 471.0, found 471.0. |

TABLE 1-continued

| Compound Number | Structure | Physical Data<br>$^1$H NMR 400 MHz (CDCl$_3$) and/or MS (m/z) |
|---|---|---|
| 247 | 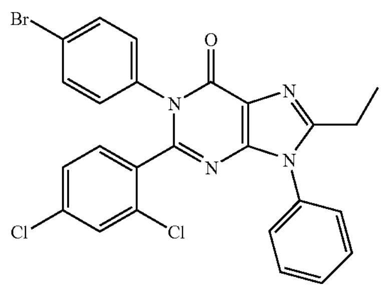 | $^1$H NMR (CDCl$_3$) δ (ppm) 7.54 (m, 3H), 7.40 (m, 4H), 7.23 (d, 1H), 7.18 (b, 1H), 7.09 (m, 2H), 6.93 (b, 1H), 2.81 (m, 2H), 1.34 (t, 3H); HPLC-MS calculated for C$_{25}$H$_{19}$BrN$_4$O (M + H$^+$): 539.0, found 539.0. |
| 248 | 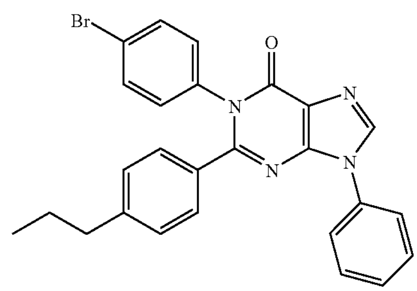 | $^1$H NMR (CDCl$_3$) δ (ppm) 8.14 (s, 1H), 7.70 (d, 2H), 7.56 (t, 2H), 7.46 (m, 3H), 7.17 (d, 2H), 7.02 (m, 4H), 2.52 (t, 2H), 1.57 (q, 2H), 0.88 (t, 3H); HPLC-MS calculated for C$_{25}$H$_{19}$BrN$_4$O (M + H$^+$): 485.1, found 485.1. |
| 249 | 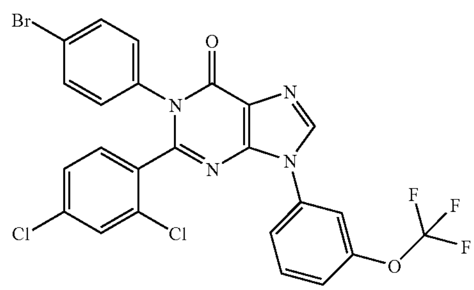 | $^1$H NMR (CDCl$_3$) δ (ppm) 8.15 (s, 1H), 7.63 (m, 3H), 7.45 (d, 2H), 7.32 (m, 2H), 7.19 (m, 3H), 6.98 (b, 1H); HPLC-MS calculated for C$_{24}$H$_{12}$BrCl$_2$F$_3$N$_4$O$_2$ (M + H$^+$): 595.0, found 595.0. |
| 250 | 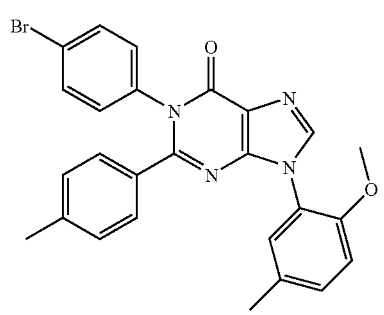 | $^1$H NMR (CDCl$_3$) δ (ppm) 8.02 (s, 1H), 7.44 (d, 2H), 7.31 (m, 1H), 7.23 (m, 1H), 7.10 (d, 2H), 7.01 (m, 5H), 3.82 (s, 3H), 2.36 (s, 3H), 2.27 (s, 3H); HPLC-MS calculated for C$_{26}$H$_{21}$BrN$_4$O$_2$ (M + H$^+$): 501.1, found 501.1. |
| 251 | 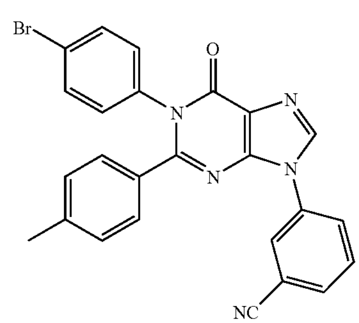 | $^1$H NMR (CDCl$_3$) δ (ppm) 8.22 (s, 1H), 8.11 (s, 1H), 7.97 (d, 1H), 7.76 (m, 1H), 7.71 (t, 1H), 7.47 (d, 2H), 7.15 (d, 2H), 7.05 (t, 4H), 2.31 (s, 3H); HPLC-MS calculated for C$_{25}$H$_{16}$BrN$_5$O (M + H$^+$): 482.0, found 482.0. |

TABLE 1-continued

| Compound Number | Structure | Physical Data $^1$H NMR 400 MHz (CDCl$_3$) and/or MS (m/z) |
|---|---|---|
| 252 | 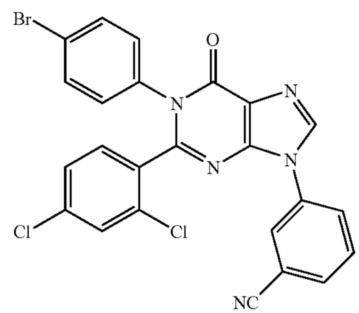 | HPLC-MS calculated for C$_{24}$H$_{12}$BrClN$_5$O (M + H$^+$): 501.0, found 501.0. |
| 253 | 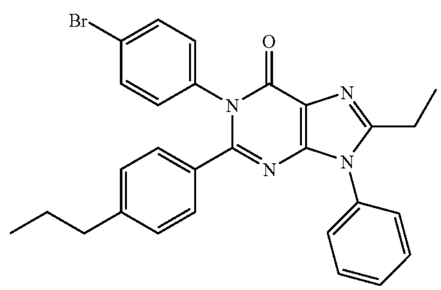 | $^1$H NMR (CDCl$_3$) δ (ppm) 7.55 (m, 3H), 7.41 (m, 4H), 7.07 (d, 2H), 7.00 (d, 2H), 6.95 (d, 2H), 2.81 (q, 2H), 2.48 (t, 2H), 1.53 (m, 2H), 1.31 (t, 3H), 0.85 (t, 3H); HPLC-MS calculated for C$_{28}$H$_{25}$BrN$_4$O (M + H$^+$): 513.1, found 513.1. |
| 254 | 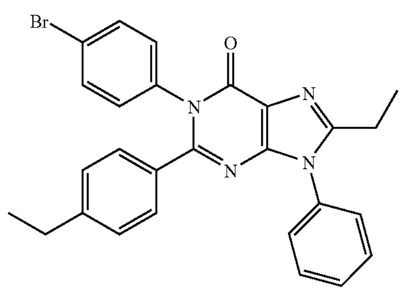 | $^1$H NMR (CDCl$_3$) δ (ppm) 7.58 (m, 3H), 7.48 (m, 4H), 7.08 (d, 2H), 7.01 (d, 2H), 6.97 (d, 2H), 2.81 (q, 2H), 2.54 (q, 2H), 1.30 (t, 3H), 1.14 (t, 3H); HPLC-MS calculated for C$_{27}$H$_{23}$BrN$_4$O (M + H$^+$): 499.1, found 499.1. |
| 255 | 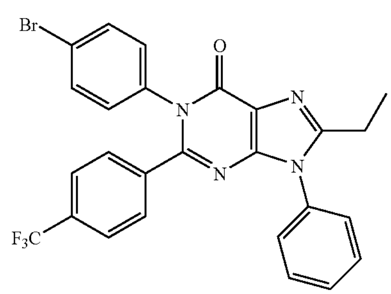 | $^1$H NMR (CDCl$_3$) δ (ppm) 7.58 (m, 3H), 7.43 (m, 6H), 7.31 (d, 2H), 7.02 (d, 2H), 2.84 (q, 2H), 1.32 (t, 3H); HPLC-MS calculated for C$_{26}$H$_{18}$BrF$_3$N$_4$O (M + H$^+$): 539.1, found 539.1. |
| 256 | 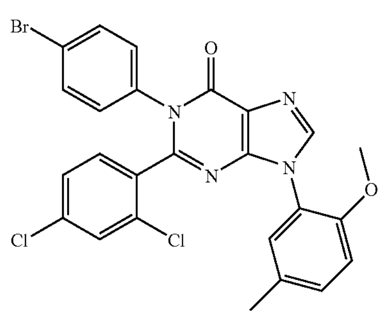 | $^1$H NMR (CDCl$_3$) δ (ppm) 8.14 (s, 1H), 7.44 (d, 2H), 7.27 (m, 4H), 7.10 (m, 2H), 6.98 (d, 2H), 3.82 (s, 3H), 2.34 (s, 3H); HPLC-MS calculated for C$_{25}$H$_{17}$BrCl$_2$N$_4$O$_2$ (M + H$^+$): 555.0, found 555.0. |

TABLE 1-continued

| Compound Number | Structure | Physical Data $^1$H NMR 400 MHz (CDCl$_3$) and/or MS (m/z) |
|---|---|---|
| 257 | 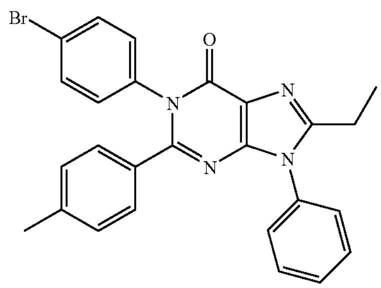 | $^1$H NMR (CDCl$_3$) δ (ppm) 7.55 (m, 3H), 7.42 (m, 4H), 7.06 (d, 2H), 7.01 (d, 2H), 6.95 (d, 2H), 2.79 (q, 2H), 2.25 (s, 3H), 1.32 (t, 3H); HPLC-MS calculated for C$_{26}$H$_{21}$BrN$_4$O (M + H$^+$): 485.1, found 485.1. |
| 258 | 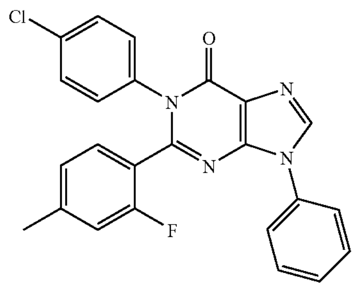 | $^1$H NMR (CDCl$_3$) δ (ppm) 8.17 (s, 1H), 7.67 (d, 2H), 7.55 (t, 2H), 7.46 (t, 1H), 7.28 (m, 2H), 7.13 (m, 3H), 6.87 (d, 1H), 6.68 (d, 1H), 2.29 (s, 3H); HPLC-MS calculated fur C$_{24}$H$_{16}$ClFN$_4$O (M + H$^+$): 431.1, found 431.1. |
| 259 | 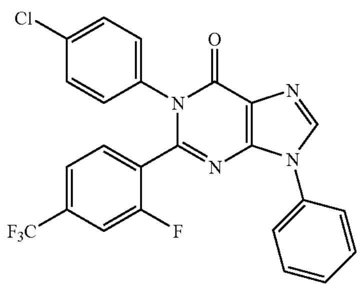 | $^1$H NMR (CDCl$_3$) δ (ppm) 8.29 (s, 1H), 7.65 (d, 2H), 7.57 (t, 2H), 7.50 (d, 1H), 7.46 (t, 1H), 7.39 (d, 1H), 7.30 (d, 2H), 7.19 (d, 1H), 7.12 (d, 2H); HPLC-MS calculated for C$_{24}$H$_{13}$ClF$_4$N$_4$O (M + H$^+$): 485.1, found 485.1. |
| 260 | 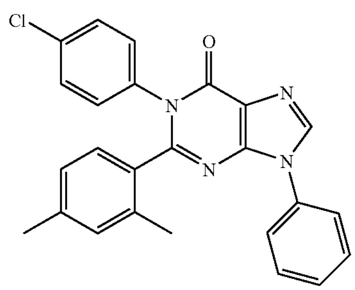 | $^1$H NMR (CDCl$_3$) δ (ppm) 8.16 (s, 1H), 7.66 (d, 2H), 7.53 (t, 2H), 7.45 (t, 1H), 7.24 (m, 2H), 7.06 (b, 2H), 6.89 (d, 2H), 6.82 (d, 1H), 2.24 (s, 3H), 2.23 (s, 3H); HPLC-MS calculated for C$_{25}$H$_{19}$ClN$_4$O (M + H$^+$): 427.1, found 427.1. |
| 262 | 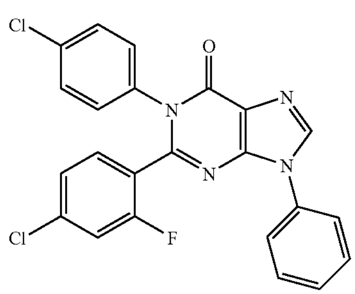 | $^1$H NMR (CDCl$_3$) δ (ppm) 8.01 (s, 1H), 7.46 (d, 2H), 7.37 (t, 2H), 7.29 (t, 1H), 7.11 (d, 2H), 7.03 (d, 1H), 6.91 (m, 3H), 6.74 (dd, 1H); HPLC-MS calculated for C$_{23}$H$_{13}$Cl$_2$FN$_4$O (M + H$^+$): 451.1, found 451.1. |

TABLE 1-continued

| Compound Number | Structure | Physical Data<br>$^1$H NMR 400 MHz (CDCl$_3$)<br>and/or MS (m/z) |
|---|---|---|
| 262 | 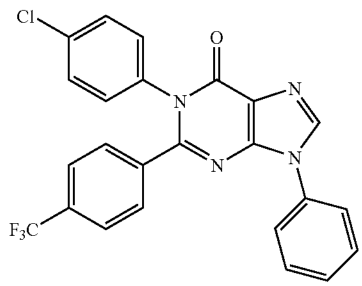 | $^1$H NMR (CDCl$_3$) δ (ppm) 8.17 (s, 1H), 7.68 (d, 2H), 7.57 (t, 2H), 7.49 (m, 3H), 7.41 (d, 2H), 7.33 (d, 2H), 7.11 (d, 2H); HPLC-MS calculated for C$_{24}$H$_{14}$ClF$_3$N$_4$O (M + H$^+$): 467.1, found 467.1. |
| 263 | 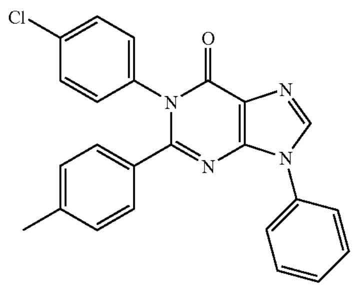 | $^1$H NMR (CDCl$_3$) δ (ppm) 8.20 (s, 1H), 7.70 (d, 2H), 7.56 (t, 2H), 7.48 (t, 1H), 7.32 (d, 2H), 7.16 (d, 2H), 7.10 (d, 2H), 7.02 (d, 2H), 2.29 (s, 3H); HPLC-MS calculated for C$_{24}$H$_{17}$ClN$_4$O (M + H$^+$): 413.1, found 413.1. |
| 264 | 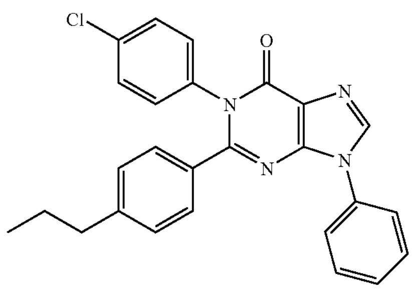 | $^1$H NMR (CDCl$_3$) δ (ppm) 8.10 (s, 1H), 7.70 (d, 2H), 7.56 (t, 2H), 7.45 (t, 1H), 7.28 (d, 2H), 7.17 (d, 2H), 7.09 (d, 2H), 7.01 (d, 2H), 2.51 (t, 2H), 1.56 (q, 2H), 0.87 (t, 3H);<br>HPLC-MS calculated for C$_{26}$H$_{21}$ClN$_4$O (M + H$^+$): 441.1, found 441.1. |
| 265 | 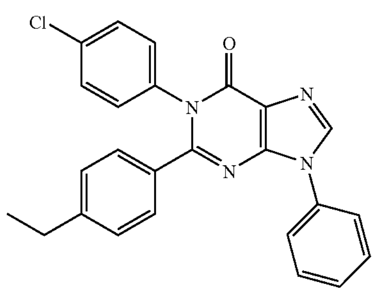 | $^1$H NMR (CDCl$_3$) δ (ppm) 8.10 (s, 1H), 7.70 (d, 2H), 7.56 (t, 2H), 7.46 (t, 1H), 7.30 (d, 2H), 7.18 (d, 2H), 7.10 (d, 2H), 7.04 (d, 2H), 2.58 (q, 2H), 1.17 (t, 3H); HPLC-MS calculated for C$_{25}$H$_{19}$ClN$_4$O (M + H$^+$): 427.1, found 427.1. |
| 266 | 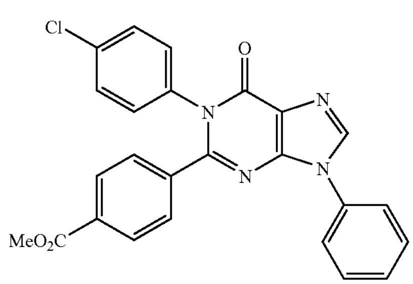 | HPLC-MS calculated for C$_{25}$H$_{19}$ClN$_4$O$_3$ (M + H$^+$): 456.9., found 456.9. |

TABLE 1-continued

| Compound Number | Structure | Physical Data $^1$H NMR 400 MHz (CDCl$_3$) and/or MS (m/z) |
|---|---|---|
| 267 | 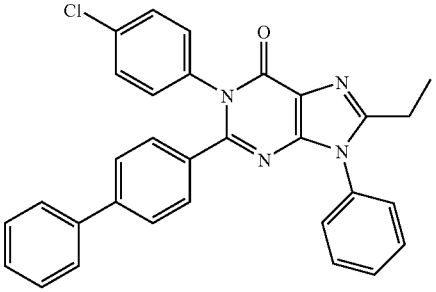 | $^1$H NMR (CDCl$_3$) δ (ppm) 7.58 (m, 3H), 7.48 (m, 2H), 7.41 (m, 6H), 7.32 (m, 3H), 7.27 (d, 2H), 7.12 (d, 2H), 2.87 (q, 2H), 1.32 (t, 3H); HPLC-MS calculated for C$_{31}$H$_{23}$ClN$_4$O (M + H$^+$): 503.2, found 503.2. |
| 268 | 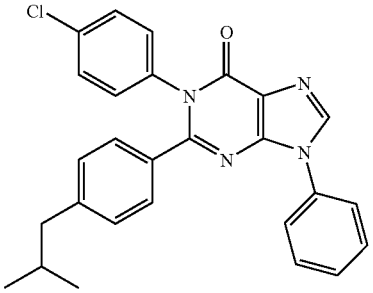 | $^1$H NMR (CDCl$_3$) δ (ppm) 8.08 (s, 1H), 7.71 (d, 2H), 7.56 (t, 2H), 7.46 (t, 1H), 7.28 (d, 2H), 7.15 (d, 2H), 7.08 (d, 2H), 6.97 (d, 2H), 2.39 (d, 2H), 1.78 (m, 1H), 0.82 (d, 6H); HPLC-MS calculated for C$_{27}$H$_{23}$ClN$_4$O (M + H$^+$): 455.2, found 455.2. |
| 269 | 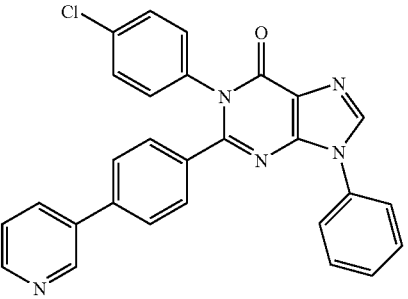 | $^1$H NMR (methanol-d$_4$) δ (ppm) 8.69 (m, 1H), 8.50 (s, 1H), 8.29 (m, 1H), 8.10 (d, 1H), 7.82 (m, 4H), 7.72 (m, 1H), 7.59 (m, 4H), 7.51 (m, 1H), 7.35 (m, 4H); HPLC-MS calculated for C$_{28}$H$_{18}$ClN$_5$O (M + H$^+$): 476.1, found 476.1. |
| 270 | 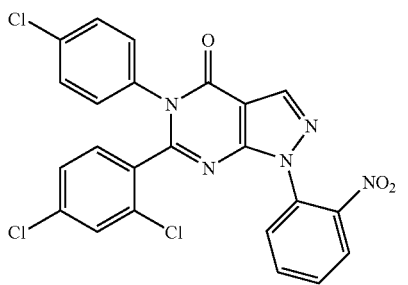 | $^1$H NMR (CDCl$_3$, 400 MHz) δ 8.40 (s, 1H), 8.07 (d, 1H), 7.87 (d, 1H), 7.79 (t, 1H), 7.61 (t, 1H), 7.33-7.27 (m, 4H), 7.22 (d, 2H), 6.97 (d, 1H). HPLC-MS calculated for C$_{23}$H$_{12}$Cl$_3$N$_5$O$_3$ (M + H$^+$) 512.0, found 512.0. |
| 271 | 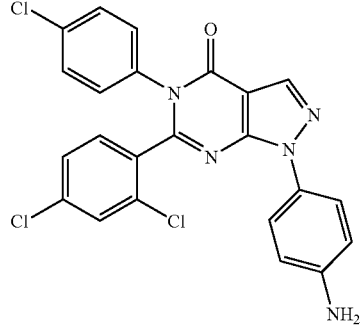 | $^1$H NMR (DMSO, 400 MHz) δ 8.78 (s, 1H), 8.15 (d, 2H), 7.97-7.95 (m, 2H), 7.90 (m, 3H), 7.84 (dd, 1H), 7.78 (m, 1H), 7.30 (d, 2H), 6.00 (s, 2H). HPLC-MS calculated for C$_{23}$H$_{14}$Cl$_3$N$_5$O (M + H$^+$) 482.0. found 482.0. |

TABLE 1-continued

| Compound Number | Structure | Physical Data $^1$H NMR 400 MHz (CDCl$_3$) and/or MS (m/z) |
|---|---|---|
| 272 | 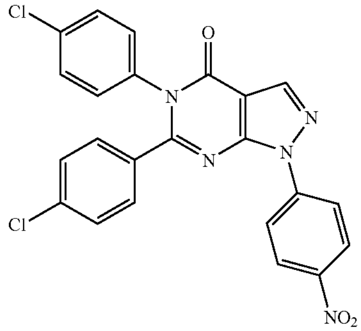 | HPLC-MS calculated for C$_{23}$H$_{13}$Cl$_2$N$_5$O$_3$ (M + H$^+$) 478.0, found 478.0. $^1$H NMR (CDCl$_3$, 400 MHz) δ 8.53 (d, 2H), 8.39 (m, 3H), 7.37 (d, 2H), 7.30 (m, 4H), 7.08 (d, 2H). HPLC-MS calculated for C$_{23}$H$_{13}$Cl$_2$N$_5$O$_3$ (M + H$^+$) 478.0, found 478.0. |
| 273 | 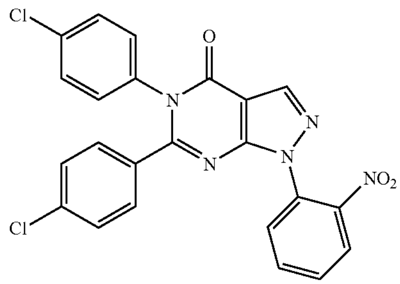 | HPLC-MS calculated for C$_{23}$H$_{13}$Cl$_2$N$_5$O$_3$ (M + H$^+$) 478.0, found 478.0. $^1$H NMR (CDCl$_3$, 400 MHz) δ 8.38 (s, 1H), 8.09 (d, 1H), 7.87 (d, 1H), 7.79 (t, 1H), 7.62 (t, 1H), 7.35 (d, 2H), 7.20 (m, 4H), 7.08 (d, 2H). HPLC-MS calculated for C$_{23}$H$_{13}$Cl$_2$N$_5$O$_3$ (M + H$^+$) 478.0, found 478.0. |
| 274 | 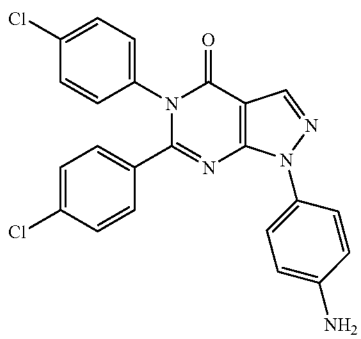 | HPLC-MS calculated for C$_{23}$H$_{15}$Cl$_2$N$_5$O (M + H$^+$) 448.1, found 448.1. |
| 275 | 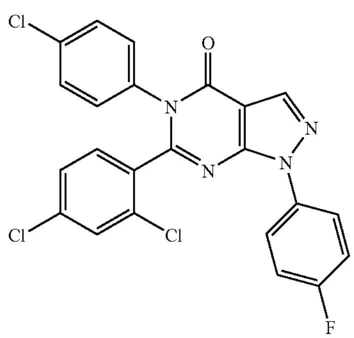 | HPLC-MS calculated for C$_{23}$H$_{12}$Cl$_3$FN$_4$O (M + H$^+$) 485.0, found 485.0. |

TABLE 1-continued

| Compound Number | Structure | Physical Data $^1$H NMR 400 MHz (CDCl$_3$) and/or MS (m/z) |
|---|---|---|
| 276 | 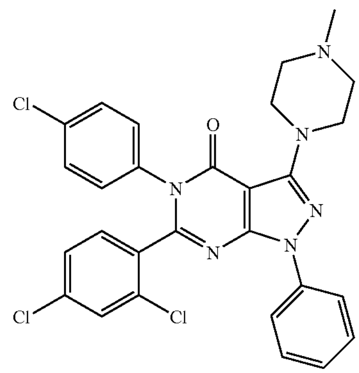 | HPLC-MS calculated for C$_{28}$H$_{23}$Cl$_3$N$_6$O (M + H$^+$) 565.1, found 565.1. |
| 277 | 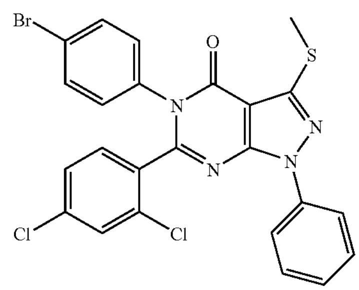 | HPLC-MS calculated for C$_{24}$H$_{15}$BrCl$_2$N$_4$OS (M + H$^+$) 557.0, found 557.0. |
| 278 | 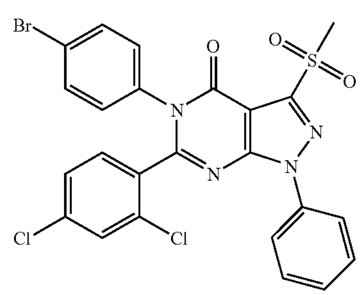 | $^1$H NMR (CDCl$_3$, 400 MHz) δ 8.05 (d, 2H), 7.59-7.40 (m, 5H), 7.35 (m, 1H), 7.21 (dd, 2H), 7.16 (d, 1H), 6.98 (m, 1H), 3.54 (s, 3H). HPLC-MS calculated for C$_{24}$H$_{15}$BrCl$_2$N$_4$O$_3$S (M + H$^+$) 591.0, found 591.0. |
| 279 | 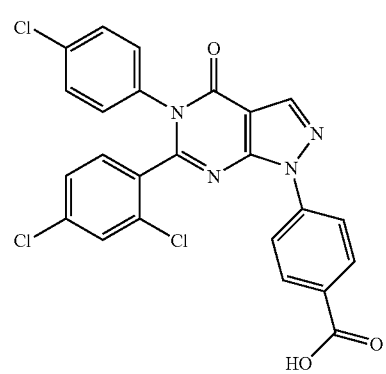 | HPLC-MS calculated for C$_{24}$H$_{13}$Cl$_3$N$_4$O$_3$ (M + H$^+$) 511.0, found 511.0. |

TABLE 1-continued

| Compound Number | Structure | Physical Data<br>¹H NMR 400 MHz (CDCl₃) and/or MS (m/z) |
|---|---|---|
| 280 | 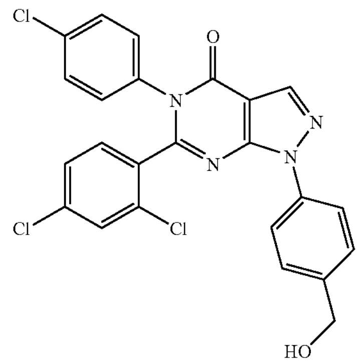 | ¹H NMR (dioxane, 400 MHz) δ 8.33 (s, 1H), 8.00 (d, 2H), 7.45 (s, 1H), 7.39 (d, 2H), 7.16 (d, 1H), 7.29-7.19 (m, 5H), 7.03 (m, 1H), 4.53 (d, 2H), 3.71 (t, 1H). HPLC-MS calculated for $C_{24}H_{15}Cl_3N_4O_2$ (M + H⁺) 497.0, found 497.0. |
| 281 | 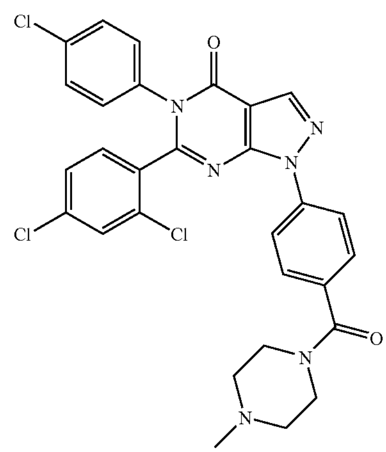 | ¹H NMR (CDCl₃, 400 MHz) δ 8.36 (s, 1H), 8.28 (d, 2H), 7.57 (d, 2H), 7.36-7.29 (m, 3H), 7.23-7.16 (m, 2H), 7.03 (m, 1H), 3.97 (m, 3H), 3.48 (m, 2H), 2.83 (m, 6H). HPLC-MS calculated for $C_{29}H_{23}Cl_3N_6O_2$ (M + H⁺) 593.1, found 593.1. |
| 282 | 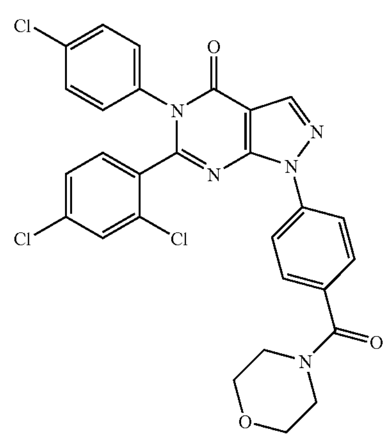 | HPLC-MS calculated for $C_{28}H_{20}Cl_3N_5O_3$ (M + H⁺) 580.1, found 580.1. |

TABLE 1-continued

| Compound Number | Structure | Physical Data $^1$H NMR 400 MHz (CDCl$_3$) and/or MS (m/z) |
|---|---|---|
| 283 | 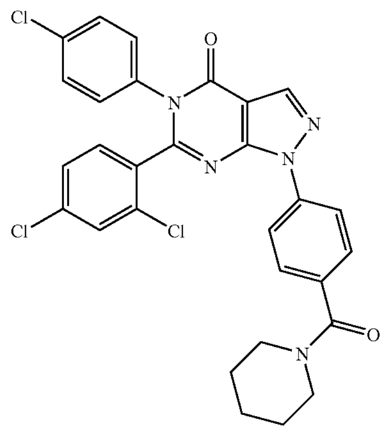 | HPLC-MS calculated for C$_{29}$H$_{22}$Cl$_3$N$_5$O$_2$ (M + H$^+$) 578.1. found 578.1. |
| 284 | 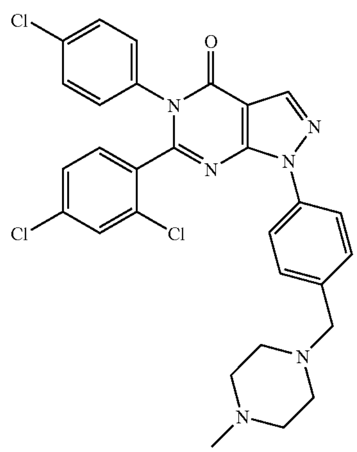 | $^1$H NMR (CDCl$_3$, 400 MHz) δ 8.34 (s, 1H), 8.06 (d, 2H), 7.44 (m, 2H), 7.34-7.28 (m, 3H), 7.18 (m, 2H), 7.03 (m, 1H), 5.31 (s, 2H), 3.66 (m, 2H), 2.89 (m, 6H), 2.71 (s, 3H). HPLC-MS calculated for C$_{29}$H$_{25}$Cl$_3$N$_6$O (M + H$^+$) 579.1, found 579.1. |
| 285 | 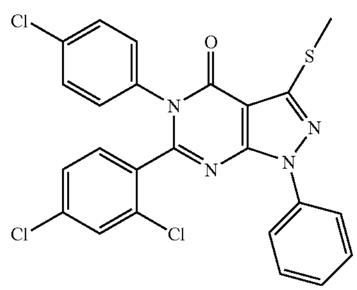 | HPLC-MS calculated for C$_{24}$H$_{15}$C$_{13}$N$_4$OS (M + H$^+$) 513.0, found 513.0. |
| 286 | 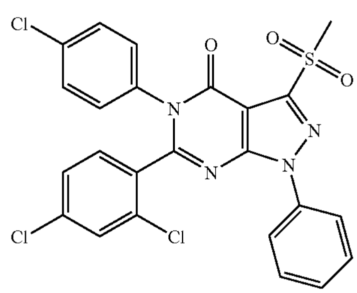 | HPLC-MS calculated for C$_{24}$H$_{15}$Cl$_3$N$_4$O$_3$S (M + H$^+$) 545.0, found 545.0. |

TABLE 1-continued

| Compound Number | Structure | Physical Data $^1$H NMR 400 MHz (CDCl$_3$) and/or MS (m/z) |
|---|---|---|
| 287 | 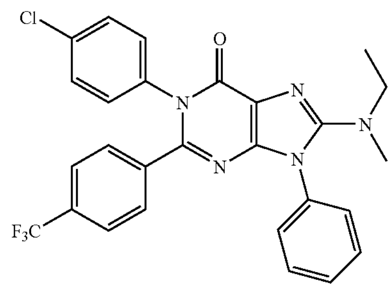 | $^1$H NMR (CDCl$_3$, 400 MHz) δ 7.54 (m, 4H), 7.47 (m, 1H), 7.42 (d, 2H), 7.30 (d, 4H), 7.08 (d, 2H), 3.17 (q, 2H), 2.90 (s, 3H), 1.03 (t, 3H). HPLC-MS calculated for C$_{27}$H$_{21}$ClF$_3$N$_5$O (M + H$^+$) 524.1, found 524.1. |
| 288 | 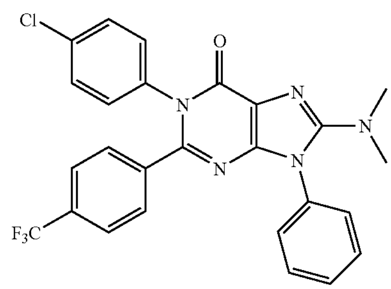 | HPLC-MS calculated for C$_{26}$H$_{19}$ClF$_3$N$_5$O (M + H$^+$) 510.1, found 510.1. |
| 289 | 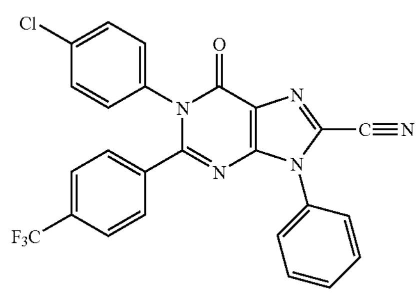 | $^1$H NMR (CDCl$_3$, 400 MHz) δ 7.64 (m, 5H), 7.52 (d, 2H), 7.38 (m, 4H), 7.12 (d, 2H), HPLC-MS calculated for C$_{25}$H$_{13}$ClF$_3$N$_5$O (M + H$^+$) 492.1, found 492.1. |
| 290 | 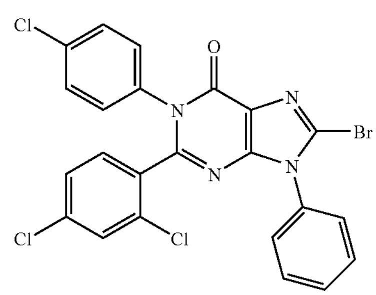 | HPLC-MS calculated for C$_{23}$H$_{12}$BrCl$_3$N$_4$O (M + H$^+$) 545.0, found 545.0. |
| 291 | 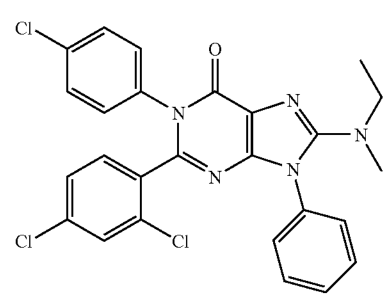 | HPLC-MS calculated for C$_{26}$H$_{20}$Cl$_3$N$_5$O (M + H$^+$) 524.1, found 524.1. |

TABLE 1-continued

| Compound Number | Structure | Physical Data <br> $^1$H NMR 400 MHz (CDCl$_3$) and/or MS (m/z) |
|---|---|---|
| 292 | 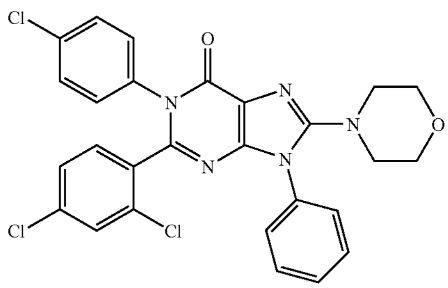 | HPLC-MS calculated for C$_{27}$H$_{20}$Cl$_3$N$_5$O$_2$ (M + H$^+$) 552.1, found 552.1. |
| 293 | 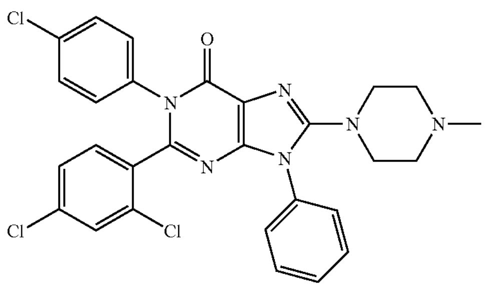 | HPLC-MS calculated for C$_{28}$H$_{23}$Cl$_3$N$_6$O (M + H$^+$) 565.1, found 565.1. |
| 294 | 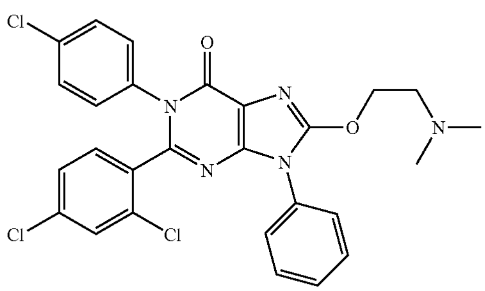 | HPLC-MS calculated for C$_{27}$H$_{22}$Cl$_3$N$_5$O$_2$ (M + H$^+$) 554.1, found 554.1. |
| 295 | 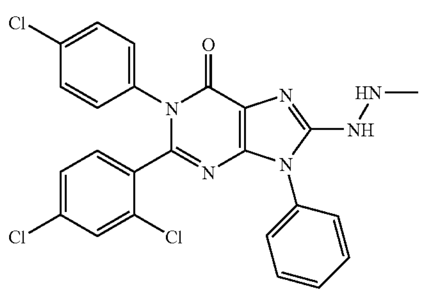 | HPLC-MS calculated for C$_{24}$H$_{17}$Cl$_3$N$_6$O (M + H$^+$) 511.1, found 511.1. |
| 296 | 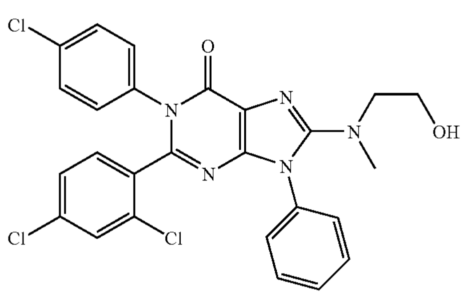 | HPLC-MS calculated for C$_{26}$H$_{20}$Cl$_3$N$_5$O$_2$ (M + H$^+$) 540.1, found 540.1. |

TABLE 1-continued

| Compound Number | Structure | Physical Data<br>$^1$H NMR 400 MHz (CDCl$_3$)<br>and/or MS (m/z) |
|---|---|---|
| 297 | 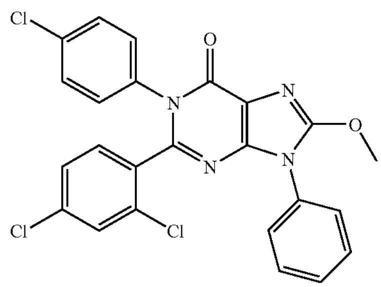 | HPLC-MS calculated for C$_{24}$H$_{15}$Cl$_3$N$_4$O$_2$ (M + H$^+$) 497.0, found 497.0. |
| 298 | 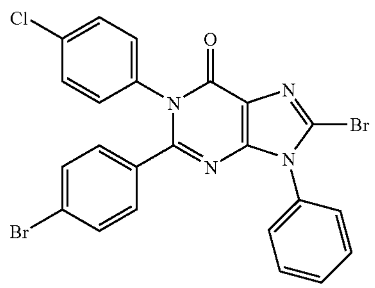 | HPLC-MS calculated for C$_{23}$H$_{13}$Br$_2$ClN$_4$O (M + H$^+$) 557.0. found 557.0. |
| 299 | 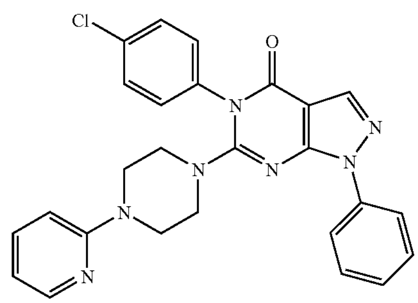 | HPLC-MS calculated for C$_{26}$H$_{22}$ClN$_7$O (M + H$^+$) 484.2, found 484.2. |
| 300 | 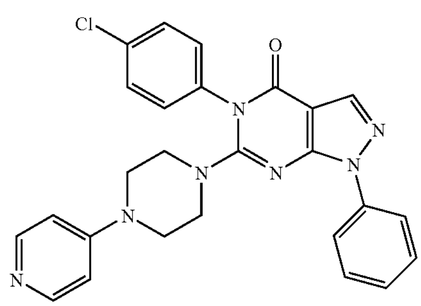 | HPLC-MS calculated for C$_{26}$H$_{22}$ClN$_7$O (M + H$^+$) 484.2, found 484.2. |
| 301 | 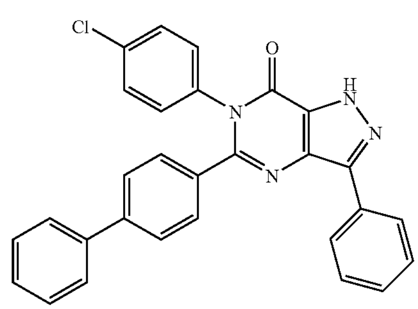 | HPLC-MS calculated for C$_{29}$H$_{19}$ClN$_4$O (M + H$^+$) 475.1, found 475.2. |

TABLE 1-continued

| Compound Number | Structure | Physical Data $^1$H NMR 400 MHz (CDCl$_3$) and/or MS (m/z) |
|---|---|---|
| 302 | 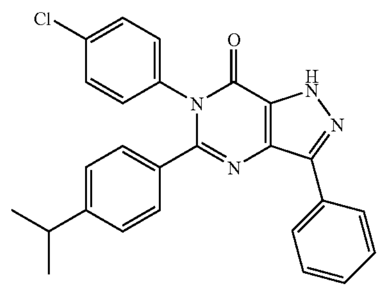 | $^1$H NMR (CDCl$_3$, 400 MHz) δ 8.42 (d, 2H), 7.48 (t, 2H), 7.39 (t, 1H), 7.32 (d, 2H), 7.26 (d, 2H), 7.11 (m, 4H), 2.86 (m, 1H), 1.22 (s, 3H), 1.20 (s, 3H); HPLC-MS calculated for C$_{26}$H$_{21}$ClN$_4$O (M + H$^+$) 441.1, found 441.2. |
| 307 | 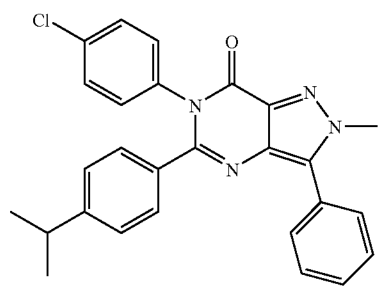 | $^1$H NMR (CDCl$_3$, 400 MHz) δ 7.65 (d, 2H), 7.54 (t, 2H), 7.47 (t, 1H), 7.27 (d, 2H), 7.16 (d, 2H), 7.09 (d, 2H), 7.02 (d, 2H), 4.19 (s, 3H), 2.80 (m, 1H), 1.16 (s, 3H), 1.14 (s, 3H); HPLC-MS calculated for C$_{27}$H$_{23}$ClN$_4$O (M + H$^+$) 455.2. found 455.2. |
| 308 | 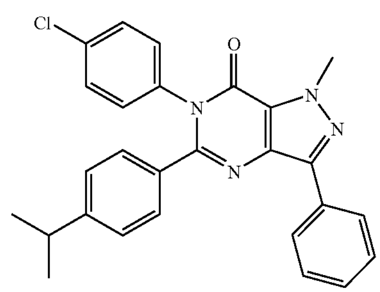 | $^1$H NMR (CDCl$_3$, 400 MHz) δ 8.37 (d, 2H), 7.46 (t, 2H), 7.35 (t, 1H), 7.32 (d, 2H), 7.25 (d, 2H), 7.10 (m, 4H), 4.37 (s, 3H), 2.86 (m, 1H), 1.21 (s, 3H), 1.19 (s, 3H); HPLC-MS calculated for C$_{27}$H$_{23}$ClN$_4$O (M + H$^+$) 455.2, found 455.2. |
| 309 | 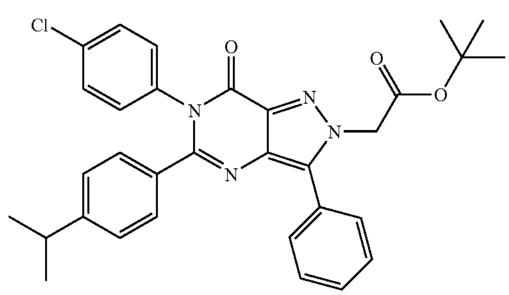 | HPLC-MS calculated for C$_{32}$H$_{31}$ClN$_4$O$_3$ (M + H$^+$) 555.2, found 555.2. |
| 310 | 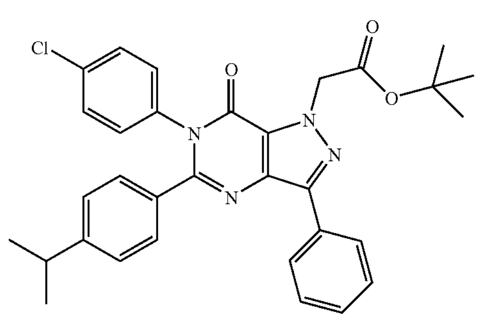 | $^1$H NMR (CD$_3$OD, 400 MHz) δ 8.37 (d, 2H), 7.45 (t, 2H), 7.36 (t, 1H), 7.30 (d, 2H), 7.24 (d, 2H), 7.09 (m, 4H), 5.35 (s, 2H), 2.85 (m, 1H), 1.48 (s, 9H), 1.21 (s, 3H), 1.19 (s, 3H); HPLC-MS calculated for C$_{32}$H$_{31}$ClN$_4$O$_3$ (M + H$^+$) 555.2, found 555.2. |

TABLE 1-continued

| Compound Number | Structure | Physical Data<br>¹H NMR 400 MHz (CDCl₃)<br>and/or MS (m/z) |
|---|---|---|
| 312 | 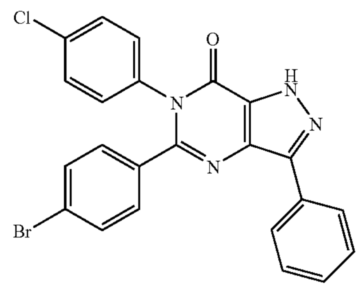 | ¹H NMR (CDCl₃, 400 MHz) δ 8.38 (d, 2H), 7.49 (t, 2H), 7.40 (m, 3H), 7.35 (d, 2H), 7.21 (d, 2H), 7.11 (d, 2H); HPLC-MS calculated for C₂₃H₁₄BrClN₄O (M + H⁺) 477.0, found 477.0. |
| 313 | 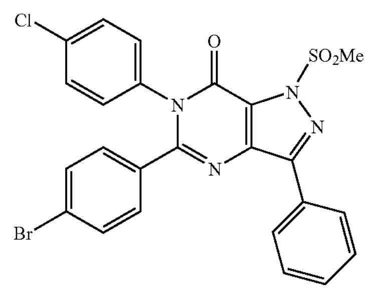 | ¹H NMR (CDCl₃, 400 MHz) δ 8.44 (d, 2H), 7.50-7.42 (m, 5H), 7.38 (d, 2H), 7.24 (d, 2H), 7.14 (d, 2H), 3.77 (s, 3H); HPLC-MS calculated for C₂₄H₁₆BrClN₄O₃S (M + H⁺) 555.0, found 555.0. |
| 315 | 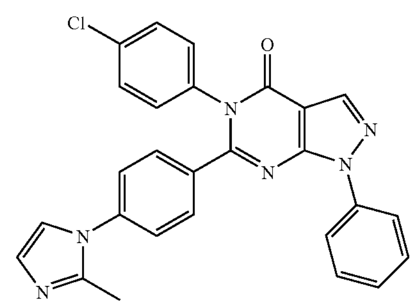 | ¹H NMR (CDCl₃, 400 MHz) δ 8.37 (s, 1H), 8.09 (d, 2H), 7.61 (d, 2H), 7.53 (t, 2H), 7.46 (d, 1H), 7.41 (t, 1H), 7.38 (d, 2H), 7.31 (d, 2H), 7.15 (m, 3H), 2.64 (s, 3H); HPLC-MS calculated for C₂₇H₁₉ClN₆O (M + H⁺) 479.1, found 479.1. |
| 316 | 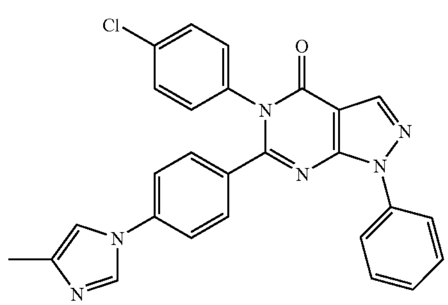 | ¹H NMR (CDCl₃, 400 MHz) δ 8.94 (s, 1H), 8.35 (s, 1H), 8.10 (d, 2H), 7.54 (m, 4H), 7.37 (m, 5H), 7.12 (m, 3H), 2.47 (s, 3H); HPLC-MS calculated for C₂₇H₁₉ClN₆O (M + H⁺) 479.1, found 479.1. |
| 317 | 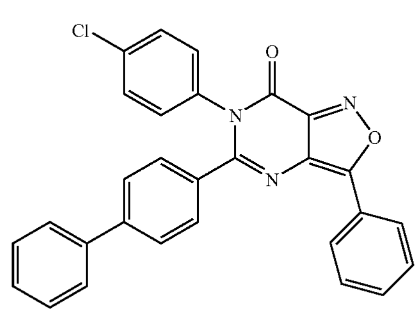 | ¹H NMR (CDCl₃, 400 MHz) δ 8.39 (dd, 2H), 7.57-7.50 (m, 7H), 7.46-7.38 (m, 5H), 7.34 (d, 2H), 7.15 (d, 2H); HPLC-MS calculated for C₂₉H₁₈ClN₃O₂ (M + H⁺) 476.1, found 476.1. |

TABLE 1-continued

| Compound Number | Structure | Physical Data<br>¹H NMR 400 MHz (CDCl₃) and/or MS (m/z) |
|---|---|---|
| 319 | 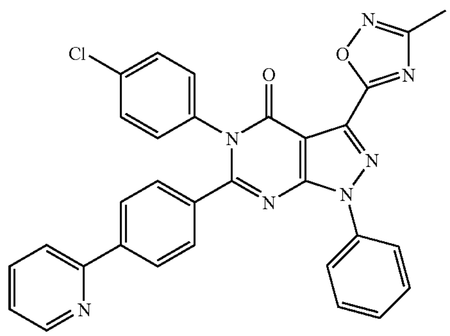 | ¹H NMR (CDCl₃, 400 MHz) δ 8.84 (d, 1H), 8.21 (dd, 2H), 8.00 (t, 1H), 7.92 (d, 2H), 7.82 (d, 1H), 7.56 (m, 4H), 7.49 (t, 1H), 7.44 (t, 1H), 7.34 (d, 2H), 7.16 (d, 2H), 2.56 (s, 3H); HPLC-MS calculated for $C_{31}H_{20}ClN_7O_2$ (M + H⁺) 558.1. found 558.1. |
| 321 | 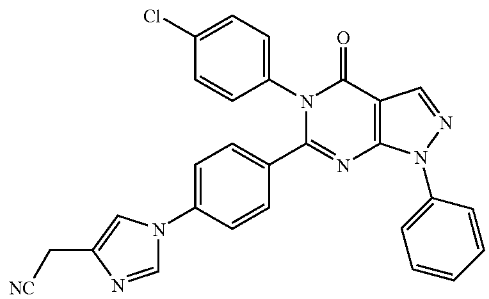 | ¹H NMR (CDCl₃, 400 MHz) δ 8.76 (s, 1H), 8.36 (s, 1H), 8.10 (dd, 2H), 7.59 (d, 2H), 7.53 (m, 3H), 7.43 (m, 3H), 7.37 (d, 2H), 7.13 (d, 2H), 4.06 (s, 2H); HPLC-MS calculated for $C_{28}H_{18}ClN_7O$ (M + H⁺) 504.1, found 504.1. |
| 322 | 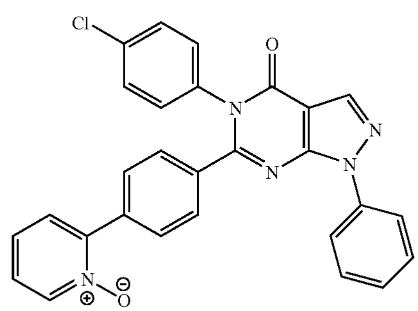 | ¹H NMR (CDCl₃, 400 MHz) δ 8.40 (d, 1H), 8.34 (s, 1H), 8.16 (dd, 2H), 7.77 (d, 2H), 7.52 (t, 2H), 7.48-7.30 (m, 8H), 7.14 (d, 2H); HPLC-MS calculated for $C_{28}H_{18}ClN_5O_2$ (M + H⁺) 492.1, found 492.1. |
| 323 | 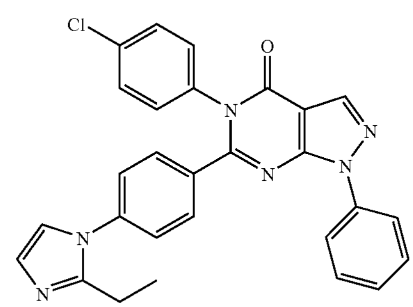 | ¹H NMR (CDCl₃, 400 MHz) δ 8.37 (s, 1H), 8.10 (d, 2H), 7.58 (d, 2H), 7.53 (t, 2H), 7.38 (m, 4H), 7.29 (d, 2H), 7.12 (m, 3H), 2.95 (q, 2H), 1.31 (t, 3H); HPLC-MS calculated for $C_{28}H_{21}ClN_6O$ (M + H⁺) 493.2, found 493.2. |
| 324 | 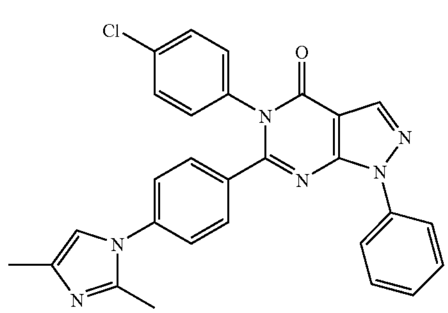 | ¹H NMR (CDCl₃, 400 MHz) δ 8.35 (s, 1H), 8.11 (d, 2H), 7.52 (m, 4H), 7.38 (m, 3H), 7.21 (d, 2H), 7.12 (d, 2H), 6.76 (s, 1H), 2.48 (s, 3H), 2.34 (s, 3H); HPLC-MS calculated for $C_{28}H_{21}ClN_6O$ (M + H⁺) 493.2, found 493.2 |

TABLE 1-continued

| Compound Number | Structure | Physical Data $^1$H NMR 400 MHz (CDCl$_3$) and/or MS (m/z) |
|---|---|---|
| 325 | 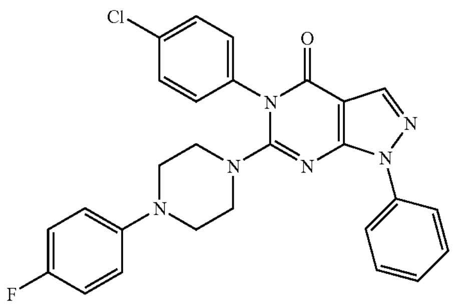 | $^1$H NMR (CDCl$_3$, 400 MHz) δ 8.19 (s, 1H), 8.08 (d, 2H), 7.52 (m, 4H), 7.35 (m, 3H), 7.04 (m, 4H), 3.49 (t, 4H), 3.07 (t, 4H); HPLC-MS calculated for C$_{27}$H$_{22}$ClFN$_6$O (M + H$^+$) 501.2, found 501.2. |
| 326 | 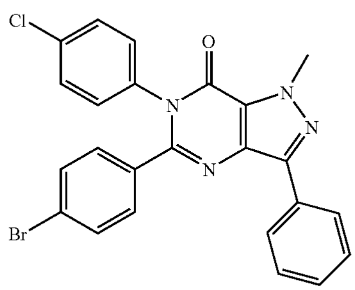 | $^1$H NMR (CDCl$_3$, 400 MHz) δ 8.34 (d, 2H), 7.46 (t, 2H), 7.37 (m, 5H), 7.21 (d, 2H), 7.10 (d, 2H), 4.37 (s, 3H); HPLC-MS calculated for C$_{24}$H$_{16}$BrClN$_4$O (M + H$^+$) 491.0, found 491.0. |
| 328 | 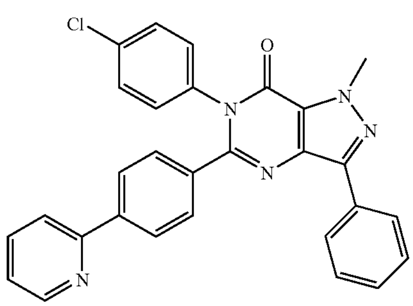 | $^1$H NMR (CDCl$_3$, 400 MHz) δ 8.92 (d, 1H), 8.36 (d, 2H), 8.08 (t, 1H), 7.84 (m, 3H), 7.55 (m, 3H), 7.47 (t, 2H), 7.37 (t, 1H), 7.34 (d, 2H), 7.15 (d, 2H), 4.39 (s, 3H); HPLC-MS calculated for C$_{29}$H$_{20}$ClN$_5$O (M + H$^+$) 490.1, found 490.1. |
| 329 | 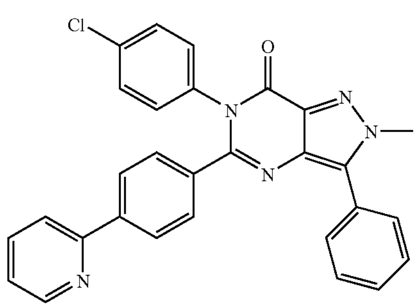 | $^1$H NMR (CDCl$_3$, 400 MHz) δ 8.66 (d, 1H), 7.83 (d, 2H), 7.73 (t, 1H), 7.67 (m, 3H), 7.55 (t, 2H), 7.48 (t, 1H), 7.38 (d, 2H), 7.28 (d, 2H), 7.23 (dd, 1H), 7.14 (d, 2H), 4.21 (s, 3H); HPLC-MS calculated for C$_{29}$H$_{20}$ClN$_5$O (M +H$^+$) 490.1, found 490.1. |

TABLE 1-continued

| Compound Number | Structure | Physical Data<br>$^1$H NMR 400 MHz (CDCl$_3$) and/or MS (m/z) |
|---|---|---|
| 331 | 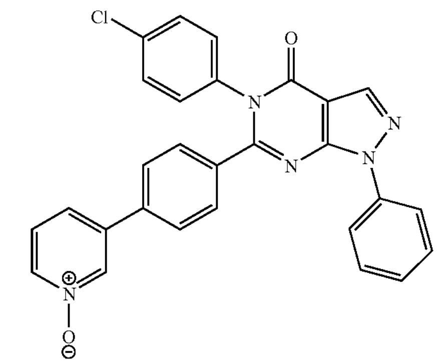 | HPLC-MS calculated for C$_{28}$H$_{18}$ClN$_5$O$_2$ (M + H$^+$) 492.1, found 492.1. |
| 333 | 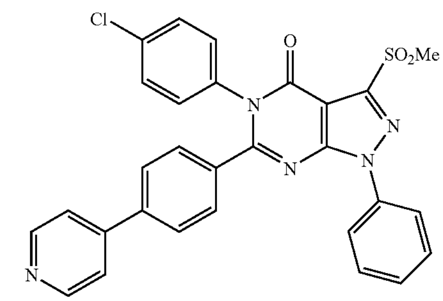 | $^1$H NMR (CDCl$_3$, 400 MHz) δ 8.72 (d, 2H), 8.10 (d, 2H), 7.60-7.49 (m, 8H), 7.45 (t, 1H), 7.37 (d, 2H), 7.17 (d, 2H), 3.55 (s, 3H); HPLC-MS calculated for C$_{29}$H$_{20}$ClN$_5$O$_3$S (M + H$^+$) 554.1, found 554.1. |
| 335 | 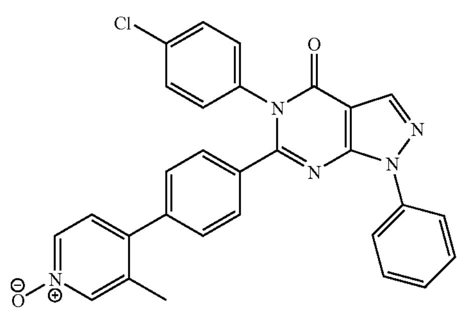 | $^1$H NMR (CDCl$_3$, 400 MHz) δ 8.35 (s, 1H), 8.23 (s, 1H), 8.19 (d, 1H), 8.13 (d, 2H), 7.52 (t, 2H), 7.45 (d, 2H), 7.37 (t, 1H), 7.34 (d, 2H), 7.22 (d, 2H), 7.18 (d, 1H), 7.12 (d, 2H), 2.21 (s, 3H); HPLC-MS calculated for C$_{29}$H$_{20}$ClN$_5$O$_2$ (M + H$^+$) 506.1, found 506.1. |
| 336 | 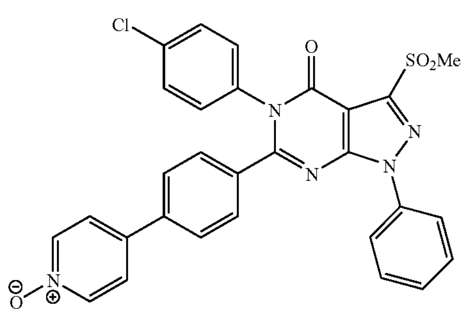 | $^1$H NMR (CDCl$_3$, 400 MHZ) δ 8.54 (d, 2H), 8.09 (d, 2H), 7.68 (d, 2H), 7.53 (m, 6H), 7.45 (t, 1H), 7.37 (d, 2H), 7.16 (d, 2H), 3.55 (s, 3H); HPLC-MS calculated for C$_{29}$H$_{20}$ClN$_5$O$_4$S (M + H$^+$) 570.1, found 570.1. |

TABLE 1-continued

| Compound Number | Structure | Physical Data $^1$H NMR 400 MHz (CDCl$_3$) and/or MS (m/z) |
|---|---|---|
| 339 | 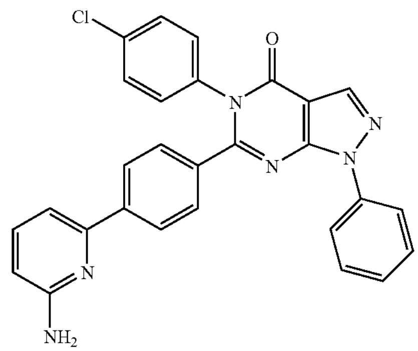 | $^1$H NMR (CDCl$_3$, 400 MHz) δ 8.33 (s, 1H), 8.16 (d, 2H), 7.87 (d, 2H), 7.52 (m, 3H), 7.42 (d, 2H), 7.36 (t, 1H), 7.32 (d, 2H), 7.12 (d, 2H), 7.07 (d, 1H), 6.51 (d, 1H); HPLC-MS calculated for C$_{28}$H$_{19}$ClN$_6$O (M + H$^+$) 491.1, found 491.1. |
| 340 | 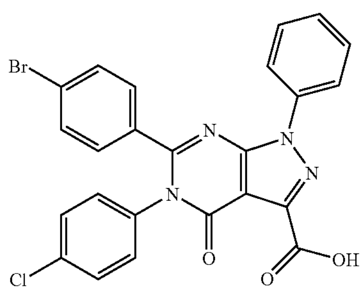 | HPLC-MS calculated C$_{24}$H$_{14}$BrClN$_4$O$_3$ (M + 1$^+$): 520.0, found: 520.0. |
| 341 | 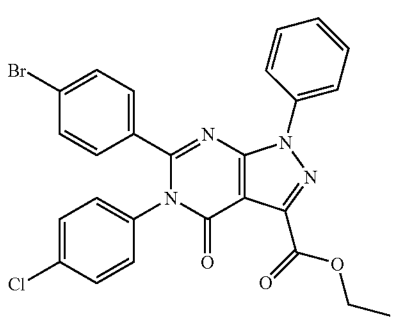 | $^1$H NMR (CDCl$_3$) δ (ppm) 8.10 (d, 2H), 7.50 (t, 2H), 7.41 (m, 3H), 7.34 (d, 2H), 7.20 (d, 2H), 7.09 (d, 2H), 4.52 (q, 2H), 1.45 (t, 3H). HPLC-MS calculated C$_{26}$H$_{18}$BrClN$_4$O$_3$ (M + 1$^+$): 549.0, found: 549.0. |
| 342 | 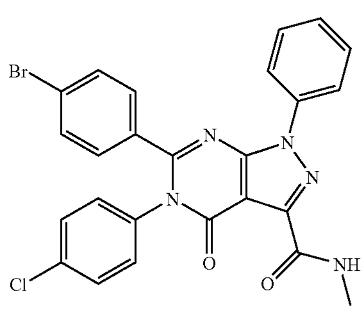 | $^1$H NMR (CDCl$_3$) δ (ppm) 9.95 (b, 1H), 8.16 (d, 2H), 7.51 (t, 2H), 7.41 (m, 5H), 7.22 (d, 2H), 7.13 (d, 2H), 3.05 (d, 3H). HPLC-MS calculated C$_{25}$H$_{17}$BrClN$_5$O$_2$ (M + 1$^+$): 534.0, found: 534.0. |

TABLE 1-continued

| Compound Number | Structure | Physical Data<br>¹H NMR 400 MHz (CDCl₃) and/or MS (m/z) |
|---|---|---|
| 343 | 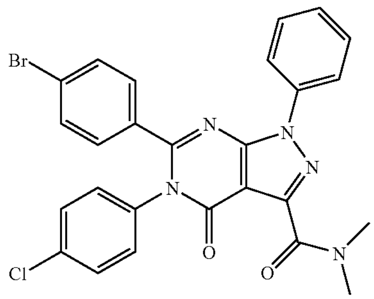 | HPLC-MS calculated<br>$C_{26}H_{19}BrClN_5O_2$ (M + 1⁺):<br>548.0, found: 548.0. |
| 344 | 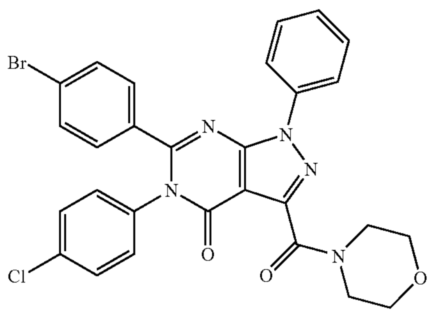 | HPLC-MS calculated<br>$C_{28}H_{21}BrClN_5O_3$ (M + 1⁺):<br>590.1, found: 590.1. |
| 345 | 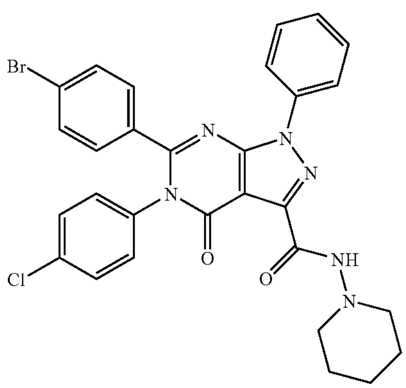 | HPLC-MS calculated<br>$C_{29}H_{24}BrClN_6O_2$ (M + 1⁺):<br>603.1, found: 603.1. |
| 346 | 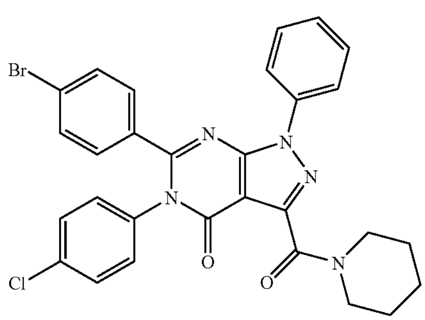 | HPLC-MS calculated<br>$C_{29}H_{23}BrClN_5O_2$ (M + 1⁺):<br>588.1, found: 588.1. |

TABLE 1-continued

| Compound Number | Structure | Physical Data<br>$^1$H NMR 400 MHz (CDCl$_3$) and/or MS (m/z) |
|---|---|---|
| 347 | 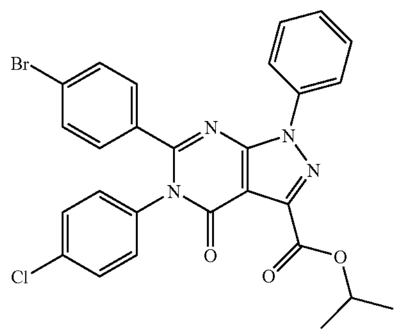 | $^1$H NMR (CDCl$_3$) δ (ppm) 8.10 (d, 2H), 7.51 (t, 2H), 7.41 (m, 3H), 7.33 (d, 2H), 7.19 (d, 2H), 7.09 (d, 2H), 5.38 (m, 1H), 1.44 (d, 6H). HPLC-MS calculated C$_{27}$H$_{20}$BrClN$_4$O$_3$ (M + 1$^+$): 563.0, found: 563.1. |
| 348 | 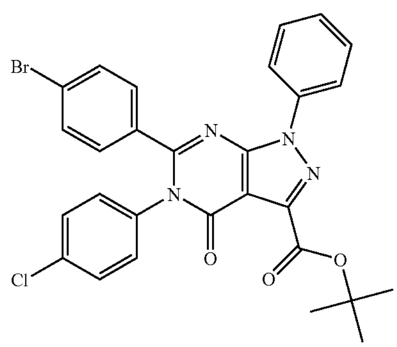 | $^1$H NMR (CDCl$_3$) δ (ppm) 8.12 (d, 2H), 7.50 (t, 2H), 7.41 (m, 3H), 7.33 (d, 2H), 7.19 (d, 2H), 7.09 (d, 2H), 1.67 (s, 9H). HPLC-MS calculated C$_{28}$H$_{22}$BrClN$_4$O$_3$ (M + 1$^+$): 577.1, found: 577.1. |
| 349 | 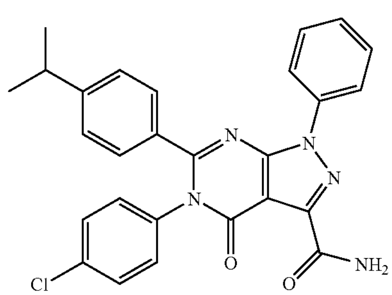 | HPLC-MS calculated C$_{27}$H$_{22}$ClN$_5$O$_2$ (M + 1$^+$): 484.2, found: 484.2. |
| 350 | 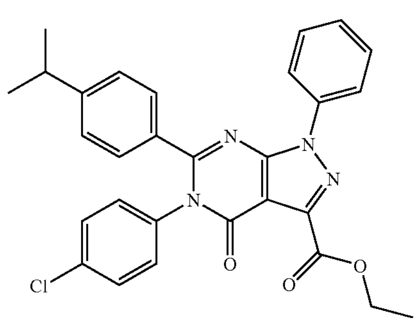 | $^1$H NMR (CDCl$_3$) δ (ppm) 8.13 (d, 2H), 7.51 (t, 2H), 7.39 (t, 1H), 7.30 (d, 2H), 7.24 (d, 2H), 7.10 (d, 2H), 4.52 (q, 2H), 2.85 (m, 1H), 1.45 (t, 3H), 1.19 (d, 6H). HPLC-MS calculated C$_{29}$H$_{25}$ClN$_4$O$_3$ (M + 1$^+$): 513.2, found: 513.2. |

TABLE 1-continued

| Compound Number | Structure | Physical Data<br>¹H NMR 400 MHz (CDCl₃) and/or MS (m/z) |
|---|---|---|
| 351 | 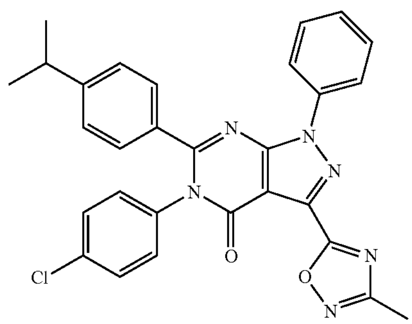 | ¹H NMR (CDCl₃) δ (ppm) 8.21 (d, 2H), 7.54 (t, 2H), 7.42 (t, 1H), 7.32 (d, 2H), 7.29 (d, 2H), 7.12 (m, 4H), 2.87 (m, 1H), 2.55 (s, 3H), 1.20 (d, 6H). HPLC-MS calculated $C_{29}H_{23}ClN_6O_2$ (M + 1⁺): 523.2, found: 523.2. |
| 352 | 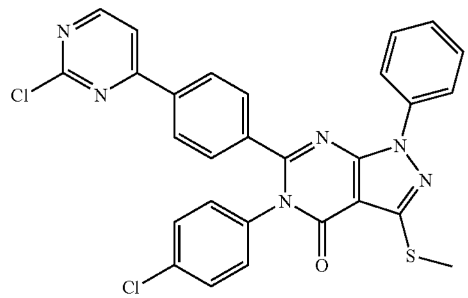 | ¹H NMR (CDCl₃) δ (ppm) 8.68 (d, 1H), 8.15 (d, 2H), 8.01 (d, 2H), 7.63 (d, 1H), 7.49 (m, 4H), 7.32 (m, 3H), 7.11 (d, 2H), 2.73 (s, 3H). HPLC-MS calculated $C_{28}H_{18}Cl_2N_6OS$ (M + 1⁺): 557.1, found: 557.1. |
| 353 | 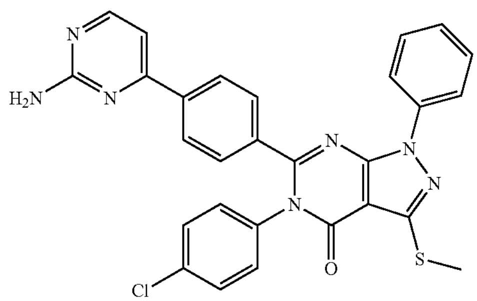 | ¹H NMR (CDCl₃) δ (ppm) 8.23 (d, 1H), 8.12 (d, 2H), 8.01 (d, 2H), 7.52 (m, 4H), 7.33 (m, 3H), 7.23 (d, 1H), 7.11 (d, 2H), 2.73 (s, 3H). HPLC-MS calculated $C_{28}H_{20}ClN_7OS$ (M + 1⁺): 538.1, found: 538.1. |
| 354 | 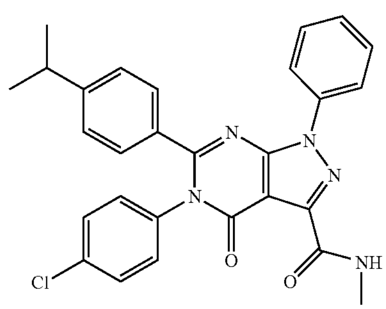 | HPLC-MS calculated $C_{28}H_{24}ClN_5O_2$ (M + 1⁺): 498.2, found: 498.2. |
| 355 | 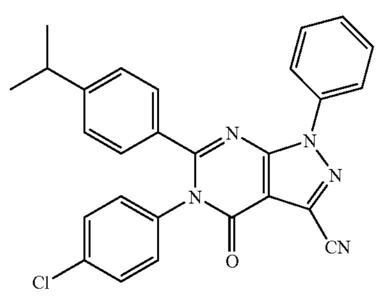 | ¹H NMR (CDCl₃) δ (ppm) 8.13 (d, 2H), 7.54 (t, 2H), 7.44 (t, 1H), 7.33 (d, 2H), 7.25 (d, 2H), 7.10 (m, 4H), 2.87 (m, 1H), 1.20 (d, 6H). HPLC-MS calculated $C_{27}H_{20}ClN_5O$ (M + 1⁺): 466.1, found: 466.1. |

TABLE 1-continued

| Compound Number | Structure | Physical Data<br>¹H NMR 400 MHz (CDCl₃) and/or MS (m/z) |
|---|---|---|
| 356 | 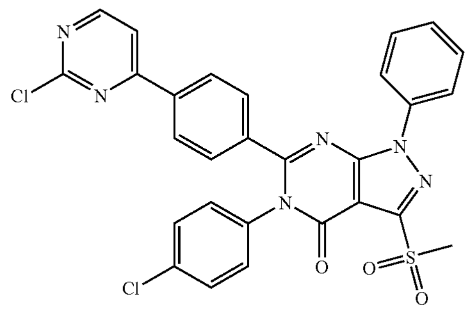 | ¹H NMR (CDCl₃) δ (ppm) 8.69 (d, 1H), 8.09 (d, 2H), 8.03 (d, 2H), 7.64 (d, 1H), 7.54 (t, 3H), 7.50 (d, 2H), 7.44 (t, 1H), 7.34 (d, 2H), 7.15 (d, 1H), 3.53 (s, 3H). HPLC-MS calculated C$_{28}$H$_{18}$Cl$_2$N$_6$O$_3$S (M + 1$^+$): 589.1, found: 589.1. |
| 357 | 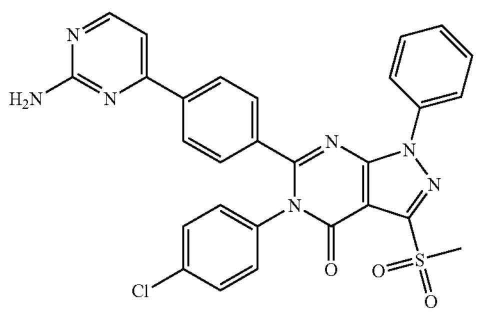 | ¹H NMR (CDCl₃) δ (ppm) 8.36 (d, 1H), 8.11 (d, 2H), 7.94 (d, 2H), 7.54 (t, 2H), 7.45 (m, 3H), 7.34 (d, 2H), 7.15 (d, 2H), 7.03 (d, 1H), 5.34 (b, 2H), 3.55 (s, 3H). HPLC-MS calculated C$_{28}$H$_{20}$ClN$_7$O$_3$S (M + 1$^+$): 570.1, found: 570.1. |
| 358 | 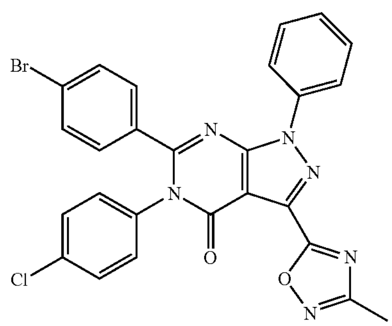 | HPLC-MS calculated C$_{26}$H$_{16}$BrClN$_6$O$_2$ (M + 1$^+$): 559.0, found: 559.0. |
| 359 | 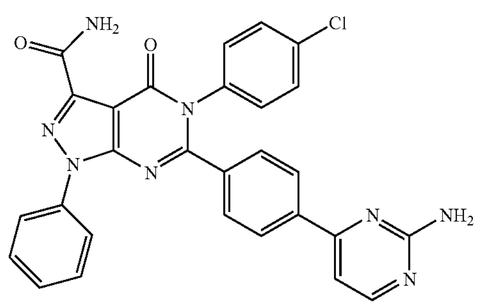 | ¹H NMR (CDCl₃) δ (ppm) 9.77 (b, 1H), 8.25 (d, 1H), 8.15 (d, 2H), 8.03 (d, 2H), 7.54 (m, 5H), 7.42 (d, 1H), 7.39 (d, 2H), 7.19 (d, 1H), 7.16 (d, 2H), 6.80 (b, 2H), 5.91 (b, 1H). HPLC-MS calculated C$_{28}$H$_{19}$ClN$_8$O$_2$ (M + 1$^+$): 535.1, found: 535.1. |
| 360 | 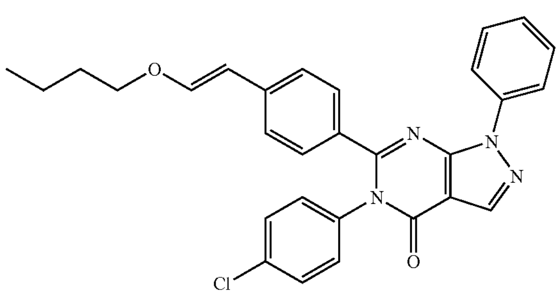 | HPLC-MS calculated C$_{29}$H$_{25}$ClN$_4$O$_2$ (M + 1$^+$): 497.2, found: 497.2. |

TABLE 1-continued

| Compound Number | Structure | Physical Data<br>¹H NMR 400 MHz (CDCl₃)<br>and/or MS (m/z) |
|---|---|---|
| 361 | 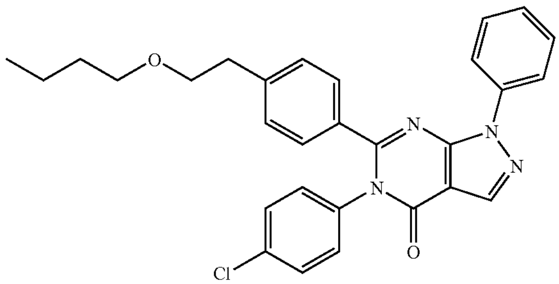 | HPLC-MS calculated<br>$C_{29}H_{27}ClN_4O_2$ (M + 1⁺): 499.2,<br>found: 499.2. |
| 362 | 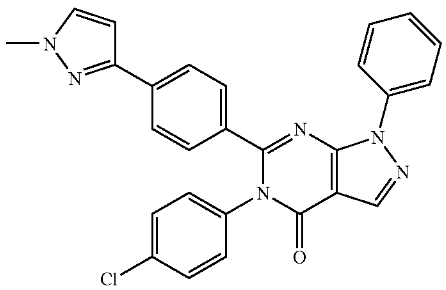 | ¹H NMR (CDCl₃) δ (ppm)<br>8.33 (s, 1H), 8.17 (d, 2H),<br>7.70 (d, 2H), 7.51 (t, 2H), 7.38<br>(m, 4H), 7.11 (d, 2H), 6.54 (d,<br>1H), 3.97 (s, 3H). HPLC-MS<br>calculated $C_{27}H_{19}ClN_6O$<br>(M + 1⁺): 479.1, found: 479.1. |
| 363 | 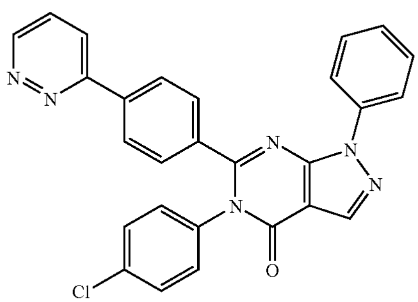 | ¹H NMR (CDCl₃) δ (ppm)<br>9.19 (b, 1H), 8.34 (s, 1H),<br>8.15 (d, 2H), 8.02 (d, 2H),<br>7.84 (d, 1H), 7.51 (m, 5H),<br>7.33 (m, 3H), 7.15 (d, 2H).<br>HPLC-MS calculated<br>$C_{27}H_{17}ClN_6O$ (M + 1⁺): 477.1,<br>found: 477.1. |
| 364 | 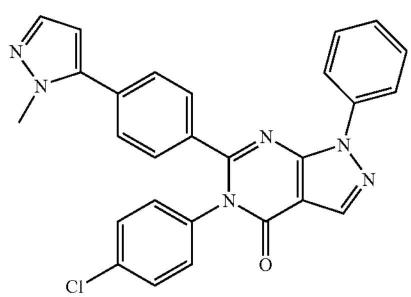 | ¹H NMR (CDCl₃) δ (ppm)<br>8.35 (s, 1H), 8.14 (d, 2H),<br>7.52 (t, 3H), 7.43 (d, 2H),<br>7.34 (m, 5H), 7.13 (d, 2H),<br>6.33 (d, 1H), 3.87 (s, 3H).<br>HPLC-MS calculated<br>$C_{27}H_{19}ClN_6O$ (M + 1⁺): 479.1,<br>found: 479.1. |
| 365 | 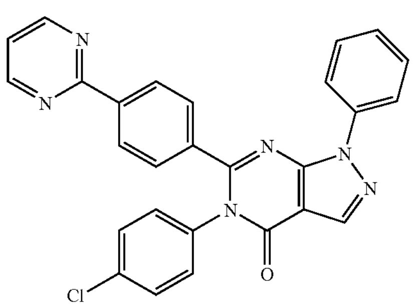 | ¹H NMR (CDCl₃) δ (ppm)<br>8.81 (d, 2H), 8.34 (t, 3H), 8.17<br>(d, 2H), 7.49 (m, 4H), 7.86 (d,<br>2H), 7.52 (t, 2H), 7.36 (t, 1H),<br>7.31 (d, 2H), 7.24 (t, 1H),<br>7.13 (d, 2H). HPLC-MS<br>calculated $C_{27}H_{17}ClN_6O$<br>(M + 1⁺): 477.1, found: 477.1. |

TABLE 1-continued

| Compound Number | Structure | Physical Data<br>$^1$H NMR 400 MHz (CDCl$_3$)<br>and/or MS (m/z) |
|---|---|---|
| 366 | 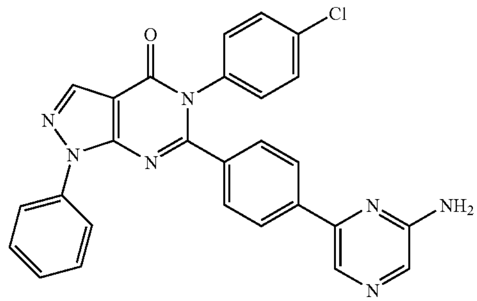 | $^1$H NMR (CDCl$_3$) δ (ppm)<br>8.34 (s, 1H), 8.32 (b, 1H), 8.15 (d, 2H), 7.99 (b, 1H), 7.86 (d, 2H), 7.52 (t, 2H), 7.46 (d, 2H), 7.37 (t, 1H), 7.31 (d, 2H), 7.12 (d, 2H). HPLC-MS calculated C$_{27}$H$_{18}$ClN$_7$O (M + 1$^+$): 492.1, found: 492.1. |
| 367 | 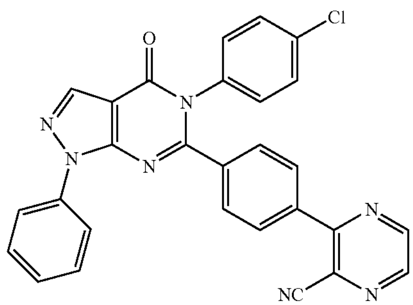 | $^1$H NMR (CDCl$_3$) δ (ppm)<br>8.84 (d, 1H), 8.68 (d, 1H), 8.36 (s, 1H), 8.14 (d, 2H), 7.94 (d, 2H), 7.53 (m, 4H), 7.37 (t, 1H), 7.33 (d, 2H), 7.13 (d, 2H). HPLC-MS calculated C$_{28}$H$_{16}$ClN$_7$O (M + 1$^+$): 502.1, found: 502.1. |
| 368 | 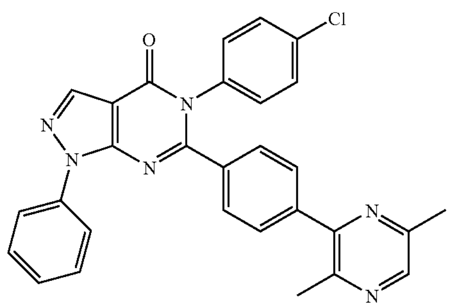 | $^1$H NMR (CDCl$_3$) δ (ppm)<br>8.35 (m, 2H), 8.16 (d, 2H), 7.49 (m, 6H), 7.35 (m, 3H), 7.14 (d, 2H), 2.58 (s, 3H), 2.52 (s, 3H). HPLC-MS calculated C$_{29}$H$_{21}$ClN$_6$O (M + 1$^+$): 505.2, found: 505.2. |
| 369 | 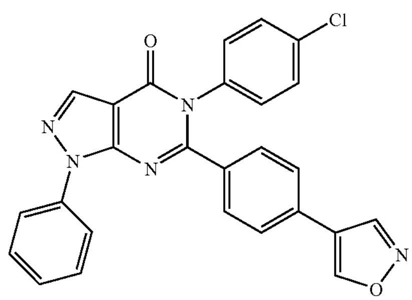 | $^1$H NMR (CDCl$_3$) δ (ppm)<br>8.70 (s, 1H), 8.54 (s, 1H), 8.34 (s, 1H), 8.14 (d, 2H), 7.51 (t, 2H), 7.35 (m, 7H), 7.12 (d, 2H). HPLC-MS calculated C$_{26}$H$_{16}$ClN$_5$O$_2$ (M + 1$^+$): 466.1, found: 466.1. |
| 370 | 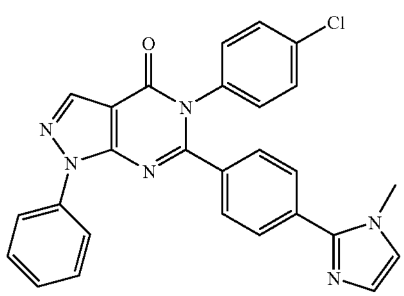 | $^1$H NMR (CDCl$_3$) δ (ppm)<br>8.35 (s, 1H), 8.12 (d, 2H), 7.65 (d, 2H), 7.55 (m, 5H), 7.39 (t, 1H), 7.33 (d, 2H), 7.16 (s, 1H), 7.07 (d, 2H). HPLC-MS calculated C$_{27}$H$_{19}$ClN$_6$O (M + 1$^+$): 479.1, found: 479.1. |

TABLE 1-continued

| Compound Number | Structure | Physical Data<br>$^1$H NMR 400 MHz (CDCl$_3$) and/or MS (m/z) |
|---|---|---|
| 371 | 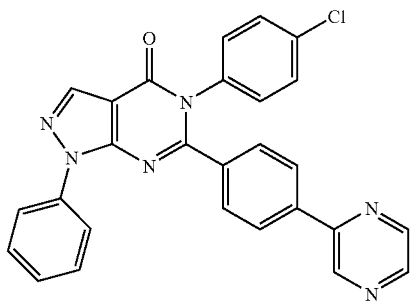 | $^1$H NMR (CDCl$_3$) δ (ppm) 9.02 (d, 1H), 8.67 (t, 1H), 8.55 (d, 1H), 8.35 (s, 1H), 8.15 (d, 2H), 7.95 (d, 2H), 7.51 (m, 4H), 7.37 (t, 1H), 7.33 (d, 2H), 7.14 (d, 2H). HPLC-MS calculated C$_{27}$H$_{17}$ClN$_6$O (M + 1$^+$): 477.1, found: 477.1. |
| 372 | 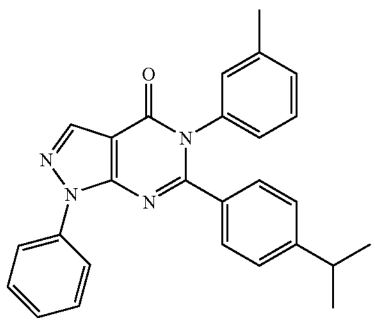 | HPLC-MS calculated C$_{27}$H$_{24}$N$_4$O (M + 1$^+$): 421.2, found: 421.2. |
| 373 | 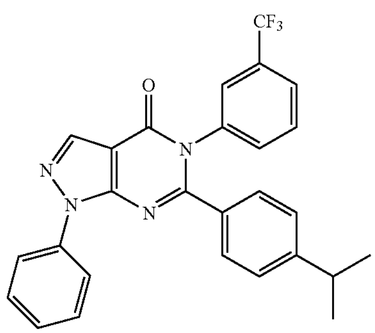 | HPLC-MS calculated C$_{27}$H$_{21}$F$_3$N$_4$O (M + 1$^+$): 475.2, found: 475.2. |
| 374 | 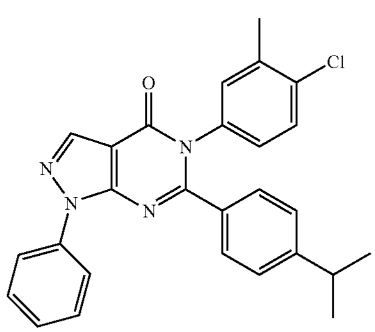 | HPLC-MS calculated C$_{27}$H$_{23}$ClN$_4$O (M + 1$^+$): 455.2, found: 455.2. |

TABLE 1-continued

| Compound Number | Structure | Physical Data $^1$H NMR 400 MHz (CDCl$_3$) and/or MS (m/z) |
|---|---|---|
| 375 | 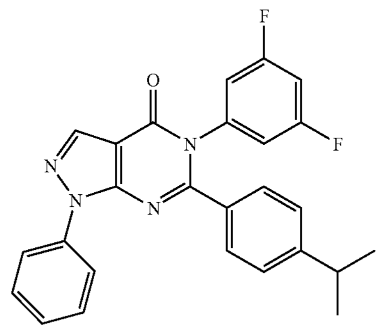 | HPLC-MS calculated C$_{26}$H$_{20}$F$_2$N$_4$O (M + 1$^+$): 443.2, found: 443.2. |
| 376 | 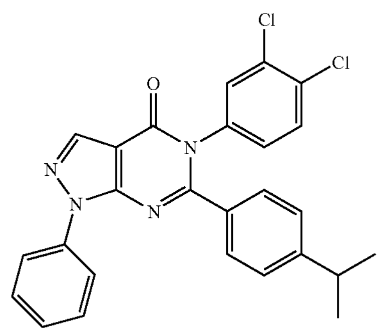 | HPLC-MS calculated C$_{26}$H$_{20}$Cl$_2$N$_4$O (M + 1$^+$): 475.1, found: 475.1. |
| 377 | 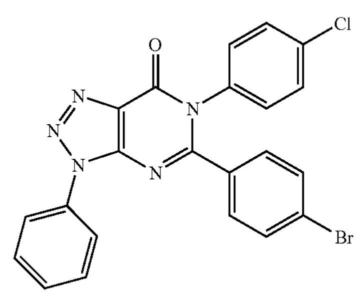 | $^1$H NMR (CDCl$_3$) δ (ppm) 8.15 (d, 2H), 7.59 (t, 2H), 7.49 (t, 1H), 7.43 (d, 2H), 7.37 (d, 2H), 7.21 (d, 2H), 7.10 (d, 2H), 2.87 (m, 1H). HPLC-MS calculated C$_{22}$H$_{13}$BrClN$_5$O (M + 1$^+$): 478.0, found: 478.0. |
| 378 | 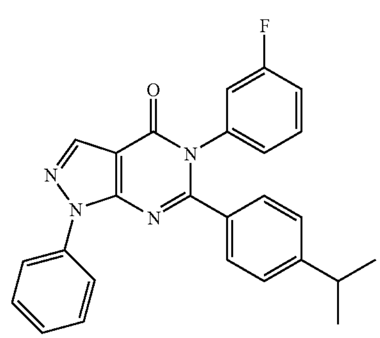 | HPLC-MS calculated C$_{26}$H$_{21}$FN$_4$O (M + 1$^+$): 425.2, found: 425.2. |

TABLE 1-continued

| Compound Number | Structure | Physical Data $^1$H NMR 400 MHz (CDCl$_3$) and/or MS (m/z) |
|---|---|---|
| 379 | 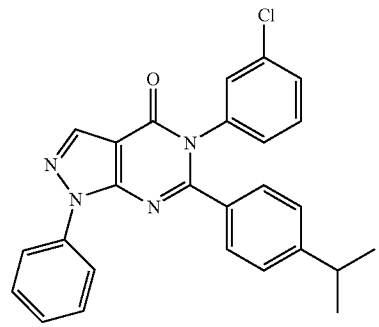 | HPLC-MS calculated C$_{26}$H$_{21}$ClN$_4$O (M + 1$^+$): 441.1, found: 441.2. |
| 380 | 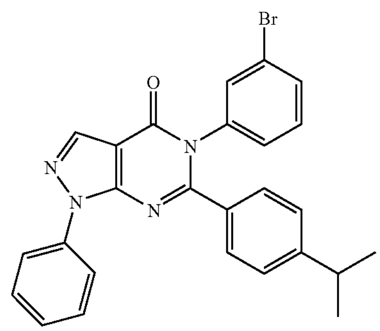 | HPLC-MS calculated C$_{26}$H$_{21}$BrN$_4$O (M + 1$^+$): 485.1, found: 485.1. |
| 381 | 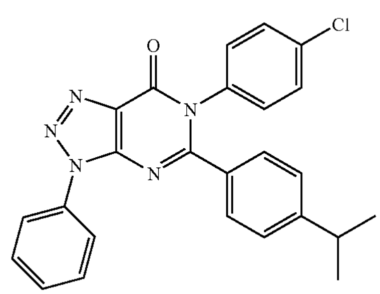 | $^1$H NMR (CDCl$_3$) δ (ppm) 8.19 (d, 2H), 7.58 (t, 2H), 7.48 (t, 1H), 7.34 (d, 2H), 7.25 (d, 2H), 7.11 (m, 4H), 2.87 (m, 1H), 1.20 (d, 6H). HPLC-MS calculated C$_{25}$H$_{20}$ClN$_5$O (M + 1$^+$): 442.1, found: 442.1. |
| 382 | 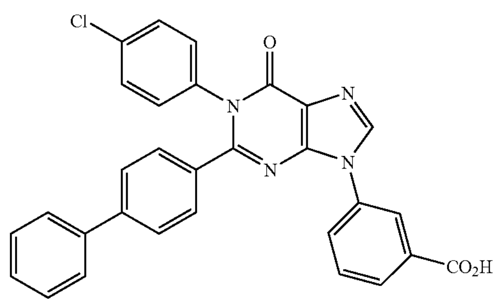 | HPLC-MS calculated for C$_{30}$H$_{19}$ClN$_4$O$_3$ (M + 1$^+$): 519.1, found 519.1. |

TABLE 1-continued

| Compound Number | Structure | Physical Data<br>¹H NMR 400 MHz (CDCl₃) and/or MS (m/z) |
|---|---|---|
| 383 | 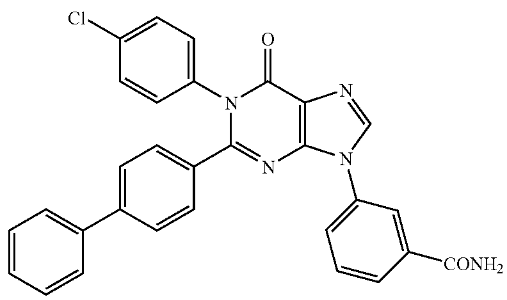 | ¹H NMR (CDCl₃) δ (ppm) 8.67 (s, 1H), 8.29 (t, 1H), 8.15 (br s, 1H), 8.02 (d, 1H), 7.98 (d, 1H), 7.71 (t, 1H) 7.64 (d, 2H), 7.58 (d, 3H), 7.46 (br s, 2H), 7.44 (m, 6H), 7.37 (m, 1H); HPLC-MS calculated for $C_{30}H_{20}ClN_5O_2$ (M + H⁺): 518.1, found 518.1. |
| 384 | 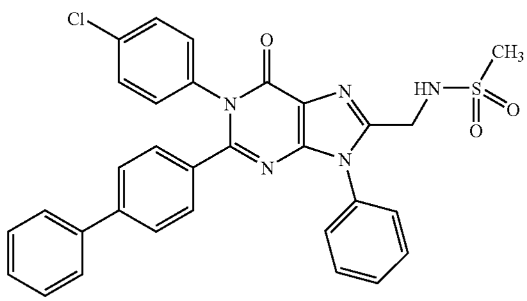 | ¹H NMR (CDCl₃) δ (ppm) 7.64 7.54 (m, 3H), 7.51 7.45 (m, 4H), 7.44 7.38 (m, 4H), 7.37 7.30 (m, 4H), 7.28 (s, 1H), 7.13 (d, 2H), 5.92 (br s, 1H), 4.48 (s, 2H), 2.99 (s, 3H); HPLC-MS calculated for $C_{31}H_{24}ClN_5O_3S$ (M + H⁺): 582.1, found 582.1. |
| 385 | 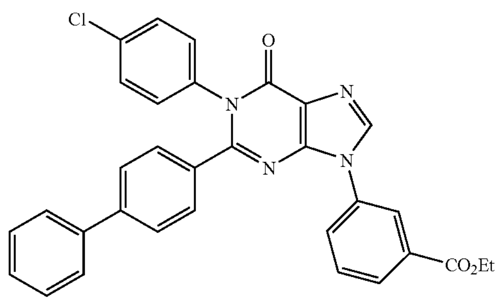 | HPLC-MS calculated for $C_{32}H_{23}ClN_4O_3$ (M + H⁺): 547.1, found 547.1. |
| 386 | 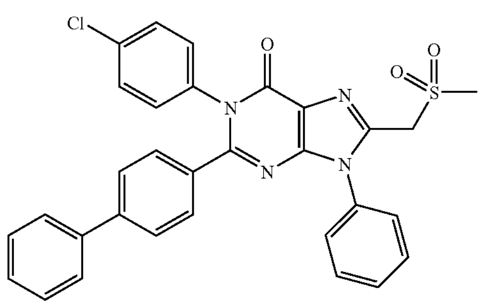 | ¹H NMR (CDCl₃) δ (ppm) 7.65 7.53 (m, 5H), 7.49 (d, 2H), 7.41 7.39 (m, 4H), 7.37 7.31 (m, 3H), 7.29 7.24 (m, 2H, partially obscured by CHCl₃), 7.16 (d, 2H), 4.43 (br s, 2H), 3.35 (br s, 3H): HPLC-MS calculated for $C_{31}H_{23}ClN_4O_3S$ (M + H⁺): 567.1, found 567.1. |
| 387 | 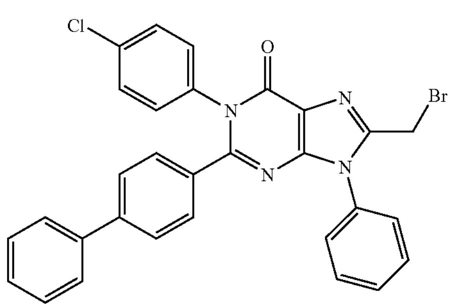 | HPLC-MS calculated for $C_{30}H_{20}BrClN_4O$ (M + H⁺): 567.1, found 567.1. |

TABLE 1-continued

| Compound Number | Structure | Physical Data $^1$H NMR 400 MHz (CDCl$_3$) and/or MS (m/z) |
|---|---|---|
| 388 | 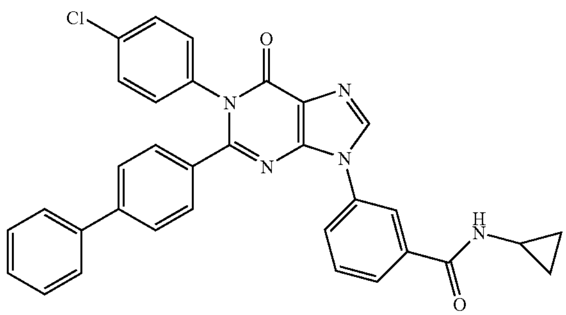 | HPLC-MS calculated for C$_{33}$H$_{24}$ClN$_5$O$_2$ (M + H$^+$): 568.1, found 568.1. |
| 389 | 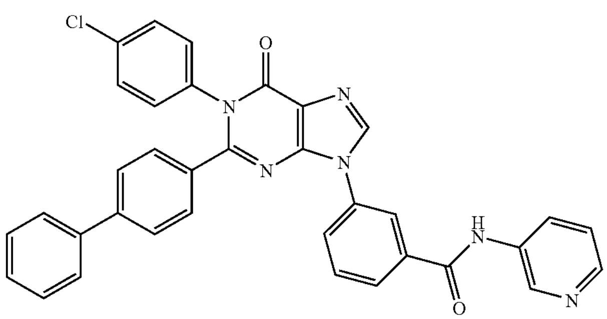 | HPLC-MS calculated for C$_{35}$H$_{23}$ClN$_6$O$_2$ (M + H$^+$): 595.1, found 595.1. |
| 390 | 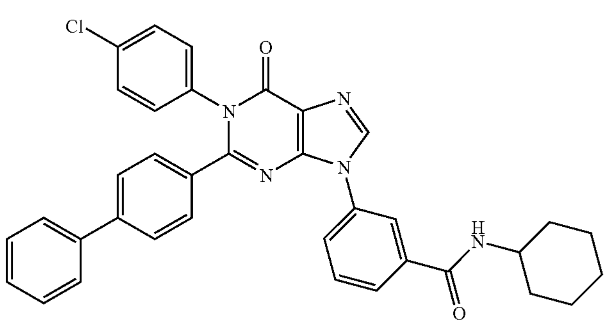 | $^1$H NMR (CDCl$_3$) δ (ppm) 8.26 (s, 1H), 8.22 (s, 1H), 7.87 (d, 1H), 7.63 (t, 1H), 7.52 (d, 2H), 7.48 7.40 (m, 4H), 7.39 7.30 (m, 5H), 7.14 (d, 2H), 6.11 (d, 1H), 3.98 (m, 1H), 2.03 (d, 2H), 1.74 (d, 2H), 1.64 (d, 1H), 1.42 (m, 2H), 1.23 (m, 3H). HPLC-MS calculated for C$_{36}$H$_{30}$ClN$_5$O$_2$ (M + H$^+$): 600.1, found 600.1. |
| 391 | 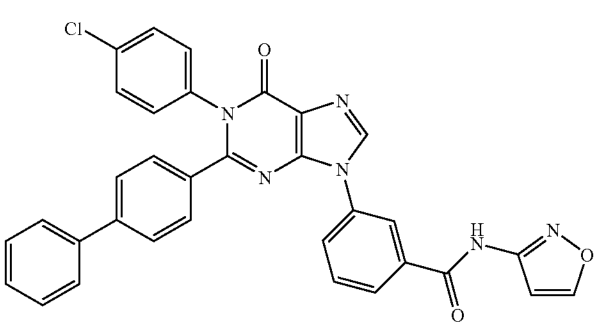 | $^1$H NMR (CDCl$_3$) δ (ppm) 9.94 (s, 1H), 8.46 (s, 1H), 8.32 (s, 1H), 8.29 (s, 1H), 8.08 (d, 1H), 8.02 (d, 1H), 7.72 (t, 1H), 7.49 (d, 2H), 7.45 (d, 2H), 7.39 (t, 2H), 7.35 7.29 (m, 5H), 7.25 (br s, 1H), 7.14 (d, 2H); HPLC-MS calculated for C$_{30}$H$_{20}$ClN$_5$O$_2$ (M + H$^+$): 585.1, found 585.1. |

TABLE 1-continued

| Compound Number | Structure | Physical Data $^1$H NMR 400 MHz (CDCl$_3$) and/or MS (m/z) |
|---|---|---|
| 392 | 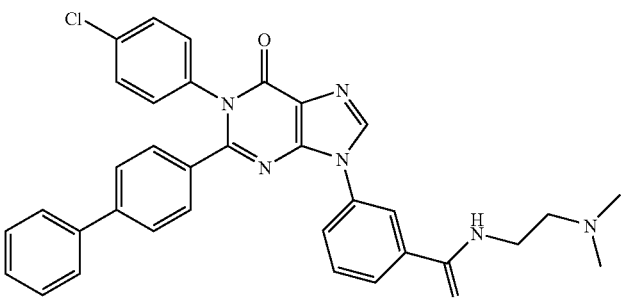 | HPLC-MS calculated for C$_{34}$H$_{29}$ClN$_6$O$_2$ (M + H$^+$): 589.1, found 589.1. |
| 393 | 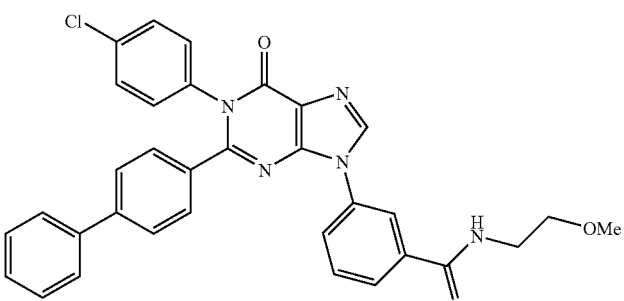 | HPLC-MS calculated for C$_{34}$H$_{29}$ClN$_6$O$_2$ (M + H$^+$): 577.1, found 577.1. |
| 394 | 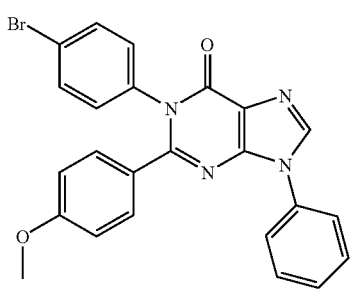 | $^1$H NMR (CDCl$_3$) δ (ppm) 8.08 (s, 1H), 7.69 (d, 2H), 7.55 (t, 2H), 7.46 (m, 3H), 7.21 (m, 2H), 7.05 (d, 2H), 6.71 (d, 2H), 3.76 (s, 3H); HPLC-MS calculated for C$_{24}$H$_{17}$BrN$_4$O$_2$ (M + H$^+$): 472.1, found 472.1. |
| 395 | 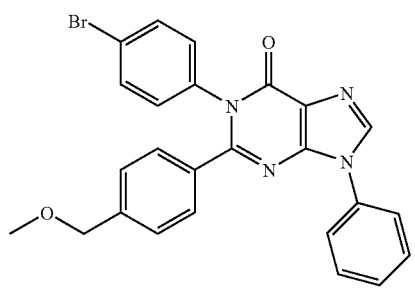 | HPLC-MS: calculated for C$_{25}$H$_{19}$ClN$_4$O$_2$ (M + 1$^+$): 443.1, found 443.1 |
| 396 | 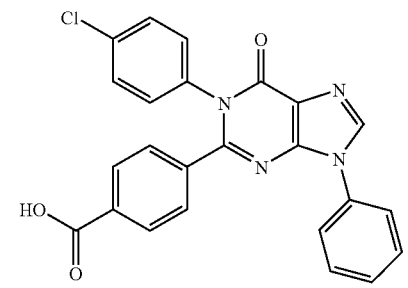 | HPLC-MS: calculated for C$_{24}$H$_{15}$ClN$_4$O$_3$ (M + 1$^+$): 443.1, found 443.1. |

TABLE 1-continued

| Compound Number | Structure | Physical Data<br>¹H NMR 400 MHz (CDCl₃)<br>and/or MS (m/z) |
|---|---|---|
| 397 | 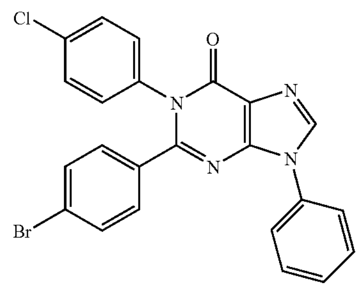 | HPLC-MS calculated for C$_{23}$H$_{14}$BrClN$_4$O (M + H$^+$): 477.0, found0477.0. |
| 398 | 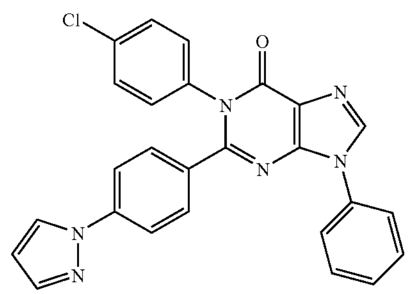 | HPLC-MS calculated for C$_{28}$H$_{18}$ClN$_5$O (M + H$^+$): 465.1, found 465.1. |
| 399 | 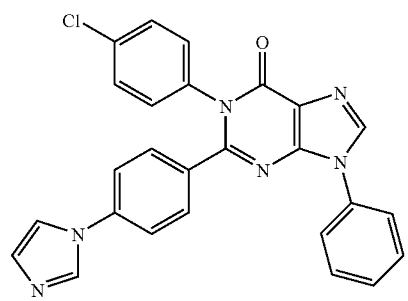 | ¹H NMR (CDCl₃) δ (ppm) 9.02 (s, 1H), 8.24 (s, 1H), 7.68 (d, 2H), 7.57 (m, 6H), 7.42 (m, 3H), 7.36 (d, 2H), 7.15 (d, 2H); HPLC-MS calculated for C$_{28}$H$_{18}$ClN$_5$O (M + H$^+$): 465.1, found 465.1. |
| 400 | 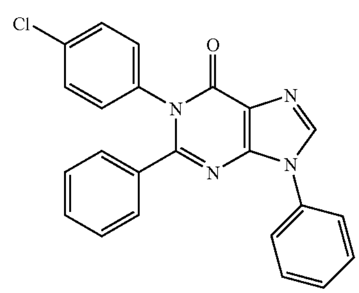 | ¹H NMR (CDCl₃) δ (ppm) 8.17 (s, 1H), 7.72 (d, 2H), 7.58 (t, 2H), 7.48 (t, 1H), 7.30 (m, 7H), 7.11 (d, 2H); HPLC-MS calculated for C$_{23}$H$_{15}$ClN$_4$O (M + H$^+$): 399.1, found 399.1. |
| 401 | 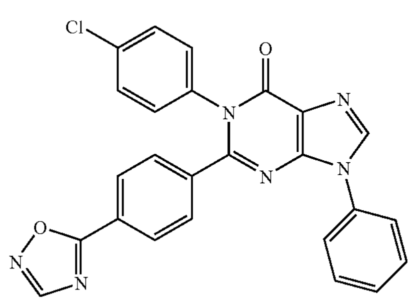 | HPLC-MS calculated for C$_{25}$H$_{15}$ClN$_6$O$_2$ (M + H$^+$): 467.1, found 467.1. |

TABLE 1-continued

| Compound Number | Structure | Physical Data<br>$^1$H NMR 400 MHz (CDCl$_3$) and/or MS (m/z) |
|---|---|---|
| 402 | 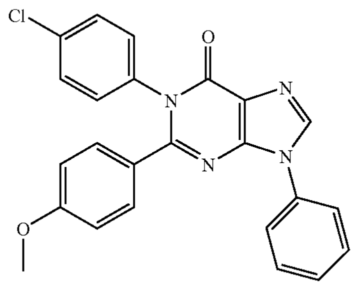 | HPLC-MS calculated for C$_{24}$H$_{17}$ClN$_4$O$_2$ (M + H$^+$): 429.1, found 429.1. |
| 403 | 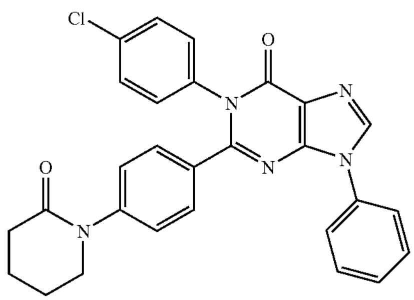 | HPLC-MS calculated for C$_{28}$H$_{22}$ClN$_5$O$_2$ (M + H$^+$): 496.1, found 496.1. |
| 404 | 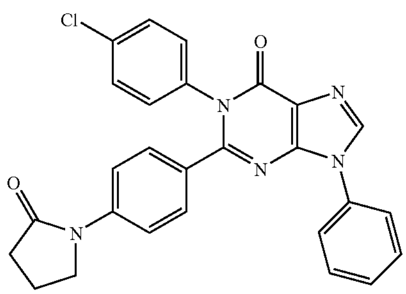 | HPLC-MS calculated for C$_{27}$H$_{22}$ClN$_5$O$_2$ (M + H$^+$): 482.1, found 482.1. |
| 405 | 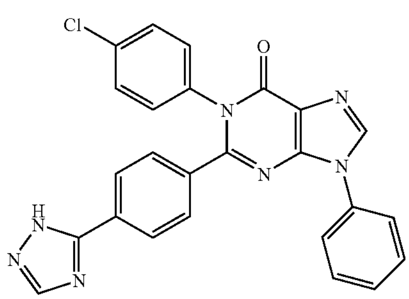 | HPLC-MS calculated for C$_{25}$H$_{16}$ClN$_7$O$_1$ (M + H$^+$): 466.1, found 466.1. |
| 406 | 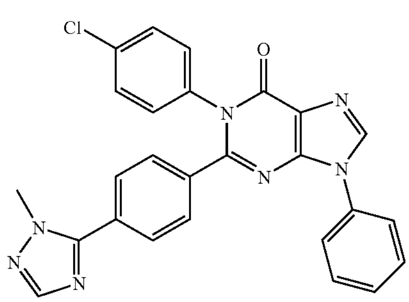 | HPLC-MS calculated for C$_{26}$H$_{18}$ClN$_7$O (M + H$^+$): 480.1, found 480.1. |

TABLE 1-continued

| Compound Number | Structure | Physical Data $^1$H NMR 400 MHz (CDCl$_3$) and/or MS (m/z) |
|---|---|---|
| 407 | 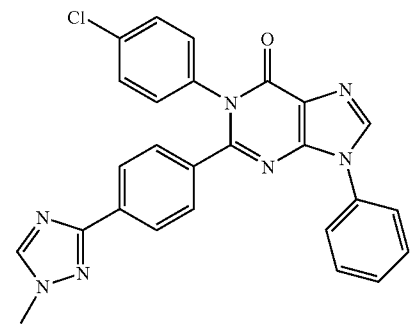 | HPLC-MS calculated for C$_{26}$H$_{18}$ClN$_7$O (M + H$^+$): 480.1, found 480.1. |
| 408 | 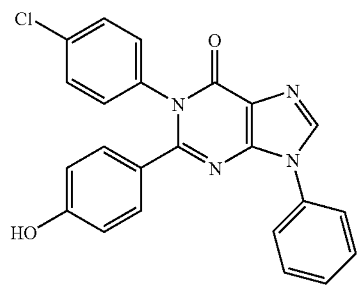 | HPLC-MS calculated for C$_{23}$H$_{15}$ClN$_4$O$_2$ (M + H$^+$): 415.1, found 415.1. |
| 409 | 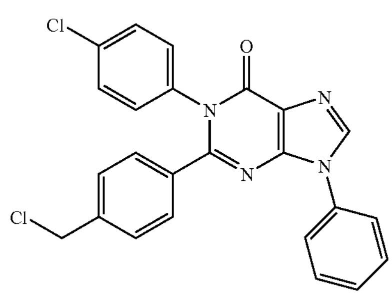 | $^1$H NMR (CDCl$_3$) δ (ppm) 8.11 (s, 1H), 7.61 (d, 2H), 7.49 (t, 2H), 7.40 (t, 1H), 7.19 (m, 6H), 7.02 (d, 2H), 4.42 (s, 2H); HPLC-MS calculated for C$_{24}$H$_{16}$Cl$_2$N$_4$O (M + H$^+$): 447.1, found 447.1. |
| 410 | 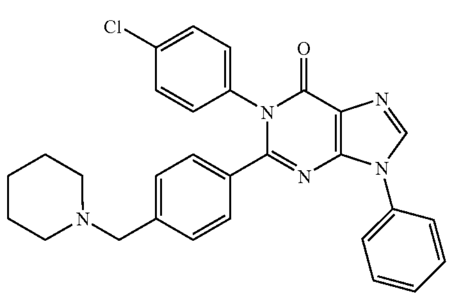 | HPLC-MS calculated for C$_{29}$H$_{26}$ClN$_5$O (M + H$^+$): 496.2, found 496.2. |
| 411 | 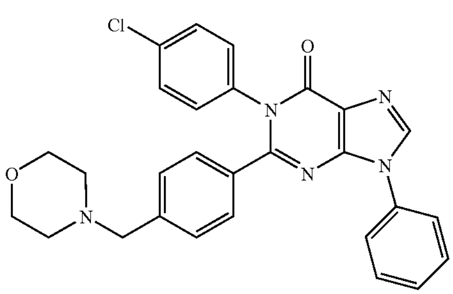 | HPLC-MS calculated for C$_{28}$H$_{24}$ClN$_5$O$_2$ (M + H$^+$): 498.2, found 498.2. |

TABLE 1-continued

| Compound Number | Structure | Physical Data $^1$H NMR 400 MHz (CDCl$_3$) and/or MS (m/z) |
|---|---|---|
| 412 | 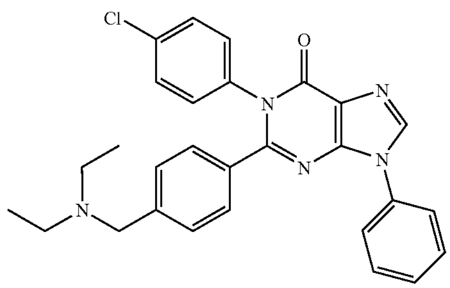 | HPLC-MS calculated for C$_{28}$H$_{26}$ClN$_5$O (M + H$^+$): 484.2, found 484.2 |
| 413 | 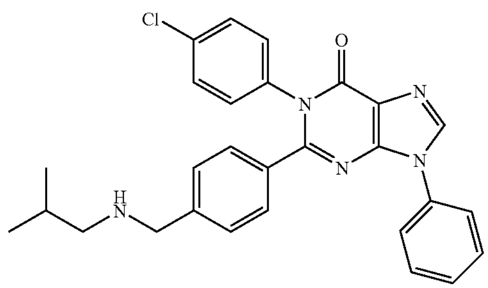 | HPLC-MS calculated for C$_{28}$H$_{26}$ClN$_5$O (M + H$^+$): 484.2, found 484.2. |
| 414 | 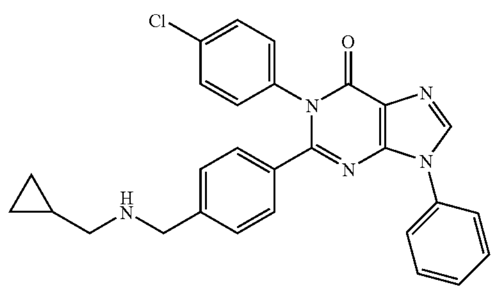 | HPLC-MS calculated for C$_{28}$H$_{24}$ClN$_5$O (M + H$^+$): 482.2, found 482.2. |
| 415 | 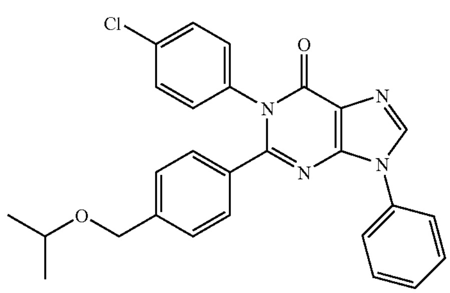 | HPLC-MS calculated for C$_{27}$H$_{23}$ClN$_4$O$_2$ (M + H$^+$): 471.2, found 471.2. |
| 416 | 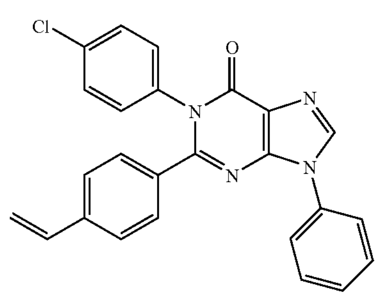 | $^1$H NMR (CDCl$_3$) δ (ppm) 8.10 (s, 1H), 7.71 (m, 3H), 7.56 (m, 3H), 7.46 (t, 2H), 7.30 (m, 2H), 7.11 (m, 3H), 6.62 (m, 1H), 5.74 (d, 1H), 5.30 (d, 1H); HPLC-MS calculated for C$_{25}$H$_{17}$ClN$_4$O (M + H$^+$): 425.1, found 425.1. |

TABLE 1-continued

| Compound Number | Structure | Physical Data<br>¹H NMR 400 MHz (CDCl₃) and/or MS (m/z) |
|---|---|---|
| 417 | 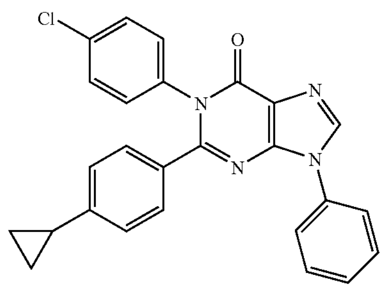 | ¹H NMR (CDCl₃) δ (ppm) 8.12 (s, 1H), 7.69 (t, 2H), 7.55 (t, 2H), 7.47 (t, 1H), 7.32 (m, 3H), 7.13 (m, 4H), 6.89 (d, 1H), 2.85 (m, 1H), 0.92 (d, 2H), 0.66 (d, 2H); HPLC-MS calculated for $C_{26}H_{19}ClN_4O$ $(M + H^+)$: 439.1, found 439.1. |
| 418 | 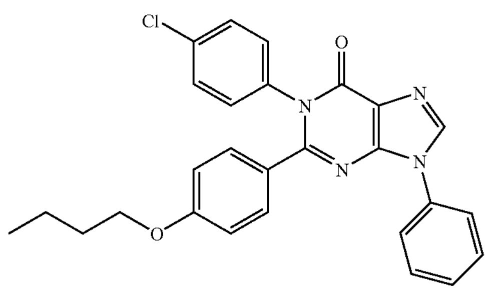 | HPLC-MS calculated for $C_{27}H_{23}ClN_4O_2$ $(M + H^+)$: 471.1, found 471.1. |
| 419 | 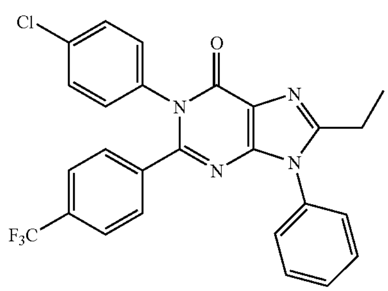 | ¹H NMR (CDCl₃) δ (ppm) 7.55 (m, 3H), 7.41 (m, 4H), 7.31 (m, 4H), 7.08 (m, 2H), 2.79 (q, 2H), 1.33 (t, 3H); HPLC-MS calculated for $C_{26}H_{18}ClF_3N_4O$ $(M + H^+)$: 494.1, found 494.1. |
| 420 | 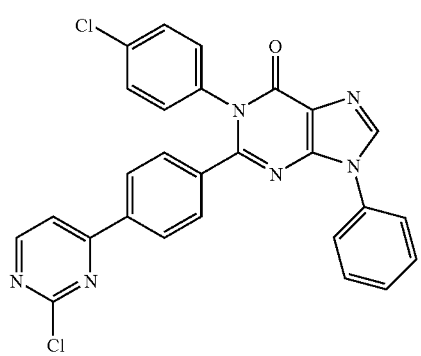 | HPLC-MS: calculated for $C_{27}H_{16}Cl_2N_6O$ $(M + 1^+)$: 511.1, found 511.1 |
| 421 | 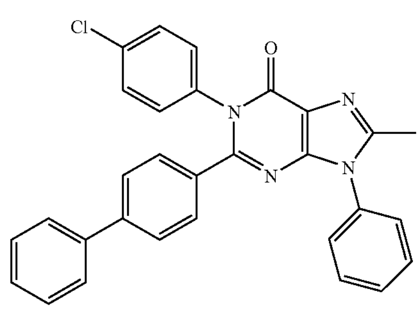 | ¹H NMR (CDCl₃) δ (ppm) 7.57 (m, 3H), 7.49 (m, 2H), 7.41 (m, 6H), 7.30 (m, 4H), 7.28 (m, 1H), 7.13 (d, 2H), 2.55 (s, 3H); HPLC-MS calculated for $C_{30}H_{21}ClN_4O$ $(M + H^+)$: 489.1, found 489.1. |

TABLE 1-continued

| Compound Number | Structure | Physical Data<br>¹H NMR 400 MHz (CDCl₃) and/or MS (m/z) |
|---|---|---|
| 422 | 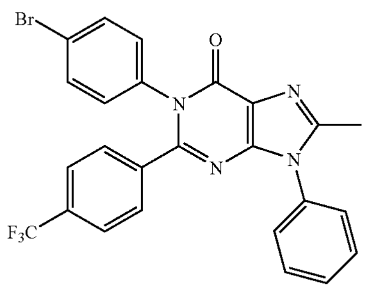 | HPLC-MS calculated for C$_{25}$H$_{16}$BrF$_3$N$_4$O (M + H$^+$): 525.1, found 525.1. |
| 423 | 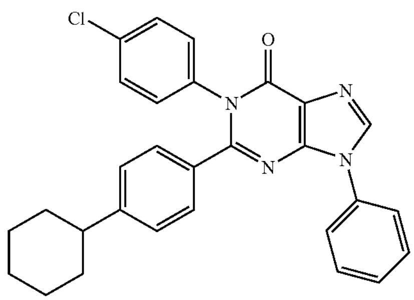 | ¹H NMR (CDCl₃) δ (ppm) 8.19 (s, 1H), 7.70 (m, 2H), 7.57 (t, 2H), 7.46 (t, 1H), 7.30 (d, 2H), 7.18 (d, 2H), 7.09 (d, 2H), 7.04 (d, 2H), 2.43 (m, 1H), 1.78 (m, 5H), 1.32 (m, 5H); HPLC-MS calculated for C$_{29}$H$_{25}$ClN$_4$O (M + H$^+$): 481.2, found 481.2. |
| 424 | 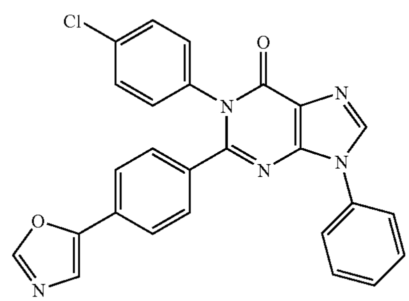 | HPLC-MS: calculated for C$_{26}$H$_{16}$ClN$_5$O (M + 1$^+$): 466.1, found 466.1. |
| 425 | 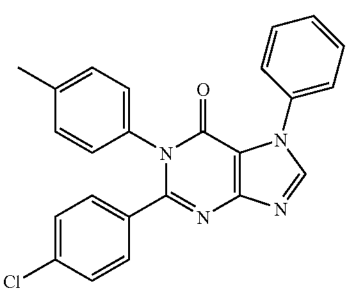 | HPLC-MS calculated for C$_{24}$H$_{17}$ClN$_4$O (M + H$^+$): 413.1, found 413.1. |
| 426 | 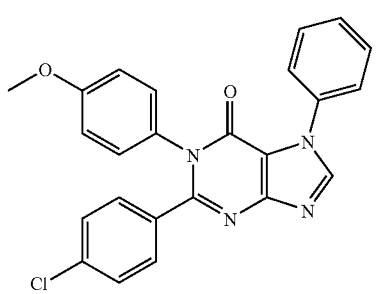 | HPLC-MS calculated for C$_{24}$H$_{17}$ClN$_4$O$_2$ (M + H$^+$): 428.1, found 428.1. |

TABLE 1-continued

| Compound Number | Structure | Physical Data<br>¹H NMR 400 MHz (CDCl₃) and/or MS (m/z) |
|---|---|---|
| 427 | 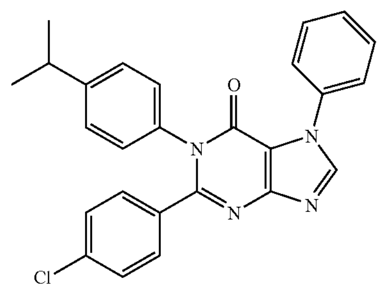 | ¹H NMR (CDCl₃) δ (ppm) 8.14 (s, 1H), 7.55 (m, 2H), 7.49 (m, 3H), 7.31 (d, 2H), 7.17 (m, 4H), 7.02 (d, 2H), 2.86 (m, 1H), 1.19 (d, 6H); HPLC-MS calculated for $C_{26}H_{21}ClN_4O$ (M + H⁺): 441.1, found 441.1. |
| 428 | 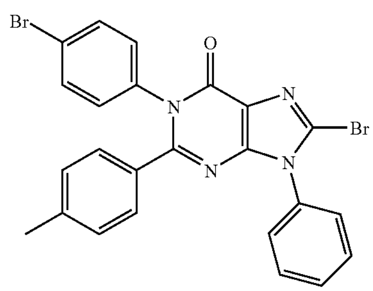 | HPLC-MS: calculated for $C_{24}H_{16}Br_2N_4O$ (M + 1⁺): 535.0, found 535.0. |
| 429 | 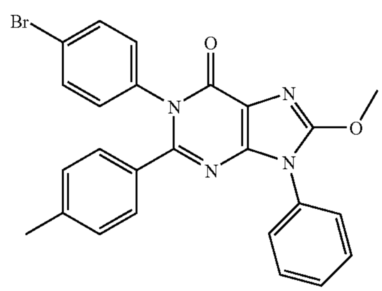 | HPLC-MS: calculated for $C_{25}H_{19}BrN_4O_2$ (M + 1⁺): 487.1, found 487.1. |
| 430 | 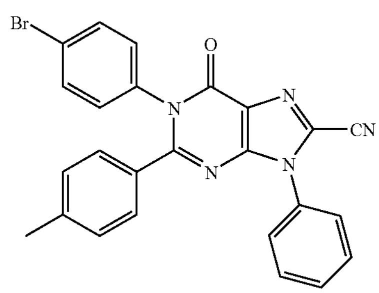 | HPLC-MS: calculated for $C_{25}H_{16}BrN_5O$ (M + 1⁺): 482.1, found 482.1. |
| 431 | 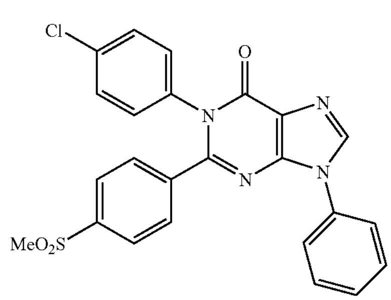 | HPLC-MS: calculated for $C_{24}H_{17}ClN_4O_3S$ (M + 1⁺): 477.1, found 477.1. |

TABLE 1-continued

| Compound Number | Structure | Physical Data $^1$H NMR 400 MHz (CDCl$_3$) and/or MS (m/z) |
|---|---|---|
| 432 | 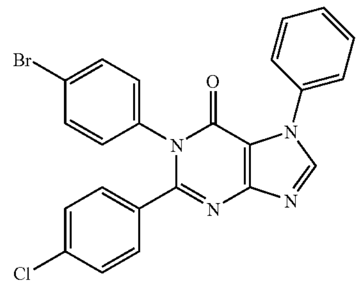 | $^1$H NMR (CDCl$_3$) δ (ppm) 8.17 (s, 1H), 7.48 (m, 7H), 7.30 (d, 2H), 7.22 (d, 2H), 7.01 (d, 2H); HPLC-MS calculated for C$_{23}$H$_{14}$BrClN$_4$O (M + H$^+$): 477.0, found 477.0. |
| 433 | 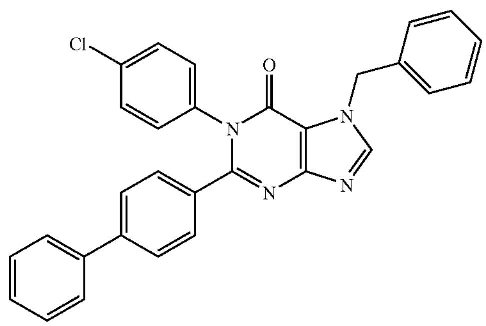 | HPLC-MS: calculated for C$_{30}$H$_{21}$ClN$_4$O (M + 1$^+$): 489.1, found 489.1. |
| 434 | 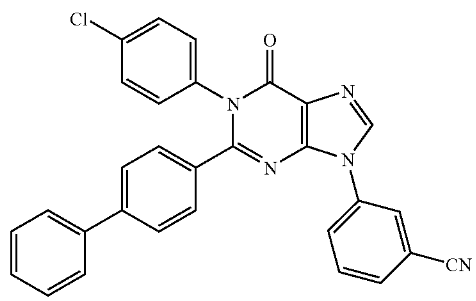 | HPLC-MS calculated for C$_{30}$H$_{18}$ClN$_5$O (M + H$^+$): 500.1, found 500.1. |
| 435 | 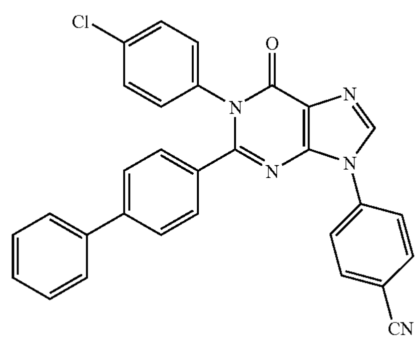 | HPLC-MS calculated for C$_{30}$H$_{18}$ClN$_5$O (M + H$^+$): 500.1, found 500.1. |
| 436 | 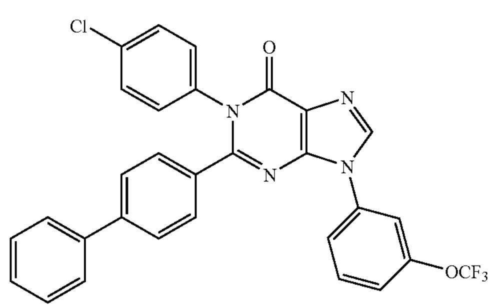 | HPLC-MS calculated for C$_{30}$H$_{18}$ClF$_3$N$_4$O$_2$ (M + H$^+$): 559.1, found 559.1. |

TABLE 1-continued

| Compound Number | Structure | Physical Data $^1$H NMR 400 MHz (CDCl$_3$) and/or MS (m/z) |
|---|---|---|
| 437 | 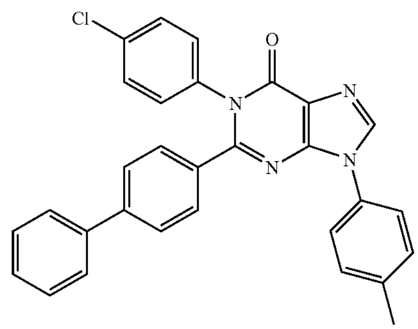 | $^1$H NMR (CDCl$_3$) δ (ppm) 8.07 (s, 1H), 7.58 (d, 2H), 7.52 (d, 2H), 7.44 (m, 4H), 7.35 (m, 7H), 7.15 (d, 2H), 2.43 (s, 3H); HPLC-MS calculated for C$_{30}$H$_{21}$ClN$_4$O (M + H$^+$): 489.1, found 489.1. |
| 438 | 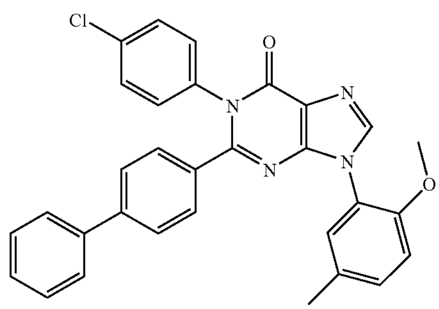 | $^1$H NMR (CDCl$_3$) δ (ppm) 8.00 (s, 1H), 7.51 (d, 2H), 7.41 (m, 4H), 7.31 (m, 6H), 7.25 (m, 2H), 7.14 (d, 2H), 6.99 (m, 1H), 3.83 (s, 3H), 2.37 (s, 3H); HPLC-MS calculated for C$_{31}$H$_{23}$ClN$_4$O$_2$ (M + H$^+$): 519.2, found 519.2. |
| 439 | 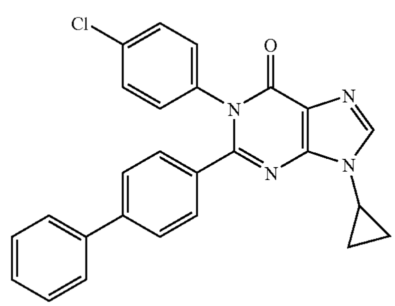 | $^1$H NMR (CDCl$_3$) δ (ppm) 8.00 (s, 1H), 7.63 (d, 2H), 7.47 (t, 2H), 7.39 (m, 1H), 7.24 (m, 3H), 7.07 (m, 3H), 6.81 (d, 2H), 1.72 (m, 1H), 0.90 (m, 2H), 0.57 (m, 2H); HPLC-MS calculated for C$_{26}$H$_{19}$ClN$_4$O (M + H$^+$): 439.1, found 439.1. |
| 440 | 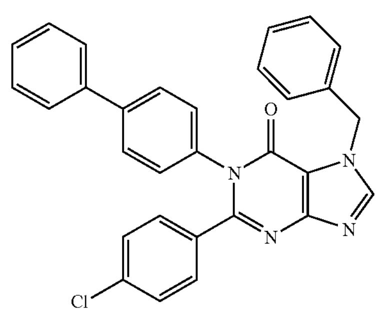 | HPLC-MS: calculated for C$_{30}$H$_{21}$ClN$_4$O (M + 1$^+$): 489.1, found 489.1. |
| 441 | 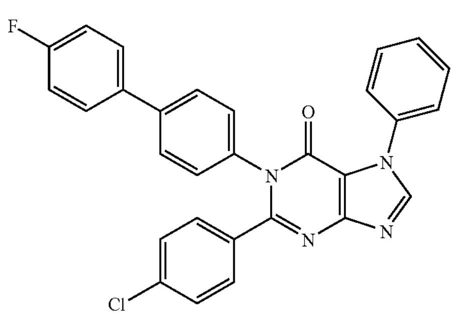 | $^1$H NMR (CDCl$_3$) δ (ppm) 8.17 (s, 1H), 7.56 (d, 2H), 7.43 (m, 7H), 7.36 (d, 2H), 7.18 (m, 4H), 7.11 (t, 2H); HPLC-MS calculated for C$_{29}$H$_{18}$ClFN$_4$O (M + H$^+$); 493.1, found 493.1. |

TABLE 1-continued

| Compound Number | Structure | Physical Data<br>$^1$H NMR 400 MHz (CDCl$_3$) and/or MS (m/z) |
|---|---|---|
| 442 | 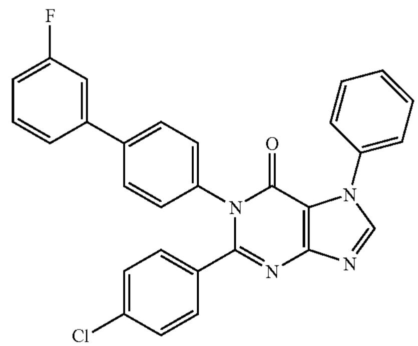 | HPLC-MS calculated for C$_{29}$H$_{18}$ClFN$_4$O (M + H$^+$): 493.1, found 493.1. |
| 443 | 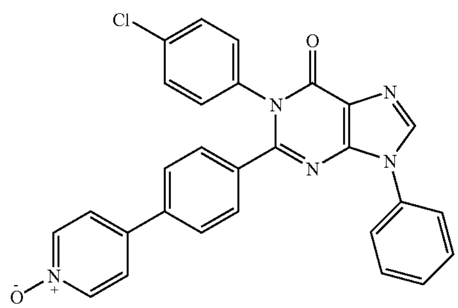 | HPLC-MS calculated for C$_{28}$H$_{18}$ClN$_5$O$_2$ (M + H$^+$): 492.1, found 492.1. |
| 444 | 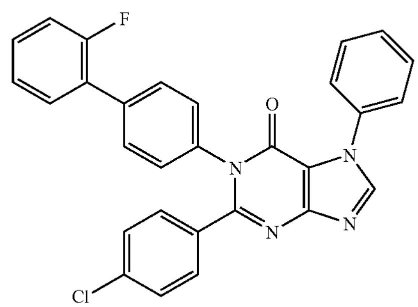 | HPLC-MS calculated for C$_{29}$H$_{18}$ClFN$_4$O (M + H$^+$): 493.1, found 493.1. |
| 445 | 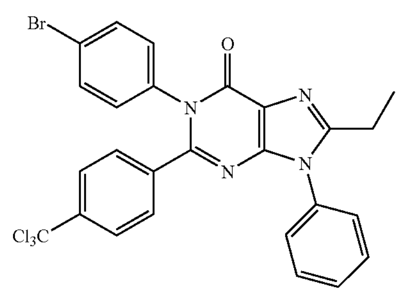 | $^1$H NMR (CDCl$_3$) δ (ppm) 7.72 (d, 2H), 7.56 (m, 3H), 7.47 (d, 2H), 7.40 (d, 2H), 7.26 (d, 2H), 7.03 (d, 2H), 2.81 (q, 2H), 1.32 (t, 3H); HPLC-MS calculated for C$_{26}$H$_{18}$BrCl$_3$N$_4$O (M + H$^+$): 587.0, found 587.0. |
| 446 | 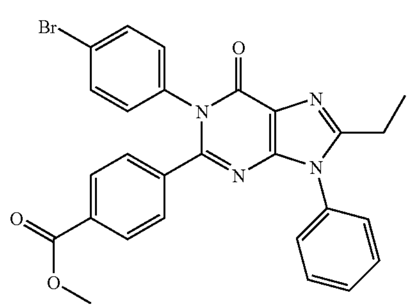 | $^1$H NMR (CDCl$_3$) δ (ppm) 7.84 (d, 2H), 7.58 (m, 3H), 7.42 (m, 4H), 7.25 (d, 2H), 7.00 (d, 2H), 3.88 (s, 3H), 2.87 (q, 2H), 1.30 (t, 3H); HPLC-MS calculated for C$_{27}$H$_{21}$BrN$_4$O$_3$ (M + H$^+$): 529.1, found 529.1. |

TABLE 1-continued

| Compound Number | Structure | Physical Data $^1$H NMR 400 MHz (CDCl$_3$) and/or MS (m/z) |
|---|---|---|
| 447 | 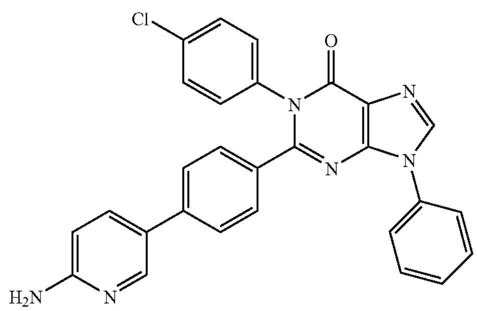 | $^1$H NMR (CDCl$_3$) δ (ppm) 8.19 (s, 1H), 7.95 (m, 2H), 7.72 (d, 2H), 7.61 (apparent t, 2H), 7.52 (apparent t, 1H), 7.42 (d, 2H), 7.35 (m, 4H), 7.17 (d, 2H), 6.95 (d, 1H); HPLC-MS calculated for C$_{28}$H$_{19}$ClN$_6$O$_2$ (M + H$^+$): 491.1, found 491.1. |
| 448 | 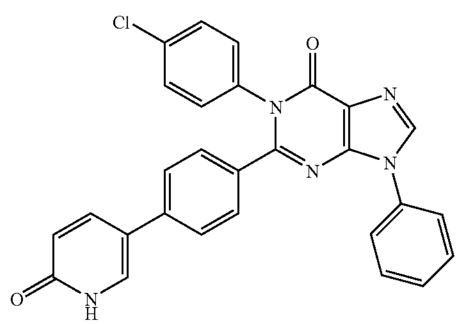 | $^1$H NMR (CDCl$_3$) δ (ppm) 8.21 (s, 1H), 8.01 (dd, 1H), 7.81 (d, 1H), 7.58 (apparent t, 2H), 7.49 (m, 1H), 7.39 (d, 2H), 7.33 (m, 3H), 7.14 (d, 2H), 6.98 (d, 1H); HPLC-MS calculated for C$_{28}$H$_{18}$ClN$_5$O$_2$ (M + H$^+$): 492.1, found 492.1. |

CB1 Biological Assays

Homogenized membranes are prepared from CHO cell clones stably expressing a human cannabinoid receptor 1 (CB1) or human cannabinoid receptor 2 (CB2). Cells are grown and scrapped from 15 cm tissue culture plates, and then subsequently centrifuged down. Cells are washed once with cold PBS, and resuspended in <20 ml of Buffer A (20 mM HEPES, pH 7.4, 10 mM EDTA, EDTA-free complete protease inhibitor cocktail [1 tablet/25 ml]). The cell suspension is homogenized on ice, using a Polytron homogenizer at 25000 rpm at three intervals of 15 seconds each. The homogenate is first centrifuged at 2000 rpm on a tabletop low speed centrifuge for 10 minutes. The supernatant, after passing through a cell strainer, is then centrifuged at 50,000×g for 25 minutes at 4° C. The pellet is resuspended into buffer B (15% glycerol, 20 mM HEPES, pH 7.4, 0.1 mM EDTA, EDTA-free complete protease inhibitor cocktail [1 tablet/10 ml]). Protein concentration of the prep is determined using the BCA Protein Assay kit using BSA as standard. The membranes are aliquoted and kept frozen at −80° C.

[$^3$H]-CP55940 ligand binding assay: Solutions of test compounds ranging from 100 μM to 0.01 nM are prepared in DMSO. The desired amount of membrane prep is diluted with ice-cold assay buffer (50 mM Tris-HCl, 2.5 mM EDTA, 5 mM MgCl$_2$, 0.05% BSA, pH 7.4) and vortexed well. 2 μl or less of compound is distributed into each well of a round-bottom 96-well polystyrene assay plate, followed by addition of 100 μl of diluted membranes (3-10 μg/well) and the mixture is kept on ice until the addition of hot CP55940 (final concentration of 0.5 nM). [$^3$H]-CP55940 is diluted 1:6300 (v/v) with cold assay buffer and 100 μl is added into each well. The reaction is carried out at room temperature for 120 minutes before the membranes are harvested onto a PerkinElmer Unifilter GF/B-96 filter plate using a Packard Filtermate Harvester. After nine washes with wash buffer (50 mM Tris-HCl, 2.5 mM EDTA, 5 mM MgCl$_2$, 0.05% BSA, pH 7), the filter is dried in a 37° C. oven for 30 minutes. MicroScint-20 is added and the plate sealed for scintillation counting on TopCount. EC$_{50}$ values are obtained by fitting the data with the sigmoidal dose response curve-fitting tool of GraphPad Prism. Eight or twelve different concentrations are used to generate a concentration response curve (using three data points per concentration).

GTPγS binding assay: Solutions of test compounds ranging from 100 μM to 0.01 nM are prepared in DMSO. The desired amount of membrane prep is diluted with ice-cold assay buffer (20 mM HEPES, pH 7.4, 100 mM NaCl, 10 mM MgCb, 0.1% Fatty acid-free BSA, 5 μM GDP) and vortexed well. 2 μl or less of compound is distributed into each well of a round-bottom 96-well polystyrene assay plate, followed by addition of 100 μl of diluted membranes (3-10 μg/well) and the mixture is kept on ice until the addition of hot GTPγS. [$^{35}$S]-GTPγS (Perkin Elmer NEG030H; 1 μCi/μl, 1250 Ci/mmol) is diluted 1:1000 (v/v) with cold assay buffer and 100 μl is added into each well. The reaction is carried out at room temperature for 90 minutes before the membranes are harvested onto PerkinElmer Unifilter GF/B-96 filter plate using a Packard Filtermate Harvester. After several washes with wash buffer (20 mM HEPES, pH 7.4, 100 mM NaCl, 10 mM MgCl$_2$), and a rinse with 95% ethanol, the filter is dried in a 37° C. oven for 30 minutes. MicroScint-20 is added and the plate sealed for scintillation counting on TopCount. EC$_{50}$ values are obtained by fitting the GTP [γ-$^{35}$S] binding data with the sigmoidal dose response curve-fitting tool of GraphPad Prism. Six or twelve different concentrations are used to generate a concentration response curve (using three data points per concentration).

For each assay, a Cheng-Prusoff correction (Cheng and Prusoff, 1973, Biochem. Pharmacol., 22:3099-3103) is used to convert the $EC_{50}$ to inhibition constant $K_i$. Thus, $$K_i = \frac{EC_{50}}{1 + [L]/K_d}$$

where [L] is the concentration of the radio-ligand used in the assay, and $K_d$ is the equilibrium binding dissociation constant for the radio-ligand.

Food Intake and Body Weight Gain

To evaluate the efficacy of compounds of the invention on inhibition of food intake and body weight gain, genetically obese ($Lep^{ob}/Lep^{ob}$) mice and diet-induced obese (DIO) mice are used in acute and sub-chronic models, respectively.

Male ob/ob mice (age 7-8 weeks old, Jackson Labs, Bar Harbor, Me.) are housed in groups of four and fed commercial standard pellet diet (Lab Diet 5001, PMI Nutrition International, LLC). Diet-induced obese mice are generated using 6-7 weeks old C57BL6 mice (Jackson Labs, Bar Harbor, Me.) placed on high fat diet (D12331, Research Diets) for 12-17 weeks. All mice are maintained on a 12-hour light/dark cycle (lights on at 06:00) in a humidity- and temperature-controlled environment with free access to food and water.

The week prior to the start of each study, mice are singly housed and a habituation to treatment is performed to establish baseline food consumption and body weight. Animals are randomized into treatment groups based on their initial body weight and food consumption.

To determine the acute effects of a single administration of a compound of the invention (test compound) on food consumption, ob/ob mice are treated with either vehicle, a known antagonist as a positive control, or with test compound(s). Similarly, to determine more chronic effects of test compound on food consumption and body weight gain, DIO mice are treated with either vehicle, a known antagonist as a positive control, or with test compound(s) for up to 7-35 days. Test compounds are dosed at ranges between 0.1 up to 100 mg/kg. Animals are treated one hour prior to the start of the dark cycle. Food intake and body weight are recorded manually using an electronic balance prior to treatment, 16 hours post-treatment, followed by daily measurements for up to 7-35 days after the start of study. Compound efficacy is determined by comparing food intake and body weight data between vehicle treated, standard positive control treated, and test compound treated mice.

Compounds of Formula I, in free form or in pharmaceutically acceptable salt form, exhibit valuable pharmacological properties, for example, as indicated by the in vitro tests described in this application. Compound of the invention show a $K_i$ of between $1 \times 10^{-5}$ and $1 \times 10^{-10}$ M, preferably less than 500 nM, more preferably less than 100 nM. Additionally, compounds of the invention show a 10 fold, preferably 20, 50 and 100 fold, selectivity for CB1 over CB2. For example, 5-(4-Bromo-phenyl)-6-(2-fluoro-phenyl)-1-phenyl-1,5-dihydro-pyrazolo[3,4-d]pyrimidin-4-one (compound 19) shows a $K_i$ of 5 μM and >5 μM for CB1 and CB2, respectively. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula Ia:

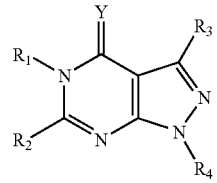

Ia in which:

Y is selected from O, $NR_7$ and S; wherein $R_7$ is selected from hydrogen, hydroxy and $C_{1-6}$alkyl;

$R_1$ is selected from $C_{3-12}$cycloalkyl, phenyl and benzyl; wherein said cycloalkyl, phenyl and benzyl of $R_1$ is optionally substituted with 1 to 3 radicals independently selected from halo, hydroxy, nitro, $C_{1-6}$alkyl, $C_{1-6}$alkoxy, halo-substituted $C_{1-6}$alkyl, halo-substituted $C_{1-6}$alkoxy, —$NR_8R_9$, —$S(O)_{0-2}R_8$, —$C(O)OR_8$ and $R_{10}$;

$R_2$ is selected from $C_{3-8}$heterocycloalkyl, $C_{5-10}$heteroaryl, phenyl and phenoxy; wherein said heterocycloalkyl, heteroaryl, phenyl or phenoxy of $R_2$ is optionally substituted with 1 to 3 radicals independently selected from halo, hydroxy, cyano, nitro, $C_{1-6}$alkyl, $C_{1-6}$alkoxy, halo-substituted $C_{1-6}$alkyl, $C_{2-6}$alkenyl, halo-substituted $C_{1-6}$alkoxy, —$XNR_8R_9$, —$XOR_8$, —$XC(O)R_8$, —XS$(O)_{0-2}R_8$, —$XC(O)NR_8R_9$, —$XC(O)OR_8$, —$XOR_{10}$, —$XNR_8XR_{10}$ and —$XR_{10}$; wherein each X is independently selected from a bond, $C_{1-4}$alkylene and $C_{2-4}$alkenylene;

$R_3$ is selected from hydrogen, methyl, methyl-sulfonyl, t-butoxy-carbonyl-methyl, amino-carbonyl-methyl, methyl-[1,2,4]oxadiazolyl, cyano-methyl, carboxy, ethoxy-carbonyl, methyl-amino-carbonyl, dimethyl-amino-carbonyl, benzyl, furanyl, pyridinyl, indolyl, morpholino-carbonyl, piperidinyl-amino-carbonyl, piperidinyl-carbonyl, isopropoxy-carbonyl, amino-carbonyl, methyl-amino-carbonyl, cyano, methyl-piperazinyl, and phenyl optionally substituted with 1 to 2 radicals independently selected from methyl, methoxy, fluoro, chloro, bromo, iodo, cyano, nitro, hydroxy-methyl, ethoxy-carbonyl, methyl-sulfonyl, dimethyl-amino, methyl-amino, cyclopropyl-aminocarbonyl, isopropoxy, trifluoromethyl and trifluoromethoxy;

$R_4$ is selected from $C_{1-6}$alkyl, halo-substituted $C_{1-6}$alkyl, $C_{6-10}$aryl, $C_{6-10}$aryl-$C_{1-4}$alkyl, $C_{5-10}$heteroaryl, $C_{3-12}$cycloalkyl, $C_{3-8}$heterocycloalkyl and $C(O)R_{11}$; wherein $R_{11}$ is selected from $C_{3-8}$heterocycloalkyl and $C_{3-8}$heteroaryl; wherein any alkyl of $R_4$ can optionally have a methylene replaced with O, $S(O)_{0-2}$ and $NR_8$; wherein any cycloalkyl, heterocycloalkyl, aryl or heteroaryl of $R_4$ can optionally be substituted with 1 to 3 radicals independently selected from halo, hydroxy, cyano, nitro, $C_{1-6}$alkyl, $C_{1-6}$alkoxy, halo-substituted-$C_{1-6}$ alkyl, halo-substituted-$C_{1-6}$alkoxy, —$XOR_8$, —$XR_{10}$, —$XC(O)R_{10}$, —$XS(O)_{0-2}R_8$, —$XNR_8R_9$, —$XC(O)NR_8R_9$, —$XC(O)NR_8R_{10}$, —$XC(O)NR_8XNR_8R_9$, —$XC(O)NR_8XOR_9$ and —$XC(O)OR_8$;

$R_8$ and $R_9$ are independently selected from hydrogen, $C_{1-6}$alkyl and $C_{2-6}$alkenyl; or $R_8$ and $R_9$ together with the nitrogen atom to which both are attached form $C_{3-8}$heterocycloalkyl or $C_{5-10}$heteroaryl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, cyano-$C_{1-6}$alkyl, nitro, $C_{1-6}$alkyl, $C_{1-6}$alkoxy, halo-substituted-$C_{1-6}$alkyl, halo-substituted-$C_{1-6}$alkoxy, hydroxy-substituted-$C_{1-6}$alkyl, hydroxy-substituted-$C_{1-6}$alkoxy, phenyl, —N(CH$_3$)$_2$, —NH(CH$_3$), —NH$_2$, S(O)$_{0-2}$—CH$_3$, —C(O)OH, and —C(O)OCH$_3$;

or a pharmaceutically acceptable salt-thereof; with the proviso that compounds of Formula Ia do not include compounds of Formula II that are set forth below:

5-(4-Isopropyl-phenyl)-1-phenyl-6-p-tolyl-1,5-dihydro-pyrazolo[3,4-d]pyrimidin-4-one;
6-(4-Bromo-phenyl)-1-phenyl-5-p-tolyl-1,5-dihydro-pyrazolo[3,4-d]pyrimidin-4-one;
1-Phenyl-5,6-di-m-tolyl-1,5-dihydro-pyrazolo[3,4-d]pyrimidin-4-one;
1-Phenyl-5,6-di-m-tolyl-1,5-dihydro-pyrazolo[3,4-d]pyrimidin-4-one;
1,5-Diphenyl-6-m-tolyl-1,5-dihydro-pyrazolo[3,4-d]pyrimidin-4-one;
1-Phenyl-5-o-tolyl-6-p-tolyl-1,5-dihydro-pyrazolo[3,4-d]pyrimidin-4-one;
5-(4-Ethoxy-phenyl)-1-phenyl-6-p-tolyl-1,5-dihydro-pyrazolo[3,4-d]pyrimidin-4-one;
5-(4-Chloro-phenyl)-1-phenyl-6-p-tolyl-1,5-dihydro-pyrazolo[3,4-d]pyrimidin-4-one;
5-(4-Isopropyl-phenyl)-1,6-diphenyl-1,5-dihydro-pyrazolo[3,4-d]pyrimidin-4-one;
5-(4-Bromo-phenyl)-6-(2-fluoro-phenyl)-1-phenyl-1,5-dihydro-pyrazolo[3,4-d]pyrimidin-4-one;
5-(4-Methoxy-phenyl)-1-phenyl-6-p-tolyl-1,5-dihydro-pyrazolo[3,4-d]pyrimidin-4-one;
6-(2-Fluoro-phenyl)-1-phenyl-5-m-tolyl-1,5-dihydro-pyrazolo[3,4-d]pyrimidin-4-one;
5-(4-Fluoro-phenyl)-6-(2-fluoro-phenyl)-1-phenyl-1,5-dihydro-pyrazolo[3,4-d]pyrimidin-4-one;
5-(4-Bromo-phenyl)-1-phenyl-6-m-tolyl-1,5-dihydro-pyrazolo[3,4-d]pyrimidin-4-one;
5-(4-Chloro-phenyl)-1-phenyl-6-m-tolyl-1,5-dihydro-pyrazolo[3,4-d]pyrimidin-4-one;
6-(2-Fluoro-phenyl)-5-(4-methoxy-phenyl)-1-phenyl-1,5-dihydro-pyrazolo[3,4-d]pyrimidin-4-one;
1-Phenyl-6-m-tolyl-5-p-tolyl-1,5-dihydro-pyrazolo[3,4-d]pyrimidin-4-one;
6-(4-Chloro-phenyl)-5-(4-fluoro-phenyl)-1-phenyl-1,5-dihydro-pyrazolo[3,4-d]pyrimidin-4-one;
5-(3-Chloro-phenyl)-1-phenyl-6-m-tolyl-1,5-dihydro-pyrazolo[3,4-d]pyrimidin-4-one;
1-Phenyl-5,6-di-p-tolyl-1,5-dihydro-pyrazolo[3,4-d]pyrimidin-4-one;
6-(4-Chloro-phenyl)-5-(4-ethoxy-phenyl)-1-phenyl-1,5-dihydro-pyrazolo[3,4-d]pyrimidin-4-one;
5-(4-Fluoro-phenyl)-1-phenyl-6-p-tolyl-1,5-dihydro-pyrazolo[3,4-d]pyrimidin-4-one;
5,6-Bis-(4-bromo-phenyl)-1-phenyl-1,5-dihydro-pyrazolo[3,4-d]pyrimidin-4-one;
5,6-Bis-(4-chloro-phenyl)-1-phenyl-1,5-dihydro-pyrazolo[3,4-d]pyrimidin-4-one;
5-(3-Chloro-phenyl)-6-(2-fluoro-phenyl)-1-phenyl-1,5-dihydro-pyrazolo[3,4-d]pyrimidin-4-one;
6-(2-Fluoro-phenyl)-1,5-diphenyl-1,5-dihydro-pyrazolo[3,4-d]pyrimidin-4-one;
1,5-Diphenyl-6-p-tolyl-1,5-dihydro-pyrazolo[3,4-d]pyrimidin-4-one;
5-(3-Chloro-phenyl)-6-(4-chloro-phenyl)-1-phenyl-1,5-dihydro-pyrazolo[3,4-d]pyrimidin-4-one;
5-(4-Methoxy-phenyl)-1,6-diphenyl-1,5-dihydro-pyrazolo[3,4-d]pyrimidin-4-one;
5-(3-Chloro-phenyl)-1-phenyl-6-p-tolyl-1,5-dihydro-pyrazolo[3,4-d]pyrimidin-4-one;
1-Phenyl-5,6-di-o-tolyl-1,5-dihydro-pyrazolo[3,4-d]pyrimidin-4-one;
6-(4-Chloro-phenyl)-1-phenyl-5-p-tolyl-1,5-dihydro-pyrazolo[3,4-d]pyrimidin-4-one;
6-(4-Bromo-phenyl)-5-(2,4-dimethyl-phenyl)-1-phenyl-1,5-dihydro-pyrazolo[3,4-d]pyrimidin-4-one;
6-(4-Chloro-phenyl)-1-phenyl-5-m-tolyl-1,5-dihydro-pyrazolo[3,4-d]pyrimidin-4-one;
6-(4-Bromo-phenyl)-1-phenyl-5-o-tolyl-1,5-dihydro-pyrazolo[3,4-d]pyrimidin-4-one;
6-(2-Fluoro-phenyl)-1-phenyl-5-o-tolyl-1,5-dihydro-pyrazolo[3,4-d]pyrimidin-4-one;
5-(4-Isopropyl-phenyl)-1-phenyl-6-m-tolyl-1,5-dihydro-pyrazolo[3,4-d]pyrimidin-4-one;
6-(4-Bromo-phenyl)-1-phenyl-5-m-tolyl-1,5-dihydro-pyrazolo[3,4-d]pyrimidin-4-one;
6-(4-Bromo-phenyl)-5-(4-ethoxy-phenyl)-1-phenyl-1,5-dihydro-pyrazolo[3,4-d]pyrimidin-4-one;
5-(4-Chloro-phenyl)-6-(2-fluoro-phenyl)-1-phenyl-1,5-dihydro-pyrazolo[3,4-d]pyrimidin-4-one;
5-(3-Chloro-phenyl)-1-phenyl-6-o-tolyl-1,5-dihydro-pyrazolo[3,4-d]pyrimidin-4-one;
5-(3,5-Dimethyl-phenyl)-1-phenyl-6-m-tolyl-1,5-dihydro-pyrazolo[3,4-d]pyrimidin-4-one;
6-(4-Bromo-phenyl)-5-(4-fluoro-phenyl)-1-phenyl-1,5-dihydro-pyrazolo[3,4-d]pyrimidin-4-one;
5-(4-Fluoro-phenyl)-1-phenyl-6-o-tolyl-1,5-dihydro-pyrazolo[3,4-d]pyrimidin-4-one;
1-Phenyl-5-m-tolyl-6-p-tolyl-1,5-dihydro-pyrazolo[3,4-d]pyrimidin-4-one; 5-(4-Bromo-phenyl)-1,6-diphenyl-1,5-dihydro-pyrazolo[3,4-d]pyrimidin-4-one;
5-(3-Chloro-phenyl)-1,6-diphenyl-1,5-dihydro-pyrazolo[3,4-d]pyrimidin-4-one;
1,6-Diphenyl-5-m-tolyl-1,5-dihydro-pyrazolo[3,4-d]pyrimidin-4-one;
5-(4-Ethoxy-phenyl)-1,6-diphenyl-1,5-dihydro-pyrazolo[3,4-d]pyrimidin-4-one;
6-(4-Bromo-phenyl)-5-(3-chloro-phenyl)-1-phenyl-1,5-dihydro-pyrazolo[3,4-d]pyrimidin-4-one;
6-(4-Chloro-phenyl)-1-phenyl-5-o-tolyl-1,5-dihydro-pyrazolo[3,4-d]pyrimidin-4-one;
6-(4-Chloro-phenyl)-5-(3,5-dimethyl-phenyl)-1-phenyl-1,5-dihydro-pyrazolo[3,4-d]pyrimidin-4-one;
1-Phenyl-6-o-tolyl-5-p-tolyl-1,5-dihydro-pyrazolo[3,4-d]pyrimidin-4-one;
1,5,6-Triphenyl-1,5-dihydro-pyrazolo[3,4-d]pyrimidin-4-one;
5-(4-Bromo-phenyl)-6-(4-chloro-phenyl)-1-phenyl-1,5-dihydro-pyrazolo[3,4-d]pyrimidin-4-one;
6-(2-Fluoro-phenyl)-5-(4-isopropyl-phenyl)-1-phenyl-1,5-dihydro-pyrazolo[3,4-d]pyrimidin-4-one;
6-(2-Fluoro-phenyl)-1-phenyl-5-p-tolyl-1,5-dihydro-pyrazolo[3,4-d]pyrimidin-4-one;
6-(4-Bromo-phenyl)-5-(4-isopropyl-phenyl)-1-phenyl-1,5-dihydro-pyrazolo[3,4-d]pyrimidin-4-one;
6-(4-Bromo-phenyl)-5-(4-chloro-phenyl)-1-phenyl-1,5-dihydro-pyrazolo[3,4-d]pyrimidin-4-one;
5-(4-Fluoro-phenyl)-1-phenyl-6-m-tolyl-1,5-dihydro-pyrazolo[3,4-d]pyrimidin-4-one;

1,6-Diphenyl-5-o-tolyl-1,5-dihydro-pyrazolo[3,4-d]pyrimidin-4-one;

5-(4-Ethoxy-phenyl)-6-(2-fluoro-phenyl)-1-phenyl-1,5-dihydro-pyrazolo[3,4-d]pyrimidin-4-one; and 1,6-Diphenyl-5-p-tolyl-1,5-dihydro-pyrazolo[3,4-d]pyrimidin-4-one.

2. The compound of claim 1 in which:

$R_1$ is selected from phenyl and cyclohexyl; wherein said phenyl and cyclohexyl are optionally substituted with 1 to 3 radicals independently selected from halo, hydroxy, nitro, $C_{1-6}$alkyl, $C_{1-6}$alkoxy, halo-substituted-$C_{1-6}$alkyl, halo-substituted-$C_{1-6}$alkoxy, —$NR_8R_9$, —$S(O)_2R_8$, —$C(O)OR_8$ and $R_{10}$; wherein $R_8$ and $R_9$ are independently selected from hydrogen, $C_{1-6}$alkyl and $C_{2-6}$alkenyl; or $R_8$ and $R_9$ together with the nitrogen atom to which both are attached form $C_{3-8}$heterocycloalkyl or $C_{5-10}$heteroaryl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, nitro, $C_{1-6}$alkyl, $C_{1-6}$alkoxy, halo-substituted-$C_{1-6}$alkyl, halo-substituted-$C_{1-6}$alkoxy, phenyl,—$N(CH_3)_2$, —$NH(CH_3)$, —$NH_2$, —$C(O)OH$, and —$C(O)OCH_3$;.

3. The compound of claim 2 in which:

$R_2$ is selected from piperazinyl, morpholino, benzthiazolyl, pyridinyl, pyrazolyl, phenyl and phenoxy; wherein said piperazinyl, morpholino, benzthiazolyl, pyridinyl, pyrazolyl, phenyl or phenoxy is optionally substituted with 1 to 3 radicals independently selected from halo, hydroxy, cyano, nitro, $C_{1-6}$alkyl, $C_{1-6}$alkoxy, halo-substituted $C_{1-6}$alkyl, halo-substituted $C_{1-6}$alkoxy, —$XNR_8R_9$, —$XOR_8$, —$XC(O)R_8$, —$XS(O)_{0-2}R_8$, —$XC(O)NR_8R_9$, —$XC(O)OR_8$, —$XOR_{10}$,—$XNR_8XR_{10}$ and $XR_{10}$; wherein each X is independently selected from a bond, $C_{1-4}$alkylene and $C_{2-4}$alkenylene; and $R_8$ and $R_9$ are independently selected from hydrogen, $C_{1-6}$alkyl and $C_{2-6}$alkenyl; or $R_8$ and $R_9$ together with the nitrogen atom to which both are attached form $C_{3-8}$heterocycloalkyl or $C_{5-10}$heteroaryl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, cyano-$C_{1-6}$alkyl, nitro, $C_{1-6}$alkyl, $C_{1-6}$alkoxy, halo-substituted-$C_{1-6}$alkyl, halo-substituted-$C_{1-6}$alkoxy, phenyl,-$N(CH_3)_2$, —$NH(CH_3)$, —$NH_2$, —$C(O)OH$, and —$C(O)OCH_3$.

4. The compound of claim 3 in which:

$R_4$ is selected from $C_{1-6}$alkyl, phenyl, $C_{5-10}$heteroaryl, $C_{3-8}$heterocycloalkyl, $C_{3-8}$heterocycloalkyl-carbonyl and $C_{3-12}$cycloalkyl; wherein any phenyl, cycloalkyl, heteroaryl or heterocycloalkyl of $R_4$ can optionally be substituted with 1 to 3 radicals independently selected from halo, hydroxy, cyano, nitro, $C_{1-6}$alkyl, $C_{1-6}$alkoxy, halo-substituted $C_{1-6}$alkyl, halo-substituted $C_{1-6}$alkoxy, —$XS(O)_{0-2}R_8$, —$XNR_8R_9$,—$XC(O)NR_8R_9$,—$XC(O)NR_8R_{10}$, —$XC(O)NR_8XNR_8R_9$, —$XC(O)NR_8XOR_9$, —$XOR_8$, —$XC(O)R_{10}$ and —$XC(O)OR_8$; wherein each X is independently selected from a bond, $C_{1-4}$alkylene and $C_{2-4}$alkenylene; each $R_8$ is independently selected from hydrogen, $C_{1-6}$alkyl and $C_{2-6}$alkenyl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, cyano-$C_{1-6}$alkyl, nitro, $C_{1-6}$alkyl, $C_{1-6}$alkoxy, halo-substituted-$C_{1-6}$alkyl, halo-substituted-$C_{1-6}$alkoxy, phenyl, —$N(CH_3)_2$, —$NH(CH_3)$, —$NH_2$, —$C(O)OH$, and —$C(O)OCH_3$.

5. The compound of claim 4, in which: Y is O.

6. The compound of claim 5 in which $R_1$ is selected from phenyl and cyclohexyl; wherein said phenyl and cyclohexyl are optionally substituted with 1 to 2 radicals independently selected from chloro, bromo, fluoro, methyl, methyl-sulfanyl, t-butyl, methoxy-carbonyl, butoxy, trifluoromethoxy, trifluoromethyl, methoxy, isopropyl, piperidinyl and phenyl optionally substituted with halo.

7. The compound of claim 6 in which $R_2$ is selected from piperazinyl, morpholino, pyridinyl, pyrazolyl, benzthiazolyl, phenyl and phenoxy; wherein said piperazinyl, morpholino, pyridinyl, pyrazolyl, benzthiazolyl, phenyl or phenoxy is optionally substituted with 1 to 2 radicals independently selected from: bromo; chloro; fluoro; iodo; hydroxy; isopropyl; methyl; cyclohexyl; oxazolyl; isoxazolyl optionally substituted with 1 to 2 methyl radicals; pyrazolidinyl; methylcarbonyl; amino-carbonyl; morpholino; thienyl; furanyl; cyclohexyl-amino optionally substituted with an amino radical; methyl-sulfonyl; trichloromethyl; methoxy-carbonyl; chloro-methyl; butoxy-ethenyl; butoxy-ethyl; trifluoromethyl; trifluoromethoxy; ethoxy-carbonyl; t-butyl; ethyl; propyl; methoxy; methoxy-methyl; carboxy; piperidinyl; piperidinyl-methyl; morpholino-methyl; diethyl-amino-methyl; isobutyl-amino-methyl; cyclopropyl-methyl-amino-methyl; isopropoxy-methyl; ethenyl; cyclopropyl; butoxy; [1,2,4]oxadiazol-5-yl optionally substituted with methyl; piperazinyl optionally substituted with 1 to 2 radicals independently selected from methyl, isopropyl and methyl-sulfonyl; 2-oxopiperidin-1-yl; 2-oxo-pyrrolidin-1-yl; 2H-[1,2,4]triazol-3-yl; 1-methyl-1H-[1,2,4]triazol-3-yl; pyrazolyl optionally substituted with methyl; pyridazinyl; pyrazinyl optionally substituted with 1 to 2 radicals independently selected from cyano and methyl; pyridinyl optionally substituted with 1 to 2 radicals independently selected from halo, methyl and amino; pyridinyl-N-oxide optionally substituted with methyl; pyrimidinyl optionally substituted with 1 to 2 radicals independently selected from halo, methyl and amino; phenyl optionally substituted with 1 to 2 radicals independently selected from halo, methyl and trifluoromethyl; imidazolyl optionally substituted with 1 to 2 radicals independently selected from methyl, ethyl and cyano-methyl; and 6-oxo-1,6-dihydro-pyridin-3-yl.

8. The compound of claim 1 in which $R_4$ is methyl, hydroxy-ethyl, t-butyl, phenyl, benzyl, cyclohexyl, cyclopropyl, pyridinyl, furanyl, morpholino-carbonyl, tetrahydro-thiopyranyl, tetrahydro-thiopyranyl 1,1-dioxide and quinolinyl; wherein said phenyl, benzyl, cyclohexyl, cyclopropyl, pyridinyl, furanyl, morpholino-carbonyl, tetrahydro-thiopyranyl, tetrahydro-thiopyranyl 1,1-dioxide and quinolinyl of $R_4$ is optionally substituted with 1 to 2 radicals independently selected from methyl, cyano, carboxy, aminocarbonyl, methoxy, trifluoromethyl, isopropoxy, methyl-sulfanyl, dimethylamino, ethoxy-carbonyl, trifluoromethoxy, cyclopropyl-aminocarbonyl, pyridinyl-aminocarbonyl, cyclohexyl-aminocarbonyl, isoxazolyl-aminocarbonyl, dimethylamino-ethyl-aminocarbonyl, methoxy-ethyl-aminocarbonyl, nitro, amino, fluoro, chloro, bromo, hydroxymethyl, methyl-piperazinyl-carbonyl, morpholino-carbonyl and piperidinyl-carbonyl.

9. The compound of claim 1 selected from:

5-(4-Chloro-phenyl)-6-(2,4-dichloro-phenyl)-1-phenyl-1,5-dihydro-pyrazolo[3,4-d]pyrimidin-4-one;
5-(4-bromo-phenyl)-1-phenyl-6-p-tolyl-1,5-dihydro-pyrazolo[3,4-d]pyrimidin-4-one;
5-(4-Chloro-phenyl)-6-(2,4-dichloro-phenyl)-1-(4-nitro-phenyl)-1,5-dihydro-pyrazolo[3,4-d]pyrimidin-4-one;
5-(4-Chloro-phenyl)-6-(2,4-dichloro-phenyl)-1-(2-nitro-phenyl)-1,5-dihydro-pyrazolo[3,4-d]pyrimidin-4-one;
1-(4-Amino-phenyl)-5-(4-chloro-phenyl)-6-(2,4-dichloro-phenyl)-1,5-dihydro-pyrazolo[3,4-d]pyrimidin-4-one;
5-(4-Bromo-phenyl)-6-(2-fluoro-phenyl)-1-quinolin-2-yl-1,5-dihydro-pyrazolo[3,4-d]pyrimidin-4-one;
5-(4-bromo-phenyl)-6-(4-fluoro-phenyl)-1-phenyl-1,5-dihydro-pyrazolo[3,4-d]pyrimidin-4-one;
5-(4-Bromo-phenyl)-1-pyridin-2-yl-6-o-tolyl-1,5-dihydro-pyrazolo[3,4-d]pyrimidin-4-one;
5-(4-Bromo-phenyl)-6-(2-fluoro-phenyl)-1-(2-hydroxy-ethyl)-1,5-dihydro-pyrazolo[3,4-d]pyrimidin-4-one;
5-(2,4-Dichloro-phenyl)-6-(2-fluoro-phenyl)-1-phenyl-1,5-dihydro-pyrazolo[3,4-d]pyrimidin-4-one;
5-(4-Bromo-phenyl)-6-(2,4-dichloro-phenyl)-1-phenyl-1,5-dihydro-pyrazolo[3,4-d]pyrimidin-4-one;
6-(2,4-Dichloro-phenyl)-5-(4-fluoro-phenyl)-1-phenyl-1,5-dihydro-pyrazolo[3,4-d]pyrimidin-4-one;
6-(4-Chloro-phenyl)-5-(2,4-dichloro-phenyl)-1-phenyl-1,5-dihydro-pyrazolo[3,4-d]pyrimidin-4-one;
5-(4-Chloro-2-fluoro-phenyl)-6-(4-chloro-phenyl)-1-phenyl-1,5-dihydro-pyrazolo[3,4-d]pyrimidin-4-one;
6-(4-Chloro-phenyl)-5-(2,4-difluoro-phenyl)-1-phenyl-1,5-dihydro-pyrazolo[3,4-d]pyrimidin-4-one;
5-(4-bromo-phenyl)-6-(2-chloro-phenyl)-1-phenyl-1,5-dihydro-pyrazolo[3,4-d]pyrimidin-4-one;
5-(4-bromo-phenyl)-6-(3-chloro-phenyl)-1-phenyl-1,5-dihydro-pyrazolo[3,4-d]pyrimidin-4-one;
5-(4-bromo-phenyl)-6-(2-bromo-phenyl)-1-phenyl-1,5-dihydro-pyrazolo[3,4-d]pyrimidin-4-one;
5-(4-bromo-phenyl)-6-(2,4-difluoro-phenyl)-1-phenyl-1,5-dihydro-pyrazolo[3,4-d]pyrimidin-4-one;
6-biphenyl-4-yl-5-(4-bromo-phenyl)-1-phenyl-1,5-dihydro-pyrazolo[3,4-d]pyrimidin-4-one;
5-(4-bromo-phenyl)-6-(3,4-dichloro-phenyl)-1-phenyl-1,5-dihydro-pyrazolo[3,4-d]pyrimidin-4-one;
6-(4-Chloro-phenyl)-1,5-diphenyl-1,5-dihydro-pyrazolo[3,4-d]pyrimidin-4-one;
5-(4-bromo-phenyl)-6-(2-fluoro-phenyl)-1-pyridin-2-yl-1,5-dihydro-pyrazolo[3,4-d]pyrimidin-4-one;
5-(4-bromo-phenyl)-1-phenyl-6-o-tolyl-1,5-dihydro-pyrazolo[3,4-d]pyrimidin-4-one;
5-(4-bromo-phenyl)-6-(3-fluoro-phenyl)-1-phenyl-1,5-dihydro-pyrazolo[3,4-d]pyrimidin-4-one;
5-(4-bromo-phenyl)-1-cyclohexyl-6-(2-fluoro-phenyl)-1,5-dihydro-pyrazolo[3,4-d]pyrimidin-4-one;
5-(4-Bromo-phenyl)-1-tert-butyl-6-(2-fluoro-phenyl)-1,5-dihydro-pyrazolo[3,4-d]pyrimidin-4-one;
5-(4-Bromo-phenyl)-6-(2-fluoro-phenyl)-1-(4-methoxy-phenyl)-1,5-dihydro-pyrazolo[3,4-d]pyrimidin-4-one;
5-(4-Bromo-phenyl)-1-(3-fluoro-phenyl)-6-(2-fluoro-phenyl)-1,5-dihydro-pyrazolo[3,4-d]pyrimidin-4-one;
4-[5-(4-Bromo-phenyl)-6-(2-fluoro-phenyl)-4-oxo-4,5-dihydro-pyrazolo[3,4-d]pyrimidin-1-yl]-benzonitrile;
5-(4-Bromo-phenyl)-6-(2-fluoro-phenyl)-1-m-tolyl-1,5-dihydro-pyrazolo[3,4-d]pyrimidin-4-one;
5-(4-Bromo-phenyl)-6-(2-fluoro-phenyl)-1-(4-trifluoromethyl-phenyl)-1,5-dihydro-pyrazolo[3,4-d]pyrimidin-4-one;
5-(4-bromo-phenyl)-6-(4-methoxy-phenyl)-1-phenyl-1,5-dihydro-pyrazolo[3,4-d]pyrimidin-4-one;
5-(4-bromo-phenyl)-1-phenyl-6-(4-trifluoromethoxy-phenyl)-1,5-dihydro-pyrazolo[3,4-d]pyrimidin-4-one;
5-(4-bromo-phenyl)-6-(4-tert-butyl-phenyl)-1-phenyl-1,5-dihydro-pyrazolo[3,4-d]pyrimidin-4-one;
5-(4-bromo-phenyl)-1-phenyl-6-(2-trifluoromethyl-phenyl)-1,5-dihydro-pyrazolo[3,4-d]pyrimidin-4-one;
5-(4-bromo-phenyl)-6-(2,6-difluoro-phenyl)-1-phenyl-1,5-dihydro-pyrazolo[3,4-d]pyrimidin-4-one;
5-(4-bromo-phenyl)-6-(2,6-dichloro-phenyl)-1-phenyl-1,5-dihydro-pyrazolo[3,4-d]pyrimidin-4-one;
5-(4-bromo-phenyl)-1-phenyl-6-(2,4,6-trifluoro-phenyl)-1,5-dihydro-pyrazolo[3,4-d]pyrimidin-4-one;
5-(4-bromo-phenyl)-6-(2-methoxy-phenyl)-1-phenyl-1,5-dihydro-pyrazolo[3,4-d]pyrimidin-4-one;
5-(4-bromo-phenyl)-1-phenyl-6-(4-trifluoromethyl-phenyl)-1,5-dihydro-pyrazolo[3,4-d]pyrimidin-4-one;
6-biphenyl-4-yl-5-(4-chloro-phenyl)-1-phenyl-1,5-dihydro-pyrazolo[3,4-d]pyrimidin-4-one;
6-(2-Fluoro-phenyl)-5-(4-methylsulfanyl-phenyl)-1-phenyl-1,5-dihydro-pyrazolo[3,4-d]pyrimidin-4-one;
5-(4-tert-Butyl-phenyl)-6-(2-fluoro-phenyl)-1-phenyl-1,5-dihydro-pyrazolo[3,4-d]pyrimidin-4-one;
4-[6-(2-Fluoro-phenyl)-4-oxo-1-phenyl-1,4-dihydro-pyrazolo[3,4-d]pyrimidin-5-yl]-benzoic acid methyl ester;
5-(4-Butoxy-phenyl)-6-(2-fluoro-phenyl)-1-phenyl-1,5-dihydro-pyrazolo[3,4-d]pyrimidin-4-one;
5-Biphenyl-4-yl-6-(2-fluoro-phenyl)-1-phenyl-1,5-dihydro-pyrazolo[3,4-d]pyrimidin-4-one;
6-(2-Fluoro-phenyl)-1-phenyl-5-(4-trifluoromethoxy-phenyl)-1,5-dihydro-pyrazolo[3,4-d]pyrimidin-4-one;
6-(2-Fluoro-phenyl)-1-phenyl-5-(4-trifluoromethyl-phenyl)-1,5-dihydro-pyrazolo[3,4-d]pyrimidin-4-one;
5-Benzyl-6-(2-fluoro-phenyl)-1-phenyl-1,5-dihydro-pyrazolo[3,4-d]pyrimidin-4-one;
5-Cyclohexyl-6-(2-fluoro-phenyl)-1-phenyl-1,5-dihydro-pyrazolo[3,4-d]pyrimidin-4-one;
5-(4-Bromo-phenyl)-6-(2-fluoro-phenyl)-1-methyl-1,5-dihydro-pyrazolo[3,4-d]pyrimidin-4-one;
5-(4-bromo-phenyl)-6-(2-fluoro-phenyl)-1-(morpholine-4-carbonyl)-1,5-dihydro-pyrazolo[3,4-d]pyrimidin-4-one;
5-(4-Bromo-phenyl)-6-(2-fluoro-phenyl)-1-(tetrahydro-thiopyran-4-yl)-1,5-dihydro-pyrazolo[3,4-d]pyrimidin-4-one;
5-(4-Bromo-phenyl)-1-(1,1-dioxo-hexahydro-1$\lambda^6$-thiopyran-4-yl)-6-(2-fluoro-phenyl)-1,5-dihydro-pyrazolo[3,4-d]pyrimidin-4-one;
5-(4-Chloro-phenyl)-6-[4-(3-methyl-[1,2,4]oxadiazol-5-yl)-phenyl]-1-phenyl-1,5-dihydro-pyrazolo[3,4-d]pyrimidin-4-one;
5-(4-Chloro-phenyl)-6-(4-isoxazol-5-yl-phenyl)-1-phenyl-1,5-dihydro-pyrazolo[3,4-d]pyrimidin-4-one;
5-(4-Chloro-phenyl)-1-phenyl-6-[4-(2H-pyrazol-3-yl)-phenyl]-1,5-dihydro-pyrazolo[3,4-d]pyrimidin-4-one;
6-(4-Acetyl-phenyl)-5-(4-chloro-phenyl)-1-phenyl-1,5-dihydro-pyrazolo[3,4-d]pyrimidin-4-one;
4-[5-(4-Chloro-phenyl)-4-oxo-1-phenyl-4,5-dihydro-1H-pyrazolo[3,4-d]pyrimidin-6-yl]-benzamide;
6-[4-(2-Amino-pyrimidin-4-yl)-phenyl]-5-(4-chloro-phenyl)-1-phenyl-1,5-dihydro-pyrazolo[3,4-d]pyrimidin-4-one;
5-(4-Chloro-phenyl)-1-phenyl-6-(4-pyrimidin-4-yl-phenyl)-1,5-dihydro-pyrazolo[3,4-d]pyrimidin-4-one;

5-(4-Chloro-phenyl)-6-[4-(2-methyl-pyrimidin-4-yl)-phenyl]-1-phenyl-1,5-dihydro-pyrazolo[3,4-d]pyrimidin-4-one;

5-(4-Chloro-phenyl)-1-phenyl-6-[4-(2H-[1,2,4]triazol-3-yl)-phenyl]-1,5-dihydro-pyrazolo[3,4-d]pyrimidin-4-one;

5-(4-Chloro-phenyl)-6-(4-[1,2,4]oxadiazol-5-yl-phenyl)-1-phenyl-1,5-dihydro-pyrazolo[3,4-d]pyrimidin-4-one;

6-Biphenyl-4-yl-5-(4-chloro-phenyl)-4-oxo-1-phenyl-4,5-dihydro-1H-pyrazolo[3,4-d]pyrimidine-3-carboxylic acid amide;

6-Biphenyl-4-yl-5-(4-chloro-phenyl)-4-oxo-1-phenyl-4,5-dihydro-1H-pyrazolo[3,4-d]pyrimidine-3-carboxylic acid ethyl ester;

5-(4-chloro-phenyl)-6-(3'-fluoro-biphenyl-4-yl)-1-phenyl-1,5-dihydro-pyrazolo[3,4-d]pyrimidin-4-one;

5-(4-chloro-phenyl)-6-(4-morpholin-4-yl-phenyl)-1-phenyl-1,5-dihydro-pyrazolo[3,4-d]pyrimidin-4-one;

5-(4-chloro-phenyl)-6-(4-imidazol-1-yl-phenyl)-1-phenyl-1,5-dihydro-pyrazolo[3,4-d]pyrimidin-4-one;

5-(4-chloro-phenyl)-1-phenyl-6-(4-pyridin-2-yl-phenyl)-1,5-dihydro-pyrazolo[3,4-d]pyrimidin-4-one;

5-(4-chloro-phenyl)-1-phenyl-6-(4-phenyl-piperazin-1-yl)-1,5-dihydro-pyrazolo[3,4-d]pyrimidin-4-one;

6-benzothiazol-2-yl-5-(4-chloro-phenyl)-1-phenyl-1,5-dihydro-pyrazolo[3,4-d]pyrimidin-4-one;

5-(4-chloro-phenyl)-1-phenyl-6-p-tolyloxy-1,5-dihydro-pyrazolo[3,4-d]pyrimidin-4-one;

5-(4-Bromo-phenyl)-1-phenyl-6-pyridin-3-yl-1,5-dihydro-pyrazolo[3,4-d]pyrimidin-4-one;

5-(4-Bromo-phenyl)-6-(2-fluoro-phenyl)-1-(tetrahydro-pyran-4-yl)-1,5-dihydro-pyrazolo[3,4-d]pyrimidin-4-one;

5-(4-Chloro-phenyl)-6-(4-iodo-phenyl)-1-phenyl-1,5-dihydro-pyrazolo[3,4-d]pyrimidin-4-one;

5-(4-Chloro-phenyl)-6-(4'-fluoro-biphenyl-4-yl)-1-phenyl-1,5-dihydro-pyrazolo[3,4-d]pyrimidin-4-one;

5-(4-Chloro-phenyl)-6-(2'-fluoro-biphenyl-4-yl)-1-phenyl-1,5-dihydro-pyrazolo[3,4-d]pyrimidin-4-one;

6-(2-Fluoro-phenyl)-1-phenyl-5-(4-piperidin-1-yl-phenyl)-1,5-dihydro-pyrazolo[3,4-d]pyrimidin-4-one;

5-(4-Chloro-phenyl)-1-phenyl-6-(4'-trifluoromethyl-biphenyl-4-yl)-1,5-dihydro-pyrazolo[3,4-d]pyrimidin-4-one;

5-(4-Chloro-phenyl)-1-phenyl-6-(4-thiophen-3-yl-phenyl)-1,5-dihydro-pyrazolo[3,4-d]pyrimidin-4-one;

5-(4-Chloro-phenyl)-6-[4-(4-methyl-piperazin-1-yl)-phenyl]-1-phenyl-1,5-dihydro-pyrazolo[3,4-d]pyrimidin-4-one;

5-(4-Chloro-phenyl)-1-phenyl-6-(4-piperidin-1-yl-phenyl)-1,5-dihydro-pyrazolo[3,4-d]pyrimidin-4-one;

6-(4-Bromo-phenyl)-5-(4-chloro-phenyl)-1-phenyl-1,5-dihydro-pyrazolo[3,4-d]pyrimidin-4-one;

5-(4-Chloro-phenyl)-6-(4-phenoxy-phenyl)-1-phenyl-1,5-dihydro-pyrazolo[3,4-d]pyrimidin-4-one;

5-(4-Bromo-phenyl)-1-phenyl-6-(4-phenyl-piperazin-1-yl)-1,5-dihydro-pyrazolo[3,4-d]pyrimidin-4-one;

5-(4-Bromo-phenyl)-6-[4-(4-fluoro-phenyl)-piperazin-1-yl]-1-phenyl-1,5-dihydro-pyrazolo[3,4-d]pyrimidin-4-one;

6-(4-Bromo-2-fluoro-phenyl)-5-(4-chloro-phenyl)-1-phenyl-1,5-dihydro-pyrazolo[3,4-d]pyrimidin-4-one;

6-(4-Bromo-2-chloro-phenyl)-5-(4-chloro-phenyl)-1-phenyl-1,5-dihydro-pyrazolo[3,4-d]pyrimidin-4-one;

5-(4-Chloro-phenyl)-6-(2-fluoro-4-morpholin-4-yl-phenyl)-1-phenyl-1,5-dihydro-pyrazolo[3,4-d]pyrimidin-4-one;

6-(2-Chloro-4-morpholin-4-yl-phenyl)-5-(4-chloro-phenyl)-1-phenyl-1,5-dihydro-pyrazolo[3,4-d]pyrimidin-4-one;

5-(4-Chloro-phenyl)-6-(3-fluoro-biphenyl-4-yl)-1-phenyl-1,5-dihydro-pyrazolo[3,4-d]pyrimidin-4-one;

6-(3-Chloro-biphenyl-4-yl)-5-(4-chloro-phenyl)-1-phenyl-1,5-dihydro-pyrazolo[3,4-d]pyrimidin-4-one;

5-(4-Chloro-phenyl)-6-(4-furan-3-yl-phenyl)-1-phenyl-1,5-dihydro-pyrazolo[3,4-d]pyrimidin-4-one;

5-(4-Chloro-phenyl)-1-phenyl-6-(4-pyridin-3-yl-phenyl)-1,5-dihydro-pyrazolo[3,4-d]pyrimidin-4-one;

5-(4-Chloro-phenyl)-1-phenyl-6-(4-pyridin-4-yl-phenyl)-1,5-dihydro-pyrazolo[3,4-d]pyrimidin-4-one;

5-(4-Chloro-phenyl)-6-[4-(3,5-dimethyl-isoxazol-4-yl)-phenyl]-1-phenyl-1,5-dihydro-pyrazolo[3,4-d]pyrimidin-4-one;

6-Biphenyl-4-yl-5-(4-chloro-phenyl)-1-(tetrahydro-pyran-4-yl)-1,5-dihydro-pyrazolo[3,4-d]pyrimidin-4-one;

5-(4-Chloro-phenyl)-6-[1-(3-fluoro-phenyl)-1H-pyrazol-4-yl]-1-phenyl-1,5-dihydro-pyrazolo[3,4-d]pyrimidin-4-one;

4-[5-(4-Chloro-phenyl)-4-oxo-1-phenyl-4,5-dihydro-1H-pyrazolo[3,4-d]pyrimidin-6-yl]-benzoic acid methyl ester;

5-(4-Bromo-phenyl)-6-morpholin-4-yl-1-phenyl-1,5-dihydro-pyrazolo[3,4-d]pyrimidin-4-one;

5-(4-Bromo-phenyl)-6-(4-isopropyl-piperazin-1-yl)-1-phenyl-1,5-dihydro-pyrazolo[3,4-d]pyrimidin-4-one;

5-(4-Chloro-phenyl)-1-phenyl-6-(4-pyrazol-1-yl-phenyl)-1,5-dihydro-pyrazolo[3,4-d]pyrimidin-4-one;

6-[4-(2-amino-cyclohexylamino)-phenyl]-5-(4-chloro-phenyl)-1-phenyl-1,5-dihydro-pyrazolo[3,4-d]pyrimidin-4-one;

6-(4-Bromo-3-fluoro-phenyl)-5-(4-chloro-phenyl)-1-phenyl-1,5-dihydro-pyrazolo[3,4-d]pyrimidin-4-one;

4-[5-(4-Chloro-phenyl)-4-oxo-1-phenyl-4,5-dihydro-1H-pyrazolo[3,4-d]pyrimidin-6-yl]-benzoic acid ethyl ester;

5-(4-Chloro-phenyl)-6-(2-fluoro-biphenyl-4-yl)-1-phenyl-1,5-dihydro-pyrazolo[3,4-d]pyrimidin-4-one;

5-(4-Chloro-phenyl)-6-(3-fluoro-4-morpholin-4-yl-phenyl)-1-phenyl-1,5-dihydro-pyrazolo[3,4-d]pyrimidin-4-one;

5-(4-Chloro-phenyl)-6-[3-fluoro-4-(4-methyl-piperazin-1-yl)-phenyl]-1-phenyl-1,5-dihydro-pyrazolo[3,4-d]pyrimidin-4-one;

5-(4-Chloro-phenyl)-6-[3-fluoro-4-(4-isopropyl-piperazin-1-yl)-phenyl]-1-phenyl-1,5-dihydro-pyrazolo[3,4-d]pyrimidin-4-one;

5-(4-Chloro-phenyl)-6-(2'-methyl-biphenyl-4-yl)-1-phenyl-1,5-dihydro-pyrazolo[3,4-d]pyrimidin-4-one;

5-(4-Chloro-phenyl)-6-(3'-methyl-biphenyl-4-yl)-1-phenyl-1,5-dihydro-pyrazolo[3,4-d]pyrimidin-4-one;

5-(4-Chloro-phenyl)-6-(4'-methyl-biphenyl-4-yl)-1-phenyl-1,5-dihydro-pyrazolo[3,4-d]pyrimidin-4-one;

5-(4-Chloro-phenyl)-6-[2-fluoro-4-(4-methyl-piperazin-1-yl)-phenyl]-1-phenyl-1,5-dihydro-pyrazolo[3,4-d]pyrimidin-4-one;

5-(4-Chloro-phenyl)-6-[2-fluoro-4-(4-isopropyl-piperazin-1-yl)-phenyl]-1-phenyl-1,5-dihydro-pyrazolo[3,4-d]pyrimidin-4-one;

6-[2-Chloro-4-(4-methyl-piperazin-1-yl)-phenyl]-5-(4-chloro-phenyl)-1-phenyl-1,5-dihydro-pyrazolo[3,4-d]pyrimidin-4-one;

6-[2-Chloro-4-(4-isopropyl-piperazin-1-yl)-phenyl]-5-(4-chloro-phenyl)-1-phenyl-1,5-dihydro-pyrazolo[3,4-d]pyrimidin-4-one;

5-(4-Chloro-phenyl)-1-phenyl-6-o-tolyloxy-1,5-dihydro-pyrazolo[3,4-d]pyrimidin-4-one;
5-(4-Chloro-phenyl)-1-phenyl-6-m-tolyloxy-1,5-dihydro-pyrazolo[3,4-d]pyrimidin-4-one;
5-(4-Chloro-phenyl)-1-phenyl-6-p-tolyl-1,5-dihydro-pyrazolo[3,4-d]pyrimidin-4-one;
5-(4-Chloro-phenyl)-1-phenyl-6-(4-trifluoromethyl-phenyl)-1,5-dihydro-pyrazolo[3,4-d]pyrimidin-4-one;
5-(4-Chloro-phenyl)-6-(4-methanesulfonyl-piperazin-1-yl)-1-phenyl-1,5-dihydro-pyrazolo[3,4-d]pyrimidin-4-one;
5-(4-Chloro-phenyl)-6-(2,4-dichloro-phenyl)-1-(2-nitro-phenyl)-1,5-dihydro-pyrazolo[3,4-d]pyrimidin-4-one;
1-(4-Amino-phenyl)-5-(4-chloro-phenyl)-6-(2,4-dichloro-phenyl)-1,5-dihydro-pyrazolo[3,4-d]pyrimidin-4-one;
5,6-Bis-(4-chloro-phenyl)-1-(4-nitro-phenyl)-1,5-dihydro-pyrazolo[3,4-d]pyrimidin-4-one;
5,6-Bis-(4-chloro-phenyl)-1-(2-nitro-phenyl)-1,5-dihydro-pyrazolo[3,4-d]pyrimidin-4-one;
1-(4-Amino-phenyl)-5,6-bis-(4-chloro-phenyl)-1,5-dihydro-pyrazolo[3,4-d]pyrimidin-4-one;
5-(4-Chloro-phenyl)-6-(2,4-dichloro-phenyl)-1-(4-fluoro-phenyl)-1,5-dihydro-pyrazolo[3,4-d]pyrimidin-4-one;
5-(4-Chloro-phenyl)-6-(2,4-dichloro-phenyl)-3-(4-methyl-piperazin-1-yl)-1-phenyl-1,5-dihydro-pyrazolo[3,4-d]pyrimidin-4-one;
5-(4-Bromo-phenyl)-6-(2,4-dichloro-phenyl)-3-methanesulfonyl-1-phenyl-1,5-dihydro-pyrazolo[3,4-d]pyrimidin-4-one;
4-[5-(4-Chloro-phenyl)-6-(2,4-dichloro-phenyl)-4-oxo-4,5-dihydro-pyrazolo[3,4-d]pyrimidin-1-yl]-benzoic acid;
5-(4-Chloro-phenyl)-6-(2,4-dichloro-phenyl)-1-(4-hydroxymethyl-phenyl)-1,5-dihydro-pyrazolo[3,4-d]pyrimidin-4-one;
5-(4-Chloro-phenyl)-6-(2,4-dichloro-phenyl)-1-[4-(4-methyl-piperazine-1-carbonyl)-phenyl]-1,5-dihydro-pyrazolo[3,4-d]pyrimidin-4-one;
5-(4-Chloro-phenyl)-6-(2,4-dichloro-phenyl)-1-[4-(morpholine-4-carbonyl)-phenyl]-1,5-dihydro-pyrazolo[3,4-d]pyrimidin-4-one;
5-(4-Chloro-phenyl)-6-(2,4-dichloro-phenyl)-1-[4-(piperidine-1-carbonyl)-phenyl]-1,5-dihydro-pyrazolo[3,4-d]pyrimidin-4-one;
5-(4-Chloro-phenyl)-6-(2,4-dichloro-phenyl)-1-[4-(4-methyl-piperazin-1-ylmethyl)-phenyl]-1,5-dihydro-pyrazolo[3,4-d]pyrimidin-4-one;
5-(4-Chloro-phenyl)-6-(2,4-dichloro-phenyl)-3-methanesulfonyl-1-phenyl-1,5-dihydro-pyrazolo[3,4-d]pyrimidin-4-one;
5-(4-chloro-phenyl)-1-phenyl-6-(4-pyridin-2-yl-piperazin-1-yl)-1,5-dihydro-pyrazolo[3,4-d]pyrimidin-4-one;
5-(4-chloro-phenyl)-1-phenyl-6-(4-pyridin-4-yl-piperazin-1-yl)-1,5-dihydro-pyrazolo[3,4-d]pyrimidin-4-one;
5-(4-chloro-phenyl)-6-[4-(1-oxy-pyridin-4-yl)-phenyl]-1-phenyl-1,5-dihydro-pyrazolo[3,4-d]pyrimidin-4-one;
5-(4-chloro-phenyl)-6-[4-(2-methyl-imidazol-1-yl)-phenyl]-1-phenyl-1,5-dihydro-pyrazolo[3,4-d]pyrimidin-4-one;
5-(4-chloro-phenyl)-6-[4-(4-methyl-imidazol-1-yl)-phenyl]-1-phenyl-1,5-dihydro-pyrazolo[3,4-d]pyrimidin-4-one;
5-(4-chloro-phenyl)-3-(3-methyl-[1,2,4]oxadiazol-5-yl)-1-phenyl-6-(4-pyridin-2-yl-phenyl)-1,5-dihydro-pyrazolo[3,4-d]pyrimidin-4-one;
(1-{4-[5-(4-chloro-phenyl)-4-oxo-1-phenyl-4,5-dihydro-1H-pyrazolo[3,4-d]pyrimidin-6-yl]-phenyl}-1H-imidazol-4-yl)-acetonitrile;
5-(4-chloro-phenyl)-6-[4-(1-oxy-pyridin-2-yl)-phenyl]-1-phenyl-1,5-dihydro-pyrazolo[3,4-d]pyrimidin-4-one;
5-(4-chloro-phenyl)-6-[4-(2-ethyl-imidazol-1-yl)-phenyl]-1-phenyl-1,5-dihydro-pyrazolo[3,4-d]pyrimidin-4-one;
5-(4-chloro-phenyl)-6-[4-(2,4-dimethyl-imidazol-1-yl)-phenyl]-1-phenyl-1,5-dihydro-pyrazolo[3,4-d]pyrimidin-4-one;
5-(4-chloro-phenyl)-6-[4-(4-fluoro-phenyl)-piperazin-1-yl]-1-phenyl-1,5-dihydro-pyrazolo[3,4-d]pyrimidin-4-one;
6-[4-(6-amino-pyridin-3-yl)-phenyl]-5-(4-chloro-phenyl)-1-phenyl-1,5-dihydro-pyrazolo[3,4-d]pyrimidin-4-one;
5-(4-chloro-phenyl)-6-[4-(1-oxy-pyridin-3-yl)-phenyl]-1-phenyl-1,5-dihydro-pyrazolo[3,4-d]pyrimidin-4-one;
5-(4-chloro-phenyl)-6-[4-(1H-imidazol-2-yl)-phenyl]-1-phenyl-1,5-dihydro-pyrazolo[3,4-d]pyrimidin-4-one;
5-(4-chloro-phenyl)-3-methanesulfonyl-1-phenyl-6-(4-pyridin-4-yl-phenyl)-1,5-dihydro-pyrazolo[3,4-d]pyrimidin-4-one;
5-(4-chloro-phenyl)-6-[4-(2-methyl-1-oxy-pyridin-4-yl)-phenyl]-1-phenyl-1,5-dihydro-pyrazolo[3,4-d]pyrimidin-4-one;
5-(4-chloro-phenyl)-6-[4-(3-methyl-1-oxy-pyridin-4-yl)-phenyl]-1-phenyl-1,5-dihydro-pyrazolo[3,4-d]pyrimidin-4-one;
5-(4-chloro-phenyl)-3-methanesulfonyl-6-[4-(1-oxy-pyridin-4-yl)-phenyl]-1-phenyl-1,5-dihydro-pyrazolo[3,4-d]pyrimidin-4-one;
5-(4-chloro-phenyl)-6-[4-(6-oxo-1,6-dihydro-pyridin-3-yl)-phenyl]-1-phenyl-1,5-dihydro-pyrazolo[3,4-d]pyrimidin-4-one;
6-[4-(4-amino-pyridin-2-yl)-phenyl]-5-(4-chloro-phenyl)-1-phenyl-1,5-dihydro-pyrazolo[3,4-d]pyrimidin-4-one;
6-[4-(6-amino-pyridin-2-yl)-phenyl]-5-(4-chloro-phenyl)-1-phenyl-1,5-dihydro-pyrazolo[3,4-d]pyrimidin-4-one;
6-(4-Bromo-phenyl)-5-(4-chloro-phenyl)-4-oxo-1-phenyl-4,5-dihydro-1H-pyrazolo[3,4-d]pyrimidine-3-carboxylic acid;
6-(4-Bromo-phenyl)-5-(4-chloro-phenyl)-4-oxo-1-phenyl-4,5-dihydro-1H-pyrazolo[3,4-d]pyrimidine-3-carboxylic acid ethyl ester;
6-(4-Bromo-phenyl)-5-(4-chloro-phenyl)-4-oxo-1-phenyl-4,5-dihydro-1H-pyrazolo[3,4-d]pyrimidine-3-carboxylic acid methylamide;
6-(4-Bromo-phenyl)-5-(4-chloro-phenyl)-4-oxo-1-phenyl-4,5-dihydro-1H-pyrazolo[3,4-d]pyrimidine-3-carboxylic acid dimethylamide;
6-(4-Bromo-phenyl)-5-(4-chloro-phenyl)-3-(morpholine-4-carbonyl)-1-phenyl-1,5-dihydro-pyrazolo[3,4-d]pyrimidin-4-one;
6-(4-Bromo-phenyl)-5-(4-chloro-phenyl)-4-oxo-1-phenyl-4,5-dihydro-1H-pyrazolo[3,4-d]pyrimidine-3-carboxylic acid piperidin-1-ylamide;
6-(4-Bromo-phenyl)-5-(4-chloro-phenyl)-1-phenyl-3-(piperidine-1-carbonyl)-1,5-dihydro-pyrazolo[3,4-d]pyrimidin-4-one;

6-(4-Bromo-phenyl)-5-(4-chloro-phenyl)-4-oxo-1-phenyl-4,5-dihydro-1H-pyrazolo[3,4-d]pyrimidine-3-carboxylic acid isopropyl ester;

6-(4-Bromo-phenyl)-5-(4-chloro-phenyl)-4-oxo-1-phenyl-4,5-dihydro-1H-pyrazolo[3,4-d]pyrimidine-3-carboxylic acid tert-butyl ester;

5-(4-Chloro-phenyl)-6-(4-isopropyl-phenyl)-4-oxo-1-phenyl-4,5-dihydro-1H-pyrazolo[3,4-d]pyrimidine-3-carboxylic acid amide;

5-(4-Chloro-phenyl)-6-(4-isopropyl-phenyl)-4-oxo-1-phenyl-4,5-dihydro-1H-pyrazolo[3,4-d]pyrimidine-3-carboxylic acid ethyl ester;

5-(4-Chloro-phenyl)-6-(4-isopropyl-phenyl)-3-(3-methyl-[1,2,4]oxadiazol-5-yl)-1-phenyl-1,5-dihydro-pyrazolo[3,4-d]pyrimidin-4-one;

5-(4-Chloro-phenyl)-6-(4-isopropyl-phenyl)-4-oxo-1-phenyl-4,5-dihydro-1H-pyrazolo[3,4-d]pyrimidine-3-carboxylic acid methylamide;

5-(4-Chloro-phenyl)-6-(4-isopropyl-phenyl)-4-oxo-1-phenyl-4,5-dihydro-1H-pyrazolo[3,4-d]pyrimidine-3-carbonitrile;

5-(4-Chloro-phenyl)-6-[4-(2-chloro-pyrimidin-4-yl)-phenyl]-3-methanesulfonyl-1-phenyl-1,5-dihydro-pyrazolo[3,4-d]pyrimidin-4-one;

6-[4-(2-Amino-pyrimidin-4-yl)-phenyl]-5-(4-chloro-phenyl)-3-methanesulfonyl-1-phenyl-1,5-dihydro-pyrazolo[3,4-d]pyrimidin-4-one;

6-(4-Bromo-phenyl)-5-(4-chloro-phenyl)-3-(3-methyl-[1,2,4]oxadiazol-5-yl)-1-phenyl-1,5-dihydro-pyrazolo[3,4-d]pyrimidin-4-one;

6-[4-(2-Amino-pyrimidin-4-yl)-phenyl]-5-(4-chloro-phenyl)-4-oxo-1-phenyl-4,5-dihydro-1H-pyrazolo[3,4-d]pyrimidine-3-carboxylic acid amide;

6-[4-(2-Butoxy-vinyl)-phenyl]-5-(4-chloro-phenyl)-1-phenyl-1,5-dihydro-pyrazolo[3,4-d]pyrimidin-4-one;

6-[4-(2-Butoxy-ethyl)-phenyl]-5-(4-chloro-phenyl)-1-phenyl-1,5-dihydro-pyrazolo[3,4-d]pyrimidin-4-one;

5-(4-Chloro-phenyl)-6-[4-(1-methyl-1H-pyrazol-3-yl)-phenyl]-1-phenyl-1,5-dihydro-pyrazolo[3,4-d]pyrimidin-4-one;

5-(4-Chloro-phenyl)-1-phenyl-6-(4-pyridazin-3-yl-phenyl)-1,5-dihydro-pyrazolo[3,4-d]pyrimidin-4-one;

5-(4-Chloro-phenyl)-6-[4-(2-methyl-2H-pyrazol-3-yl)-phenyl]-1-phenyl-1,5-dihydro-pyrazolo[3,4-d]pyrimidin-4-one;

5-(4-Chloro-phenyl)-1-phenyl-6-(4-pyrimidin-2-yl-phenyl)-1,5-dihydro-pyrazolo[3,4-d]pyrimidin-4-one;

6-[4-(6-Amino-pyrazin-2-yl)-phenyl]-5-(4-chloro-phenyl)-1-phenyl-1,5-dihydro-pyrazolo[3,4-d]pyrimidin-4-one;

3-{4-[5-(4-Chloro-phenyl)-4-oxo-1-phenyl-4,5-dihydro-1H-pyrazolo[3,4-d]pyrimidin-6-yl]-phenyl}-pyrazine-2-carbonitrile;

5-(4-Chloro-phenyl)-6-[4-(3,6-dimethyl-pyrazin-2-yl)-phenyl]-1-phenyl-1,5-dihydro-pyrazolo[3,4-d]pyrimidin-4-one;

5-(4-Chloro-phenyl)-6-[4-(4-isoxazol-4-yl-phenyl)-1-phenyl-1,5-dihydro-pyrazolo[3,4-d]pyrimidin-4-one;

5-(4-Chloro-phenyl)-6-[4-(1-methyl-1H-imidazol-2-yl)-phenyl]-1-phenyl-1,5-dihydro-pyrazolo[3,4-d]pyrimidin-4-one;

5-(4-Chloro-phenyl)-1-phenyl-6-(4-pyrazin-2-yl-phenyl)-1,5-dihydro-pyrazolo[3,4-d]pyrimidin-4-one;

6-(4-Isopropyl-phenyl)-1-phenyl-5-m-tolyl-1,5-dihydro-pyrazolo[3,4-d]pyrimidin-4-one;

6-(4-Isopropyl-phenyl)-1-phenyl-5-(3-trifluoromethyl-phenyl)-1,5-dihydro-pyrazolo[3,4-d]pyrimidin-4-one;

5-(4-Chloro-3-methyl-phenyl)-6-(4-isopropyl-phenyl)-1-phenyl-1,5-dihydro-pyrazolo[3,4-d]pyrimidin-4-one;

5-(3,5-Difluoro-phenyl)-6-(4-isopropyl-phenyl)-1-phenyl-1,5-dihydro-pyrazolo[3,4-d]pyrimidin-4-one;

5-(3,4-Dichloro-phenyl)-6-(4-isopropyl-phenyl)-1-phenyl-1,5-dihydro-pyrazolo[3,4-d]pyrimidin-4-one;

5-(3-Fluoro-phenyl)-6-(4-isopropyl-phenyl)-1-phenyl-1,5-dihydro-pyrazolo[3,4-d]pyrimidin-4-one;

5-(3-Chloro-phenyl)-6-(4-isopropyl-phenyl)-1-phenyl-1,5-dihydro-pyrazolo[3,4-d]pyrimidin-4-one; and 5-(3-Bromo-phenyl)-6-(4-isopropyl-phenyl)-1-phenyl-1,5-dihydro-pyrazolo[3,4-d]pyrimidin-4-one;

or a pharmaceutically acceptable salt thereof.

10. A composition comprising a pharmaceutically acceptable carrier and a compound:

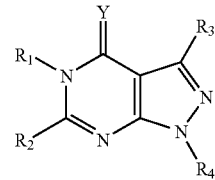

Ia in which:

Y is selected from O, NR$_7$ and S; wherein R$_7$ is selected from hydrogen, hydroxy and C$_{1-6}$alkyl;

R$_1$ is selected from C$_{3-12}$cyclolalkyl, phenyl and benzyl; wherein said cycloalkyl, phenyl and benzyl of R$_1$ is optionally substituted with 1 to 3 radicals independently selected from halo, hydroxy, nitro, C$_{1-6}$alkyl, C$_{1-6}$alkoxy, halo-substituted C$_{1-6}$alkyl, halo-substituted C$_{1-6}$alkoxy, —NR$_8$R$_9$, —S(O)$_{0-2}$R$_8$, —C(O)OR$_8$ and R$_{10}$;

R$_2$ is selected from C$_{3-8}$heterocycloalkyl, C$_{5-10}$heteroaryl, phenyl and phenoxy; wherein said heterocycloalkyl, heteroaryl, phenyl or phenoxy of R$_2$ is optionally substituted with 1 to 3 radicals independently selected from halo, hydroxy, cyano, nitro, C$_{1-6}$alkyl, C$_{1-6}$alkoxy, halo-substituted C$_{1-6}$alkyl, C$_{2-6}$alkenyl, halo-substituted C$_{1-6}$alkoxy, —XNR$_8$R$_9$, —XOR$_8$, —XC(O)R$_8$, —XS(O)$_{0-2}$R$_8$, —XC(O)NR$_8$R$_9$, —XC(O)OR$_8$, —XOR$_{10}$, —XNR$_8$XR$_{10}$ and —XR$_{10}$; wherein each X is independently selected from a bond, C$_{1-4}$alkylene and C$_{2-4}$alkenylene;

R$_3$ is selected from hydrogen, methyl, methyl-sulfonyl, t-butoxy-carbonyl-methyl, amino-carbonyl-methyl, methyl-[1,2,4]oxadiazolyl, cyano-methyl, carboxy, ethoxy-carbonyl, methyl-amino-carbonyl, dimethyl-amino-carbonyl, benzyl, furanyl, pyridinyl, indolyl, morpholino-carbonyl, piperidinyl-amino-carbonyl, piperidinyl-carbonyl, isopropoxy-carbonyl, amino-carbonyl, methyl-amino-carbonyl, cyano, methyl-piperazinyl, and phenyl optionally substituted with 1 to 2 radicals independently selected from methyl, methoxy, fluoro, chloro, bromo, iodo, cyano, nitro, hydroxy-methyl, ethoxy-carbonyl, methyl-sulfonyl, dimethyl-amino, methyl-amino, cyclopropyl-aminocarbonyl, isopropoxy, trifluoromethyl and trifluoromethoxy;

R$_4$ is selected from C$_{1-6}$alkyl, halo-substituted C$_{1-6}$alkyl, C$_{6-10}$aryl, C$_{6-10}$aryl-C$_{1-4}$alkyl, C$_{5-10}$heteroaryl, C$_{3-12}$cycloalkyl, C$_{3-8}$heterocycloalkyl and C(O)R$_{11}$; wherein R$_{11}$ is selected from C$_{3-8}$heterocycloalkyl and C$_{3-8}$heteroaryl; wherein any alkyl of R$_4$ can optionally have a methylene replaced with O, S(O)$_{0-2}$ and NR$_8$;

wherein any cycloalkyl, heterocycloalkyl, aryl or heteroaryl of $R_4$ can optionally be substituted with 1 to 3 radicals independently selected from halo, hydroxy, cyano, nitro, $C_{1-6}$alkyl, $C_{1-6}$alkoxy, halo-substituted-$C_{1-6}$ alkyl, halo-substituted-$C_{1-6}$alkoxy, —$XOR_8$, —$XR_{10}$, —$XC(O)R_{10}$, —$XS(O)_{0-2}R_8$, —$XNR_8R_9$, —$XC(O)NR_8R_9$, —$XC(O)NR_8R_{10}$, —$XC(O)NR_8XNR_8R_9$, —$XC(O)NR_8XOR_9$ and —$XC(O)OR_8$;

$R_8$ and $R_9$ are independently selected from hydrogen, $C_{1-6}$alkyl and $C_{2-6}$alkenyl; or $R_8$ and $R_9$ together with the nitrogen atom to which both are attached form $C_{3-8}$heterocycloalkyl or $C_{5-10}$heteroaryl; and $R_{10}$ is selected from $C_{5-10}$heteroaryl, $C_{3-8}$heterocycloalkyl, $C_{3-12}$cycloalkyl and phenyl; wherein said heteroaryl or heterocycloalkyl of $R_{10}$ or the combination of $R_8$ and $R_9$ and additionally the cycloalkyl or phenyl of $R_{10}$ is optionally substituted with 1 to 3 radicals independently selected from halo, hydroxy, cyano, cyano-$C_{1-6}$alkyl, nitro, $C_{1-6}$alkyl, $C_{1-6}$alkoxy, halo-substituted-$C_{1-6}$alkyl, halo-substituted-$C_{1-6}$alkoxy, hydroxy-substituted-$C_{1-6}$alkyl, hydroxy-substituted-$C_{1-6}$alkoxy, phenyl —$N(CH_3)_2$, —$NH(CH_3)$, —$NH_2$, $S(O)_{0-2}$—$CH_3$, —$C(O)OH$, and —$C(O)OCH_3$;

or the pharmaceutically acceptable salts thereof;

with the proviso that compounds of Formula Ia do not include compounds of Formula II that are set forth below:

5-(4-Isopropyl-phenyl)-1-phenyl-6-p-tolyl-1,5-dihydro-pyrazolo[3,4-d]pyrimidin-4-one;
6-(4-Bromo-phenyl)-1-phenyl-5-p-tolyl-1,5-dihydro-pyrazolo[3,4-d]pyrimidin-4-one;
1-Phenyl-5,6-di-m-tolyl-1,5-dihydro-pyrazolo[3,4-d]pyrimidin-4-one;
1-Phenyl-5,6-di-m-tolyl-1,5-dihydro-pyrazolo[3,4-d]pyrimidin-4-one;
1,5-Diphenyl-6-m-tolyl-1,5-dihydro-pyrazolo[3,4-d]pyrimidin-4-one;
1-Phenyl-5-o-tolyl-6-p-tolyl-1,5-dihydro-pyrazolo[3,4-d]pyrimidin-4-one;
5-(4-Ethoxy-phenyl)-1-phenyl-6-p-tolyl-1,5-dihydro-pyrazolo[3,4-d]pyrimidin-4-one;
5-(4-Chloro-phenyl)-1-phenyl-6-p-tolyl-1,5-dihydro-pyrazolo[3,4-d]pyrimidin-4-one;
5-(4-Isopropyl-phenyl)-1,6-diphenyl-1,5-dihydro-pyrazolo[3,4-d]pyrimidin-4-one;
5-(4-Bromo-phenyl)-6-(2-fluoro-phenyl)-1-phenyl-1,5-dihydro-pyrazolo[3,4-d]pyrimidin-4-one;
5-(4-Methoxy-phenyl)-1-phenyl-6-p-tolyl-1,5-dihydro-pyrazolo[3,4-d]pyrimidin-4-one;
6-(2-Fluoro-phenyl)-1-phenyl-5-m-tolyl-1,5-dihydro-pyrazolo[3,4-d]pyrimidin-4-one;
5-(4-Fluoro-phenyl)-6-(2-fluoro-phenyl)-1-phenyl-1,5-dihydro-pyrazolo[3,4-d]pyrimidin-4-one;
5-(4-Bromo-phenyl)-1-phenyl-6-m-tolyl-1,5-dihydro-pyrazolo[3,4-d]pyrimidin-4-one;
5-(4-Chloro-phenyl)-1-phenyl-6-m-tolyl-1,5-dihydro-pyrazolo[3,4-d]pyrimidin-4-one;
6-(2-Fluoro-phenyl)-5-(4-methoxy-phenyl)-1-phenyl-1,5-dihydro-pyrazolo[3,4-d]pyrimidin-4-one;
1-Phenyl-6-m-tolyl-5-p-tolyl-1,5-dihydro-pyrazolo[3,4-d]pyrimidin-4-one;
6-(4-Chloro-phenyl)-5-(4-fluoro-phenyl)-1-phenyl-1,5-dihydro-pyrazolo[3,4-d]pyrimidin-4-one;
5-(3-Chloro-phenyl)-1-phenyl-6-m-tolyl-1,5-dihydro-pyrazolo[3,4-d]pyrimidin-4-one;
1-Phenyl-5,6-di-p-tolyl-1,5-dihydro-pyrazolo[3,4-d]pyrimidin-4-one;
6-(4-Chloro-phenyl)-5-(4-ethoxy-phenyl)-1-phenyl-1,5-dihydro-pyrazolo[3,4-d]pyrimidin-4-one;
5-(4-Fluoro-phenyl)-1-phenyl-6-p-tolyl-1,5-dihydro-pyrazolo[3,4-d]pyrimidin-4-one;
5,6-Bis-(4-bromo-phenyl)-1-phenyl-1,5-dihydro-pyrazolo[3,4-d]pyrimidin-4-one;
5,6-Bis-(4-chloro-phenyl)-1-phenyl-1,5-dihydro-pyrazolo[3,4-d]pyrimidin-4-one;
5-(3-Chloro-phenyl)-6-(2-fluoro-phenyl)-1-phenyl-1,5-dihydro-pyrazolo[3,4-d]pyrimidin-4-one;
6-(2-Fluoro-phenyl)-1,5-diphenyl-1,5-dihydro-pyrazolo[3,4-d]pyrimidin-4-one;
1,5-Diphenyl-6-p-tolyl-1,5-dihydro-pyrazolo[3,4-d]pyrimidin-4-one;
5-(3-Chloro-phenyl)-6-(4-chloro-phenyl)-1-phenyl-1,5-dihydro-pyrazolo[3,4-d]pyrimidin-4-one;
5-(4-Methoxy-phenyl)-1,6-diphenyl-1,5-dihydro-pyrazolo[3,4-d]pyrimidin-4-one;
5-(3-Chloro-phenyl)-1-phenyl-6-p-tolyl-1,5-dihydro-pyrazolo[3,4-d]pyrimidin-4-one;
1-Phenyl-5,6-di-o-tolyl-1,5-dihydro-pyrazolo[3,4-d]pyrimidin-4-one;
6-(4-Chloro-phenyl)-1-phenyl-5-p-tolyl-1,5-dihydro-pyrazolo[3,4-d]pyrimidin-4-one;
6-(4-Bromo-phenyl)-5-(2,4-dimethyl-phenyl)-1-phenyl-1,5-dihydro-pyrazolo[3,4-d]pyrimidin-4-one;
6-(4-Chloro-phenyl)-1-phenyl-5-m-tolyl-1,5-dihydro-pyrazolo[3,4-d]pyrimidin-4-one;
6-(4-Bromo-phenyl)-1-phenyl-5-o-tolyl-1,5-dihydro-pyrazolo[3,4-d]pyrimidin-4-one;
6-(2-Fluoro-phenyl)-1-phenyl-5-o-tolyl-1,5-dihydro-pyrazolo[3,4-d]pyrimidin-4-one;
5-(4-Isopropyl-phenyl)-1-phenyl-6-m-tolyl-1,5-dihydro-pyrazolo[3,4-d]pyrimidin-4-one;
6-(4-Bromo-phenyl)-1-phenyl-5-m-tolyl-1,5-dihydro-pyrazolo[3,4-d]pyrimidin-4-one;
6-(4-Bromo-phenyl)-5-(4-ethoxy-phenyl)-1-phenyl-1,5-dihydro-pyrazolo[3,4-d]pyrimidin-4-one;
5-(4-Chloro-phenyl)-6-(2-fluoro-phenyl)-1-phenyl-1,5-dihydro-pyrazolo[3,4-d]pyrimidin-4-one;
5-(3-Chloro-phenyl)-1-phenyl-6-o-tolyl-1,5-dihydro-pyrazolo[3,4-d]pyrimidin-4-one;
5-(3,5-Dimethyl-phenyl)-1-phenyl-6-m-tolyl-1,5-dihydro-pyrazolo[3,4-d]pyrimidin-4-one;
6-(4-Bromo-phenyl)-5-(4-fluoro-phenyl)-1-phenyl-1,5-dihydro-pyrazolo[3,4-d]pyrimidin-4-one;
5-(4-Fluoro-phenyl)-1-phenyl-6-o-tolyl-1,5-dihydro-pyrazolo[3,4-d]pyrimidin-4-one;
1-Phenyl-5-m-tolyl-6-p-tolyl-1,5-dihydro-pyrazolo[3,4-d]pyrimidin-4-one; 5-(4-Bromo-phenyl)-1,6-diphenyl-1,5-dihydro-pyrazolo[3,4-d]pyrimidin-4-one;
5-(3-Chloro-phenyl)-1,6-diphenyl-1,5-dihydro-pyrazolo[3,4-d]pyrimidin-4-one;
1,6-Diphenyl-5-m-tolyl-1,5-dihydro-pyrazolo[3,4-d]pyrimidin-4-one;
5-(4-Ethoxy-phenyl)-1,6-diphenyl-1,5-dihydro-pyrazolo[3,4-d]pyrimidin-4-one;
6-(4-Bromo-phenyl)-5-(3-chloro-phenyl)-1-phenyl-1,5-dihydro-pyrazolo[3,4-d]pyrimidin-4-one;
6-(4-Chloro-phenyl)-1-phenyl-5-o-tolyl-1,5-dihydro-pyrazolo[3,4-d]pyrimidin-4-one;
6-(4-Chloro-phenyl)-5-(3,5-dimethyl-phenyl)-1-phenyl-1,5-dihydro-pyrazolo[3,4-d]pyrimidin-4-one;
1-Phenyl-6-o-tolyl-5-p-tolyl-1,5-dihydro-pyrazolo[3,4-d]pyrimidin-4-one;

1,5,6-Triphenyl-1,5-dihydro-pyrazolo[3,4-d]pyrimidin-4-one;

5-(4-Bromo-phenyl)-6-(4-chloro-phenyl)-1-phenyl-1,5-dihydro-pyrazolo[3,4-d]pyrimidin-4-one;

6-(2-Fluoro-phenyl)-5-(4-isopropyl-phenyl)-1-phenyl-1,5-dihydro-pyrazolo[3,4-d]pyrimidin-4-one;

6-(2-Fluoro-phenyl)-1-phenyl-5-p-tolyl-1,5-dihydro-pyrazolo[3,4-d]pyrimidin-4-one;

6-(4-Bromo-phenyl)-5-(4-isopropyl-phenyl)-1-phenyl-1,5-dihydro-pyrazolo[3,4-d]pyrimidin-4-one;

6-(4-Bromo-phenyl)-5-(4-chloro-phenyl)-1-phenyl-1,5-dihydro-pyrazolo[3,4-d]pyrimidin-4-one;

5-(4-Fluoro-phenyl)-1-phenyl-6-m-tolyl-1,5-dihydro-pyrazolo[3,4-d]pyrimidin-4-one;

1,6-Diphenyl-5-o-tolyl-1,5-dihydro-pyrazolo[3,4-d]pyrimidin-4-one;

5-(4-Ethoxy-phenyl)-6-(2-fluoro-phenyl)-1-phenyl-1,5-dihydro-pyrazolo[3,4-d]pyrimidin-4-one; and 1,6-Diphenyl-5-p-tolyl-1,5-dihydro-pyrazolo[3,4-d]pyrimidin-4-one.

11. A compound selected from the group consisting of:

4-[6-(2-Fluoro-phenyl)-4-oxo-1-phenyl-1,4-dihydro-pyrazolo[3,4-d]pyrimidin-5-yl]-benzonitrile;

6-(2-Fluoro-phenyl)-1-phenyl-5-pyridin-3-yl-1,5-dihydro-pyrazolo[3,4-d]pyrimidin-4-one;

5-(4-Bromo-phenyl)-6-(2,4-dichloro-phenyl)-3-methylsulfanyl-1-phenyl-1,5-dihydro-pyrazolo[3,4-d]pyrimidin-4-one;

5-(4-Chloro-phenyl)-6-(2,4-dichloro-phenyl)-3-methylsulfanyl-1-phenyl-1,5-dihydro-pyrazolo[3,4-d]pyrimidin-4-one;

5-(4-Chloro-phenyl)-6-[4-(2-chloro-pyrimidin-4-yl)-phenyl]-3-methylsulfanyl-1-phenyl-1,5-dihydro-pyrazolo[3,4-d]pyrimidin-4-one; and 6-[4-(2-Amino-pyrimidin-4-yl)-phenyl]-5-(4-chloro-phenyl)-3-methylsulfanyl-1-phenyl-1,5-dihydro-pyrazolo[3,4-d]pyrimidin-4-one;

or a pharmaceutically acceptable salt thereof.

* * * * *